US012678492B2

(12) United States Patent
Connor et al.

(10) Patent No.: US 12,678,492 B2
(45) Date of Patent: Jul. 14, 2026

(54) COMBINATION THERAPY WITH ANTIBODY-DRUG CONJUGATES AND HYALURONIDASES

(71) Applicant: HALOZYME, INC., San Diego, CA (US)

(72) Inventors: Robert Connor, San Diego, CA (US); David Kang, San Diego, CA (US); Tara Nekoroski, San Diego, CA (US); Michael Labarre, San Diego, CA (US)

(73) Assignee: HALOZYME, INC., San Diego, CA (US)

( * ) Notice: Subject to any disclaimer, the term of this patent is extended or adjusted under 35 U.S.C. 154(b) by 0 days.

(21) Appl. No.: 19/315,951

(22) Filed: Sep. 2, 2025

(65) Prior Publication Data

US 2026/0061038 A1      Mar. 5, 2026

Related U.S. Application Data

(63) Continuation of application No. PCT/US2025/018582, filed on Mar. 5, 2025.

(60) Provisional application No. 63/673,280, filed on Jul. 19, 2024, provisional application No. 63/561,701, filed on Mar. 5, 2024.

(51) Int. Cl.
*A61K 38/40* (2006.01)
*A61K 38/47* (2006.01)
*A61K 47/68* (2017.01)

(52) U.S. Cl.
CPC ........ *A61K 38/47* (2013.01); *A61K 47/68031* (2023.08); *A61K 47/68033* (2023.08); *A61K 47/68035* (2023.08); *A61K 47/68037* (2023.08); *A61K 47/6849* (2017.08); *A61K 47/6851* (2017.08); *C12Y 302/01035* (2013.01)

(58) Field of Classification Search
CPC ............ C07K 16/283; C07K 2317/622; C07K 2319/00; A61P 37/00; C12Y 302/01035
See application file for complete search history.

(56) References Cited

U.S. PATENT DOCUMENTS

| | | | |
|---|---|---|---|
| 7,767,429 | B2 | 8/2010 | Bookbinder et al. |
| 7,829,081 | B2 | 11/2010 | Bookbinder et al. |
| 7,846,431 | B2 | 12/2010 | Bookbinder et al. |
| 7,871,607 | B2 | 1/2011 | Bookbinder et al. |
| 8,105,586 | B2 | 1/2012 | Bookbinder et al. |
| 8,187,855 | B2 | 5/2012 | Baker et al. |
| 8,202,517 | B2 | 6/2012 | Bookbinder et al. |
| 8,257,699 | B2 | 9/2012 | Bookbinder et al. |
| 8,343,487 | B2 | 1/2013 | Baker et al. |
| 8,431,124 | B2 | 4/2013 | Bookbinder et al. |
| 8,431,380 | B2 | 4/2013 | Bookbinder et al. |
| 8,450,470 | B2 | 5/2013 | Bookbinder et al. |
| 8,580,252 | B2 | 11/2013 | Bookbinder et al. |

| | | | |
|---|---|---|---|
| 8,765,685 | B2 | 7/2014 | Bookbinder et al. |
| 8,772,246 | B2 | 7/2014 | Bookbinder et al. |
| 8,927,249 | B2 | 1/2015 | Wei et al. |
| 9,221,882 | B2 | 12/2015 | Skerra et al. |
| 9,284,543 | B2 | 3/2016 | Wei et al. |
| 9,447,401 | B2 | 9/2016 | Wei et al. |
| 9,677,061 | B2 | 6/2017 | Bookbinder et al. |
| 9,677,062 | B2 | 6/2017 | Bookbinder et al. |
| 9,725,515 | B2 | 8/2017 | Anderson et al. |
| 9,873,748 | B2 | 1/2018 | Chen et al. |
| 9,913,822 | B2 | 3/2018 | Maneval et al. |
| 9,968,676 | B2 | 5/2018 | Adler et al. |
| 10,077,318 | B2 | 9/2018 | Bhakta et al. |
| 10,117,886 | B2 | 11/2018 | Cheng et al. |
| 10,385,135 | B2 | 8/2019 | Jansson et al. |
| 10,646,569 | B2 | 5/2020 | Shenoy |
| 10,766,965 | B2 | 9/2020 | Chaulagain et al. |
| 10,799,597 | B2 | 10/2020 | Goldenberg |
| 10,842,743 | B2 | 11/2020 | Roth et al. |
| 10,918,736 | B2 | 2/2021 | Kim et al. |
| 11,041,149 | B2 | 6/2021 | Wei et al. |
| 11,364,283 | B2 | 6/2022 | Npo et al. |
| 11,414,489 | B2 | 8/2022 | Rosengren et al. |
| 12,371,683 | B2 | 7/2025 | Park et al. |
| 2020/0282071 | A1 | 9/2020 | Friedrich et al. |
| 2021/0363270 | A1 | 11/2021 | Park et al. |
| 2021/0393713 | A1 | 12/2021 | Hordeaux et al. |
| 2022/0168403 | A1 | 6/2022 | Kapur et al. |
| 2023/0181712 | A1 | 6/2023 | Umaña et al. |
| 2023/0250408 | A1 | 8/2023 | Park et al. |
| 2023/0372342 | A1 | 11/2023 | Walker et al. |
| 2023/0405095 | A1 | 12/2023 | Han et al. |

(Continued)

FOREIGN PATENT DOCUMENTS

| | | |
|---|---|---|
| CN | 113827718 A | 12/2021 |
| CN | 114432269 A | 5/2022 |

(Continued)

OTHER PUBLICATIONS

International Search Report and Written Opinion for International Application No. PCT/US2025/018582, mailed Jul. 9, 2025, 30 pages.

(Continued)

*Primary Examiner* — Tekchand Saidha
*Assistant Examiner* — Mohammad Y Meah
(74) *Attorney, Agent, or Firm* — Haynes Beffel & Wolfeld LLP; Andrew L. Dunlap; Hannah W. Powell

(57) ABSTRACT

Provided are combination dosing regimens comprising administering an antibody-drug conjugate and hyaluronidase. Combinations and compositions containing the antibody-drug conjugate and hyaluronidase are provided. The dosing regimens and combinations are for treating or preventing cancer.

37 Claims, 67 Drawing Sheets

Specification includes a Sequence Listing.

(56) References Cited

U.S. PATENT DOCUMENTS

| | | | |
|---|---|---|---|
| 2024/0115569 A1 | 4/2024 | Noble et al. |
| 2024/0307549 A1 | 9/2024 | Kulke et al. |
| 2025/0009850 A1 | 1/2025 | Park et al. |
| 2025/0051453 A1 | 2/2025 | Verheesen et al. |
| 2025/0084171 A1 | 3/2025 | van der Woning et al. |

FOREIGN PATENT DOCUMENTS

| | | |
|---|---|---|
| CN | 114539538 B | 3/2023 |
| CN | 119524152 A | 2/2025 |
| EP | 2907504 B1 | 6/2017 |
| EP | 4272729 A1 | 11/2023 |
| EP | 4424301 A1 | 9/2024 |
| WO | 2009/111066 A1 | 9/2009 |
| WO | 2009117085 A1 | 9/2009 |
| WO | 2010/077297 A1 | 7/2010 |
| WO | 2013/102144 A1 | 7/2013 |
| WO | 2017/161206 A1 | 9/2017 |
| WO | 2017/195792 A1 | 11/2017 |
| WO | 2017/217525 A1 | 12/2017 |
| WO | 2020/022791 A1 | 1/2020 |
| WO | 2020/197230 A1 | 10/2020 |
| WO | 2021/050953 A1 | 3/2021 |
| WO | 2021150079 A1 | 7/2021 |
| WO | 2022005499 A1 | 1/2022 |
| WO | 2022141232 A1 | 7/2022 |
| WO | 2023/019556 A1 | 2/2023 |
| WO | 2023/042096 A1 | 3/2023 |
| WO | 2023/056403 A1 | 4/2023 |
| WO | 2023/075506 A1 | 5/2023 |
| WO | 2023/141297 A2 | 7/2023 |
| WO | 2023/156614 A1 | 8/2023 |
| WO | 2023/201119 A1 | 10/2023 |
| WO | 2023/209036 A1 | 11/2023 |
| WO | 2024/058648 A1 | 3/2024 |
| WO | 2024/091417 A1 | 5/2024 |
| WO | 2024/095173 A1 | 5/2024 |
| WO | 2024/138188 A1 | 6/2024 |
| WO | 2024/159948 A1 | 8/2024 |
| WO | 2024/240173 A1 | 11/2024 |
| WO | 2024/249889 A1 | 12/2024 |
| WO | 2025/103501 A1 | 5/2025 |
| WO | 2024/254278 A3 | 6/2025 |
| WO | 2025/124463 A1 | 6/2025 |

OTHER PUBLICATIONS

Mcnulty, FDA Approves Sacituzumab Govitecan for Pre-Treated HR+/HER2-Metastatic Breast Cancer, AJMC, Feb. 3, 2023, <https://www.ajmc.com/view/fda-approves-sacituzumab-govitecan-for-pre-treated-hr-her2--metastatic-breast-cancer>.

FIG. 5

Trodelvy

4493L

4498R

4593L

Trodelvy + rHuPH20

Pre-Image Not Useable

AID 4493L: Trodelvy

Epidermis/
Dermis

Subcutaneous

Muscle

AID 4493R: Trodelvy + rHuPH20

Epidermis/
Dermis

Subcutaneous

Muscle

AID 4493: Naive

Epidermis/
Dermis

Subcutaneous

Muscle

AID 4498R: Trodelvy

Epidermis/
Dermis

Subcutaneous

Muscle

AID 4498L: Trodelvy + rHuPH20

Epidermis/
Dermis

Subcutaneous

Muscle

AID 4498: Naive

Epidermis/
Dermis

Subcutaneous

Muscle

AID 4593L: Trodelvy

Epidermis/
Dermis

Subcutaneous

Muscle

AID 4593R: Trodelvy + rHuPH20

Epidermis/
Dermis

Subcutaneous

Muscle

AID 4593: Naive

Epidermis/
Dermis

Subcutaneous

Muscle

ADC 4493L        4498R        4593L

ADC + rHuPH20

Pre-Image Not
Useable 4493R        4498L        4593R

FIG. 17C

AID #4493L:ADC

Pre          Post-T1          Post-T24h

Post-T48h          Post-T72h

AID #4493R:ADC
+ rHuPH20

Image Not
Taken

Pre          Post-T1          Post-T24h

Post-T48h          Post-T72h

AID #4498R:ADC

Pre           Post-T1           Post-T24h

Post-T48h           Post-T72h

AID #4498L:ADC
+ rHuPH20

Pre           Post-T1           Post-T24h

Post-T48h           Post-T72h

AID #4593L:ADC

Pre                          Post-T1                          Post-T24h

Post-T48h                          Post-T72h

AID #4593R:ADC
+ rHuPH20

Pre                          Post-T1                          Post-T24h

Post-T48h                          Post-T72h

AID 4493L: ADC

Epidermis/
Dermis

Subcutaneous

Muscle

AID 4493R ADC + rHuPH20

Epidermis/
Dermis

Subcutaneous

Muscle

AID 4493: Naive

AID 4498R: ADC

AID 4498L: ADC + rHuPH20

AID 4498: Naive

AID 4593L: ADC

Epidermis/Dermis

Subcutaneous

Muscle

AID 4593R: ADC + rHuPH20

Epidermis/Dermis

Subcutaneous

Muscle

AID 4593: Naive

Pre-injection

ADC-Site Q7

Pre          T$_0$          T$_{0.5h}$

ADC + rHuPH20-Site Q2

Pre          T$_0$          T$_{0.5h}$

ADC-Site Q3

ADC + rHuPH20-Site Q6

ADC-Site Q5

Pre  $T_0$  $T_{1h}$  $T_{1.5h}$  $T_{2h}$

ADC + rHuPH20-Site Q4

Pre  $T_0$  $T_{1h}$  $T_{1.5h}$  $T_{2h}$

ADC-Site Q1

Pre          T$_0$          T$_{2h}$          T$_{3h}$          T$_{3.5h}$          T$_{4h}$

ADC + rHuPH20-Site Q8

Pre          T$_0$          T$_{2h}$          T$_{3h}$          T$_{3.5h}$          T$_{4h}$

Injection Site #7: ADC - 0.5 hour

Injection Site #2: ADC + rHuPH20 - 0.5 hour

Injection Site #3: ADC - 1 hour

Dermis

Subcutaneous

Muscle

Injection Site #6: ADC + rHuPH20 - 1 hour

Dermis

Subcutaneous

Muscle

Injection Site #5: ADC - 2 hours

Injection Site #4: ADC + rHuPH20 - 2 hours

Injection Site #1: ADC - 4 hours

Dermis

Subcutaneous

Muscle

Injection Site #8: ADC + rHuPH20 - 4 hours

Dermis

Subcutaneous

Muscle

Injection Site #9: Naive

Dermis

Subcutaneous

Muscle

Injection Site #10: Naive

Dermis

Subcutaneous

Muscle

T0                              T2h

ADC

ADC +
rHuPH20

● ADC
▲ ADC + rHuPH20

● ADC
▲ ADC+ rHuPH20

FIG. 33

ADC

ADC + rHuPH20

Naïve SC

= 560 mg Q3W IV

= 520 mg Q2W SC with rHuPH20

= 560 mg Q3W IV

= 780 mg Q3W SC with rHuPH20

= 560 mg Q3W IV

= 1000 mg Q4W SC with rHuPH20

— = 420 mg Q3W IV

— = 430 mg Q2W SC with rHuPH20

···· = 420 mg Q3W IV

— = 640 mg Q3W SC with rHuPH20

— = 420 mg Q3W IV

— = 850 mg Q4W SC with rHuPH20

Example 4

— = 252 mg Q3W IV
— = 250 mg Q2W SC with rHuPH20

— = 252 mg Q3W IV
— = 370 mg Q3W SC with rHuPH20

— = 252 mg Q3W IV
— = 490 mg Q4W SC with rHuPH20

Time (days)

= 140 mg Q3W IV
= 150 mg Q2W SC with rHuPH20

= 140 mg Q3W IV
= 220 mg Q3W SC with rHuPH20

= 140 mg Q3W IV
= 290 mg Q4W SC with rHuPH20

Example 7

— = 420 mg Q3W IV
— = 400 mg Q2W SC with rHuPH20

— = 420 mg Q3W IV
— = 600 mg Q3W SC with rHuPH20

— = 420 mg Q3W IV
— = 800 mg Q4W SC with rHuPH20

Time (days)

Example 8

— = 5.25 mg Q3W IV
— = 4.8 mg Q2W SC with rHuPH20

— = 5.25 mg Q3W IV
— = 7.1 mg Q3W SC with rHuPH20

— = 5.25 mg Q3W IV
— = 9.5 mg Q4W SC with rHuPH20

```
                        SEQUENCE LISTING

Sequence total quantity: 57
SEQ ID NO: 1            moltype = AA  length = 509
FEATURE                 Location/Qualifiers
REGION                  1..509
                        note = precursor human PH20
source                  1..509
                        mol_type = protein
                        organism = Homo sapiens
SEQUENCE: 1
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS ATMFIVSILF LIISSVASL                                   509

SEQ ID NO: 2            moltype = AA  length = 474
FEATURE                 Location/Qualifiers
REGION                  1..474
                        note = Mature PH20
source                  1..474
                        mol_type = protein
                        organism = Homo sapiens
SEQUENCE: 2
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLSATMFI VSILFLIISS VASL        474

SEQ ID NO: 3            moltype = AA  length = 482
FEATURE                 Location/Qualifiers
REGION                  1..482
                        note = precursor soluble rHuPH20
source                  1..482
                        mol_type = protein
                        organism = Homo sapiens
SEQUENCE: 3
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
```

```
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQI    480
FY                                                                  482

SEQ ID NO: 4          moltype = AA   length = 447
FEATURE               Location/Qualifiers
REGION                1..447
                      note = soluble rHuPH20 1-447
source                1..447
                      mol_type = protein
                      organism = Homo sapiens
SEQUENCE: 4
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIFY                                       447

SEQ ID NO: 5          moltype = AA   length = 446
FEATURE               Location/Qualifiers
REGION                1..446
                      note = soluble rHuPH20 1-446
source                1..446
                      mol_type = protein
                      organism = Homo sapiens
SEQUENCE: 5
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQIF                                        446

SEQ ID NO: 6          moltype = AA   length = 445
FEATURE               Location/Qualifiers
REGION                1..445
                      note = soluble rHuPH20 1-445
source                1..445
                      mol_type = protein
                      organism = Homo sapiens
SEQUENCE: 6
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQI                                         445

SEQ ID NO: 7          moltype = AA   length = 444
FEATURE               Location/Qualifiers
REGION                1..444
                      note = soluble rHuPH20 1-444
source                1..444
                      mol_type = protein
                      organism = Homo sapiens
SEQUENCE: 7
LNFRAPPVIP NVPFLWAWNA PSEFCLGKFD EPLDMSLFSF IGSPRINATG QGVTIFYVDR     60
LGYYPYIDSI TGVTVNGGIP QKISLQDHLD KAKKDITFYM PVDNLGMAVI DWEEWRPTWA    120
RNWKPKDVYK NRSIELVQQQ NVQLSLTEAT EKAKQEFEKA GKDFLVETIK LGKLLRPNHL    180
WGYYLFPDCY NHHYKKPGYN GSCFNVEIKR NDDLSWLWNE STALYPSIYL NTQQSPVAAT    240
LYVRNRVREA IRVSKIPDAK SPLPVFAYTR IVFTDQVLKF LSQDELVYTF GETVALGASG    300
IVIWGTLSIM RSMKSCLLLD NYMETILNPY IINVTLAAKM CSQVLCQEQG VCIRKNWNSS    360
DYLHLNPDNF AIQLEKGGKF TVRGKPTLED LEQFSEKFYC SCYSTLSCKE KADVKDTDAV    420
DVCIADGVCI DAFLKPPMET EEPQ                                          444

SEQ ID NO: 8          moltype = AA   length = 443
FEATURE               Location/Qualifiers
REGION                1..443
                      note = soluble rHuPH20 1-443
source                1..443
```

```
                             mol_type = protein
                             organism = Homo sapiens
SEQUENCE: 8
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEP                                          443

SEQ ID NO: 9                 moltype = AA   length = 442
FEATURE                      Location/Qualifiers
REGION                       1..442
                             note = soluble rHuPH20 1-442
source                       1..442
                             mol_type = protein
                             organism = Homo sapiens
SEQUENCE: 9
LNFRAPPVIP NVPFLWAWNA PSEFCLGKFD EPLDMSLFSF IGSPRINATG QGVTIFYVDR   60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EE                                           442

SEQ ID NO: 10                moltype = AA   length = 450
FEATURE                      Location/Qualifiers
REGION                       1..450
                             note = hyaluronidase
source                       1..450
                             mol_type = protein
                             organism = Bos taurus
SEQUENCE: 10
MRPFSLEVSL HLPWAMAAHL LPVCTLFLNL LSMTQGSRDP VVPNQPFTTI WNANTEWCMK   60
KHGVDVDISI FDVVTNPGQT FRGPNMTIFY SSQLGTYPYY TSAGEPVFGG LPQNASLNAH  120
LARTFQDILA AMPEPRFSGL AVIDWEAWRP RWAFNWDTKD IYRQRSRALV QKQHPDWLAP  180
RVEAAAQDQF EGAAEEWMAG TLKLGQALRP QGLWGFYNFP ECYNYDFKSP NYTGRCPLNI  240
CAQNDQLGWL WGQSRALYPS IYLPAALEGT KKTQMFVQHR VAEAFRVAAG AGDPKLPVLP  300
YMQLFYDMTN HFLPAEELEH SLGESAAQGA AGVVLWVSWL STSTKESCQA IKEYVDTTLG  360
PSILNVTSGA RLCSQVLCSG HGRCARRPSY PKARLILNST SFSIKPTPGG GPLTLQGALS  420
LEDRLRMAVE FECRCYRGWR GTRCEQWGMW                                   450

SEQ ID NO: 11                moltype = AA   length = 331
FEATURE                      Location/Qualifiers
REGION                       1..331
                             note = hyaluronidase A
source                       1..331
                             mol_type = protein
                             organism = synthetic construct
SEQUENCE: 11
SERPKRVFNI YWNVPTFMCH QYDLYFDEVT NFNIKRNSKD DFQGDKIAIF YDPGEFPALL   60
SLKDGKYKKR NGGVPQEGNI TIHLQKFIEN LDKIYPNRNF SGIGVIDFER WRPIFRQNWG  120
NMKIHKNFSI DLVRNEHPTW NKKMIELEAS KRFEKYARFF MEETLKLAKK TRKQADWGYY  180
GYPYCFNMSP NNLVPECDVT AMHENDKMSW LFNNQNVLLP SVYVRQELTP DQRIGLVQGR  240
VKEAVRISNN LKHSPKVLSY WWYVQDETN TFLTETDVKK TFQEIVINGG DGIIIWGSSS  300
DVNSLSKCKR LQDYLLTVLG PIAINVTEAV N                                 331

SEQ ID NO: 12                moltype = AA   length = 340
FEATURE                      Location/Qualifiers
REGION                       1..340
                             note = hyaluronidase B
source                       1..340
                             mol_type = protein
                             organism = synthetic construct
SEQUENCE: 12
DRTIWPKKGF SIYWNIPTHF CHNFGVYFKE LKQFNIKYNS MNNFRGETIS LFYDPGNFPS   60
MVLLKNGTYE IRNEGVPQKG NLTIHLEQFT KELDEIYPKK IAGGIGVIHF HNWRPIFRRN  120
VDNLKINKDI SIDLVRKEHP KWDKSMIEKE ASNRFETSAK IFMEKTLKLA KEIRKKTEWG  180
YHGYPHCLSG STDKPSFDCD ALSMSENDKM SWLFNNQNVL LPSIYLKNVL KPDEKIHLVQ  240
ERLKEAIRIS KNFKHLPKVL PYWWYTYQDK ESIFLTEADV KNTFKEILTN GADGIIIWGV  300
SYELTDRKRC EKLKEYLMKI LGPIAFKVTK AVKENTPLNF                        340

SEQ ID NO: 13                moltype = AA   length = 382
FEATURE                      Location/Qualifiers
REGION                       1..382
```

```
                              note = hyaluronidase
source                        1..382
                              mol_type = protein
                              organism = Apis mellifera
SEQUENCE: 13
MSRPLVITEG MMIGVLLMLA PINALLLGFV QSTPDNNKTV REFNVYWNVP TFMCHKYGLR    60
FEEVSEKYGI LQNWMDKFRG EEIAILYDPG MFPALLKDPN GNVVARNGGV PQLGNLTKHL   120
QVFRDHLINQ IPDKSFPGVG VIDFESWRPI FRQNWASLQP YKKLSVEVVR REHPFWDDQR   180
VEQEAKRRFE KYGQLFMEET LKAAKRMRPA ANWGYYAYPY CYNLTPNQPS AQCEATTMQE   240
NDKMSWLFES EDVLLPSVYL RWNLTSGERV GLVGGRVKEA LRIARQMTTS RKKVLPYYWY   300
KYQDRRDTDL SRADLEATLR KITDLGADGF IIWGSSDDIN TKAKCLQFRE YLNNELGPAV   360
KRIALNNNAN DRLTVDVSVD QV                                           382

SEQ ID NO: 14                 moltype = AA   length = 331
FEATURE                       Location/Qualifiers
REGION                        1..331
                              note = hyaluronidase
source                        1..331
                              mol_type = protein
                              organism = Dolichovespula maculata
SEQUENCE: 14
SERPKRVFNI YWNVPTFMCH QYGLYFDEVT NFNIKHNSKD DFQGDKISIF YDPGEFPALL    60
PLKEGNYKIR NGGVPQEGNI TIHLQRFIEN LDKTYPNRNF NGIGVIDFER WRPIFRQNWG   120
NMMIHKKFSI DLVRNEHPFW DKKMIELEAS KRFEKYARLF MEETLKLAKK TRKQADWGYY   180
GYPYCFNMSP NNLVPDCDAT AMLENDKMSW LFNNQNVLLP SVYIRHELTP DQRVGLVQGR   240
VKEAVRISNN LKHSPKVLSY WWYVYQDDTN TFLTETDVKK TFQEIAINGG DGIIIWGSSS   300
DVNSLSKCKR LREYLLTVLG PITVNVTETV N                                 331

SEQ ID NO: 15                 moltype = AA   length = 367
FEATURE                       Location/Qualifiers
REGION                        1..367
                              note = hyaluronidase
source                        1..367
                              mol_type = protein
                              organism = synthetic construct
SEQUENCE: 15
YVSLSPDSVF NIITDDISHQ ILSRSNCERS KRPKRVFSIY WNVPTFMCHQ YGMNFDEVTD    60
FNIKHNSKDN FRGETISIYY DPGKFPALMP LKNGNYEERN GGVPQRGNIT IHLQQFNEDL   120
DKMTPDKNFG GIGVIDFERW KPIFRQNWGN TEIHKKYSIE LVRKEHPKWS ESMIEAEATK   180
KFEKYARYFM EETLKLAKKT RKRAKWGYYG FPYCYNVTPN NPGPDCDAKA TIENDRLSWM   240
YNNQEILFPS VYVRHEQKPE ERVYLVQGRI KEAVRISNNL EHSPSVLAYW WYVYQDKMDI   300
YLSETDVEKT FQEIVTNGGD GIIIWGSSSD VNSLSKCKRL REYLLNTLGP FAVNVTETVN   360
GRSSLNF                                                           367

SEQ ID NO: 16                 moltype = AA   length = 462
FEATURE                       Location/Qualifiers
REGION                        1..462
                              note = hyaluronidase
source                        1..462
                              mol_type = protein
                              organism = Mus musculus
SEQUENCE: 16
MLGLTQHAQK VWRMKPFSPE VSPGSSPATA GHLLRISTLF LTLLELAQVC RGSVVSNRPF    60
ITVWNGDTHW CLTEYGVDVD VSVFDVVANK EQSFQGSNMT IFYREELGTY PYYTPTGEPV   120
FGGLPQNASL VTHLAHTFQD IKAAMPEPDF SGLAVIDWEA WRPRWAFNWD SKDIYRQRSM   180
ELVQAEHPDW PETLVEAAAK NQFQEAAEAW MAGTLQLGQV LRPRGLWGYY GFPDCYNNDF   240
LSLNYTGQCP VFVRDQNDQL GWLWNQSYAL YPSIYLPAAL MGTGKSQMYV RHRVQEALRV   300
AIVSRDPHVP VMPYVQIFYE MTDYLLPLEE LEHSLGESEA QGVAGAVLWL SSDKTSTKES   360
CQAIKAYMDS TLGPFIVNVT SAALLCSEAL CSGHGRCVRH PSYPEALLTL NPASFSIELT   420
HDGRPPSLKG TLSLKDRAQM AMKFRCRCYR GWRGKWCDKR GM                     462

SEQ ID NO: 17                 moltype = AA   length = 473
FEATURE                       Location/Qualifiers
REGION                        1..473
                              note = Hyaluronidase 2
source                        1..473
                              mol_type = protein
                              organism = Mus musculus
SEQUENCE: 17
MRAGLGPIIT LALVLEVAWA GELKPTAPPI FTGRPFVVAW NVPTQECAPR HKVPLDLRAF    60
DVKATPNEGF FNQNITTFYY DRLGLYPRFD AAGTSVHGGV PQNGSLCAHL PMLKESVERY   120
IQTQEPGGLA VIDWEEWRPV WVRNWQEKDV YRQSSRQLVA SRHPDWPSDR VMKQAQYEFE   180
FAARQFMLNT LRYVKAVRPQ HLWGFYLFPD CYNHDYVQNM ESYTGRCPDV EVARNDQLAW   240
LWAESTALFP SVYLDETLAS VSHSRNFVSF RVREALRVAH THHANHALPV YVFTRPTYTR   300
GLTGLSQVDL ISTIGESAAL GSAGVIFWGD SEDASSMETC QYLKNYLTQL LVPYIVNVSW   360
ATQYCSWTQC HGHGRCVRRN PSANTFLHLN ASSFRLVPGH TPSEPQLRPE GQLSEADLNY   420
LQKHFRCQCY LGWGGEQCQR NYKGAAGNAS RAWAGSHLTS LLGLVAVALT WTL          473

SEQ ID NO: 18                 moltype = AA   length = 412
```

-continued

```
FEATURE              Location/Qualifiers
REGION               1..412
                     note = hyalurinidase 3
source               1..412
                     mol_type = protein
                     organism = Mus musculus
SEQUENCE: 18
MIMHLGLMMV VGLTLCLMHG QALLQVPEHP FSVVWNVPSA RCKAHFGVHL PLDALGIVAN   60
HGQHFHGQNI SIFYKNQFGL YPYFGPRGTA HNGGIPQAVS LDHHLARAAH QILHSLGSSF  120
AGLAVLDWEE WYPLWAGNWG PHRQVYLAAS WVWTQQMFPG LDPQEQLHKA HTSFEQAARA  180
LMEYTLQLGR TLRPSGLWGF YRYPACGNGW HKMASNYTGH CHAAITTQNT QLRWLWAASS  240
ALFPSIYLPP RLPLAYRQAF VRHRLEEAFR VALLEHSHPL PVLAYSRLTH RSSGRFLSLD  300
DLMQTIGVSA ALGTAGVVLW GDLSFSSSEE KCWRLHDYLV GTLGPYVINV TKADMACSHQ  360
RCHGHGRCAR KDPGQMEAFL HLQPDDSLGA WNSFRCHCYS GWAGPTCLEP KP          412

SEQ ID NO: 19         moltype = AA  length = 435
FEATURE               Location/Qualifiers
REGION                1..435
                      note = hyalauronidase
source                1..435
                      mol_type = protein
                      organism = Sus scrofa
SEQUENCE: 19
MAAHLLPICT LFLNLLSVAQ GSRDPVVLNR PFTTIWNANT QWCLKRHGVD VDVSVFEVVV   60
NPGQTFRGPN MTIFYSSQLG TYPYYTSAGE PVFGGLPQNA SLDVHLNRTF KDILAAMPES  120
NFSGLAVIDW EAWRPRWAFN WDAKDIYRQR SRALVQKQHP DWPAPWVEAA AQDQFQEAAQ  180
TWMAGTLKLG QTLRPHGLWG FYGFPDCYNY DFQSSNYTGQ CPPGVSAQND QLGWLWGQSR  240
ALYPSIYLPS ALEGTNKTQL YVQHRVNEAF RVAAAAGDPN LPVLPYAQIF HDMTNRLLSR  300
EELEHSLGES AAQGAAGVVL WVSWENTRTK ESCQSIKEYV DTTLGPFILN VTSGALLCSQ  360
AVCSGHGRCV RRPSHTEALP ILNPSSFSIK PTPGGGPLTL QGALSLKDRV QMAEEFQCRC  420
YPGWRGTWCE QQGTR                                                   435

SEQ ID NO: 20         moltype = AA  length = 419
FEATURE               Location/Qualifiers
REGION                1..419
                      note = hyaluronidase 3
source                1..419
                      mol_type = protein
                      organism = Sus scrofa
SEQUENCE: 20
MTMQLGLALV LGVAMCLGCG QPLLRAPERP FCVLWNVPSA RCKARFGVHL PLEALGITAN   60
HGQRFHGQNI TIFYKSQLGL YPYFGPRGTA HNGGIPQAVS LDHHLARAAY QIHRSLRPGF  120
TGLAVLDWEE WCPLWAGNWG RRQAYQAASC AWAQRVYPNL DPQEQLCKAR AGFEEAARAL  180
MEDTLRLGRM LRPHGLWGFY HYPACGNGWH GTASNYTGHC HAAALARNTQ LYWLWAASSA  240
LFPSIYLPPG LPPAYHQAFV RYRLEEAFRV ALVGHPHPLP VLAYARLTHR NSGRFLSQDE  300
LVQTIGVSAA LGASGVVLWG DLSFSSSEEE CWHLRGYLVG TLGPYVINVT RAAMACSHQR  360
CHGHGRCAWQ DPGQLKVFLH LHPGGSPGAW ESFSCRCYWG WAGPTCQEPR PELGPEEAT   419

SEQ ID NO: 21         moltype = AA  length = 449
FEATURE               Location/Qualifiers
REGION                1..449
                      note = hyaluronidase 1
source                1..449
                      mol_type = protein
                      organism = Rattus norvegicus
SEQUENCE: 21
MKPFSPEVSP DPCPATAAHL LRTYTLFLTL LELAQGCRGS MVSNRPFITV WNADTHWCLK   60
DHGVDVDVSV FDVVANKEQN FQGPNMTIFY REELGTYPYY TPTGEPVFGG LPQNASLVTH  120
LAHAFQDIKA AMPEPDFSGL AVIDWEAWRP RWAFNWDSKD IYQQRSMELV RAEHPDWPET  180
LVEAEAQGQF QEAAEAWMAG TLQLGQVLRP RGLWGYYGFP DCYNYDFLSP NYTGQCSLSI  240
HDQNDQLGWL WNQSYALYPS IYLPAALMGT GKSQMYVRYR VQEAFRLALV SRDPHVPIMP  300
YVQIFYEKTD YLLPLEELEH SLGESAAQGA AGAVLWISSE KTSTKESCQA IKAYMDSTLG  360
PPILNVTSAA LLCSEALCSG RGRCVRHPSY PEALLTLSPA SFSIEPTHDG RPLSLKGTLS  420
LKDRAQMAMK FKCRCYRGWS GEWCKKQDM                                    449

SEQ ID NO: 22         moltype = AA  length = 473
FEATURE               Location/Qualifiers
REGION                1..473
                      note = hyaluronidase 2
source                1..473
                      mol_type = protein
                      organism = Rattus norvegicus
SEQUENCE: 22
MRAGLGPIIT LALVLEVAWA SELKPTAPPI FTGRPFVVAW NVPTQECAPR HKVPLDLRAF   60
DVEATPNEGF FNQNITTFYY DRLGLYPRFD AAGMSVHGGV PQNGSLCAHL PMLKEAVERY  120
IQTQEPAGLA VIDWEEWRPV WVRNWQEKDV YRQSSRQLVA SRHPDWPSDR IVKQAQYEFE  180
FAARQFMLNT LRYVKAVRPQ HLWGFYLFPD CYNHDYVQNW DSYTGRCPDV EVAQNDQLAW  240
LWAENTALFP SVYLDKTLAS SKHSRNFVSF RVQEALRVAH THHANHALPV YVFTRPTYTR  300
RLTELNQMDL ISTIGESAAL GSAGVIFWGD SVYASSMENC QNLKKYLTQT LVPYIVNVSW  360
```

```
ATQYCSWTQC HGHGRCVRRN PSASTFLHLS PSSFRLVPGR TPSEPQLRPE GELSEDDLSY  420
LQMHFRCHCY LGWGGEQCQW NHKRAAGDAS RAWAGAHLAS LLGLVAMTLT WTL         473

SEQ ID NO: 23            moltype = AA  length = 412
FEATURE                  Location/Qualifiers
REGION                   1..412
                         note = hyaluronidase 3
source                   1..412
                         mol_type = protein
                         organism = Rattus norvegicus
SEQUENCE: 23
MITQLGLTLV VGLTLCLVHV QALLQVPEFP FSVLWNVPSA RCKTRFGVHL PLDALGIIAN  60
HGQRFHGQNI TIFYKNQFGL YPYFGPRGTA HNGGIPQAVS LDHHLAQAAH QILHNLGSSF  120
AGLAVLDWEE WYPLWAGNWG THRQVYQAAS WAWAQQMFPD LNPQEQLHKA QTGFEQAARA  180
LMEHTLRLGQ MLRPHGLWGF YRYPVCGNGW HNMASNYTGH CHPAIITRNT QLRWLWAASS  240
ALFPSIYLPP RLPPAYHQTF VRHRLEEAFR VALTGHAHPL PVLAYVRLTH RSSGRFLSLD  300
DLMQTIGVSA ALGAAGVVLW GDLSVSSSEE ECWRLHDYLV GTLGPYVINV TKAATACSHQ  360
RCHGHGRCSW KDPGQMEAFL HLQPDDNLGA WKSFRCRCYL GWSGPTCLEP KP          412

SEQ ID NO: 24            moltype = AA  length = 545
FEATURE                  Location/Qualifiers
REGION                   1..545
                         note = PH20
source                   1..545
                         mol_type = protein
                         organism = Oryctolagus cuniculus
SEQUENCE: 24
MGVLKFKHIF FGSAVELSGV FQIVFIFLLI PCCLTANFRA PPVIPNVPFL WAWNAPTEFC  60
LGKSGEPLDM SLFSLFGSPR KNKTGQGITI FYVDRLGYYP YIDPHTGAIV HGRIPQLGPL  120
QQHLTKLRQE ILYYMPKDNV GLAVIDWEEW LPTWLRNWKP KDIYRIKSIE LVKSQHPQYN  180
HSYATEKAKR DFEKAGKDFM EETLKLGRLL RPNHLWGYYL FPDCYNHHYD KPNLYKGSCF  240
DIEKKRNDDL SWLWKESTAL FPSVYLTSRA RSATALSKLY VVRNRVHEAI RVSKIPDDKS  300
PLPNFVYTRL VFTDQIFQFL SHHDLVYTIG EIVALGASGI VVWGSQSLAR SMKSCLHLDN  360
YMKTILNPYL INVTLAAKMC NQVLCQEQGV CTRKNWNPND VLHLNPGNFA IQLGSNGTYK  420
VDGKPTLTDL EQFSKNFQCS CYTNLNCKER TDMNNVRTVN VCAVENVCID TNVGPQAVTY  480
APKEKKDVAH ILSNTTSINS STTMSLPFPR KHVSGCLLVL CMYSQYLNIC YRLVAIGIQH  540
GYYLK                                                             545

SEQ ID NO: 25            moltype = AA  length = 476
FEATURE                  Location/Qualifiers
REGION                   1..476
                         note = hyaluronidase 2
source                   1..476
                         mol_type = protein
                         organism = Ovis aries
SEQUENCE: 25
MWTGLGPAVT LALVLVVAWA TELKPTAPPI FTGRPFVVAW DVPTQDCGPR HKMPLDPKDM  60
KAFDVQASPN EGFVNQNITI FYRDRLGMYP HFNSVGRSVH GGVPQNGSLW VHLEMLKGHV  120
EHYIRTQEPA GLAVIDWEDW RPVWVRNWQD KDVYRRLSRQ LVASHHPDWP PERIVKEAQY  180
EFEFAARQFM LETLRFVKAF RPRHLWGFYL FPDCYNHDYV QNWETYTGRC PDVEVSRNDQ  240
LSWLWAESTA LFPSVYLEET LASSTHGRNF VSFRVQEALR VADVHHANHA LPVYVFTRPT  300
YSRGLTGLSE MDLISTIGES AALGAAGVIL WGDAGFTTSN ETCRRLKDYL TRSLVPYVVN  360
VSWAAQYCSW AQCHGHGRCV RRDPNAHTFL HLSASSFRLV PSHAPDEPRL RPEGELSWAD  420
RNHLQTHFRC QCYLGWGGEQ CQWDRRRAAG GASGAWAGSH LTGLLAVAVL AFTWTS      476

SEQ ID NO: 26            moltype = AA  length = 414
FEATURE                  Location/Qualifiers
REGION                   1..414
                         note = hyaluronidase 3
source                   1..414
                         mol_type = protein
                         organism = Pongo pygmaeus
SEQUENCE: 26
MTTRLGPALV LGVALCLGCG QPLPQVPERP FSVLWNVPSA HCKSRFGVHL PLNALGIIAN  60
RGQHFHGQNM TIFYKNQLGL YPYFGPKGTA HNGGIPQALP LDRHLALAAY QIHHSLRPGF  120
AGPAVLDWEE WCPLWAGNWG RRRAYQAASW AWAQQVFPDL DPQEQLYKAY TGFEQAARAL  180
MEDTLRVAQA LRPHGLWGFY HYPACGNGWH SMASNYTGRC HAATLARNTQ LHWLWAASSA  240
LFPSIYLPPR LPPAHHQAFV RHRLEEAFRV ALVGHLPVLA YVRLTHRRSG RFLSQDDLVQ  300
TIGVSAALGA AGVVLWGDLS LSSSEEECWH LHDYLVDTLG PYGINVTRAA MACSHQRCHG  360
HGRCARRDPG QMEAFLHLWP DGSLGDWKSF SCHCYWGWAG PTCQEPRLGP KEAV        414

SEQ ID NO: 27            moltype = AA  length = 510
FEATURE                  Location/Qualifiers
REGION                   1..510
                         note = PH20
source                   1..510
                         mol_type = protein
                         organism = Macaca fascicularis
SEQUENCE: 27
```

```
MGVLKFKHIF FRSFVKSSGV SQIVFTFLLI PCCLTLNFRA PPIIPNVPFL WAWNAPSEFC    60
LGKFNEPLDM SLFTLMGSPR INVTGQGVTI FYVDRLGYYP YIDLTTGVTV HGGIPQKVSL   120
QDHLDKSKQD ILFYMPVDNL GMAVIDWEEW RPTWARNWKP KDVYKNRSIE LVQQQNVQLS   180
LPQATDKAKQ EFEKAGKDFM LETIKLGRSL RPNHLWGYYL FPDCYNHHYR KPGYNGSCFD   240
VEIKRNDDLS WLWNESTALY PSIYLNTQQS VVVATLYVRN RVREAIRVSK IPDAKNPLPV   300
FVYARLVFTD QVLKFLSREE LVSTLGETVA LGASGIVIWG SLSITRSMKS CLLLDTYMET   360
ILNPYIINVT LAAKMCSQVL CQEQGVCIRK DWNSSDYLHL NPDNFDIRLE KGGKFTVHGK   420
PTVEDLEEFS EKFYCSCYTN LSCKEKADVK DTDAVDVCIA DGVCIDASLK PPVETEGSPP   480
IFYNTSSSTV STTMFIVNIL FLIISSVASL                                   510

SEQ ID NO: 28          moltype = AA  length = 529
FEATURE                Location/Qualifiers
REGION                 1..529
                       note = PH20
source                 1..529
                       mol_type = protein
                       organism = Cavia porcellus
SEQUENCE: 28
MGAFTFKHSF FGSFVECSGV LQTVFIFLLI PCCLADKRAP PLIPNVPLLW VWNAPTEFCI    60
GGTNQPLDMS FFSIVGTPRK NITGQSITLY YVDRLGYYPY IDPHTGAIVH GGLPQLMNLQ   120
QHLRKSRQDI LFYMPTDSVG LAVIDWEEWR PTWTRNWRPK DIYRNKSIEL VKSQHPQYNH   180
SYAVAVAKRD FERTGKAFML ETLKLGKSLR PSSLWGYYLF PDCYNTHFTK PNYDGHCPPI   240
ELQRNNDLQW LWNDSTALYP SVYLTSRVRS SQNGALYVRN RVHESIRVSK LMDDKNPLPI   300
YVYIRLVFTD QTTTFLELDD LVHSVGEIVP LGVSGIIIWG SLSLTRSLVS CIGLENYMKG   360
TLLPYLINVT LAAKMCGQVL CKNQGICTRK DWNTNTYLHL NATNFDIELQ QNGKFVVHGK   420
PSLEDLQEFS KNFHCSCYTN VACKDRLDVH NVRSVNVCTA NNICIDAVLN PPSLDDDDEP   480
PITDDTSQNQ DSISDITSSA PPSSHILPKD LSWCLFLLSI FSQHWKYLL                529

SEQ ID NO: 29          moltype = AA  length = 512
FEATURE                Location/Qualifiers
REGION                 1..512
                       note = PH20
source                 1..512
                       mol_type = protein
                       organism = Rattus norvegicus
SEQUENCE: 29
MGELQFKWLF WRSFAESGGT FQTVLIFLFI PYSLTVDYRA TPVLSDTTFV WVWNVPTEAC    60
VENVTEPIDL SFFSLIGSPR KTAIGQPVTL FYVDRLGNYP HIDAQQTEHH GGIPQKGDLT   120
THLVKAKEDV ERYIPTDKLG LAIIDWEEWR PTWMRNWTPK DIYRNKSIEL VQAADPAINI   180
TEATVRAKAQ FEGAAKEFME GTLKLGKHIR PKHLWGFYLF PDCYNNKFQV DNYDGQCPDV   240
EKKRNDDLDW LWKESTGLYP SVYLKKDLKS SRKATLYVRY RVLESIRVSK VSDESNPVPI   300
FVYIRLVFTD HVSEYLLEDD LVNTIGEIVA QGTSGIIIWD AMSLAQRSAG CPILRQYMKT   360
TLNPYIVNVT LAAKMCSQTL CKEKGMCSRK TESSDAYLHL DPSSFSINVT EAGKYEVLGK   420
PEVKDLEYFS EHFKCSCFSK MTCEETSDMR SIQDVNVCMG DNVCIKATLG PNSAFHLLPG   480
KGLLLMTTLA HILHHLPHDI FVFPWKMLVS TP                                 512

SEQ ID NO: 30          moltype = AA  length = 512
FEATURE                Location/Qualifiers
REGION                 1..512
                       note = PH20
source                 1..512
                       mol_type = protein
                       organism = Mus musculus
SEQUENCE: 30
MGELRFKHLF WGSFVESGGT FQTVLIFLLI PCSLTVDYRA APILSNTTFL WIWNVPTERC    60
VGNVNDPIDL SFFSLIGSPR KTATGQPVTL FYVDRLGLYP HIDANQAEHY GGIPQRGDYQ   120
AHLRKAKTDI EHYIPDDKLG LAIIDWEEWR PTWLRNWKPK DNYRNKSIEL VQSTNPGLSI   180
TEATQKAIQQ FEEAGRKFME GTLHLGKFLR PNQLWGYYLF PDCYNNKFQD PKYDGQCPAV   240
EKKRNDNLKW LWKASTGLYP SVYLKKDLKS NRQATLYVRY RVVEAIRVSK VGNASDPVPI   300
FVYIRLVFTD RTSEYLLEDD LVNTIGEIVA LGTSGIIIWD AMSLAQRAAG CPILHKYMQT   360
TLNPYIVNVT LAAKMCSQTL CNEKGMCSRR KESSDVYLHL NPSHFDIMLT ETGKYEVLGN   420
PRVGDLEYFS EHFKCSCFSR MTCKETSDVK NVQDVNVCVG DNVCIKAKVE PNPAFYLLPG   480
KSLLFMTTLG HVLYHLPQDI FVFPRKTLVS TP                                 512

SEQ ID NO: 31          moltype = AA  length = 807
FEATURE                Location/Qualifiers
REGION                 1..807
                       note = hyaluronidase
source                 1..807
                       mol_type = protein
                       organism = Staphylococcus aureus
SEQUENCE: 31
MTYRIKKWQK LSTITLLMAG VITLNGGEFR SVDKHQIAVA DTNVQTPDYE KLRNTWLDVN    60
YGYDKYDENN PDMKKKFDAT EKEATNLLKE MKTESGRKYL WSGAETLETN SSHMTRTYRN   120
IEKIAEAMRN PKTTLNTDEN KKKVKDALEW LHKNAYGKEP DKKVKELSEN FTKTTGKNTN   180
LNWWDYEIGT PKSLTNTLIL LNDQFSNEEK KKFTAPIKTF APDSDKILSS VGKAELAKGG   240
NLVDISKVKL LECIIEEDKD MMKKSIDSFN KVFTYVQDSA TGKERNGFYK DGSYIDHQDV   300
PYTGAYGVVL LEGISQMMPM IKETPFNDKT QNDTTLKSWI DDGFMPLIYK GEMMDLSRGR   360
AISRENETSH SASATVMKSL LRLSDAMDDS TKAKYKKIVK SSVESDSSYK QNDYLNSYSD   420
```

-continued

```
IDKMKSLMTD NSISKNGLTQ QLKIYNDMDR VTYHNKDLDF AFGLSMTSKN VARYESINGE   480
NLKGWHTGAG MSYLYNSDVK HYHDNFWVTA DMKRLSGTTT LDNEILKDTD DKKSSKTFVG   540
GTKVDDQHAS IGMDFENQDK TLTAKKSYFI LNDKIVFLGT GIKSTDSSKN PVTTIENRKA   600
NGYTLYTDDK QTTNSDNQEN NSVFLESTDT KKNIGYHFLN KPKITVKKES HTGKWKEINK   660
SQKDTQKTDE YYEVTQKHSN SDNKYGYVLY PGLSKDVFKT KKDEVTVVKQ EDDFHVVKDN   720
ESVWAGVNYS NSTQTFDINN TKVEVKAKGM FILKKKDDNT YECSFYNPES TNSASDIESK   780
ISMTGYSITN KNTSTSNESG VHFELTK                                       807

SEQ ID NO: 32          moltype = AA  length = 371
FEATURE                Location/Qualifiers
REGION                 1..371
                       note = hyaluronidase
source                 1..371
                       mol_type = protein
                       organism = synthetic construct
SEQUENCE: 32
MTENIPLRVQ FKRMSADEWA RSDVILLEGE IGFETDTGFA KFGDGQNTFS KLKYLTGPKG   60
PKGDTGLQGK TGGTGPRGPA GKPGTTDYDQ LQNKPDLGAF AQKEETNSKI TKLESSKADK   120
SAVYSKAESK IELDKKLSLT GGIVTGQLQF KPNKSGIKPS SSVGGAINID MSKSEGAAMV   180
MYTNKDTTDG PLMILRSDKD TFDQSAQFVD YSGKTNAVNI VMRQPSAPNF SSALNITSAN   240
EGGSAMQIRG VEKALGTLKI THENPNVEAK YDENAAALSI DIVKKQKGGK GTAAQGIYIN   300
STSGTAGKML RIRNKNEDKF YVGPDGGFHS GANSTVAGNL TVKDPTSGKH AATKDYVDEK   360
IAELKKLILK K                                                        371

SEQ ID NO: 33          moltype = AA  length = 1628
FEATURE                Location/Qualifiers
REGION                 1..1628
                       note = hyaluronidase
source                 1..1628
                       mol_type = protein
                       organism = Clostridium perfringens
SEQUENCE: 33
MNKNIRKIIT STVLAAMTIS VLPSNLVVFA TDGITENFYE IYPKPQEISY SGGEFQISDE   60
INIVYDDGID TYTKKRVDEV LEASNLEATV SNEIVPGKTN FLVGINESGG VVDNYFNKNI   120
PHDESFFDEK MDANIVSVKD GVIGVIGEDT DSAFYGVTTL KHVFNQLEEG NKIQSFRADD   180
YAEVAHRGFI EGYYGNPWSN EDRAELMKFG GDYKLNQYVF APKDDPYHNS KWRDLYPEEK   240
LSEIKKLAQV GNETKNRYVY ALHPFMNNPV RFDTEENYQN DLGVIKAKFT QLLENDVRQF   300
AILADDASAP AQGASMYVKL LTDLTRWLEE QQSTYPDLKT DLMFCPSDYY GNGSSAQLKE   360
LNKAEDNVSI VMTGGRIWGE VDENFANNFM NNISTEGHPG RAPFFWINWP CSDNSKQHLI   420
MGGNDTFLHP GVDPSKIDGI VLNPMQQAEA NKSALFAIAD YAWNIWDNKE EADENWNDSF   480
KYMDHGTAEE TNSSLALREI SKHMINQNMD GRVRPLQESV ELAPKLEAFK QKYDSGASIK   540
EDALELIAEF TNLQKAADYY KNNPGNERTR DQIIYWLNCW EDTMDAAIGY LKSAIAIEEG   600
DDEAAWANYS EAQGAFEKSK TYGFHYVDHT EYAEVGVQHI VPFIKSMGQN LSVVIGSIVD   660
PNRIIATYIS NRQDAPTGNP DNIFDNNAST ELVYKNPNRI DVGTYVGVKY SNPITLNNVE   720
FLMGANSNPN DTMQKAKIQY TVDGREWIDL EEGVEYTMPG AIKVENLDLK VRGVRLIATE   780
ARENTWLGVR DINVNKKEDS NSGVEFNPSL IRSESWQVYE GNEANLLDGD DNTGVWYKTL   840
NGDTSLAGEF IGLDLGKEIK LDGIRFVIGK NGGGSSDKWN KPFKLEYSLDN ESWTTIKEYD   900
KTGAPAGKDV IEESFETPIS AKYIRLTNME NINKWLTFSE FAIISDELEN AGNKENVYTN   960
TELDLLSLAK EDVTKLIPTD DISLNHGEYI GVKLNRIKDL SNINLEISND TGLKLQSSMN   1020
GVEWTEITDK NTLEDGRYVR LINTSNEAVN FNLTKFEVNS NEVYEPSLVD AYVGDDGAKK   1080
AVDGDLKTRV KFLGAPSTGD TIVYDLGQEI LVDNLKYVVL DTEVDHVRDG KIQLSLDGET   1140
WTDAITIGDG VENGVDDMFS TPLKNGYKHG NQSGGIVPID SAYVEGDNLN QKARYVRILF   1200
TAPYRHRWTV INELMINNGE YISTVNDPTY ISNPIEERGF APSNLRDGNL TTSYKPNTNN   1260
GEISEGSITY RLSEKTDVRK VTIVQSGSSI SNAKVMARVG DGSENVTDQW VQLGTLSNSL   1320
NEFINRDYNN IYEIKIEWTD VAPNIYEIIT LNQEFEFPVN DSLKAKYDEL INLSGDEYTL   1380
SSFETLKEAL NEAKSILDDS NSSQKKIDKA LEKLNKAEER LDLRATDFED FNKVLTLGNS   1440
LVEEEYTAES WALFSEVLEA ANEANKNKAD YTQDQINQIV IDLDASIKAL VKETPEVDKT   1500
NLGELINQGK SLLDESVEGF NVGEYHKGAK DGLTVEINKA EEVFNKEDAT EEEINLAKES   1560
LEGAIARFNS LLIEESTGDF NGNGKIDIGD LAMVSKNIGS TTNTSLDLNK DGSIDEYEIS   1620
FINHRILN                                                            1628

SEQ ID NO: 34          moltype = AA  length = 435
FEATURE                Location/Qualifiers
REGION                 1..435
                       note = Hyaluronidase-1 [Precursor]
source                 1..435
                       mol_type = protein
                       organism = Homo sapiens
SEQUENCE: 34
MAAHLLPICA LFLTLLDMAQ GFRGPLLPNR PFTTVWNANT QWCLERHGVD VDVSVFDVVA   60
NPGQTFRGPD MTIFYSSQLG TYPYYTPTGE PVFGGLPQNA SLIAHLARTF QDILAAIPAP   120
DFSGLAVIDW EAWRPRWAFN WDTKDIYRQR SRALVQAQHP DWPAPQVEAV AQDQFQGAAR   180
AWMAGTLQLG RALRPRGLWG FYGFPDCYNY DFLSPNYTGQ CPSGIRAQND QLGWLWGQSR   240
ALYPSIYMPA VLEGTGKSQM YVQHRVAEAF RVAVAAGDPN LPVLPYVQIF YDTTNHFLPL   300
DELEHSLGES AAQGAAGVVL WVSWENTRTK ESCQAIKEYM DTTLGPFILN VTSGALLCSQ   360
ALCSGHGRCV RRTSHPKALL LLNPASFSIQ LTPGGGPLSL RGALSLEDQA QMAVEFKCRC   420
YPGWQAPWCE RKSMW                                                    435

SEQ ID NO: 35          moltype = AA  length = 473
```

-continued

```
FEATURE              Location/Qualifiers
REGION               1..473
                     note = Hyaluronidase-2 [Precursor]
source               1..473
                     mol_type = protein
                     organism = Homo sapiens
SEQUENCE: 35
MRAGPGPTVT LALVLAVAWA MELKPTAPPI FTGRPFVVAW DVPTQDCGPR LKVPLDLNAF   60
DVQASPNEGF VNQNITIFYR DRLGLYPRFD SAGRSVHGGV PQNVSLWAHR KMLQKRVEHY  120
IRTQESAGLA VIDWEDWRPV WVRNWQDKDV YRRLSRQLVA SRHPDWPPDR IVKQAQYEFE  180
FAAQQFMLET LRYVKAVRPR HLWGFYLFPD CYNHDYVQNW ESYTGRCPDV EVARNDQLAW  240
LWAESTALFP SVYLDETLAS SRHGRNFVSF RVQEALRVAR THHANHALPV YVFTRPTYSR  300
RLTGLSEMDL ISTIGESAAL GAAGVILWGD AGYTTSTETC QYLKDYLTRL LVPYVVNVSW  360
ATQYCSRAQC HGHGRCVRRN PSASTFLHLS TNSFRLVPGH APGEPQLRPV GELSWADIDH  420
LQTHFRCQCY LGWSGEQCQW DHRQAAGGAS EAWAGSHLTS LLALAALAFT WTL         473

SEQ ID NO: 36        moltype = AA  length = 417
FEATURE              Location/Qualifiers
REGION               1..417
                     note = Hyaluronidase-3 [Precursor]
source               1..417
                     mol_type = protein
                     organism = Homo sapiens
SEQUENCE: 36
MTTQLGPALV LGVALCLGCG QPLPQVPERP FSVLWNVPSA HCEARFGVHL PLNALGIIAN   60
RGQHFHGQNM TIFYKNQLGL YPYFGPRGTA HNGGIPQALP LDRHLALAAY QIHHSLRPGF  120
AGPAVLDWEE WCPLWAGNWG RRRAYQAASW AWAQQVFPDL DPQEQLYKAY TGFEQAARAL  180
MEDTLRVAQA LRPHGLWGFY HYPACGNGWH SMASNYTGRC HAATLARNTQ LHWLWAASSA  240
LFPSIYLPPR LPPAHHQAFV RHRLEEAFRV ALVGHRHPLP VLAYVRLTHR RSGRFLSQDD  300
LVQSIGVSAA LGAAGVVLWG DLSLSSSEEE CWHLHDYLVD TLGPYVINVT RAAMACSHQR  360
CHGHGRCARR DPGQMEAFLH LWPDGSLGDW KSFSCHCYWG WAGPTCQEPR PGPKEAV     417

SEQ ID NO: 37        moltype = AA  length = 481
FEATURE              Location/Qualifiers
REGION               1..481
                     note = Hyaluronidase-4
source               1..481
                     mol_type = protein
                     organism = Homo sapiens
SEQUENCE: 37
MKVLSEGQLK LCVVQPVHLT SWLLIFFILK SISCLKPARL PIYQRKPFIA AWNAPTDQCL   60
IKYNLRLNLK MFPVIGSPLA KARGQNVTIF YVNRLGYYPN YTSQGVPING GLPQNISLQV  120
HLEKADQDIN YYIPAEDFSG LAVIDWEYWR PQWARNWNSK DVYRQKSRKL ISDMGKNVSA  180
TDIEYLAKVT FEESAKAFMK ETIKLGIKSR PKGLWGYYLY PDCHNYNVYA PNYSGSCPED  240
EVLRNNELSW LWNSSAALYP SIGVWKSLGD SENILRFSKF RVHESMRIST MTSHDYALPV  300
FVYTRLGYRD EPLFFLSKQD LVSTIGESAA LGAAGIVIWG DMNLTASKAN CTKVKQFVSS  360
DLGSYIANVT RAAEVCSLHL CRNNGRCIRK MWNAPSYLHL NPASYHIEAS EDGEFTVKGK  420
ASDTDLAVMA DTFSCHCYQG YEGADCREIK TADGCSGVSP SPGSLMTLCL LLLASYRSIQ  480
L                                                                 481

SEQ ID NO: 38        moltype = AA  length = 467
FEATURE              Location/Qualifiers
REGION               1..467
                     note = sHuPH20 precursor 1-467
source               1..467
                     mol_type = protein
                     organism = Homo sapiens
SEQUENCE: 38
MGVLKFKHIF FRSFVKSSGV SQIVFTFLLI PCCLTLNFRA PPVIPNVPFL WAWNAPSEFC   60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDA                467

SEQ ID NO: 39        moltype = AA  length = 477
FEATURE              Location/Qualifiers
REGION               1..477
                     note = sHuPH20 precursor 1-477
source               1..477
                     mol_type = protein
                     organism = Homo sapiens
SEQUENCE: 39
MGVLKFKHIF FRSFVKSSGV SQIVFTFLLI PCCLTLNFRA PPVIPNVPFL WAWNAPSEFC   60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
```

```
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEE       477

SEQ ID NO: 40              moltype = AA  length = 478
FEATURE                    Location/Qualifiers
REGION                     1..478
                           note = sHuPH20 precursor 1-478
source                     1..478
                           mol_type = protein
                           organism = Homo sapiens
SEQUENCE: 40
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEP      478

SEQ ID NO: 41              moltype = AA  length = 479
FEATURE                    Location/Qualifiers
REGION                     1..479
                           note = sHuPH20 precursor 1-479
source                     1..479
                           mol_type = protein
                           organism = Homo sapiens
SEQUENCE: 41
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQ     479

SEQ ID NO: 42              moltype = AA  length = 480
FEATURE                    Location/Qualifiers
REGION                     1..480
                           note = sHuPH20 precursor 1-480
source                     1..480
                           mol_type = protein
                           organism = Homo sapiens
SEQUENCE: 42
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQI    480

SEQ ID NO: 43              moltype = AA  length = 481
FEATURE                    Location/Qualifiers
REGION                     1..481
                           note = sHuPH20 precursor 1-481
source                     1..481
                           mol_type = protein
                           organism = Homo sapiens
SEQUENCE: 43
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL    120
QDHLDKAKKD ITFYMPVDNL GMAVIDWEEW RPTWARNWKP KDVYKNRSIE LVQQQNVQLS    180
LTEATEKAKQ EFEKAGKDFL VETIKLGKLL RPNHLWGYYL FPDCYNHHYK KPGYNGSCFN    240
VEIKRNDDLS WLWNESTALY PSIYLNTQQS PVAATLYVRN RVREAIRVSK IPDAKSPLPV    300
FAYTRIVFTD QVLKFLSQDE LVYTFGETVA LGASGIVIWG TLSIMRSMKS CLLLDNYMET    360
ILNPYIINVT LAAKMCSQVL CQEQGVCIRK NWNSSDYLHL NPDNFAIQLE KGGKFTVRGK    420
PTLEDLEQFS EKFYCSCYST LSCKEKADVK DTDAVDVCIA DGVCIDAFLK PPMETEEPQI    480
F                                                                    481

SEQ ID NO: 44              moltype = AA  length = 483
FEATURE                    Location/Qualifiers
REGION                     1..483
                           note = sHuPH20 precursor 1-483
source                     1..483
```

```
                         mol_type = protein
                         organism = Homo sapiens
SEQUENCE: 44
MGVLKFKHIF FRSFVKSSGV SQIVFTFLLI PCCLTLNFRA PPVIPNVPFL WAWNAPSEFC    60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYN                                                                483

SEQ ID NO: 45            moltype = AA   length = 432
FEATURE                  Location/Qualifiers
REGION                   1..432
                         note = sHuPH20 mature 36-467
source                   1..432
                         mol_type = protein
                         organism = Homo sapiens
SEQUENCE: 45
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DA                                                      432

SEQ ID NO: 46            moltype = AA   length = 448
FEATURE                  Location/Qualifiers
REGION                   1..448
                         note = sHuPH20 mature 36-483
source                   1..448
                         mol_type = protein
                         organism = Homo sapiens
SEQUENCE: 46
LNFRAPPVIP NVPFLWAWNA PSEFCLGKFD EPLDMSLFSF IGSPRINATG QGVTIFYVDR    60
LGYYPYIDSI TGVTVNGGIP QKISLQDHLD KAKKDITFYM PVDNLGMAVI DWEEWRPTWA   120
RNWKPKDVYK NRSIELVQQQ NVQLSLTEAT EKAKQEFEKA GKDFLVETIK LGKLLRPNHL   180
WGYYLFPDCY NHHYKKPGYN GSCFNVEIKR NDDLSWLWNE STALYPSIYL NTQQSPVAAT   240
LYVRNRVREA IRVSKIPDAK SPLPVFAYTR IVFTDQVLKF LSQDELVYTF GETVALGASG   300
IVIWGTLSIM RSMKSCLLLD NYMETILNPY IINVTLAAKM CSQVLCQEQG VCIRKNWNSS   360
DYLHLNPDNF AIQLEKGGKF TVRGKPTLED LEQFSEKFYC SCYSTLSCKE KADVKDTDAV   420
DVCIADGVCI DAFLKPPMET EEPQIFYN                                     448

SEQ ID NO: 47            moltype = DNA   length = 1446
FEATURE                  Location/Qualifiers
misc_feature             1..1446
                         note = DNA encoding soluble rHuPH20 precursor
source                   1..1446
                         mol_type = other DNA
                         organism = Homo sapiens
SEQUENCE: 47
atgggagtgc taaaattcaa gcacatcttt ttcagaagct ttgttaaatc aagtggagta    60
tcccagatag ttttcacctt ccttctgatt ccatgttgct tgactctgaa tttcagagca   120
cctcctgtta ttccaaatgt gcctttcctc tgggcctgga atgccccaag tgaattttgt   180
cttgaaaat ttgatgagcc actagatatg agcctcttct ctttcatagg aagcccccga   240
ataaacgcca ccgggcaagg tgttacaata ttttatgttg atagacttgg ctactatcct   300
tacatagatt caatcacagg agtaactgtg aatggaggaa tcccccagaa gatttcctta   360
caagaccatc tggacaaagc taagaaagac attacatttt atatgccagt agacaatttg   420
ggaatggctg ttattgactg gggaagaatgg agacccactt gggcaagaaa ctggaaacct   480
aaagatgttt acaagaatag gtctattgaa ttggttcagc aacaaaatgt acaacttagt   540
ctcacagagg ccactgagaa agcaaaacaa gaatttgaaa aggcagggaa ggatttcctg   600
gtagagacta taaaattggg aaaattactt cggccaaatc acttgtgggg ttattatctt   660
tttccggatt gttacaacca tcactataag aaacccggtt acaatggaag ttgcttcaat   720
gtagaaataa aagagaatga tgatctcagc tggttgtgga atgaaagcac tgctctttac   780
ccatccattt atttgaacac tcagcagtct cctgtagctg ctacactcta tgtgcgcaat   840
cgagttcggg aagccatcag agtttccaaa atacctgatg caaaaagtcc acttccggtt   900
tttgcatata cccgcatagt ttttactgat caagttttga aattcctttc tcaagatgaa   960
cttgtgtata catttggcga aactgttgct ctgggtgctt ctggaattgt aatatgggga   1020
accctcagta taatgcgaag tatgaaatct tgcttgctcc tagacaatta catggagact   1080
atactgaatc cttacataat caacgtcaca ctagcagcca aatgtgtag ccaagtgctt   1140
tgccaggagc aagagtgtgt tataaggaaa aactggaatt caagtgacta tcttcacctc   1200
aacccagata attttgctat tcaacttgag aaaggtggaa agttcacagt acgtggaaaa   1260
ccgacacttg aagcctgga gcaatttttct gaaaaatttt attgcagctg ttatagcacc   1320
ttgagttgta aggagaaagc tgatgtaaaa gacactgatg ctgttgatgt gtgtattgct   1380
gatggtgtct gtatagatgc ttttctaaaa cctcccatgg agacagaaga acctcaaatt   1440
```

-continued

```
ttctac                                                                  1446

SEQ ID NO: 48              moltype = AA   length = 509
FEATURE                    Location/Qualifiers
REGION                     1..509
                           note = PH20 variant P48A
source                     1..509
                           mol_type = protein
                           organism = Homo sapiens
SEQUENCE: 48
MGVLKFKHIF FRSFVKSSGV SQIVFTFLLI PCCLTLNFRA PPVIPNVAFL WAWNAPSEFC   60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYNASPSTLS ATMFIVSILF LIISSVASL                                     509

SEQ ID NO: 49              moltype = AA   length = 509
FEATURE                    Location/Qualifiers
REGION                     1..509
                           note = precursor PH20 variant L499W
source                     1..509
                           mol_type = protein
                           organism = Homo sapiens
SEQUENCE: 49
MGVLKFKHIF FRSFVKSSGV SQIVFTFLLI PCCLTLNFRA PPVIPNVPFL WAWNAPSEFC   60
LGKFDEPLDM SLFSFIGSPR INATGQGVTI FYVDRLGYYP YIDSITGVTV NGGIPQKISL   120
QDHLDKAKKD ITFYMPVDNL GMAVIDWEEW RPTWARNWKP KDVYKNRSIE LVQQQNVQLS   180
LTEATEKAKQ EFEKAGKDFL VETIKLGKLL RPNHLWGYYL FPDCYNHHYK KPGYNGSCFN   240
VEIKRNDDLS WLWNESTALY PSIYLNTQQS PVAATLYVRN RVREAIRVSK IPDAKSPLPV   300
FAYTRIVFTD QVLKFLSQDE LVYTFGETVA LGASGIVIWG TLSIMRSMKS CLLLDNYMET   360
ILNPYIINVT LAAKMCSQVL CQEQGVCIRK NWNSSDYLHL NPDNFAIQLE KGGKFTVRGK   420
PTLEDLEQFS EKFYCSCYST LSCKEKADVK DTDAVDVCIA DGVCIDAFLK PPMETEEPQI   480
FYNASPSTLS ATMFIVSIWF LIISSVASL                                     509

SEQ ID NO: 50              moltype = DNA   length = 6630
FEATURE                    Location/Qualifiers
misc_feature               1..6630
                           note = HZ24 vector
source                     1..6630
                           mol_type = other DNA
                           organism = synthetic construct
SEQUENCE: 50
tcaatattgg ccattagcca tattattcat tggttatata gcataaatca atattggcta   60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg acccccgccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtccg ccccctattg acgtcaatga   420
cggtaaatgg cccgcctggc attatgccca gtacatgacc ttacgggact ttcctacttg   480
gcagtacatc tacgtattag tcatcgctat taccatggtg atgcggtttt ggcagtacac   540
caatgggcgt ggatagcggt ttgactcacg gggatttcca agtctccacc ccattgacgt   600
caatgggagt ttgttttggc accaaaatca acgggacttt ccaaaatgtc gtaataaccc   660
cgccccgttg acgcaaatgg gcggtaggcg tgtacggtgg gaggtctata taagcagagc   720
tcgtttagtg aaccgtcaga tcactagaag ctttattgcg gtagtttatc acagttaaat   780
tgctaacgca gtcagtgctt ctgacacaac agtctcgaac ttaagctgca gaagttggtc   840
gtgaggcact gggcaggtaa gtatcaaggt tacaagacag gtttaaggag accaatagaa   900
actgggcttg tcgagacaga gaagactctt gcgtttctga taggcaccta ttggtcttac   960
tgacatccac tttgcctttc tctccacagg tgtccactcc cagttcaatt acagctctta   1020
aggctagagt acttaatacg actcactata ggctagcctc gaggaactga aattgggagca   1080
catctttttc agaagctttg ttaaatcaag tggagtatcc cagatagttt tcaccttcct   1140
tctgattcca tgttgcttga ctctgaattt cagagcacct cctgttattc caaatgtgcc   1200
tttcctctgg gcctggaatg ccccaagtga attttgtctt ggaaaatttg atgagccact   1260
agatatgagc ctcttctctt tcataggaag cccccgaata aacgccaccg ggcaaggtgt   1320
tacaatattt tatgttgata gacttggcta ctatccttac atagattcaa tcacaggaat   1380
aactgtgaat ggaggaatcc cccagaagat ttccttacaa gaccatctgg acaaagctaa   1440
gaaagacatt acatttttata tgccagtaga caatttggga atggctgtta ttgactggga   1500
agaatgggaga cccacttggg caagaaactg gaaacctaaa gatgtttaca agaataggtc   1560
tattgaattg gttcagcaac aaaatgtaca acttagtctc acagaggcca ctgagaaagc   1620
aaaacaagaa tttgaaaagg caggggaagga tttcctggta gagactataa aattgggaaa   1680
attacttcgg ccaaatcact gtgggggtta ttatcttttt ccggattgtt acaaccatca   1740
ctataagaaa cccggttaca atggaagttg cttcaatgta gaaataaaaa gaaatgatga   1800
tctcagctgg ttgtggaatg aaagcactgc tctttaccca tccatttatt gaacactca   1860
gcagtctcct gtagctgcta cactctatgt gcgcaatcga gttcgggaag ccatcagagt   1920
ttccaaaata cctgatgcaa aaagtccact tccggttttt gcatatacc gcatagtttt   1980
```

-continued

```
tactgatcaa gttttgaaat tcctttctca agatgaactt gtgtatacat ttggcgaaac    2040
tgttgctctg ggtgcttctg gaattgtaat atggggaacc ctcagtataa tgcgaagtat    2100
gaaatcttgc ttgctcctag acaattacat ggagactata ctgaatcctt acataatcaa    2160
cgtcacacta gcagccaaaa tgtgtagcca agtgctttgc caggagcaag gagtgtgtat    2220
aaggaaaaac tggaattcaa gtgactatct tcacctcaac ccagataatt ttgctattca    2280
acttgagaaa ggtggaaagt tcacagtacg tggaaaaccg acacttgaag acctggagca    2340
attttctgaa aaattttatt gcagctgtta tagcaccttg agttgtaagg agaaagctga    2400
tgtaaaagac actgatgctg ttgatgtgtg tattgctgat ggtgtctgta tagatgcttt    2460
tctaaaacct cccatggaga cagaagaacc tcaaattttc tactgaggat ccatagctaa    2520
cgcccctctc cctccccccc ccctaacgtt actggccgaa gccgcttgga ataaggccga    2580
tgtgcgtttg tctatatgtt attttccacc atattgccgt cttttggcaa tgtgagggcc    2640
cggaaacctg gccctgtctt cttgacgagc attcctaggg gtctttcccc tctcgccaaa    2700
ggaatgcaag gtctgttgaa tgtcgtgaag gaagcagttc ctctggaagc ttcttgaaga    2760
caaacaacgt ctgtagcgac cctttgcagg cagcggaacc ccccacctgg cgacaggtgc    2820
ctctgcggcc aaaagccacg tgtataagat acacctgcaa aggcggcaca accccagtgc    2880
cacgttgtga gttggatagt tgtggaaaga gtcaaatggc tctcctcaag cgtattcaac    2940
aaggggctga aggatgccca gaaggtaccc cattgtatgg gatctgatct ggggcctcgg    3000
tgcacatgct ttacatgtgt ttagtcgagg ttaaaaaaac gtctaggccc cccgaaccac    3060
ggggacgtgg ttttcctttg aaaaacacga tgataagctt gccacaaccc acagcggccg    3120
ctgccatcat ggttcgacca ttgaactgca tcgtcgccgt gtcccaaaat atggggattg    3180
gcaagaacgg agacctaccc tggcctccgc tcaggaacga gttcaagtac ttccaaagaa    3240
tgaccacaac ctcttcagtg gaaggtaaac agaatctggt gattatgggt aggaaaacct    3300
ggttctccat tcctgagaag aatcgacctt taaaggacag aattaatata gttctcagta    3360
gagaactcaa agaaccacca cgaggagctc attttcttgc caaaagtttg gatgatgcct    3420
taagacttat tgaacaaccg gaattggcaa gtaaagtaga catggtttgg atagtcggag    3480
gcagttctgt ttaccaggaa gccatgaatc aaccaggcca cctcagactc tttgtgacaa    3540
ggatcatgca ggaatttgaa agtgacacgt ttttcccaga aattgatttg gggaaatata    3600
aacttctccc agaataccca ggcgtcctct ctgaggtcca ggaggaaaaa ggcatcaagt    3660
ataagtttga agtctacgag aagaaagact aaacgcgtgg tacctctaga gtcgacccgg    3720
gcggccgctt cgagcagaca tgataagata cattgatgag tttggacaaa ccacaactag    3780
aatgcagtga aaaaaatgct ttatttgtga aatttgtgat gctattgctt tatttgtaac    3840
cattataagc tgcaataaac aagttaacaa caacaattgc attcatttta tgtttcaggt    3900
tcaggggggg atgtgggagg ttttttaaag caagtaaaac ctctacaaat gtggtaaaat    3960
cgataaggat ccgggctggc gtaatagcga agaggcccgc accgatcgcc cttcccaaca    4020
gttgcgcagc ctgaatggcg aatggacgcg ccctgtagcg gcgcattaag cgcggcgggt    4080
gtggtggtta cgcgcagcgt gaccgctaca cttgccagcg ccctagcgcc cgctcctttc    4140
gctttcttcc cttcctttct cgccacgttc gccggctttc cccgtcaagc tctaaatcgg    4200
gggctccctt tagggttccg atttagtgct ttacggcacc tcgaccccaa aaaacttgat    4260
tagggtgatg gttcacgtag tgggccatcg ccctgatgaa cggttttcg ccctttgacg    4320
ttggagtcca cgttctttaa tagtggactc ttgttccaaa ctggaacaac actcaaccct    4380
atctcggtct attcttttga tttataaggg attttgccga tttcggccta ttggttaaaa    4440
aatgagctga tttaacaaaa atttaacgcg aattttaaca aaatattaac gcttacaatt    4500
tcctgatgcg gtattttctc cttacgcatc tgtgcggtat ttcacaccgc atatggtgca    4560
ctctcagtac aatctgctct gatgccgcat agttaagcca gccccgacac ccgccaacac    4620
ccgctgacgc gccctgacgg gcttgtctgc tcccggcatc cgcttacaga caagctgtga    4680
ccgtctccgg gagctgcatg tgtcagaggt tttcaccgtc atcaccgaaa cgcgcgagac    4740
gaaagggcct cgtgatacgc ctatttttat aggttaatgt catgataata atggtttctt    4800
agacgtcagg tggcactttt cggggaaatg tgcgcggaac ccctatttgt ttattttct    4860
aaatacattc aaatatgtat ccgctcatga dacaataacc ctgataaatg cttcaataat    4920
attgaaaaag gaagagtatg agtattcaac atttccgtgt cgcccttatt ccttttttg    4980
cggcatttttg ccttcctgtt tttgctcacc cagaaacgct ggtgaaagta aaagatgctg    5040
aagatcagtt gggtgcacga gtgggttaca tcgaactgga tctcaacagc ggtaagatcc    5100
ttgagagttt cgccccgaa gaacgttttc caatgatgag cacttttaaa gttctgctat    5160
gtggcgcggt attatcccgt attgacgccg ggcaagagca actcggtcgc cgcatacact    5220
attctcagaa tgacttggtt gagtactcac cagtcacaga aaagcatctt acggatggca    5280
tgacagtaag agaattatgc agtgctgcca taaccatgag tgataacact gcggccaact    5340
tacttctgac aacgatcgga ggaccgaagg agctaaccgc ttttttgcac aacatggggg    5400
atcatgtaac tcgccttgat cgttgggaac cggagctgaa tgaagccata ccaaacgacg    5460
agcgtgacac cacgatgcct gtagcaatgg caacaacgtt gcgcaaacta ttaactggcg    5520
aactacttac tctagcttcc cggcaacaat taatagactg gatggaggcg gataaagttg    5580
caggaccact tctgcgctcg gcccttccgg ctggctggtt tattgctgat aaatctggag    5640
ccggtgagcg tgggtctcgc ggtatcattg cagcactggg gccagatggt aagccctccc    5700
gtatcgtagt tatctacacg acggggagtc aggcaactat ggatgaacga aatagacaga    5760
tcgctgagat aggtgcctca ctgattaagc attggtaact gtcagaccaa gtttactcat    5820
atatacttta gattgattta aaacttcatt tttaatttaa aaggatctag gtgaagatcc    5880
tttttgataa tctcatgacc aaaatccctt aacgtgagtt ttcgttccac tgagcgtcag    5940
accccgtaga aaagatcaaa ggatcttctt gagatccttt ttttctgcgc gtaatctgct    6000
gcttgcaaac aaaaaaacca ccgctaccag cggtggtttg tttgccggat caagagctac    6060
caactcttt tccgaaggta actggcttca gcagagcgca gataccaaat actgttcttc    6120
tagtgtagcc gtagttaggc caccacttca agaactctgt agcaccgcct acatacctcg    6180
ctctgctaat cctgttacca gtggctgctg ccagtggcga taagtcgtgt cttaccgggt    6240
tggactcaag acgatagtta ccggataagg cgcagcggtc gggctgaacg ggggggttcgt    6300
gcacacagcc cagcttggag cgaacgacct acaccgaact gagataccta cagcgtgagc    6360
tatgagaaag cgccacgctt cccgaaggga gaaaggcgga caggtatccg gtaagcggca    6420
gggtcggaac aggagagcgc acgagggagc ttccaggggg aaacgcctgg tatctttata    6480
gtcctgtcgg gtttcgccac ctctgacttg agcgtcgatt tttgtgatgc tcgtcagggg    6540
gcggagcct atggaaaaac gccagcaacg cggcctttt acggttcctg gccttttgct    6600
ggccttttgc tcacatggct cgacagatct                                    6630
```

-continued

```
SEQ ID NO: 51          moltype = DNA  length = 1449
FEATURE                Location/Qualifiers
misc_feature           1..1449
                       note = PH20 mRNA sequence from 3D35M cells
source                 1..1449
                       mol_type = other DNA
                       organism = Homo sapiens SEQUENCE: 51
atgggagtgc taaaattcaa gcacatcttt ttcagaagct ttgttaaatc aagtggagta  60
tcccagatag ttttcacctt ccttctgatt ccatgttgct tgactctgaa tttcagagca  120
cctcctgtta ttccaaatgt gcctttcctc tgggcctgga atgccccaag tgaattttgt  180
cttggaaaat ttgatgagcc actagatatg agcctcttct ctttcatagg aagccccga   240
ataaacgcca ccgggcaagg tgttacaata ttttatgttg atagacttgg ctactatcct  300
tacatagatt caatcacagg agtaactgtg aatggaggaa tcccccagaa gatttcctta  360
caagaccatc tggacaaagc taagaaagac attacatttt atatgccagt agacaatttg  420
ggaatggctg ttattgactg ggaagaatgg agacccactt gggcaagaaa ctggaaacct  480
aaagatgttt acaagaatag gtctattgaa ttggttcagc aacaaaatgt acaacttagt  540
ctcacagagg ccactgagaa agcaaaacaa gaatttgaaa aggcagggaa ggatttcctg  600
gtagagacta taaaattggg aaaattactt cggccaaatc acttgtgggg ttattatctt  660
tttccggatt gttacaacca tcactataag aaacccggtt acaatggaag ttgcttcaat  720
gtagaaataa aaagaaatga tgatctcagc tggttgtgga atgaaagcac tgctctttac  780
ccatccattt atttgaacac tcagcagtct cctgtagctg ctacactcta tgtgcgcaat  840
cgagttcggg aagccatcag agtttccaaa atacctgatg caaaaagtcc acttccggtt  900
tttgcatata cccgcatagt ttttactgat caagtttttga aattcctttc tcaagatgaa  960
cttgtgtata catttggcga aactgttgct ctgggtgctt ctggaattgt aatatgggga  1020
accctcagta taatgcgaag tatgaaatct tgcttgctcc tagacaatta catggagact  1080
atactgaatc cttacataat caacgtcaca ctagcagcca aaatgtgtag tcaagtgctt  1140
tgccaggagc aaggagtgtg tataaggaaa aactggaatt caagtgacta tcttcacctc  1200
aacccagata attttgctat tcaacttgag aaaggtggaa agttcacagt acgtggaaaa  1260
ccgacacttg aagacctgga gcaatttct gaaaaatttt attgcagctg ttatagcacc  1320
ttgagttgta aggagaaagc tgatgtaaaa gacactgatg ctgttgatgt gtgtattgct  1380
gatggtgtct gtatagatgc ttttctaaaa cctcccatgg agacagaaga acctcaaatt  1440
ttctactga                                                          1449

SEQ ID NO: 52          moltype = DNA  length = 18
FEATURE                Location/Qualifiers
misc_feature           1..18
                       note = AP07
source                 1..18
                       mol_type = other DNA
                       organism = synthetic construct SEQUENCE: 52
agccattccc aaattgtc                                                 18

SEQ ID NO: 53          moltype = DNA  length = 18
FEATURE                Location/Qualifiers
misc_feature           1..18
                       note = AP08
source                 1..18
                       mol_type = other DNA
                       organism = synthetic construct SEQUENCE: 53
ctcccagttc aattacag                                                 18

SEQ ID NO: 54          moltype = DNA  length = 18
FEATURE                Location/Qualifiers
misc_feature           1..18
                       note = AP09
source                 1..18
                       mol_type = other DNA
                       organism = synthetic construct SEQUENCE: 54
cgttagctat ggatcctc                                                 18

SEQ ID NO: 55          moltype = DNA  length = 22
FEATURE                Location/Qualifiers
misc_feature           1..22
                       note = AP10
source                 1..22
                       mol_type = other DNA
                       organism = synthetic construct SEQUENCE: 55
cgagacagag aagactcttg cg                                            22

SEQ ID NO: 56          moltype = DNA  length = 22
FEATURE                Location/Qualifiers
misc_feature           1..22
                       note = AP12
source                 1..22
```

-continued

```
                        mol_type = other DNA
                        organism = synthetic construct
SEQUENCE: 56
cattcaacag accttgcatt cc                                              22

SEQ ID NO: 57          moltype = AA  length = 17
FEATURE                Location/Qualifiers
REGION                 1..17
                       note = C-terminal peptide cleaved from soluble rHuPH20 aa
                        431-447
source                 1..17
                       mol_type = protein
                       organism = Homo sapiens
SEQUENCE: 57
DAFKLPPMET EEPQIFY                                                    17
```

1

COMBINATION THERAPY WITH ANTIBODY-DRUG CONJUGATES AND HYALURONIDASES

FIELD OF THE INVENTION

The inventions herein relate to compositions, combination dosing regimen comprising administering an antibody-drug conjugate and hyaluronidase, and methods of treating or preventing diseases using such compositions and dosing regimen.

INCORPORATION BY REFERENCE OF SEQUENCE LISTING

An electronic version of the Sequence Listing is filed herewith, the contents of which are incorporated by reference in their entirety. The electronic file was created on Apr. 15, 2025, is 102,000 bytes in size, and is titled 063995-5123-WO_Corrected.xml.

BACKGROUND

Patient surveys have shown that the majority of patients would prefer to receive a long-acting injectable regimen at fewer intervals rather than taking intravenous injections. Currently, all available antibody-drug conjugates are administered via intravenous administration.

A safety concern when treating patients with injectable suspensions is injection site reactions. Combining an antibody-drug conjugate with other drug products can alter the injection site reaction profile of an antibody-drug conjugate. Combining an antibody-drug conjugate with other drug products also may alter the pharmacokinetic (pK) profile of an antibody-drug conjugate.

Long-acting injectable treatments are limited by patient experience and side effects. Achieving an injectable suspension with a high concentration of drug in order to dose less frequently and overcome the non-compliance problem with treatment regimens, whilst maintaining product stability, avoiding drug-drug interactions, and avoiding patient side effects is desirable.

There is a need in the art for a treatment and prevention with antibody-drug conjugates that can be dosed at fewer intervals without increasing injection site reactions.

SUMMARY

Provided are combination dosing regimens, comprising administering hyaluronidase; and administering an antibody-drug conjugate. Also provided are methods of treating or preventing breast cancer or urothelial cancer, comprising administering to a patient in need of treatment or prevention the combination dosing regimen as described herein. Provided are combinations and kits, comprising a composition comprising a soluble hyaluronidase; and antibody-drug conjugate.

Soluble hyaluronidase can be administered with an antibody-drug conjugate to allow a larger amount of antibody-drug conjugate to be administered to a patient at in a single dose than the amounts of antibody-drug conjugate administered alone. Thus, methods, regimens, and combinations provided herein can be administered less frequently.

In an aspect of the present disclosure, a combination dosing regimen is provided. In an embodiment, the combination dosing regimen includes administering a soluble hyaluronidase, and administering an antibody-drug conjugate. The soluble hyaluronidase may be a soluble PH20 hyaluronidase such as, for example, rHuPH20. In an embodiment, the hyaluronidase has the sequence set forth as residues 36-482 set forth in SEQ ID NO: 1 (i.e., SEQ ID NO: 4) or 36-483 set forth in SEQ ID NO: 1 (i.e., SEQ ID NO: 46) or has at least 98% sequence identity to the sequence set forth in SEQ ID NO: 4 or SEQ ID NO: 46. In an embodiment, the soluble hyaluronidase comprises amino acids 36-464 of SEQ ID NO: 1, or comprises a sequence of amino acids that has at least 85% sequence identity to a sequence of amino acids that contains at least amino acids 36-464 of SEQ ID NO:1, and retains hyaluronidase activity. In an embodiment, the soluble hyaluronidase comprises a sequence of amino acids that has at least 86%, 87%, 88%, 89%, 90%, 91%, 92%, 93%, 94%, 95%, 96%, 97%, 98% or 99% sequence identity to a sequence of amino acids that contains at least amino acids 36-464 of SEQ ID NO:1 and retains hyaluronidase activity.

In an embodiment, the soluble hyaluronidase has (a) amino acids set forth as residues 36-465 of SEQ ID NO: 1, 36-466 of SEQ ID NO: 1, 36-467 of SEQ ID NO: 1, 36-468 of SEQ ID NO: 1, 36-469 of SEQ ID NO: 1, 35-470 of SEQ ID NO: 1, 36-471 of SEQ ID NO: 1, 36-472 of SEQ ID NO: 1, 36-474 of SEQ ID NO: 1, 36-475 of SEQ ID NO: 1, 36-476 of SEQ ID NO: 1, 35-477 of SEQ ID NO: 1, 36-478 of SEQ ID NO: 1 (i.e., SEQ ID NO: 8), 36-479 of SEQ ID NO: 1 (i.e., SEQ ID NO: 7), 36-480 of SEQ ID NO: 1 (i.e., SEQ ID NO: 6), 36-481 of SEQ ID NO: 1 (i.e., SEQ ID NO: 5), 36-482 of SEQ ID NO: 1 (i.e., SEQ ID NO: 4), 36-483 of SEQ ID NO: 1 (i.e., SEQ ID NO: 46), 35-484 of SEQ ID NO: 1, 36-485 of SEQ ID NO: 1, 36-486 of SEQ ID NO: 1, 36-487 of SEQ ID NO: 1, 36-488 of SEQ ID NO: 1, 36-489 of SEQ ID NO: 1, 36-490 of SEQ ID NO: 1, 35-491 of SEQ ID NO: 1, 36-492 of SEQ ID NO: 1, 36-493 of SEQ ID NO: 1, 36-494 of SEQ ID NO: 1, 36-495 of SEQ ID NO: 1, 36-496 of SEQ ID NO: 1, 36-497 of SEQ ID NO: 1, 35-498 of SEQ ID NO: 1, 36-499 of SEQ ID NO: 1, and 36-500 of SEQ ID NO: 1, or an N-terminally truncated variant thereof lacking residues 36, 36-37, 36-38, 36-39, or 36-40. In an embodiment, the soluble hyaluronidase is a variant soluble hyaluronidase that has at least 91% sequence identity to a soluble hyaluronidase of (a). In an embodiment, the soluble hyaluronidase has at least 95% sequence identity to a soluble hyaluronidase of (a) or the variant thereof. In an embodiment, the soluble hyaluronidase comprises the replacement F204P, and has increased stability relative the unmodified PH20 that does not comprise F204P; and (a) T341S, L342W, S343E, I344N, M345T, S347T, M348K, K349E, L352Q, L353A, L3541, D355K, N356E, E359D and I361T;

(b) L342W, S343E, I344N, M345T, S347T, M348K, K349E, L352Q, L353A, L3541, D355K, N356E, E359D and I361T;

(c) M345T, S347T, M348K, K349E, L352Q, L353A, L354I, D355K, N356E, E359D, I361T and N363G;

(d) T341G, L342W, S343E, I344N, M345T, S347T, M348K, K349E, L352Q, L353A, L354I, D355K, N356E, E359D and I361T;

(e) T341A, L342W, S343E, I344N, M345T, S347T, M348K, K349E, L352Q, L353A, L354I, D355K, N356E, E359D and I361T;

(f) T341C, L342W, S343E, I344N, M345T, S347T, M348K, K349E, L352Q, L353A, L354I, D355K, N356E, E359D and I361T;

(g) T341D, L342W, S343E, I344N, M345T, S347T, M348K, K349E, L352Q, L353A, L354I, D355K, N356E, E359D and I361T;

(h) I344N, M345T, S347T, M348K, K349E, L352Q, L353A, L354I, D355K, N356E, E359D and I361T, and (i) S343E, I344N, M345T, S347T, M348K, K349E, L352Q, L353A, L354I, D355K, N356E, E359D and I361T.

The increased stability is reflected as increased stability in denaturing condition or at elevated temperatures.

In an embodiment, the soluble hyaluronidase is a variant modified polypeptide or catalytically active portion thereof that comprises one or more amino acid residue substitutions selected from among T341A, T341C, T341D, T341G, T341S, L342W, S343E, I344N, M348K, and N363G; numbering is with reference to SEQ ID NO:1; modifications comprise insertions, deletions, and replacements of amino acids; the polypeptides have an N-terminus, at residue 36, 37, 38, 39, or 40, and a C-terminus at a residue corresponding to residues 465 to 500.

In an embodiment, the modified PH20 comprises amino acid residue substitutions selected from among: T341S, L342W, S343E, I344N, M345T, S347T, M348K, K349E, L352Q, L353A, L354I, D355K, N356E, E359D and I361T. In an embodiment, the soluble hyaluronidase comprises amino acid modifications selected from one or more up to all of the following T341S, L342W, S343E, I344N, M345T, S347T, M348K, K349E, L352Q, L353A, L354I, D355K, N356E, E359D and I361T. In an embodiment, the C-terminus of variant PH20 polypeptide is at a residue corresponding to amino acid 467, 468, 469, 470, or 471 with reference to SEQ ID NO:1.

In an embodiment, the soluble hyaluronidase comprises the sequence of amino acids set forth in SEQ ID NO:2 or is a catalytically active fragment thereof.

In an embodiment, the soluble hyaluronidase is administered at a dose of 2000 to 60,000 U, preferably at a dose of 2,000 U to 15,000 U, preferably at a dose of 10,000 U. In an embodiment, the antibody-drug conjugate is administered at a dose of 10 mg/kg. In an embodiment, the antibody-drug conjugate is administered at a dose of at least or at 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 30 mg/kg, 40 mg/kg, 50 mg/kg, 60 mg/kg, 70 mg/kg, 80 mg/kg, 90 mg/kg, and 100 mg/kg. In an embodiment, the antibody-drug conjugate is administered at a dose of at least 0.05 mg/kg.

In an embodiment, the hyaluronidase and antibody-drug conjugate are administered subcutaneously.

In an embodiment, the combination dosing regimen includes, in a first step administering the soluble hyaluronidase to a patient; and in a second step administering the antibody-drug conjugate to the patient.

In an embodiment, the soluble hyaluronidase and antibody-drug conjugate are administered in the same composition. In an embodiment, the soluble hyaluronidase and antibody-drug conjugate are administered once a day. In an embodiment, the soluble hyaluronidase and antibody-drug conjugate are administered on day one and day eight of a twenty-one-day treatment cycle for three cycles. In an embodiment, the soluble hyaluronidase and antibody-drug conjugate are administered on day one and day 15 of a twenty-one-day treatment cycle. In an embodiment, the soluble hyaluronidase and antibody-drug conjugate are administered on day one, day 15 and day 29 of a forty-two-day treatment cycle. In an embodiment, the soluble hyaluronidase and antibody-drug conjugate are administered on day one and day 8 and day 15 of a twenty-eight-day treatment cycle. In an embodiment, the soluble hyaluronidase and antibody-drug conjugate are administered on day one and day 4 and day 7 of an induction cycle. In an embodiment, the soluble hyaluronidase and antibody-drug conjugate are administered Q1, Q2, Q3, or Q4.

In an embodiment, the soluble hyaluronidase is administered at a rate of: about 0.05 mL/sec to about 1.0 mL/sec, about 0.05 mL/sec to about 0.10 mL/sec, about 0.10 mL/sec to about 0.20 mL/sec, about 0.20 mL/sec to about 0.30 mL/sec, about 0.30 mL/sec to about 0.40 mL/sec, about 0.40 mL/sec to about 0.50 mL/sec, about 0.50 mL/sec to about 0.60 mL/sec, about 0.60 mL/sec to about 0.70 mL/sec, about 0.70 mL/sec to about 0.80 mL/sec, about 0.80 mL/sec to about 0.90 mL/sec, about 0.90 mL/sec to about 1.00 mL/sec, about 0.10 mL/sec to about 0.90 mL/sec, about 0.20 mL/sec to about 0.80 mL/sec, about 0.30 mL/sec to about 0.70 mL/sec, about 0.40 mL/sec to about 0.60 mL/sec, or about 0.45 mL/sec to about 0.55 mL/sec.

In an embodiment, administration during the combined dosing regimen takes: about 10 seconds to about 60 seconds, about 10 seconds to about 20 seconds, about 20 seconds to about 30 seconds, about 30 seconds to about 40 seconds, about 40 seconds to about 50 seconds, about 50 seconds to about 60 seconds, about 20 seconds to about 50 seconds, about 30 seconds to about 40 seconds, at least or less than about 10 seconds to about 60 seconds, at least or less than about 10 seconds to about 20 seconds, at least or less than about 20 seconds to about 30 seconds, at least or less than about 30 seconds to about 40 seconds, at least or less than about 40 seconds to about 50 seconds, at least or less than about 50 seconds to about 60 seconds, at least or less than about 20 seconds to about 50 seconds, or at least or less than about 30 seconds to about 40 seconds.

In an embodiment, swelling (bleb) volume is reduced following the administration into a subject when compared to a formulation that does not comprise the soluble hyaluronidase.

In an embodiment, administration of a high volume has reduced back leakage compared to a formulation that does not comprise the soluble hyaluronidase.

In an embodiment, safety profile is improved and/or the adverse events or side effects are reduced in comparison to administration of the antibody-drug conjugate without the soluble hyaluronidase. In an embodiment, safety profile is improved and/or the adverse events or side effects are reduced in comparison to intravenous administration of the antibody-drug conjugate without hyaluronidase.

In an aspect of the present disclosure, a method of treating (i) a locally advanced or metastatic breast cancer, or (ii) locally advanced or metastatic urothelial cancer is provided. In an embodiment, the method includes administering to a patient in need of treatment, a combination dosing regimen including administering a soluble hyaluronidase and administering an antibody-drug conjugate. In an embodiment, the locally advanced or metastatic breast cancer may be unresectable locally advanced or metastatic triple-negative breast cancer (mTNBC) in adult subjects who have received two or more prior systemic therapies, at least one of them for metastatic disease, or unresectable locally advanced or metastatic hormone receptor (HR)-positive, human epidermal growth factor receptor 2 (HER2)-negative breast cancer in adult subjects who have received endocrine-based therapy and at least two additional systemic therapies in the metastatic setting. In an embodiment, the locally advanced or metastatic urothelial cancer may be in adult subjects who have previously received a platinum-containing chemotherapy and either programmed death receptor-1 (PD-1) or programmed death-ligand 1 (PD-L1) inhibitor.

In an aspect of the present disclosure, a combination is provided. In an embodiment, the combination includes a soluble hyaluronidase and an antibody-drug conjugate. In an embodiment, the soluble hyaluronidase and the antibody-drug conjugate are in separate compositions. In an embodiment, the soluble hyaluronidase and the antibody-drug conjugate are co-formulated. In an embodiment, the soluble hyaluronidase and antibody-drug conjugate are in separate compositions in a container with at least two compartments.

In an aspect, a kit including a combination disclosed herein is provided.

In an aspect, a multi-compartment container is provided. In an embodiment, the multi-compartment container may include a suspension including antibody-drug conjugate in a first compartment and a soluble hyaluronidase in a second compartment.

BRIEF DESCRIPTION OF DRAWINGS

The following detailed description of embodiments of the hyaluronidase formulations for high volume administration, will be better understood when read in conjunction with the appended drawings of exemplary embodiments.

FIG. 5 is a chart of individual swelling height (mm) after SC injection of Trodelvy and Trodelvy+rHuPH20–caliper measurement.

FIG. 6A: Composite images of minipigs treated with Trodelvy. FIG. 6B: Composite 3D images of minipigs treated with Trodelvy+rHuPH20.

FIG. 11 is a chart of the qualitative assessment of post-injection induration (firmness).

FIG. 12A provides an image of the histological staining of minipig AID #4493 after injection with Trodelvy. FIG. 12B provides an image of the histological staining of minipig AID #4493 after injection with Trodelvy+rHuPH20. FIG. 12C provides an image of the histological staining of the naïve skin of minipig AID #4493. FIG. 12D provides an image of the histological staining of minipig AID #4498 after injection with Trodelvy. FIG. 12E provides an image of the histological staining of minipig AID #4498 after injection with Trodelvy+rHuPH20.

FIG. 12 F provides an image of the histological staining of the naïve skin of minipig AID #4498.

FIG. 12G provides an image of the histological staining of minipig AID #4593 after injection with Trodelvy. FIG. 12H provides an image of the histological staining of minipig AID #4593 after injection with Trodelvy+rHuPH20. FIG. 12I provides an image of the histological staining of the naïve skin of minipig AID #4593.

FIG. 13 is a chart of mean injection time (seconds±SEM) of ADC and ADC+rHuPH20.

FIG. 14 is a chart of mean (mg±SEM) and individual weights of back-leakage of Trodelvy and Trodelvy+rHuPH20.

FIGS. 15A-15C show swelling amounts after SC injection of ADC and ADC+rHuPH20. FIG. 15A is a chart of individual swelling volumes (mL) after SC injection of ADC and ADC+rHuPH20 taken by caliper measurement. FIG. 15B is a chart of individual swelling area (cc) after SC injection of ADC and ADC+rHuPH20 taken by caliper measurement. FIG. 15C is a chart of individual swelling height (mm) after SC injection of ADC and ADC+rHuPH20 taken by caliper measurement.

FIGS. 17A-17C show bleb size after SC injection of ADC and ADC+rHuPH20. FIG. 17A is a chart of individual bleb volume (mL) after SC injection of ADC and ADC+rHuPH20 measured by 3D imaging. FIG. 17B is a chart of individual bleb area (cm$^2$) after SC injection of ADC and ADC+rHuPH20 measured by 3D imaging. FIG. 17C is a chart of individual bleb height (mm) after SC injection of ADC and ADC+rHuPH20 measured by 3D imaging.

FIG. 20A shows injection sites post dosing with ADC for AID #4493L. FIG. 20B shows injection sites post dosing with ADC+rHuPH20 for AID #4493R. FIG. 20C shows injection sites post dosing with ADC for AID #4498R. FIG. 20D shows injection sites post dosing with ADC+rHuPH20 for AID #4498L. FIG. 20E shows injection sites post dosing with ADC for AID #4593L. FIG. 20F shows injection sites post dosing with ADC+rHuPH20 for AID #4593R.

FIG. 21A shows H&E staining of AID #4493L: ADC.

FIG. 21B shows H&E staining of AID #4493R: ADC+rHuPH20. FIG. 21C shows H&E staining of AID #4493: naïve skin. FIG. 21D shows H&E staining of AID #4498R: ADC. FIG. 21E shows H&E staining of AID #4498L: ADC+rHuPH20. FIG. 21F shows H&E staining of AID #4498: naïve skin. FIG. 21G shows H&E staining of AID #4593L: ADC. FIG. 21H shows H&E staining of AID #4593R: ADC+rHuPH20. FIG. 21I shows H&E staining of AID #4593: naïve skin.

FIG. 28A shows H&E staining of injection Site #7—ADC—0.5 hour exposure. FIG. 28B shows H&E Staining of Injection Site #2—ADC+rHuPH20—0.5 hour exposure. FIG. 28C shows H&E Staining of Injection Site #3—ADC—1 hour exposure. FIG. 28D shows H&E Staining of Injection Site #6—ADC+rHuPH20—1 hour exposure. FIG. 28E shows H&E Staining of Injection Site #5—ADC—2 hour exposure. FIG. 28F shows H&E Staining of Injection Site #4—ADC+rHuPH20—2 hour exposure. FIG. 28G shows H&E Staining of Injection Site #1—ADC—4 hour exposure. FIG. 28H shows H&E Staining of Injection Site #8—ADC+rHuPH20—4 hour exposure. FIG. 28I shows H&E Staining of Injection Site #9—Naïve skin. FIG. 28J shows H&E Staining of Injection Site #10—Naïve skin.

FIGS. 30-30B show bleb size post-injection of ADC and ADC+rHuPH20. FIG. 30B shows a chart of bleb height of ADC and ADC+rHuPH20.

FIG. 32A is a chart comparison of post-injection swelling of ADC and ADC+rHuPH20 at T0. FIG. 32B is a chart comparison of post-injection induration of ADC and ADC+rHuPH20 at T0. FIG. 32C is a chart comparison of post-injection swelling of ADC and ADC+rHuPH20 from T0 to T2h. FIG. 32D is a chart comparison of post-injection induration of ADC and ADC+rHuPH20 from T0 to T2h.

FIG. 33 is a chart comparing post-injection back-leakage of ADC and ADC+rHuPH20.

FIG. 34A is a chart comparing post-injection bleb volume of ADC and ADC+rHuPH20. FIG. 34B is a chart comparing post-injection bleb height of ADC and ADC+rHuPH20.

FIG. 35A is chart comparing post-injection swelling at T0. FIG. 35B is chart comparing post-injection induration at T0. FIG. 35C is chart comparing post-injection swelling from T0 to T2h. FIG. 35D is chart comparing post-injection induration from T0 to T2h.

FIG. 36A is a chart comparing delivery time of ADC v. ADC+rHuPH20.

FIG. 37A is a chart comparing bleb volume post-injection with ADC v. ADC+rHuPH20. FIG. 37B is a chart comparing bleb area post-injection with ADC v. ADC+rHuPH20. FIG. 37C is a chart comparing bleb height post-injection with ADC v. ADC+rHuPH20.

FIG. 38A is a chart comparing post-injection swelling post-injection with ADC and ADC+rHuPH20. FIG. 38B is a chart comparing post-injection induration post-injection with ADC and ADC+rHuPH20.

DETAILED DESCRIPTION

A. Definitions

Figures 1, 2:
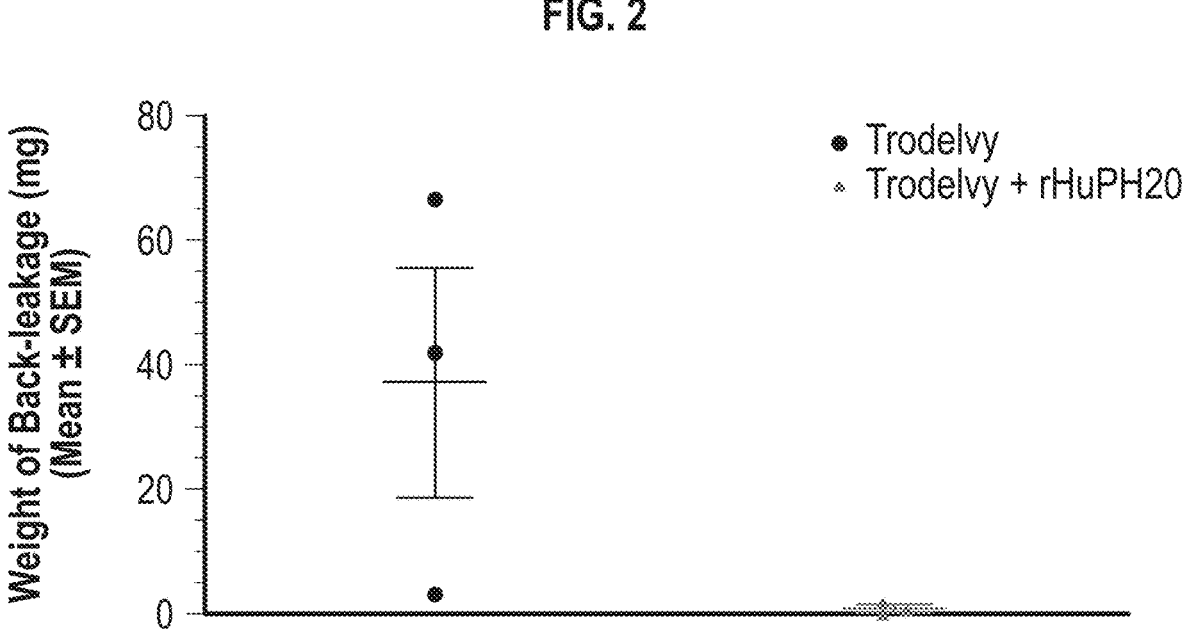
FIG. 1 is a chart of mean injection time (seconds±SEM) of Trodelvy and Trodelvy+rHuPH20.
FIG. 2 is a chart of mean (mg±SEM) and individual weights of back-leakage.

Unless defined otherwise, all technical and scientific terms used herein have the same meaning as is commonly understood by one of skill in the art to which the invention(s) belong. All patents, patent applications, published applications and publications, GenBank® sequences, databases, websites and other published materials referred to throughout the entire disclosure herein, unless noted otherwise, are incorporated by reference in their entirety. If there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein the term 'combination dosing regimen' refers to at least two components administered together to a patient.

As used herein, the term 'treatment' or 'treating' refers to alleviating the specified condition, eliminating or reducing the symptoms of the condition, slowing or eliminating the progression, invasion, or spread of the condition and reducing or delaying the reoccurrence of the condition in a previously afflicted subject.

As used herein, the term 'prevention' or 'preventing' refers to precluding developing a disease, disorder, or condition or reducing the risk of developing the disease, disorder, or condition or reducing the symptoms thereof.

As used herein the term 'injection site reaction' means side effects at or near the spot where the infusion/injection was received. This includes pain or discomfort, redness, swelling, itching, bruising, lumps, infection complications (cellulitis or abscess), and irritation.

As used herein, a soluble hyaluronidase is a hyaluronidase of form thereof that is not GPI anchored, and that is soluble under physiological conditions and is secreted upon expression. Hyaluronidases, such as ovine and bovine hyaluronidases occur as soluble hyaluronidases. Human PH20 hyaluronidase does not occur as a soluble hyaluronidase. It is known in the art that removal of all or a part of the GPI anchor results in soluble forms.

As used herein the term 'rHuPH20' refers to the soluble hyaluronidase composition produced upon expression in a mammalian cell, such as a CHO cell, or other cell that effects glycosylation, of nucleic acid encoding residues 36-482 of SEQ ID NO:1. For expression in cells the encoding nucleic acid is linked to the native (residues 1-35 of SEQ ID NO:1) or a heterologous signal sequence for trafficking and secretion of the encoded polypeptides. The resulting secreted soluble glycoprotein is a heterogeneous mixture of polypeptides, including polypeptides that terminate at residues 479, 480, 481, and 482, and are composed of residues 36-479, 36-480, 36-481, and 36-482 with reference to SEQ ID NO:1. Shorter C-terminally truncated forms also may be included.

As used herein, "combination therapy" refers to a treatment in which a subject if given two or more therapeutic agents, such as at least two or at least three therapeutic agents, for treating a single disease.

As used herein, "hyaluronidase activity" refers to the ability to enzymatically catalyse the cleavage of hyaluronic acid. The United States Pharmacopeia (USP) XXII assay for hyaluronidase determines hyaluronidase activity indirectly by measuring the amount of higher molecular weight hyaluronic acid, or hyaluronan, (HA) substrate remaining after the enzyme is allowed to react with the HA for 30 min at 37° C. (USP XXII-NF XVII (1990) 644-645 United States Pharmacopeia Convention, Inc, Rockville, MD). A Reference Standard solution can be used in an assay to ascertain the relative activity, in units, of any hyaluronidase. In vitro assays to determine the hyaluronidase activity of hyaluronidases, such as PH20, including soluble PH20 and esPH20, are known in the art and described herein. Exemplary assays include the micro turbidity assay that measures cleavage of hyaluronic acid by hyaluronidase indirectly by detecting the insoluble precipitate formed when the uncleaved hyaluronic acid binds with serum albumin and the biotinylated-hyaluronic acid assay that measures the cleavage of hyaluronic acid indirectly by detecting the remaining biotinylated-hyaluronic acid non-covalently bound to microtiter plate wells with a streptavidin-horseradish peroxidase conjugate and a chromogenic substrate. Reference Standards can be used, for example, to generate a standard curve to determine the activity in Units of the hyaluronidase being tested.

As used herein, specific activity refers to Units of activity per mg protein. The milligrams of hyaluronidase is defined by the absorption of a solution of at 280 nm assuming a molar extinction coefficient of approximately 1.7, in units of M−1 cm−1.

As used herein, "neutral active" refers to the ability of a PH20 polypeptide to enzymatically catalyse the cleavage of hyaluronic acid at neutral pH (e.g. at or about pH 7.0).

As used herein, a "GPI-anchor attachment signal sequence" is a C-terminal sequence of amino acids that directs addition of a preformed GPI-anchor to the polypeptide within the lumen of the ER. GPI-anchor attachment signal sequences are present in the precursor polypeptides of GPI-anchored polypeptides, such as GPI-anchored PH20 polypeptides. The C-terminal GPI-anchor attachment signal sequence typically contains a predominantly hydrophobic region of 8-20 amino acids, preceded by a hydrophilic spacer region of 8-12 amino acids, immediately downstream of the ω-site, or site of GPI-anchor attachment. GPI-anchor attachment signal sequences can be identified using methods well known in the art, such as but not limited to, in silico methods and algorithms (see, e.g. Udenfriend et al. (1995) *Methods Enzymol.* 250:571-582, Eisenhaber et al., (1999) *J. Biol. Chem.* 292: 741-758, Fankhauser et al., (2005) *Bioinformatics* 21:1846-1852, Omaetxebarria et al., (2007)*Proteomics* 7:1951-1960, Pierleoni et al., (2008)*BMC Bioinformatics* 9:392), including those that are readily available on bioinformatic websites, such as the ExPASy Proteomics tools site (e.g. the World Wide Web site expasy.ch/tools/).

As used herein, sequence identity refers to the relatedness between or among polypeptides among nucleic acid molecules. Sequence identity can be assessed by aligning two sequences and counting the number of differences between the aligned portion and the sequence to which it is compared. Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson (1988) Proc. Natl. Acad. Sci. USA 85:2444 (other programs include the GCG program package (Devereux (1984) Nucleic Acids Research 12:387), BLASTP, BLASTN, FASTA (Altschul (1990) J. Mol. Biol. 215:403); Guide to Huge Computers, Bishop, ed., Academic Press, 1994, and Carrillo (1988) SIAM J. Applied Math 48:1073). For example, the BLAST function of the National Center for Biotechnology Information database can be used to determine identity. Other commercially or publicly available programs include, DNAStar "MegAlign" program and the University of Wisconsin Genetics Computer Group (UWG) "Gap" program. Percent homology or identity of proteins and/or nucleic acid molecules can be determined, for example, by comparing sequence information using a GAP computer program (e.g. Needleman (1970) J. Mol. Biol. 48:443, as revised by Smith and Waterman (1981) Adv. Appl. Math. 2:482. Briefly, the GAP program defines similarity as the number of aligned symbols (i.e. nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov (1986) Nucl. Acids Res. 14:6745, as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide.

As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e. 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "denaturing condition" or "denaturation condition" refers to any condition or agent that, when exposed to a protein, affects or influences the degradation or denaturation of the protein, generally as a result of a loss or partial loss of the tertiary or secondary structure of the protein. Denaturing conditions can result in effects such as loss or reduction in activity, loss or reduction of solubility, aggregation and/or crystallization.

As used herein, "resistance to a denaturation condition" refers to any amount of decreased reduction or elimination of a property or activity of the protein associated with or caused by denaturation. For example, denaturation is associated with or causes increased crystallization or aggregation, reduced solubility or decreased activity. Hence, resistance to denaturation means that the protein exhibits decreased aggregation or crystallization, increased solubility or increased or greater activity (e.g. hyaluronidase activity) when exposed to a denaturing condition compared to a reference protein (e.g. unmodified enzyme).

As used herein, stability of a modified PH20 hyaluronidase means that it exhibits resistance to denaturation caused by a denaturation condition or denaturing agent.

For clarity of disclosure, and not by way of limitation, the detailed description is divided into the subsections that follow.

B. Overview

Provided are combination dosing regimens, comprising administering a hyaluronidase; and administering an antibody-drug conjugate. The agents in the dosing regimens can be administered sequentially, intermittently, serially, in the same composition, and/or in other combinations of the agents. The combination dosing regimens described herein are dosing regimens suitable to be provided to a patient in order to treat or prevent cancer.

In an embodiment of the combination dosing regimens provided are dosing regimens suitable for treating an cancer. In an alternative embodiment, the combination dosing regimen provided herein is for preventing cancer. The combination dosing regimen is administered to a patient in need of treatment for cancer.

In embodiments herein, provided are combination dosing regimens in which an antibody-drug conjugate and a soluble hyaluronidase are administered.

C. Antibody-Drug Conjugates

In embodiments herein, antibody-drug conjugates (ADC) are comprised of a monoclonal antibody (mAb), a cytotoxic payload, and a chemical linker. Once the ADC reaches the target cells, the mAb component recognizes and binds to the cell surface antigens, and the ADC-antigen complex is then internalized within the cancer cell by endocytosis to form an early endosome, which, following a maturation, forms late endosomes and finally fuses with lysosomes. The cytotoxic drug payload is then released from the mAb via either a chemical reaction or enzyme digestion in the lysosomes, and exerts its cytotoxic effect, causing cell apoptosis or death.

In addition to the cytotoxic properties from the payload, the Fc portion of the monoclonal antibody aids in immune-related cytotoxicities, such as antibody-dependent cell mediated cytotoxicity (ADCC), antibody-dependent phagocytosis (ADP), and complement-dependent cytotoxicity (CDC). Genetic engineering technologies have advanced to enhance the effector function of the antibody in the Fc region. Additionally, the binding of the antibody component of ADC with the specific antigen epitope of cancer cells can inhibit the downstream signal transduction of the antigen receptor.

An appropriate selection of target antigen is central to the design of an ADC. First, the antigen should be expressed, either exclusively or predominantly, in the tumor cells to reduce the off-target toxicity. Secondly, the binding to the target antigen should ideally lead to the internalization of the antigen-antibody complex. Additionally, it should ideally be on the surface rather than intracellular for it to be recognized, and lastly, it should not be secretory since a secreted antigen in the circulation would cause the undesirable ADC to bind outside of the tumor sites. Exemplary target antigens for ADC include but are not limited to, CD19, CD22, CD30, CD33, and CD79b in hematological malignancies and HER2, trop2, nectin4, tissue factor, and folate receptor alpha (FRα) in solid cancers.

An ideal antibody moiety should facilitate an effective internalization, have high antigen affinity, preserve long plasma half-life, and demonstrate low immunogenicity. The mAb are large-sized and account for over 90% of the mass of any given ADC. This is favorable because it encounters reduced distribution or permeation into healthy tissue, including those normally functioning as metabolizing and eliminating organs. No such problem is encountered at the tumor site as the vasculature in the tumor is characteristically leaky and allows the distribution and permeation of the ADC to the tumor cells.

In an embodiment, there are two types of linkers in the ADC, including cleavable and non-cleavable. The cleavable linkers are either chemically labile (hydrazone bond and disulfide bond) or enzymatically labile. Hydrazone linkers are generally stable in alkaline environments and are hydrolyzed in low pH environments, such as that in the lysosome and endosome. Hence, the cleavage of ADC with hydrazone linkers occurs predominantly in the lysosome and endosome upon internalization, with occasional hydrolysis in the plasma, resulting in off-target, systemic toxicity. Similarly, a disulfide bond linker can be stable in the plasma while specifically releasing the active payloads in the cancer cells with an elevated reductive glutathione level. The enzyme sensitive linkers are sensitive to the lysosomal protease that is generally overexpressed in cancer cells, enabling an accurate drug release in the cells after internalization. ADC with non-cleavable linkers are resistant to chemical or enzymatic digestion in the plasma and will require complete degradation of the antibody within the late endosomes and lysosome to release the payload. Therefore, ADC with non-cleavable linkers may have the lowest off-target systemic toxicity due to increased plasma stability and thus they are most suitable in the treatment of tumors with homogenous antigen expression. In an embodiment, some of the ADC have been engineered to have desirable "off-target effect" for "by-stander killing" extending the cytotoxic effect to the low or negative antigen-expressing cells in the tumor proximity. For this mechanism to work, several characteristics of the ADC molecules are crucial: namely, a cleavable linker and a non-polar, freely membrane-permeable payload. Conversely, to reduce the undesirable systemic toxicity from payload molecules permeating out of the tumor cells, ionizable payloads (e.g. containing carboxylic acids) can be used.

In an embodiment, the cytotoxic payloads should ideally have the following properties. High potency, in vitro high cytotoxic activity (sub-nanomolar half maximal inhibitory concentration ($IC_{50}$) value), high stability in the systemic circulation, sufficient solubility in the aqueous environment of antibody and biochemical properties to allow easier conjugation to the antibody, low immunogenicity, small molecular weight, and a long half-life. In an embodiment, there are mainly two classes of cytotoxic drugs used as payloads, microtubule inhibitors or DNA damaging agents.

In an embodiment, auristatins and maytansines payloads are both cytotoxic agents that work as tubulin inhibitors.

Auristatin is a dolastatin synthetic analog. There are two auristatin derivatives: one is monomethyl auristatin E (MMAE) and the other is monomethyl auristatin F (MMAF). These two cytotoxic agents differ structurally wherein the phenylalanine present at the C-terminus renders MMAF membrane-impermeable, whereas the MMAE can exit the cell and thus diffuse to nearby cells and kill them through the bystander effects. In an embodiment, the cytoxic agent is selected from maytansinoids which are natural cytotoxic agents isolated from the cortex of *Maytenus serrata*, which possesses a macrolide structure.

In an embodiment, the cytotoxic agents are selected from calicheamicins, pyrrolobenzodiazepines and topoisomerase inhibitors which are DNA-damaging agents that act through DNA double strand breaks, crosslinking, and intercalation, respectively. Both gemtuzumab ozogamicin and inotuzumab Ozogamicin have N-acetyl gamma calicheamicin as a payload. Calicheamicins belong to a class of potent anti-tumor antibiotics that cleave the DNA in a site-specific, double-stranded manner. Pyrrolobenzodiazepines are another class of antibiotics derived from *Streptomyces* species and is used as a cytotoxic payload in Loncastuximab Tesirine. SN-38 and Deruxtecan are topoisomerase inhibitors that are the cytotoxic components of Sacituzumab Govitecan and Trastuzumab Deruxtecan, respectively. Any of the above cytotoxic agents are embodied in the ADC.

In addition to the choice of the antibody, the linker, and the payload, the method of conjugation is also important for the successful structure of ADC. In an embodiment, the lysine and cysteine residues on the antibody provide the accessible reaction sites for conjugation. In an embodiment, a varying number (0-8) of small-molecule toxins may be attached to an antibody, as the conventional conjugation methods are random, resulting in a wide drug-antibody ratio (DAR) distribution. In an embodiment, the ideal DALR is 2-4. A low DALR can lower the efficacy, while a high DALR may increase the drug potency.

Exemplary ADC, antigen targets, linkers and cytotoxins for use in the present invention are included in the table below.

| ADC | Antigen Target | Linker | Cytotoxin | Payload Target | Dose |
|---|---|---|---|---|---|
| Gemtuzumab ozogamicin (Mylotarg) | CD33 | Cleavable acid-labile hydrazone | N-acetyl gamma Calicheamicin dimethyl hydrazide (cytotoxic antibiotic) | Minor groove of DNA | 2-3 mg/m$^2$ mono 3-6 mg/m$^2$ combo |
| Brentuximab vedotin (Adcetris) | CD30 | Cleavable (enzymatic) | Monomethyl auristatin E (microtubule-targeting) | Tubulin-microtubule | 1.8-180 mg/m$^2$ mono 1.2-120 mg/m$^2$ combo |
| Ado-Trastuzumab emtansine (Kadcyla) | Her-2 | Non-cleavable (thioether) | DM1, derivative of maytansine (emtansine) (microtubule-targeting) | Tubulin-microtubule | 3.6 mg/kg |
| Inotuzumab ozogamicin (Besponsa) | CD22 | Cleavable acid-labile hydrazone linker (chemical) | N-acetyl gamma Calicheamicin imethyl hydrazide (cytotoxic antibiotic) | Minor groove of DNA | 0.5-0.8 mg/m$^2$ |
| Polatuzumab vedotin (Polivy) | CD79b | Cleavable (Enzymatic) | Monomethyl auristatin E (microtubule-targeting) | Tubulin-microtubule | 1.8 mg/kg |

-continued

| ADC | Antigen Target | Linker | Cytotoxin | Payload Target | Dose |
|---|---|---|---|---|---|
| Enfortumab vedotin- (Padcev) | Nectin-4 | Cleavable (Enzymatic) | Monomethyl auristatin E (microtubule-targeting) | Tubulin-microtubule | 1.25-125 mg/kg |
| Fam-Trastuzumab deruxtecan (Enhertu) | Her-2 | Cleavable (Enzymatic) | Topoisomerase I inhibitor (exatecan derivative) (DNA-targeting) | DNA Topoisomerase I | 5.4-6.4 mg/kg |
| Sacituzumab govitecan (Trodelvy) | Trop-2 | Cleavable acid-labile hydrazone (chemical) | SN-38 (active metabolite) of Irinotecan, topoisomerase-1 inhibitor (DNA-targeting) | DNA Topoisomerase I | 10 mg/kg |
| Loncastuximab Tesirine (Zynlonta) | CD19 | Cleavable (Enzymatic) | SG3199, alkylating agent (Pyrrolobenzod iazepine dimer) (DNA-targeting) | DNA crosslinking | 0.15-0.075 mg/kg |
| Tisotumab vedotin (Tivdak) | Tissue factor (TF) CF-III | Cleavable (Enzymatic) | Monomethyl auristatin E (microtubule-targeting) | Tubulin-microtubule | 2 mg/kg |
| Mirvetuximab soravtansine-gynx (Elahere) (FRα) | Folate factor alpha | Cleavable Disufide bond based (chemical) | DM4 (maytansinoid derivative ravtansine) (microtubule-targeting) | Tubulin-microtubule | 6 mg/kg |
| Datopotamab deruxtecan (Datroway) | Trop-2 | Protease cleavable | Deruxtecan | DNA Topoisomerase I | 6 mg/kg |
| Anvatabart opadotin (ARX788) | Erb-b2 receptor tyrosine kinase-2 | Stable (non-cleavable) | AS269 | Tubulin-microtubule | 1.3-1.5 mg/kg |
| AZD0901 | Claudin-18 | Protease cleavable | Monomethyl auristatin E | Tubulin-microtubule | 1.8-2.2 mg/kg |
| DB-1303 | Erb-b2 receptor tyrosine kinase-2 | Cathepsin cleavable | P1003 | DNA Topoisomerase I | 8 mg/kg |
| Rinatabart sesutecan | Folate receptor alpha | Cleavable | Exatecan | DNA Topoisomerase I | 120 mg/m$^2$ |
| DS-7300 | CD276 | Protease cleavable | Deruxtecan | DNA Topoisomerase I | 12 mg/kg |
| Luveltamab tazevibulin (Luvelta) | Folate receptor alpha | Protease cleavable | 3-aminophenyl hemiasterlin | Tubulin-microtubulin | 4.3-5.2 mg/kg |
| Patritumab deruxtecan | Erb-b2 receptor tyrosine kinase-3 | Protease cleavable | Exatecan | DNA Topoisomerase I | 5.6 mg/kg |
| Raludotatug deruxtecan | Cadherin 6 | Protease cleavable | Exatecan | DNA Topoisomerase I | 4.8, 5.6, 6.4 mg/kg |
| Sacituzumab triumotecan (SKB264) | Tumor associated calcium signal transducer 4 | pH sensitive and enzyme cleavable | Belotecan | DNA Topoisomerase I | 4 mg/kg |
| Sigvotatug vedotin | Integrin subunit beta-6 secretory leukocyte peptidase inhibitor | Protease cleavable | Monomethyl auristatin E | Tubulin-microtubulin | 1.8 mg/kg |

-continued

| ADC | Antigen Target | Linker | Cytotoxin | Payload Target | Dose |
|---|---|---|---|---|---|
| Telisotuzumab adizutecan (ABBV-400) | Met-proto-oncogene receptor tyrosine kinase | Cleavable | Adizutecan | DNA Topoisomerase I | 2.4-3 mg/kg |
| Telisotuzumab vidotin (Teliso-V) | Met-proto-oncogene receptor tyrosine kinase | Protease cleavable | Monomethyl auristatin E | Tubulin-microtubulin | 1.9 mg/kg |
| Zilovertamab vedotin | ROR1 | Protease cleavable | Monomethyl auristatin E | Tubulin-microtubulin | 1.5-2.5 mg/kg |

In embodiments herein, an antibody-drug conjugate is provided in a suspension. The suspension includes any suitable suspension of an antibody-drug conjugate, such as those exemplified. Combinations and treatment regimens are provided herein in which an antibody-drug conjugate is administered in combination with a soluble hyaluronidase.

D. Soluble Hyaluronidases

Soluble hyaluronidases include any that, upon expression, are secreted from a cell and exist in soluble form. Such soluble hyaluronidases include, for example, but are not limited to, bacterial soluble hyaluronidases, non-human soluble hyaluronidases, such as bovine PH20 and ovine PH20, human soluble PH20, and variants thereof. Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g. DG44 CHO cells).

Soluble PH20 hyaluronidase is available and sold, for example, under the trademark ENHANZE®. ENHANZE® technology provides to a drug delivery technology, employing the soluble hyaluronidases to facilitate the delivery of injected drugs and fluids. When co-formulated with other drugs or administered with other drugs, the ENHANZE® technology reduces treatment burden for patients. It can allow for large volume subcutaneous injections with increased dispersion and absorption of co-administered therapies.

rHuPH20 refers to the composition produced upon expression in a cell, such as CHO cell, of nucleic acid encoding residues 36-482 of SEQ ID NO: 26, generally linked to the native or a heterologous signal sequence (residues 1-35 of SEQ ID NO: 26). rHuPH20 is produced by expression of a nucleic acid molecule, such as encoding amino acids 1-482 (set forth in SEQ ID NO: 26) in a mammalian cell. Translational processing removes the 35 amino acid signal sequence. As produced in the culture medium there is heterogeneity at the C-terminus such that the product, designated rHuPH20, includes a mixture of species that can include any one or more of the polypeptides 36-480, 36-481, and 36-482 of SEQ ID NO: 26, and some shorter polypeptides, in various abundance. rHuPH20 and forms of soluble hyaluronidase are produced in cells, such as CHO cells, for example DG44 CHO cells, that facilitate N-glycosylation. PH20 is a glycoprotein, and as known in the art, requires glycosylation retain activity. See, e.g. U.S. Pat. Nos. 8,927,249 and 9,284,543 (and PCT Publication No. WO 2010/077297), which describe the effects of glycosylation and partial glycosylation and elimination of glycosylation on the activity of soluble forms of PH20. These patents and publications also describe and exemplify I soluble C-terminally truncated forms of PH20.

1. Forms of Soluble Human PH20

Soluble hyaluronidases include bovine and ovine PH20, and recombinant and humanized forms thereof. Human PH20 in nature includes a GPI anchor and exists linked to sperm cells; it is not soluble. C-terminally-truncated forms thereof are soluble. Soluble forms of recombinant human PH20 have been produced and can be used in the compositions, combinations and methods described herein. Descriptions of and production of such soluble forms of PH20 are described, for example, in U.S. Pat. Nos. 7,767, 429; 8,202,517; 8,431,380; 8,431,124; 8,450,470; 8,765, 685; 8,772,246; 7,871,607; 7,846,431; 7,829,081; 8,105, 586; 8,187,855; 8,257,699; 8,580,252; 9,677,061; and 9,677,062, each incorporated by reference herein. The soluble hyaluronidases, thus include forms of human PH20, which are neutral active hyaluronidases and which require glycosylation for activity.

SEQ ID NO: 1 sets forth the sequence of the precursor polypeptides; the mature PH20 polypeptide (residues 36-509); soluble forms also include those with amino acid truncations at the N-terminal, such as deletions of the first one, two, three, or fours residues, such that the resulting polypeptides have an N-terminus, for example, at residue 36, 37, 38, 39, or 40, and a C-terminus at a residue from 465 to 500, and variants thereof, including, but not limited to, variants discussed below, variants known in the art, and allelic variants.

Hyaluronidases for use in the compositions, combinations and methods herein are soluble neutral active hyaluronidases. Exemplary thereof are the soluble C-terminally truncated forms of mature human PH20. Soluble forms that have hyaluronidase activity, include but are not limited to, those that are truncated at residues from 465 to 500 of SEQ ID NO: 1, and that are, upon expression, secreted. Exemplary thereof are polypeptides that have sequence 36-465 of SEQ ID NO: 1, 36-466 of SEQ ID NO: 1, 36-467 of SEQ ID NO: 1, 36-468 of SEQ ID NO: 1, 36-469 of SEQ ID NO: 1, 35-470 of SEQ ID NO: 1, 36-471 of SEQ ID NO: 1, 36-472 of SEQ ID NO: 1, 36-474 of SEQ ID NO: 1, 36-475 of SEQ ID NO: 1, 36-476 of SEQ ID NO: 1, 35-477 of SEQ ID NO: 1, 36-478 of SEQ ID NO: 1, 36-479 of SEQ ID NO: 1, 36-480 of SEQ ID NO: 1, 36-481 of SEQ ID NO: 1, 36-482 of SEQ ID NO: 1, 36-483 of SEQ ID NO: 1, 35-484 of SEQ ID NO: 1, 36-485 of SEQ ID NO: 1, 36-486 of SEQ ID NO: 1, 36-487 of SEQ ID NO: 1, 36-488 of SEQ ID NO: 1, 36-489 of SEQ ID NO: 1, 36-490 of SEQ ID NO: 1, 35-491 of SEQ ID NO: 1, 36-492 of SEQ ID NO: 1, 36-493 of SEQ ID NO: 1, 36-494 of SEQ ID NO: 1, 36-495 of SEQ ID NO: 1, 36-496 of SEQ ID NO: 1, 36-497 of SEQ ID NO: 1, 35-498 of SEQ ID NO: 1, 36-499 of SEQ ID NO: 1, and 36-500 of SEQ ID NO:1, as well as N-terminally truncated forms of each of the preceding that lack two to five residues at the N-terminus, such as for example 37-368 of SEQ ID NO: 1, 38-468 of SEQ ID NO: 1, and any others that exhibit hyaluronidase activity at neutral pH, such as pH in the range of 7.0-7.4.

Thus, such soluble forms include truncated forms of the mature form of human PH20 lacking all or a portion of the C-terminal GPI anchor, so long as the hyaluronidase is soluble and retains hyaluronidase activity. Soluble forms are secreted upon expression in mammalian cells, and are encoded with a signal sequence, such are residues 1-35 of SEQ ID NO: 1 or a heterologous signal sequence that is cleaved by the cell to effect secretion. Soluble forms are forms that, when expressed in a cell, lack the signal peptide. Also included among soluble hyaluronidases are variants of the soluble PH20 polypeptides that exhibit hyaluronidase activity. Variants include polypeptides having at least 60%, 70%, 80%, 85%, 90%, 91%, 92%, 93%, 94%, 95%, 96%, 97%, 98%, 99% or more sequence identity to any of the PH20 polypeptides 36-465 of SEQ ID NO: 1, 36-466 of SEQ ID NO: 1, 36-467 of SEQ ID NO: 1, 36-468 of SEQ ID NO: 1, 36-469, 35-470 of SEQ ID NO: 1, 36-471 of SEQ ID NO: 1, 36-472 of SEQ ID NO: 1, 36-474 of SEQ ID NO: 1, 36-475 of SEQ ID NO: 1, 36-476 of SEQ ID NO: 1, 35-477 of SEQ ID NO: 1, 36-478 of SEQ ID NO: 1, 36-479 of SEQ ID NO: 1, 36-480 of SEQ ID NO: 1, 36-481 of SEQ ID NO: 1, 36-482 of SEQ ID NO: 1, 36-483 of SEQ ID NO: 1, 35-484 of SEQ ID NO: 1, 36-485 of SEQ ID NO: 1, 36-486 of SEQ ID NO: 1, 36-487 of SEQ ID NO: 1, 36-488 of SEQ ID NO: 1, 36-489 of SEQ ID NO: 1, 36-490 of SEQ ID NO: 1, 35-491 of SEQ ID NO: 1, 36-492 of SEQ ID NO: 1, 36-493 of SEQ ID NO: 1, 36-494 of SEQ ID NO: 1, 36-495 of SEQ ID NO: 1, 36-496 of SEQ ID NO: 1, 36-497 of SEQ ID NO: 1, 35-498 of SEQ ID NO: 1, 36-499 of SEQ ID NO: 1, and 36-500 of SEQ ID NO:1. Amino acid variants include conservative and non-conservative insertions, or deletions, or replacements, and include the modifications, singly or combinations of the modifications detailed, for example, in U.S. Pat. No. 11,041,149 and International PCT publication No. WO 2013/102144. U.S. Pat. No. 11,041,149 and International PCT publication No. WO 2013/102144 describe a systematic analysis and results identifying the effects of amino acid modifications at each residue in PH20 to thereby provide a structure/function map of PH20; a skilled person can identify replacement residues and consequent alterations in properties and activities, such as for effecting increases in enzymatic activity, stability in denaturing conditions, and also residues whose replacement or deletion decreases or eliminates enzymatic activity.

It is understood that residues that are important or otherwise required for the activity of a hyaluronidase, such as any described above or known to those of skill in the art, are generally invariant and, except for possible conservative amino acid substitutions, cannot be changed. These include, for example, active site residues. For example, amino acid residues 111, 113 and 176 (corresponding to residues in the mature PH20 polypeptide) of a human PH20 polypeptide, or soluble form thereof, are generally invariant and are not altered. Other residues that confer glycosylation and formation of disulfide bonds required for proper folding also can be invariant.

The soluble human PH20 hyaluronidase is GPI-anchored and is rendered soluble by truncation at the C-terminus by removal of all or a part of the GPI anchor. Such truncation can remove all of the GPI anchor attachment sequence or can remove only some of the GPI anchor attachment sequence. The resulting polypeptide, however, is soluble. In instances where the soluble hyaluronidase retains a portion of the GPI anchor attachment signal sequence, 1, 2, 3, 4, 5, 6, 7 or more amino acid residues in the GPI anchor attachment signal sequence can be retained, provided the polypeptide is soluble. Polypeptides containing one or more amino acids of the GPI anchor are termed extended soluble hyaluronidases. One of skill in the art can determine whether a polypeptide is GPI-anchored using methods well known in the art. Such methods include, but are not limited to, using known algorithms to predict the presence and location of the GPI anchor attachment signal sequence and ω-site, and performing solubility analyses before and after digestion with phosphatidylinositol-specific phospholipase C (PI-PLC) or D (PI-PLD).

Extended soluble hyaluronidases, which terminate for example, at residues 495, 496, 497, 498, 499, and 500, with reference to SEQ ID NO:1, can be produced by making C-terminal truncations to any naturally GPI-anchored hyaluronidase such that the resulting polypeptide is soluble and contains one or more amino acid residues from the GPI anchor attachment signal sequence (see, e.g. U.S. Pat. No. 8,927,249). These include hyaluronidases that are neutral active, soluble, contain amino acid substitutions, and have at least 60%, 70%, 80%, 85%, 90%, 91%, 92%, 93%, 94%, 95%.

Typically, for use in the compositions, combinations and methods herein, a soluble human hyaluronidase, such as a soluble human PH20, is used, such as a PH20 and variants having, for example, at least 91% or 95% or 98% sequence identity thereto, including those with 1 to 5 N-terminal residues deleted. Hyaluronidases used in the regimens, combinations, compositions, and methods herein can be recombinantly produced or can be purified or partially purified from natural sources, such as, for example, from testes extracts. Methods for production of recombinant proteins, including recombinant hyaluronidases, are well known in the art.

Recombinant soluble forms of human PH20 have been generated and can be used in the compositions, combinations and methods provided herein. For example, with reference to SEQ ID NO: 1, which sets forth the sequence of full length precursor PH20, which includes a signal sequence (residues 1-35), soluble forms include, but are not limited to, C-terminal truncated polypeptides of human PH20 set forth in SEQ ID NO: 1 having a C-terminal amino acid residue 467 of the sequence of amino acids set forth in SEQ ID NO: 1, 468 of the sequence of amino acids set forth in SEQ ID NO: 1, 469 of the sequence of amino acids set forth in SEQ ID NO: 1, 470 of the sequence of amino acids set forth in SEQ ID NO: 1, 471 of the sequence of amino acids set forth in SEQ ID NO: 1, 472 of the sequence of amino acids set forth in SEQ ID NO: 1, 473 of the sequence of amino acids set forth in SEQ ID NO: 1, 474 of the sequence of amino acids set forth in SEQ ID NO: 1, 475 of the sequence of amino acids set forth in SEQ ID NO: 1, 476 of the sequence of amino acids set forth in SEQ ID NO: 1, 477 of the sequence of amino acids set forth in SEQ ID NO: 1 (i.e., SEQ ID NO: 39), 478 of the sequence of amino acids set forth in SEQ ID NO: 1 (i.e., SEQ ID NO: 40), 479 of the sequence of amino acids set forth in SEQ ID NO: 1 (i.e., SEQ ID NO: 41), 480 of the sequence of amino acids set forth in SEQ ID NO: 1 (i.e., SEQ ID NO: 42), 481 of the sequence of amino acids set forth in SEQ ID NO: 1 (i.e., SEQ ID NO: 43), 482 of the sequence of amino acids set forth in SEQ ID NO: 1 (i.e., SEQ ID NO: 3), 483 of the sequence of amino acids set forth in SEQ ID NO: 1 (i.e., SEQ ID NO: 44), 484 of the sequence of amino acids set forth in SEQ ID NO: 1, 485 of the sequence of amino acids set forth in SEQ ID NO: 1, 486 of the sequence of amino acids set forth in SEQ ID NO: 1, 487 of the sequence of amino acids set forth in SEQ ID NO: 1, 488 of the sequence of amino acids set forth in SEQ ID NO: 1, 489 of the sequence of amino acids set forth in SEQ ID NO: 1, 490 of the sequence of amino acids set forth in SEQ ID NO: 1, 491 of the sequence of amino acids set forth in SEQ ID NO: 1, 492 of the sequence of amino acids set forth in SEQ ID NO: 1, 493 of the sequence of amino acids set forth in SEQ ID NO: 1, 494 of the sequence of amino acids set forth in SEQ ID NO: 1, 495 of the sequence of amino acids set forth in SEQ ID NO: 1, 496 of the sequence of amino acids set forth in SEQ ID NO: 1, 497 of the sequence of amino acids set forth in SEQ ID NO: 1, 498 of the sequence of amino acids set forth in SEQ ID NO: 1, 499 of the sequence of amino acids set forth in SEQ ID NO: 1 or 500 of the sequence of amino acids set forth in SEQ ID NO: 1, or polypeptides that exhibit at least 85%, 90%, 91%, 92%, 93%, 94%, 95%, 96%, 97%, 98%, 99%, or more sequence identity thereto, when aligned with the unmodified sequence of the soluble PH20, have activity at neutral pH, and are soluble (secreted into the medium when expressed in a mammalian cell). Soluble forms of human PH20 generally include those that contain amino acids 36-464 set forth in SEQ ID NO: 1 and terminate at any of residues, 465-500 and optionally include a 1-3 amino acid deletion at the N-terminus (i.e. lack residues 36, 36-37, or 36-38 of SEQ ID NO:1). For example, when expressed in mammalian cells, the 35 amino acid N-terminal signal sequence (residues 1-35 of SEQ ID NO:1) is cleaved during processing, and a soluble form of the protein is secreted. Thus, the mature soluble polypeptides include those that contain amino acids 36 to 467 of SEQ ID NO: 1, 468 of SEQ ID NO: 1, 469 of SEQ ID NO: 1, 470 of SEQ ID NO: 1, 471 of SEQ ID NO: 1, 472 of SEQ ID NO: 1, 473 of SEQ ID NO: 1, 474 of SEQ ID NO: 1, 475 of SEQ ID NO: 1, 476 of SEQ ID NO: 1, 477 of SEQ ID NO: 1 (i.e., SEQ ID NO: 9), 478 of SEQ ID NO: 1 (i.e., SEQ ID NO: 8), 479 of SEQ ID NO: 1 (i.e., SEQ ID NO: 7), 480 of SEQ ID NO: 1 (i.e., SEQ ID NO: 6),481 of SEQ ID NO: 1 (i.e., SEQ ID NO: 5),482 of SEQ ID NO: 1 (i.e., SEQ ID NO: 4), 483 of SEQ ID NO: 1 (i.e., SEQ ID NO: 46), and up to and including 500 of SEQ ID NO: 1. Exemplary of soluble hyaluronidases are soluble human PH20 polypeptides that are 442 (i.e., SEQ ID NO: 9), 443 (i.e., SEQ ID NO: 8), 444 (i.e., SEQ ID NO: 7), 445 (i.e., SEQ ID NO: 6), 446 (i.e., SEQ ID NO: 5) or 447 (i.e., SEQ ID NO: 4) amino acids in length, such as set forth those set forth above, and variants thereof that have, for example, at least 85%, 86%, 87%, 88%, 89%, 90%, 91%, 92%, 93%, 94%, 95%, 96%, 97%, 98% or 99% sequence identity thereto and retains hyaluronidase activity. The generation of such soluble forms of recombinant human PH20 are described, for example, in U.S. Pat. Nos. 7,767,429; 8,202,517; 8,431,380; 8,431,124; 8,450,470; 8,765,685; 8,772,246; 7,871,607; 7,846,431; 7,829,081; 8,105,586; 8,187,855; 8,257,699; 8,580,252; 9,677,061; and 9,677,062.

Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g. DG44 CHO cells).

The composition that recombinantly produced from mammalian cells, such as CHO cells, has been referred to rHuPH20. It refers to the composition produced upon expression in a cell, such as CHO cell, of nucleic acid encoding residues 36-482 of SEQ ID NO: 1 (i.e., SEQ ID NO: 4), generally linked to the native (residues 1-35 of SEQ ID NO: 1; residues 1-482 of SEQ ID NO: 1 are set forth in SEQ ID NO: 3) or a heterologous signal sequence. rHuPH20 is produced by expression of a nucleic acid molecule, such as encoding amino acids 1-482 (set forth in SEQ ID NO: 1; residues 1-482 of SEQ ID NO: 1 are set forth in SEQ ID NO: 3) or 36 to 482 (residues 36-482 of SEQ ID NO: 4) with a heterologous signal sequence. Post translational processing removes the 35 amino acid signal sequence, resulting in polypeptide or a mixture of polypeptides, including those set forth in SEQ ID NO:4-8. As produced in the culture medium there is heterogeneity at the C-terminus such that the product, designated rHuPH20, includes a mixture of species that can include any one or more of SEQ ID NO: 4-8 in various abundance. Generally, the soluble hyaluronidases, rHuPH20 is produced in cells that facilitate correct N-glycosylation to retain activity, such as CHO cells (e.g. DG44 CHO cells). Human soluble PH20 hyaluronidase requires glycosylation for activity. When produced recombinantly from a vector encoding residues 36-582, the most abundant species is the 446 amino acid polypeptides corresponding to residues 36-481 of SEQ ID NO: 1(i.e., SEQ ID NO: 5). The particular distribution of resulting polypeptides can depend upon the particular method of production. An exemplary method for production of high levels of PH20 is detailed, for example in U.S. Pat. Nos. 8,187,855 and 8,343,487.

2. Glycosylation of Hyaluronidases

Glycosylation, including N- and O-linked glycosylation, of some hyaluronidases, including the soluble PH20 hyaluronidases, can be important for their catalytic activity and stability. For some hyaluronidases, removal of N-linked glycosylation can result in near complete inactivation of the hyaluronidase activity. For such hyaluronidases, the presence of N-linked glycans can be important for generating an active enzyme.

N-linked oligosaccharides fall into several primary types (oligomannose, complex, hybrid, sulfated), all of which have (Man) 3-GlcNAc-GlcNAc- cores attached via the amide nitrogen of Asn residues that fall within -Asn-Xaa-Thr/Ser-sequences (where Xaa is not Pro). Glycosylation at an -Asn-Xaa-Cys-site has been reported for coagulation protein C. In some instances, a hyaluronidase, such as a PH20 hyaluronidase, can contain N-glycosidic and O-glycosidic linkages. For example, PH20 has O-linked oligosaccharides as well as N-linked oligosaccharides. There are six potential N-linked glycosylation sites at N82, N166, N235, N254, N368, N393 of human PH20 exemplified in SEQ ID NO: 1.

3. Variants

As discussed above, variants of PH20 are known to those of skill in the art, or readily can be prepared in view of the skill and knowledge in the art. Variants include those with amino acid replacements, insertions, and deletions. Variants of the soluble PH20 polypeptides that have altered properties, such as increased stability and/or activity, have been produced. U.S. Pat. No. 9,447,401 and family members U.S. Pat. Nos. 10,865,400, 11,041,149 and 11,066,656 describe and provide a structure/function map of human PH20 detailing the effects of amino acid replacements at every residue in the catalytic domain of PH20. These patents provide about 7000 examples in which the effects of replacing each amino acid with 15 other amino acids on activity and stability were identified and described. By virtue of those patents, and earlier publications/patents, describing virtually all variants of soluble PH20 polypeptides are known in the art. A skilled person readily can prepare soluble hyaluronidases and variants thereof and know the properties of the resulting hyaluronidase.

Other variants also are known to those of skill in the art, and can be used in the combinations, regimens, and methods described herein. For example, see, International PCT Publication No. WO2020/022791 and WO2020197230A which are incorporated by reference, and which describe modified PH20 polypeptides. These polypeptides, which include variants of the PH20 polypeptides that generally span residues 38-468, and include replacements, insertions, and deletions. The variants include for example one or more amino acid residues changes S343E, I344N, M345T, M348K, K349E, L353A, L354I, N356E, and I361T (with reference to SEQ ID NO:1), and others, including about 15 amino acid variations, and truncations at the N-terminus and C-terminus. Variants that contain such modifications and others are set forth in SEQ ID NO: 60-115 of International PCT publication No. WO2020/022791. Exemplary of these polypeptides is the polypeptide of SEQ ID NO:99, therein. International PCT Publication No. WO2021/150079 provides variant PH20 polypeptides described as having increased stability relative to unmodified PH20, such as those in rHuPH20. These variant polypeptides have been shown to have PH20 activity and are described as having use for subcutaneous co-administration with other agents.

E. Methods of Administration, Regimens, and Combinations

1. Methods of Administration

In an embodiment, each of the hyaluronidase and antibody-drug conjugate can be administered to a patient via injection. In an embodiment the hyaluronidase and antibody-drug conjugate is administered subcutaneously. For example, the hyaluronidase and antibody-drug conjugate can be administered to a patient subcutaneously in the abdominal tissue, leg or arm. The hyaluronidase and antibody-drug conjugate can be administered separately or in the same composition.

The compositions for administration to a patient via an injection (e.g. subcutaneously) also may comprise suitable inert additives, stabilizers, carriers, or excipients. In an embodiment, the injectable composition comprises histidine. In an embodiment, the injectable composition comprises sodium chloride. In an embodiment, the injectable composition comprises polysorbate. In an embodiment, the polysorbate comprises polysorbate 80. In an embodiment, the injectable composition comprises an antioxidant. In an embodiment, the antioxidant comprises methionine.

It is shown and described herein that when an antibody-drug conjugate is administered in combination with the hyaluronidase, dispersion of the co-injected drugs or co-delivered is enhanced. By depolymerizing hyaluronan, hyaluronidase temporarily facilitates dispersion by reducing the viscosity of interstices. The permeability barrier in these tissues is restored to pre-injection levels within 24 to 48 hours after injection of hyaluronidase. This allows for higher volumes in a single injection of the antibody-drug conjugate to be administered to the patient.

When administered in separate compositions, the hyaluronidase and antibody-drug conjugate are injected as close to the same site as possible. For example, in an embodiment, hyaluronidase is first injected to a patient at a first injection site and subsequently the antibody-drug conjugate is injected at the same injection site or at an injection site as close to the first injection site as possible.

In an embodiment, the antibody-drug conjugate is administered at a concentration of about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg and 100 mg/kg. In an embodiment, the antibody-drug conjugate is administered a concentration of about 100 mg/kg.

2. Regimens

Provided are regimens for administration of an antibody-drug conjugate in combination with a soluble hyaluronidase. The antibody-drug conjugate generally is formulated as a solution for subcutaneous injection at effective concentrations, and the hyaluronidase is provided as a composition containing an effective concentration of soluble hyaluronidase for delivery of an effective amount of hyaluronidase in about 0.5 mL to 10 mL, such as 1 mL to 5 mL, or 1 mL to 3 mL. The antibody-drug conjugate and hyaluronidase can be administered separately or co-formulated for administration in a single composition. When administered separately, they can be administered in any order, but generally the hyaluronidase is administered first. The antibody-drug conjugate and/or hyaluronidase can be provided as separate compositions, such as suspension and solutions, or can be provided as a co-formulation.

As described herein, the hyaluronidase and antibody-drug conjugate can be administered together or sequentially or any other defined regimen. For example, in some embodiments, the hyaluronidase is administered to a patient before the antibody-drug conjugate is administered i.e. in a first step hyaluronidase is administered to a patient; and in a second step the antibody-drug conjugate is administered to a patient. In an embodiment an antibody-drug conjugate is administered to the patient as soon as possible after hyaluronidase has been administered to the patient i.e. immediately after hyaluronidase has been administered to the patient.

In accord with regimens and compositions provided herein, the hyaluronidase is administered in an amount suitable to allow a dose of from about 100 mg of an antibody-drug conjugate to be administered to the patient. Exemplary ranges include, but are not limited to, an amount suitable to allow a dose from 10 mg to 2000 mg be administered to the patient, or dose of at least 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, 1800 mg, 1900 mg or 2000 mg or more to be administered to a patient. In other embodiments, the hyaluronidase is administered in an amount suitable to allow a dose of at least or at about an 100 mg to be administered. It is understood that a skilled practitioner can determine a particular dose, which can depend upon various parameters include the mass of the patient, the age of the patient, and other conditions of the patient.

In an exemplary embodiment, an antibody-drug conjugate is administered at a dose of from 100 mg to 2000 mg, such as, but not limited to, a dose of from 900 mg to 2000 mg, such as for example, a dose of at least or at 10 mg to 1000 mg, such as for example, a dose of at least or at 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, 1800 mg, 1900 mg or 2000 mg. Exemplary thereof the antibody-drug conjugate is administered at a dose of 1000 mg to 2000 mg or in amounts in between such doses. For example, an antibody-drug conjugate is administered at a dose of about 1500 mg, or at a dose of about 1750 mg, or at a dose of about 1900 mg, or at a dose of about 1950 mg.

In an embodiment, the amount of the disclosed formulation administered to the subject is dependent on the subject being treated, the severity of the disorder or condition, the rate of administration, the disposition of the compounds, and/or the discretion of the prescribing physician. In an embodiment, an effective dosage of the antibody-drug conjugate in the disclosed formulation is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect, for example by dividing such larger doses into several small doses for administration throughout the day. Low dose administration of an antibody-drug conjugate in combination with hyaluronidase is possible due to decreased residence time at the site of administration.

In an embodiment, the disclosed formulation is administered to the subject in multiple doses. Dosing may be about once, twice, three times, four times, five times, six times, or more than six times per day. Dosing may be about once a month, once every three weeks (Q3W) every two weeks (Q2W), once a week (QW), or once every other day. In some embodiments, dosing may be once every five weeks (Q5W), once every six weeks (Q6W), once every seven weeks (Q7W), once every eight weeks (Q8W), once every nine weeks (Q9W), once every ten weeks (Q10W), once every eleven weeks (Q11W), once every twelve weeks (Q12W), once every thirteen weeks (Q13W), once every fourteen weeks (Q14W) or once every fifteen weeks (Q15W). In one embodiment, the disclosed formulation is administered about once per day to about 6 times per day. In one embodiment, the administration of the disclosed formulation continues for less than about 7 days. In yet another embodiment the administration continues for more than about 6, 10, 14, 28 days, two months, six months, or one year. In some cases, continuous dosing is achieved and maintained as long as necessary.

Hyaluronidases have been used clinically since the 1950s. For example, rHuPH20, approved by the FDA in 2004, has been shown to be well tolerated in clinical evaluation of [subcutaneous] doses of up to 96,000 U, wherein U is USP units. For example, for purposes herein, hyaluronidase is administered at a dose of from 2000 to 15,000 U, such as, but not limited to from 5,000 to 15,000 U, such as 6,000 to 12,000 U, 8,000 to 12,000 U, such as at or about a dose of about 10,000 U, for example 10,000 U. The hyaluronidase is administered in injection volumes that range from at or about 0.5 mL to 10 mL, such as 1 mL to 5 mL, or at or about1 mL to 3 mL, such as a 1 mL injection; the volume is a function of the specific activity of a particular formulation of the hyaluronidase. The particular amount depends upon parameters understood by those of skill in the art. Co-administration of an antibody-drug conjugate with hyaluronidase, as noted, allows for administration of a higher doses and larger volumes of the antibody-drug conjugate potentially affording a longer interval between injections. This can increase the convenience of long-acting regimens and can result in better adherence to therapy and positively impact treatment outcomes and acceptability.

As discussed above, the combination of an antibody-drug conjugate and hyaluronidase can allow less frequent dosing compared to administration of the antibody-drug conjugate alone, in dosing regimens that do not include a hyaluronidase. For example, in accord with the instant disclosure, hyaluronidase and antibody-drug conjugate are administered once every 3 months to once every year, such as once every 3 months, once every 4 months, once every 5 months or once every 6 months or other intervals that are longer than 3 months and less than 6 months, 9 months, or one year. In an exemplary regimen, hyaluronidase and antibody-drug conjugate are administered once every 3 months.

In an embodiment, combination dosing regimen is provided that comprises administering hyaluronidase; and an antibody-drug conjugate, wherein hyaluronidase is administered at a dose of from 4,000 to 15,000 U; and the antibody-drug conjugate is administered at a dose of from 10 to 100 mg/kg wherein the combination dosing regimen is administered once every 3 months to once every 6 months.

In another embodiment, provided is a combination dosing regimen comprising administering hyaluronidase; and administering an antibody-drug conjugate, wherein hyaluronidase is administered at a dose of from 6,000 to 12,000 U; and the antibody-drug conjugate is administered at a dose of from 10 to 100 mg/kg. Wherein the combination dosing regimen is administered once every 3 months to once every 6 months.

In another embodiment, provided a combination dosing regimen comprising administering hyaluronidase; and administering an antibody-drug conjugate, wherein hyaluronidase is administered at a dose of 10,000 U; and the antibody-drug conjugate is administered at a dose of from 10 mg/kg to 100 mg/kg. In this regime the antibody-drug conjugate has a concentration of 10 to 100 mg/kg, and the combination dosing regimen is administered once every 3 months.

The regimens provided herein are for treating or preventing cancer, comprising administering to a patient in need of treatment or prevention a combination dosing regimen described herein. Prevention, as described herein, includes reducing the risk of infection. Hence in embodiments herein, provide are methods of treating a cancer, the method comprising administering to a patient a combination dosing regimen described herein. In an alternative embodiment, provided is a method of preventing cancer, the method comprising administering to a human the combination dosing regimen described herein. In the first method, the patient has been diagnosed with cancer; in the latter, the subject has not been diagnosed with a cancer, but, generally is a subject at risk of exposure to an antibody-drug conjugate.

In a further aspect, the combination dosing regimens as described herein are for use in the treatment or prevention of cancer. In an embodiment, the combination dosing regimens described herein are for use in the treatment of cancer. In an alternative embodiment, the present invention provides the combination dosing regimen as described herein for use in the prevention of cancer.

In an embodiment, cancers for treatment or prevention as described herein include but are not limited to, anaplastic large cell lymphoma (ALCL), peripheral T-cell lymphoma (PTCL), adult T-cell leukemia/lymphoma, cutaneous T-cell lymphoma (CTCL), extra-nodal NK-T-cell lymphoma, non-Hodgkin's lymphoma, diffuse large B-cell lymphoma, particularly EBV-positive diffuse large B-cell lymphoma, B cell acute lymphoblastic leukemia, breast cancer, lung cancer, gastric cancer, ovarian cancer, colon cancer, gastric cancer, endometrial cancer, cervical cancer, colorectal cancer, esophageal cancer, squamous cell carcinoma, pancreatic cancer, prostate cancer, stomach cancer, thyroid cancer, glioma, melanoma, urinary bladder cancer, urogenital cancer and uterine cancer.

3. Combinations, Compositions and Kits

Provided herein are compositions, combinations, and kits. The combinations comprise a composition containing the hyaluronidase; and a composition that is suspension comprising an antibody-drug conjugate. The compositions comprising the antibody-drug conjugate are formulated as a suspension in amounts for administering a dose of the antibody-drug conjugate, such as in an amount that is 10 mg to 2000 mg, such as such as, but not limited to, a dose of from 10 mg to 1000 mg, such as for example, a dose of at least or at 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, 1800 mg, 1900 mg or 2000 mg as detailed above. Each of the compositions can be formulated for single dosage or multiple dosage administration or for dilution as appropriate.

The hyaluronidase is formulated for administration of a dose from 2000 to 15,000 U, such as, but not limited to from 5,000 to 15,000 U, such as 6,000 to 12,000 U, 8,000 to 12,000 U, such as at or about a dose of about 10,000 U, for example 10,000 U. Compositions containing hyaluronidase for administration are well known, and generally are formulated at a pH of about 7 to about 7.4, in appropriate buffers, salts, stabilizers and surfactant as needed. See e.g. U.S. Pat. No. 7,767,429. Variants, as described herein, that are more stable in denaturing conditions, such as those described in U.S. Pat. No. 9,447,401 and family members and variants designed for increased activity and/or stability can be formulated. The hyaluronidase and antibody-drug conjugate can be co-formulated as suspensions or mixed prior to use for administration in a single composition. The compositions containing both are formulated to deliver an appropriate dose of each.

The combinations can contain the two compositions or the single co-formulations, and optionally instructions for use. The combinations can be packaged as kits. Exemplary combinations and kits can include a syringe or other container containing the hyaluronidase, and a syringe or other container containing the antibody-drug conjugate. Alternatively, the antibody-drug conjugate and hyaluronidase can be provided in a dual compartment container, such as a dual compartment where the compositions are separated, such as by a membrane that can be punctured prior to administration. In these aspects, the hyaluronidase and antibody-drug conjugate are as described herein.

The syringe or other container may be sized and shaped to hold a volume of the hyaluronidase corresponding to a volume selected from:
(a) 3 mL to 5 mL, 3 mL to 10 mL, 3 mL to 15 mL, 3 mL to 20 mL, 3 mL to 25 mL, 3 ml to 30 mL, 3 mL to 35 mL, 3 mL to 40 mL, 3 mL to 45 mL, 3 mL to 50 mL, 5 mL to 10 mL, 5 mL to 15 mL, 5 mL to 20 mL, 5 mL to 25 mL, 5 mL to 30 mL, 5 mL to 35 mL, 5 mL to 40 mL; 5 mL to 45 mL, 5 mL to 50 mL, 10 mL to 15 mL; 10 mL to 20 mL; 10 mL to 25 mL; 10 mL to 30 mL; 10 mL to 35 mL; 10 mL to 40 mL, 10 mL to 50 mL;
(b) about 3 mL to about 5 mL, about 3 mL to about 10 mL, about 3 mL to about 15 mL, about 3 mL to about 20 mL, about 3 mL to about 25 mL, about 3 ml to about 30 mL, about 3 mL to about 35 mL, about 3 mL to about 40 mL, about 3 mL to about 45 mL, about 3 mL to about 50 mL, about 5 mL to about 10 mL, about 5 mL to about 15 mL, about 5 mL to about 20 mL, about 5 mL to about 25 mL, about 5 mL to about 30 mL, about 5 mL to about 35 mL, about 5 mL to about 40 mL; about 5 mL to about 45 mL, about 5 mL to about 50 mL, about 10 mL to about 15 mL; about 10 mL to about 20 mL; about 10 mL to about 25 mL; about 10 mL to about 30 mL; about 10 mL to about 35 mL; about 10 mL to about 40 mL, about 10 mL to about 50 mL;
(c) at least about 3 mL, at least about 3.5 mL, at least about 4 mL, at least about 4.5 mL, at least about 5.5 mL, at least about 6 mL, at least about 6.5 mL, at least about 7 mL, at least about 7.5 mL, at least about 8 mL, at least about 8.5 mL, at least about 9 mL, at least about 9.5 mL, at least about 10 mL, at least about 10.5 mL, at least about 11 mL, at least about 11.5 mL, at least about 12 mL, at least about 12.5 mL, at least about 13 mL, at least about 13.5 mL, at least about 14 mL, at least about 14.5 mL, at least about 15 mL, at least about 15.5 mL, at least about 16 mL, at least about 16.5 mL, at least about 17 mL, at least about 17.5 mL, at least about 18 mL, at least about 18.5 mL, at least about 19 mL, at least about 19.5 mL, at least about 20 mL, at least about 25 mL, at least about 30 mL, at least about 35 mL, at least about 40 mL, at least about 45 mL, at least about 50 mL; and
(d) at least 3 mL, at least 3.5 mL, at least 4 mL, at least 4.5 mL, at least 5.5 mL, at least 6 mL, at least 6.5 mL, at least 7 mL, at least 7.5 mL, at least 8 mL, at least 8.5 mL, at least 9 mL, at least 9.5 mL, at least 10 mL, at least 10.5 mL, at least 11 mL, at least 11.5 mL, at least 12 mL, at least 12.5 mL, at least 13 mL, at least 13.5 mL, at least 14 mL, at least 14.5 mL, at least 15 mL, at least 15.5 mL, at least 16 mL, at least 16.5 mL, at least 17 mL, at least 17.5 mL, at least 18 mL, at least 18.5 mL, at least 19 mL, at least 19.5 mL, at least 20 mL, at least 25 mL, at least 30 mL, at least 35 mL, at least 40 mL, at least 45 mL, at least 50 mL.

The hyaluronidase may be delivered at a rate of approximately 0.08-0.75 mL/sec. For example, this would provide target delivery time ranges of 13-120 seconds for a 10 mL dose volume. 10 mL of the hyaluronidase may be delivered at a rate of 0.33 mL/sec. In one embodiment, the hyaluronidase is delivered at a rate of.
(a) 0.5 mL/10 sec., 0.75 mL/10 sec., 1 mL/10 sec., 1.25 mL/10 sec., 1.5 mL/10 sec., 1.75 mL/10 sec, 2 mL/10 sec., 2.25 mL/10 sec, 2.5 mL/10 sec., 2.75 mL/10 sec, 3 mL/10 sec., 3.25 mL/10 sec, 3.5 mL/10 sec., 3.75 mL/10 sec, 4 mL/10 sec., 4.25 mL/10 sec., 4.5 mL/10 sec., 4.75 mL/10 sec, 5 mL/10 sec;
(b) 2 mL/30 sec., 2.5 mL/30 sec., 3 mL/30 sec., 3.5 mL/30 sec., 4 mL/30 sec., 4.5 mL/30 sec., 5 mL/30 sec., 5.5 mL/30 sec., 6 mL/30 sec., 6.5 mL/30 sec., 7 mL/30 sec., 7.5 mL/30 sec., 8 mL/30 sec., 8.5 mL/30 sec., 9 mL/30 sec., 9.5 mL/30 sec., 10 mL/30 sec., 10.5 mL/30 sec.; and (c) 4 mL/min, 5 mL/min, 6 mL/min, 7 mL/min, 8 mL/min, 9 mL/min, 10 mL/min, 11 mL/min, 12 mL/min, 13 mL/min, 14 mL/min, 15 mL/min, 16 mL/min, 17 mL/min, 18 mL/min, 19 mL/min, 20 mL/min, 21 mL/min.

The hyaluronidase may be delivered at a delivery time of approximately of 13-120 seconds. In one embodiment, the hyaluronidase is delivered at a delivery time of.

(a) about 10 seconds, about 12 seconds, about 16 seconds, about 18 seconds, about 20 seconds, about 22 seconds, about 24 seconds, about 26 seconds, about 28 seconds, about 30 seconds, about 32 seconds, about 34 seconds, about 36 seconds, about 38 seconds, about 40 seconds, about 42 seconds, about 44 seconds, about 46 seconds, about 48 seconds, about 50 seconds, about 52 seconds, about 54 seconds, about 56 seconds, about 58 seconds, about 60 seconds, about 65 seconds, about 70 seconds, about 75 seconds, about 80 seconds, about 85 seconds, about 90 seconds, about 95 seconds, about 100 seconds, about 105 seconds, about 110 seconds, about 115 seconds, or about 120 seconds.

(b) about 10 seconds to about 120 seconds, about 12 seconds to about 115 seconds, about 16 seconds to about 110 seconds, about 18 seconds to about 105 seconds, about 20 seconds to about 100 seconds, about 22 seconds to about 95 seconds, about 24 seconds to about 90 seconds, about 26 seconds to about 85 seconds, about 28 seconds to about 80 seconds, about 30 seconds to about 75 seconds, about 32 seconds to about 70 seconds, about 34 seconds to about 65 seconds, about 36 seconds to about 60 seconds, about 38 seconds to about 58 seconds, about 40 seconds to about 56 seconds, about 42 seconds to about 54 seconds, about 44 seconds to about 52 seconds or about 46 seconds to about 50 seconds.

In an embodiment, the compositions and combinations described herein can comprise one or more of inactive ingredients, including but not limited to, a divalent cation, a buffer, a pH adjusting agent, an anti-oxidation agent, a tonicity modifier, a surfactant, and other inactive ingredients/agents described below. Provided below is a description of the inactive ingredients that can be included in the hyaluronidase compositions and combinations described herein. The inactive ingredients are exemplary only and provide a platform from which minor adjustments can be made. It is understood that very small changes in the concentrations of the various excipients and other components (e.g. +15% of the stated concentrations), or small changes in pH, can be made while retaining some if not all of the hyaluronan degrading enzyme stability. Further changes also can be made by adding or removing excipients. For example, the type of stabilizing surfactant can be changed.

Divalent Cation

In some embodiments, the hyaluronidase compositions and combinations provided herein comprise an amount of a divalent cation to achieve at least 50%, and generally at least 70%, of the initial enzymatic activity of the hyaluronidase at temperatures of between or approximately between 37° C. to 42° C., such as at least or about or approximately 37° C. or 40° C., for at least three (3) days and generally at least one month (e.g. 4 weeks) as described herein. For example, the amount of divalent cation is an amount to achieve at least 75%, 80%, 85%, 86%, 87%, 88%, 89%, 90%, 91%, 92%, 93%, 94%, 95%, 96%, 97%, 98%, 99% or more of the initial enzymatic activity of the hyaluronidase for at least three (3) days, and generally for at least 4 weeks at temperatures between or approximately between 37° C. to 42° C., such as at least or about or approximately 40° C.

For example, hyaluronidase compositions and combinations provided herein can contain an amount of Lys-Lys, salt, derivative, analogue or mimetic thereof, to achieve at least 50%, and generally at least 70%, of the initial enzymatic activity of the hyaluronan-degrading enzyme at temperatures between or approximately between 37° C. to 42° C., such as at least or about or approximately 40° C., for at least three (3) days and generally for at least 4 weeks. Such a hyaluronidase composition or combination provided herein may contain between or about between 5 mM to 300 mM Lys-Lys, such as 10 mM to 200 mM, 50 mM to 150 mM or 10 mM to 50 mM. For example, a hyaluronidase composition or combination provided herein may contain at least or about at least or 5 mM, 10 mM, 20 mM, 30 mM, 40 mM, 50 mM, 60 mM, 70 mM, 80 mM, 90 mM, 100 mM, 125 mM, 150 mM, 200 mM, 300 mM or more Lys-Lys.

In another example, the hyaluronidase compositions or combinations provided herein can contain an amount of $MgCl_2$, a derivative, an analogue or a mimetic thereof, to achieve at least 50%, and generally at least 70%, of the initial enzymatic activity of the hyaluronidase at temperatures between or approximately between 37° C. to 42° C., such as at least or about or approximately 40° C., for at least three (3) days and generally for at least 4 weeks. The hyaluronidase compositions and combinations provided herein may contain between or about between 5 mM to 300 mM $MgCl_2$, such as 10 mM to 200 mM, 50 mM to 150 mM or 10 mM to 50 mM. For example, the hyaluronidase compositions and combinations provided herein may contain at least or about at least or 5 mM, 10 mM, 20 mM, 30 mM, 40 mM, 50 mM, 60 mM, 70 mM, 80 mM, 90 mM, 100 mM, 125 mM, 150 mM, 200 mM, 300 mM or more $MgCl_2$.

As discussed below, formulations containing a divalent cation (e.g. Lys-Lys), if necessary, also can contain a tonicity modifier (e.g. NaCl).

If necessary, the pH of the hyaluronidase compositions and combinations described herein can be adjusted using acidifying agents to lower the pH or alkalizing agents to increase the pH. Exemplary acidifying agents include, but are not limited to, acetic acid, citric acid, sulfuric acid, hydrochloric acid, monobasic sodium phosphate solution, and phosphoric acid. Exemplary alkalizing agents include, but are not limited to, dibasic sodium phosphate solution, sodium carbonate, or sodium hydroxide.

Any buffer can be used in the compositions and combinations provided herein so long as it does not adversely affect the stability of the composition/combination and supports the requisite pH range required. Examples of particularly suitable buffers include Tris, succinate, acetate, phosphate buffers, histidine, citrate, aconitate, malate and carbonate. Those of skill in the art, however, will recognize that the compositions and combinations provided herein are not limited to a particular buffer, so long as the buffer provides an acceptable degree of pH stability, or "buffer capacity" in the range indicated. Generally, a buffer has an adequate buffer capacity within about 1 pH unit of its pK. Buffer suitability can be estimated based on published pK tabulations or can be determined empirically by methods well known in the art. The pH of the solution can be adjusted to the desired endpoint within the range as described above, for example, using any acceptable acid or base.

Buffers that can be included in the compositions and combinations provided herein include, but are not limited to, Tris (Tromethamine), histidine, phosphate buffers, such as dibasic sodium phosphate, and citrate buffers. For example, the buffer can be a histidine hydrochloride (histidine/HCl) buffer. Generally, the buffering agent is present in an amount herein to maintain the pH range of the composition or combination between or about between 6.5 to 7.8, for example between or about between 6.8 to 7.8 such as between or about between 7.0 to 7.6. Such buffering agents can be present in the compositions and combinations at concentrations between or about between 1 mM to 100 mM, such as 10 mM to 50 mM or 20 mM to 40 mM, such as at or about 30 mM. For example, such buffering agents can be present in the compositions and combinations in a concentration of or about or at least 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, or more.

In some examples, a buffering agent is not required. In an embodiment, the hyaluronidase compositions and combinations described herein comprise a surfactant. The surfactants generally are non-ionic surfactants. Surfactants that can be included in the compositions and combinations herein include, but are not limited to, partial and fatty acid esters and ethers of polyhydric alcohols such as of glycerol, or sorbitol, poloxamers and polysorbates. For example, exemplary surfactants in the compositions and combinations herein include any one or more of poloxamer 188 (PLURONICS® such as PLURONIC® F68), TETRON-ICS®, polysorbate 20, polysorbate 80, PEG 400, PEG 3000, Tween® (e.g. Tween® 20 or Tween® 80), Triton® X-100, SPAN®, MYRJ®, BRIJ®, CREMOPHOR®, polypropylene glycols or polyethylene glycols. In some examples, the compositions and combinations herein contain poloxamer 188, polysorbate 20, polysorbate 80, generally poloxamer 188 (pluronic F68).

In the compositions and combinations provided herein, the total amount of the one or more surfactants as a percentage (%) of mass concentration (w/v) in the compositions and combinations herein can be, for example, between from or between about from 0.0% to 1.0%, such as between or about between 0.0% to 0.0005%, 0.0005% to 0.005%, 0.001% to 0.01%, 0.01% to 0.5%, 0.01% to 0.1% or 0.01% to 0.02%. For example, the compositions and combinations provided herein can contain at or about 0.001%, 0.005%, 0.01%, 0.015%, 0.02%, 0.025%, 0.03%, 0.035%, 0.04%, 0.045%, 0.05%, 0.055%, 0.06%, 0.065%, 0.07%, 0.08%, or 0.09% surfactant.

Anti-Oxidation Agent

The compositions and combinations provided herein also can contain antioxidants to reduce or prevent oxidation, in particular oxidation of the hyaluronidase. Exemplary antioxidants include, but are not limited to, cysteine, tryptophan and methionine. In particular examples, the anti-oxidant is methionine. The compositions and combinations provided herein can include an antioxidant at a concentration from between or from about between 5 mM to or to about 50 mM, such as 5 mM to 40 mM, 5 mM to 20 mM or 10 mM to 20 mM. For example, methionine can be provided in the compositions and combinations herein at a concentration from between or from about between 5 mM to or to about 50 mM, such as 5 mM to 40 mM, 5 mM to 20 mM or 10 mM to 20 mM. For example, an antioxidant, for example methionine, can be included at a concentration that is or is about or is at least 5 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 35 mM, 40 mM, 45 mM or 50 mM. In some examples, compositions and combinations described herein contain 10 mM to 20 mM methionine, such as or about or at least 10 mM or 20 mM methionine.

Tonicity Modifier

Optionally, the stable hyaluronidase compositions and combinations provided herein can contain a tonicity modifier.

For example, in some embodiments, a tonicity modifier is included in the compositions and combinations herein to produce a solution with the desired osmolality. The compositions and combinations provided herein have an osmolality of between or about between 245 mOsm/kg to 500 mOsm/kg. For example, the osmolality is or is about or at least 245 mOsm/kg, 250 mOsm/kg, 255 mOsm/kg, 260 mOsm/kg, 265 mOsm/kg, 270 mOsm/kg, 275 mOsm/kg, 280 mOsm/kg, 285 mOsm/kg, 290 mOsm/kg, 295 mOsm/kg, 300 mOsm/kg, 350 mOsm/kg, 400 mOsm/kg, 450 mOsm/kg or 500 mOsm/kg. Typically, a tonicity modified is included in the compositions and combinations herein that contain a divalent cation, such as Lys-Lys, in a concentration that is less than 100 mM, such as less than 80 mM, 70 mM, 60 mM, 50 mM, 40 mM, 30 mM, 20 mM, 10 mM or less. For example, a tonicity modified is included in the compositions and combinations herein that contain a divalent cation, such as Lys-Lys, at a concentration of between or about between 10 mM to 50 mM, such as about or approximately 10 mM, 15 mM, 20 mM, 25 mM, 30 mM, 35 mM, 40 mM, 45 mM or 50 mM.

Tonicity modifiers include, but are not limited to, glycerin, NaCl, amino acids, polyalcohols, trehalose, and other salts and/or sugars. For example, the compositions and combinations provided herein can optionally include NaCl as a tonicity modifier. The NaCl can be included at a concentration of between or about between 0 mM to 200 mM, such as generally 30 mM to 100 mM, 50 mM to 160 mM, for example 50 mM to 120 mM or 80 mM to 140 mM. Generally, the NaCl is less than 150 mM, and generally less than 140 mM, 130 mM, 120 mM, 110 mM, 100 mM, 90 mM, 80 mM, 70 mM, 60 mM, 50 mM, 40 mM, 30 mM, 20 mM, 10 mM or less. The particular amount can be empirically determined in order to retain enzyme activity and/or tonicity.

In another example, glycerin (glycerol) is optionally included in the compositions and combinations described herein. For example, the compositions and combinations provided herein typically contain less than 60 mM glycerin, such as less than 55 mM, less than 50 mM, less than 45 mM, less than 40 mM, less than 35 mM, less than 30 mM, less than 25 mM, less than 20 mM, less than 15 mM, 10 mM or less.

Other Agents or Excipients

The stable compositions and combinations provided herein can optionally contain one or more other agents, carriers, excipients or preservatives. For example, exemplary stabilizers that optionally can be included in the hyaluronidase compositions and combinations provided herein include, but are not limited to, amino acids, amino acid derivatives, amines, sugars, polyols, salts and buffers, surfactants, and other agents. For example, included among the types of stabilizers that optionally can be contained in the formulations herein is an amino acid stabilizer or a hyaluronidase inhibitor (e.g. a hyaluronidase substrate, such as hyaluronan). Exemplary amino acid stabilizers, amino acid derivatives or amines include, but are not limited to, L-Arginine, Glutamine, glycine, Lysine, Methionine, Proline, Lys-Lys, Gly-Gly, Trimethylamine oxide (TMAO) or betaine. Exemplary of sugars and polyols include, but are not limited to, glycerol, sorbitol, mannitol, inositol, sucrose or trehalose. Exemplary of salts and buffers include, but are not limited to, magnesium chloride, sodium sulfate, Tris such as Tris (100 mM), or sodium Benzoate. Exemplary surfactants include, but are not limited to, poloxamer 188 (e.g. Pluronic® F68), polysorbate 80 (PS80), polysorbate 20 (PS20). Other stabilizers include, but are not limited to, hyaluronic acid (HA), human serum albumin (HSA), phenyl butyric acid, taurocholic acid, polyvinylpyrolidone (PVP) or zinc.

In an embodiment, the hyaluronidase compositions and combinations also can optionally contain an amount of preservative(s) that, when combined with the components set forth above, result in a stable composition or combination. When included, the preservatives are present in a sufficient concentration to provide the anti-microbial requirements of, for example, the United States Pharmacopoeia (USP) and the European Pharmacopoeia (EP). Typically, formulations that meet EP (EPA or EPB) anti-microbial requirements contain more preservative than those formulated only to meet USP anti-microbial requirements. Generally, when included, the compositions and combinations provided herein contain preservative(s) in an amount that exhibits anti-microbial activity by killing or inhibiting the propagation of microbial organisms in a sample of the composition as assessed in an antimicrobial preservative effectiveness test (APET). Non-limiting examples of preservatives that can be included in the compositions and combinations provided herein include, but are not limited to, phenol, meta-cresol (m-cresol), methylparaben, benzyl alcohol, thimerosal, benzalkonium chloride, 4-chloro-1-butanol, chlorhexidine dihydrochloride, chlorhexidine digluconate, L-phenylalanine, EDTA, bronopol (2-bromo-2-nitropropane-1,3-diol), phenylmercuric acetate, glycerol (glycerin), imidurea, chlorhexidine, sodium dehydroacetate, orthocresol (o-cresol), para-cresol (p-cresol), chlorocresol, cetrimide, benzethonium chloride, ethylparaben, propylparaben or butylparaben and any combination thereof. In one example, the compositions and combinations contain at least one phenolic preservative. For example, the composition or combination contains phenol, m-cresol or phenol and m-cresol. When included in the compositions and combinations provided herein, the total amount of the one or more preservative agents as a percentage (%) of mass concentration (w/v) in the composition and combination can be, for example, between from or between about from 0.1% to 0.4%, such as 0.1% to 0.3%, 0.15% to 0.325%, 0.15% to 0.25%, 0.1% to 0.2%, 0.2% to 0.3%, or 0.3% to 0.4%, and generally less than 0.4% (w/v) preservative, for example, at least or about at least 0.1%, 0.12%, 0.125%, 0.13%, 0.14%, 0.15%, 0.16%, 0.17%, 0.175%, 0.18%, 0.19%, 0.2%, 0.25%, 0.3%, 0.325%, 0.35% but less than 0.4% total preservative.

Optionally, the compositions and combinations can include carriers such as a diluent, adjuvant, excipient, or vehicle with which the formulation is administered. Examples of suitable pharmaceutical carriers are described in "Remington's Pharmaceutical Sciences" by E. W. Martin. Such compositions will contain a therapeutically effective amount of the compound, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions.

For example, pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidone, celluloses and derivatives thereof, povidone, crospovidones and other such binders known to those of skill in the art.

For example, an excipient protein can be added to the composition or combination that can be any of a number of pharmaceutically acceptable proteins or peptides. Generally, the excipient protein is selected for its ability to be administered to a mammalian subject without provoking an immune response. For example, human serum albumin is generally well-suited for use in pharmaceutical formulations. Other known pharmaceutical protein excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The excipient is included in the composition or combination at a sufficient concentration to prevent adsorption of the protein to the holding vessel or vial. The concentration of the excipient will vary according to the nature of the excipient and the concentration of the protein in the composition or combination.

A composition or combination, if desired, also can contain minor amounts of wetting or emulsifying agents, or pH buffering agents, for example, acetate, sodium citrate, cyclodextrin derivatives, sorbitan monolaurate, triethanolamine sodium acetate, triethanolamine oleate, and other such agents.

In an embodiment, the injectable combination comprises a hyaluronidase and Gemtuzumab ozogamicin. For example, Gemtuzumab ozogamicin is mixed with an inert additive, carrier, or excipient selected from dextran (e.g.

dextran 40), sodium chloride, sodium phosphate dibasic anhydrous, sodium phosphate monobasic monohydrate, and sucrose. For example, Gemtuzumab ozogamicin is mixed with each dextran (e.g. dextran 40), sodium chloride, sodium phosphate dibasic anhydrous, sodium phosphate monobasic monohydrate, and sucrose. In an embodiment, the injectable combination comprises a hyaluronidase and Brentuximab vedotin. For Example, Brentuximab vedotin is mixed with an inert additive, carrier, or excipient selected from trehalose dihydrate, sodium citrate dihydrate, citric acid monohydrate, and polysorbate (e;g., polysorbate 80). For example, Brentuximab vedotin is mixed with each of trehalose dihydrate, sodium citrate dihydrate, citric acid monohydrate, and polysorbate (e;g., polysorbate 80). In an embodiment, the injectable combination comprises a hyaluronidase and Ado-Trastuzumab emtansine. For example, Ado-Trastuzumab emtansine is mixed with an inert additive, carrier, or excipient selected from polysorbate (e.g. polysorbate 20), sodium succinate, and sucrose. For example, Ado-Trastuzumab emtansine is mixed with each of polysorbate (e.g. polysorbate 20), sodium succinate, and sucrose. In an embodiment, the injectable combination comprises a hyaluronidase and Inotuzumab ozogamicin. For example, Inotuzumab ozogamicin emtansine is mixed with an inert additive, carrier, or excipient selected from polysorbate (e.g. polysorbate 80), sodium chloride, sucrose, and tromethamine. For example, Inotuzumab ozogamicin emtansine is mixed with each of polysorbate (e.g. polysorbate 80), sodium chloride, sucrose, and tromethamine. In an embodiment, the injectable combination comprises a hyaluronidase and Polatuzumab vedotin. For example, Polatuzumab vedotin is mixed with an inert additive, carrier, or excipient selected from polysorbate (e.g. polysorbate 20), sodium hydroxide, succinic acid, and sucrose. For example, Polatuzumab vedotin is mixed with each of polysorbate (e.g. polysorbate 20), sodium hydroxide, succinic acid, and sucrose. In an embodiment, the injectable combination comprises a hyaluronidase and Enfortumab vedotin. For example, Enfortumab vedotin is mixed with an inert additive, carrier, or excipient selected from histidine, histidine hydrochloride monohydrate, polysorbate (e.g. polysorbate 20), and trehalose dihydrate. For example, Enfortumab vedotin is mixed with each of histidine, histidine hydrochloride monohydrate, polysorbate (e.g. polysorbate 20), and trehalose dihydrate. In an embodiment, the injectable combination comprises a hyaluronidase and Fam-Trastuzumab deruxtecan. For example, Fam-Trastuzumab deruxtecan is mixed with an inert additive, carrier, or excipient selected from histidine (e.g. L-histidine), histidine hydrochloride monohydrate (e.g. L-histidine hydrochloride monohydrate), polysorbate (e.g. polysorbate 80), and sucrose. For example, Fam-Trastuzumab deruxtecan is mixed with each of histidine (e.g. L-histidine), histidine hydrochloride monohydrate (e.g. L-histidine hydrochloride monohydrate), polysorbate (e.g. polysorbate 80), and sucrose. In an embodiment, the injectable combination comprises a hyaluronidase and Sacituzumab govitecan. For example, Sacituzumab govitecan is mixed with an inert additive, carrier, or excipient selected from 2-(N-morpholino)ethane sulfonic acid (MES), polysorbate (e.g. polysorbate 80), trehalose dihydrate, and sodium chloride. In an embodiment, Sacituzumab govitecan is mixed with each of 2-(N-morpholino)ethane sulfonic acid (MES), polysorbate (e.g. polysorbate 80), trehalose dihydrate, and sodium chloride. In an embodiment, the injectable combination comprises a hyaluronidase and Loncastuximab Tesirine. For example, Loncastuximab Tesirine is mixed with an inert additive, carrier, or excipient selected from histidine (e.g.

L-histidine), histidine monohydrochloride (e.g. L-histidine monohydrochloride), polysorbate (e.g. polysorbate 20), and sucrose. For example, Loncastuximab Tesirine is mixed with each of histidine (e.g. L-histidine), histidine monohydrochloride (e.g. L-histidine monohydrochloride), polysorbate (e.g. polysorbate 20), and sucrose. In an embodiment, the injectable combination comprises a hyaluronidase and Tisotumab vedotin. For example, Tisotumab vedotin is mixed with an inert additive, carrier, or excipient selected from mannitol (e.g. d-mannitol), histidine (e.g. L-histidine), histidine monohydrochloride (e.g. L-histidine monohydrochloride), and sucrose. For example, Tisotumab vedotin is mixed with an each of mannitol (e.g. d-mannitol), histidine (e.g. L-histidine), histidine monohydrochloride (e.g. L-histidine monohydrochloride), and sucrose. In an embodiment, the injectable combination comprises a hyaluronidase and Mirvetuximab soravtansine-gynx. For example, Mirvetuximab soravtansine-gynx is mixed with an inert additive, carrier, or excipient selected from acetic acid (e.g. glacial acetic acid), polysorbate (e.g. polysorbate 20), sodium acetate, and sucrose. For example, Mirvetuximab soravtansine-gynx is mixed with each of acetic acid (e.g. glacial acetic acid), polysorbate (e.g. polysorbate 20), sodium acetate, and sucrose.

3. Methods of Administration

In an embodiment, each of the hyaluronidase and antibody-drug conjugate can be administered to a patient via injection. In an embodiment the hyaluronidase and antibody-drug conjugate are administered subcutaneously. For example, the hyaluronidase and antibody-drug conjugate can be administered to a patient subcutaneously in the abdominal tissue. The hyaluronidase and antibody-drug conjugate can be administered separately or in the same composition.

In an embodiment, the hyaluronidase and antibody-drug conjugate are administered topically by mucosal delivery. In an embodiment, the mucosal delivery is selected from the group consisting of buccal delivery, pulmonary delivery, ocular delivery, nasal delivery, intranasal delivery, vaginal delivery, and oral delivery. In an embodiment, the hyaluronidase is administered directly to a mucosal tissue of the human subject, including at the affected site. In an embodiment, the mucosal tissue is selected from the group consisting of anterior nostril, nasal sinus, vaginal, esophagus, urethral, sublingual and buccal.

In an embodiment, various delivery systems are known and can be used to administer the hyaluronidase in combination with an antibody-drug conjugate. For example, the hyaluronidase can be encapsulated in liposomes, microparticles, microcapsules for topical delivery. In addition, pulmonary administration can also be used, such as inhalers or nebulizers, and aerosol formulations.

If the hyaluronidase and antibody-drug conjugate comprise pulmonary or intranasal administration, the composition can be formulated in the form of an aerosol, spray, mist or drip. In particular, the hyaluronidase and antibody-drug conjugate can be provided by the use of suitable propellants (such as dichlorodifluoromethane, trichlorofluoromethane, dichlorotetrafluoroethane, carbon dioxide, or other suitable gases). Aerosol sprays are delivered from pressurized packaging or sprayers. In the case of pressurized aerosols, the dosage unit can be determined by providing a valve that can deliver a metered amount. Capsules and cartridges (made of, for example, gelatin) containing powder mixtures of compounds and suitable powder bases such as lactose or starch can be formulated and used in inhalers.

If the hyaluronidase and antibody-drug conjugate is administered topically, including directly to the affected site, the compositions can be in the form of ointment, cream, transdermal patch, lotion, gel, shampoo, spray, aerosol, solution, emulsion. With regard to non-sprayable topical dosage forms, it is generally employed to include a carrier or one or more excipients compatible with topical application, and the dynamic viscosity is preferably greater than the viscosity of water to a semi-solid or solid form. Suitable formulations include (but are not limited to) solutions, suspensions, emulsions, creams, ointments, powders, wipes, ointments, which are sterilized or used to affect various properties such as osmotic pressure, if necessary, adjuvants (such as preservatives, stabilizers, wetting agents, buffers or salts) are present in the composition.

Other suitable topical dosage forms include sprayable aerosol formulations, where the active ingredient, optionally combined with a solid or liquid inert carrier, is mixed and encapsulated with a pressurized volatile substance (such as a gaseous propellant such as freon) or encapsulated in a squeeze bottle. If necessary, a moisturizing agent or humectant may also be added to the composition.

In an embodiment, it may be necessary to locally administer the hyaluronidase to the affected site in need of treatment; this may be achieved by, for example, but not limited to, topical administration, local infusion, injection, or by means of an implant. The implant may be a porous or non-porous material, including membranes and matrices, such as silicone membranes, polymers, fibrous matrices or collagen matrices.

In an embodiment, the invention provides a composition for transdermal delivery containing the hyaluronidase, antibody-drug conjugate and a pharmaceutical excipient suitable for transdermal delivery. Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The transdermal compositions also may comprise suitable solid or gel phase carriers or excipients, which are compounds that allow increased penetration of, or assist in the delivery of, the hyaluronidase and antibody-drug conjugate across the stratum corneum permeability barrier of the skin. There are many of these penetration-enhancing molecules known to those skilled in the field of topical formulation. Examples of such carriers and excipients include, but are not limited to, humectants (e.g. urea), glycols (e.g. ethylene glycol, propylene glycol), alcohols (e.g. methanol, ethanol, propanol, including isopropanol and n-propanol; butanol, including n-butanol, isobutanol, tert-butanol, and sec-butanol; pentanol, including 1-pentanol, 2-pentanol, 3-pentanol, 2-methyl-1-butanol, 3-methyl-1-butanol, 2-methyl-2-butanol, 2-methyl-3-butanol, and 2,2-dimethylpropanol; and hexanol, including hexan-1-ol, hexan-2-ol, hexan-3-ol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2,3-dimethylbutan-1-ol, 3,3-dimethylbutan-1-ol, 2,3-dimethylbutan-2-ol, 3,3-dimethylbutan-2-ol, and 2-ethylbutan-1-ol), fatty acids (e.g.

oleic acid, α-linolenic acid, linoleic acid, γ-linolenic acid, palmitoleic acid), surfactants (e.g. isopropyl myristate and sodium lauryl sulfate), pyrrolidones (e.g. N-methyl-2-pyrrolidone, 2-pyrrolidone), glycerol monolaurate, sulfoxides (e.g. dimethyl sulfoxide, decylmethylsulfoxide), terpenes (e.g. menthol, 1,8-cineole, limonene, menthone, nerolidol), amines, amides, alkanes, alkanols, water, calcium carbonate, calcium phosphate, various sugars, starches, cellulose derivatives, gelatin, and polymers such as polyethylene glycols and polypropylene glycols.

Another exemplary formulation for delivery hyaluronidase and antibody-drug conjugate employs transdermal delivery devices ("patches"). Such transdermal patches may be used to provide continuous or discontinuous infusion of the hyaluronidase in controlled amounts, either with or without another active pharmaceutical ingredient. The construction and use of transdermal patches for the delivery of pharmaceutical agents is known. See, e.g. U.S. Pat. Nos. 5,023,252; 4,992,445 and 5,001,139 incorporated by reference herein. Such patches may be constructed for continuous, pulsatile, or on demand delivery of hyaluronidase and antibody-drug conjugate.

A diverse range of delivery methods may be utilized to cater to a wide range of medical needs. These methods offer patients and healthcare providers options based on the nature of the medication, dosage requirements, and the specific condition being treated. In some embodiments, an injector, or other handheld devices for injections that allow patients to self-administer preset doses, is used to administer the hyaluronidase and antibody-drug conjugate to the affected site. In some embodiments, the autoinjector is a prefilled syringe, a high volume autoinjector or a large volume autoinjector. The injector may be button actuated or needle guard actuated and may be configured to deliver a single dose or a plurality of doses.

A wearable administration apparatus may be utilized to administer the hyaluronidase and antibody-drug conjugate to the affected site in cases that require prolonged delivery. In some embodiments, an on-body injector, or other wearable device that deliver a larger volume of medication subcutaneously over an extended period, is used to administer the hyaluronidase and antibody-drug conjugate to the affected site. In some embodiments, a patch pump, or other wearable device adhering to the skin that delivers medication subcutaneously through an injection site, is used to administer the hyaluronidase and antibody-drug conjugate to the affected site. In some embodiments, a wearable infusion pump, or other device worn on the body for continuous subcutaneous infusion of medication, is used to administer the hyaluronidase and antibody-drug conjugate to the affected site.

An implantable administration apparatus may be utilized to administer the hyaluronidase and antibody-drug conjugate. The implantable apparatus may be made of porous or non-porous materials (such as silicone membranes, polymers, fibrous matrices, or collagen matrices) that release medication gradually over time. In some embodiments, a subcutaneous impact, or other implant specifically designed to be placed beneath the skin for controlled and sustained release of medication, is used to administer the hyaluronidase and antibody-drug conjugate to the affected site. In some embodiments, an intramuscular implant, or other implant designed for insertion into muscle tissue, providing a localized and sustained release of medication, is used to administer the hyaluronidase to the affected site. In some embodiments, an intradermal implant, or other implant placed within the dermal layer of the skin for targeted and controlled delivery of medication, is used to administer the hyaluronidase and antibody-drug conjugate to the affected site. In some embodiments, topical administration, or other application directly onto the skin, including creams, gels, ointments, and transdermal patches, is used to administer the hyaluronidase and antibody-drug conjugate to the affected site.

The compositions for administration to a patient via an injection (e.g. subcutaneously) also may comprise suitable inert additives, carriers, or excipients. In an embodiment, the injectable composition or combination comprises histidine. In an embodiment, the injectable composition comprises sodium chloride. In an embodiment, the injectable composition comprises polysorbate. In an embodiment, the polysorbate comprises polysorbate 80. In an embodiment, the injectable composition comprises an antioxidant. In an embodiment, the antioxidant comprises methionine.

In an embodiment, the injectable combination comprises a hyaluronidase and Gemtuzumab ozogamicin. In an embodiment, Gemtuzumab ozogamicin is mixed with an inert additive, carrier, or excipient selected from dextran (e.g. dextran 40), sodium chloride, sodium phosphate dibasic anhydrous, sodium phosphate monobasic monohydrate, and sucrose. In an embodiment, Gemtuzumab ozogamicin is mixed with each dextran (e.g. dextran 40), sodium chloride, sodium phosphate dibasic anhydrous, sodium phosphate monobasic monohydrate, and sucrose. In an embodiment, the injectable combination comprises a hyaluronidase and Brentuximab vedotin. In an embodiment, Brentuximab vedotin is mixed with an inert additive, carrier, or excipient selected from trehalose dihydrate, sodium citrate dihydrate, citric acid monohydrate, and polysorbate (e;g., polysorbate 80). In an embodiment, Brentuximab vedotin is mixed with each of trehalose dihydrate, sodium citrate dihydrate, citric acid monohydrate, and polysorbate (e;g., polysorbate 80). In an embodiment, the injectable combination comprises a hyaluronidase and Ado-Trastuzumab emtansine. In an embodiment, Ado-Trastuzumab emtansine is mixed with an inert additive, carrier, or excipient selected from polysorbate (e.g. polysorbate 20), sodium succinate, and sucrose. In an embodiment, Ado-Trastuzumab emtansine is mixed with each of polysorbate (e.g. polysorbate 20), sodium succinate, and sucrose. In an embodiment, the injectable combination comprises a hyaluronidase and Inotuzumab ozogamicin. In an embodiment, Inotuzumab ozogamicin emtansine is mixed with an inert additive, carrier, or excipient selected from polysorbate (e.g. polysorbate 80), sodium chloride, sucrose, and tromethamine. In an embodiment, Inotuzumab ozogamicin emtansine is mixed with each of polysorbate (e.g. polysorbate 80), sodium chloride, sucrose, and tromethamine. In an embodiment, the injectable combination comprises a hyaluronidase and Polatuzumab vedotin. In an embodiment, Polatuzumab vedotin is mixed with an inert additive, carrier, or excipient selected from polysorbate (e.g. polysorbate 20), sodium hydroxide, succinic acid, and sucrose. In an embodiment, Polatuzumab vedotin is mixed with each of polysorbate (e.g. polysorbate 20), sodium hydroxide, succinic acid, and sucrose. In an embodiment, the injectable combination comprises a hyaluronidase and Enfortumab vedotin. In an embodiment, Enfortumab vedotin is mixed with an inert additive, carrier, or excipient selected from histidine, histidine hydrochloride monohydrate, polysorbate (e.g. polysorbate 20), and trehalose dihydrate. In an embodiment, Enfortumab vedotin is mixed with each of histidine, histidine hydrochloride monohydrate, polysorbate (e.g. polysorbate 20), and trehalose dihydrate. In an embodiment, the injectable combination comprises a hyaluronidase and Fam-Trastuzumab deruxtecan. In an embodiment, Fam-Trastuzumab deruxtecan is mixed with an inert additive, carrier, or excipient selected from histidine (e.g. L-histidine), histidine hydrochloride monohydrate (e.g. L-histidine hydrochloride monohydrate), polysorbate (e.g. polysorbate 80), and sucrose. In an embodiment, Fam-Trastuzumab deruxtecan is mixed with each of histidine (e.g. L-histidine), histidine hydrochloride monohydrate (e.g. L-histidine hydrochloride monohydrate), polysorbate (e.g. polysorbate 80), and sucrose. In an embodiment, the injectable combination comprises a hyaluronidase and Sacituzumab govitecan. In an embodiment, Sacituzumab govitecan is mixed with an inert additive, carrier, or excipient selected from 2-(N-morpholino)ethane sulfonic acid (MES), polysorbate (e.g. polysorbate 80), trehalose dihydrate, and sodium chloride. In an embodiment, Sacituzumab govitecan is mixed with each of 2-(N-morpholino)ethane sulfonic acid (MES), polysorbate (e.g. polysorbate 80), trehalose dihydrate, and sodium chloride. In an embodiment, the injectable combination comprises a hyaluronidase and Loncastuximab Tesirine. In an embodiment, Loncastuximab Tesirine is mixed with an inert additive, carrier, or excipient selected from histidine (e.g. L-histidine), histidine monohydrochloride (e.g. L-histidine monohydrochloride), polysorbate (e.g. polysorbate 20), and sucrose. In an embodiment, Loncastuximab Tesirine is mixed with each of histidine (e.g. L-histidine), histidine monohydrochloride (e.g. L-histidine monohydrochloride), polysorbate (e.g. polysorbate 20), and sucrose. In an embodiment, the injectable combination comprises a hyaluronidase and Tisotumab vedotin. In an embodiment, Tisotumab vedotin is mixed with an inert additive, carrier, or excipient selected from mannitol (e.g. d-mannitol), histidine (e.g. L-histidine), histidine monohydrochloride (e.g. L-histidine monohydrochloride), and sucrose. In an embodiment, Tisotumab vedotin is mixed with an each of mannitol (e.g. d-mannitol), histidine (e.g. L-histidine), histidine monohydrochloride (e.g. L-histidine monohydrochloride), and sucrose. In an embodiment, the injectable combination comprises a hyaluronidase and Mirvetuximab soravtansine-gynx. In an embodiment, Mirvetuximab soravtansine-gynx is mixed with an inert additive, carrier, or excipient selected from acetic acid (e.g. glacial acetic acid), polysorbate (e.g. polysorbate 20), sodium acetate, and sucrose. In an embodiment, Mirvetuximab soravtansine-gynx is mixed with each of acetic acid (e.g. glacial acetic acid), polysorbate (e.g. polysorbate 20), sodium acetate, and sucrose.

In an embodiment, the injection of a high volume of the disclosed formulation in a subject leads to fewer side effects in the subject compared to an identical subject administered the same volume of a comparable formulation that does not comprise the hyaluronidase. In an embodiment, the injection of a high volume disclosed elsewhere herein with the disclosed formulation has reduced back leakage compared similar formulation that does not comprise the hyaluronidase. In an embodiment, the back leakage is reduced about 54%, about 56%, about 58%, about 60%, about 62%, about 64%, about 66%, about 68%, about 70%, about 72%, about 74%, about 76%, or about 78% when a high volume of the disclosed formulation is administered to a subject using a HVAI fitted with a 23 gauge needle compared to a similar formulation that does not comprise the hyaluronidase. In an embodiment, the back leakage is reduced about 62%, about 64%, about 68%, about 70%, about 72%, about 74%, about 76%, about 78%, about 80%, about 82%, about 84%, or about 86% when a high volume of the disclosed formulation is administered to a subject using a HVAI fitted with a 25 gauge needle compared to a similar formulation that does not comprise the hyaluronidase.

In an embodiment, the swelling (bleb) volume is reduced following the injection of the disclosed formulation into a subject when compared to a similar formulation that does not comprise the hyaluronidase. In an embodiment, the swelling height is reduced following the injection of the disclosed formulation when compared to a similar formulation that does not comprise the hyaluronidase. In an embodiment, the swelling size is reduced following the injection of the disclosed formulation when compared to a similar formulation that does not comprise the hyaluronidase. In an embodiment, the swelling area is reduced following the injection of the disclosed formulation when compared to a similar formulation that does not comprise the hyaluronidase. In an embodiment, the swelling induration following the initial injection of the disclosed formulation is minimized compared to a similar formulation that does not comprise the hyaluronidase. In an embodiment, the swelling resolves quicker when the disclosed formulation is injected compared to a similar formulation that does not comprise the hyaluronidase. In an embodiment, the disclosed formulation permits for more consistent delivery (i.e., time to delivery, reduction in bleb swelling volume, height and induration) from injection to injection, compared to a similar formulation that does not comprise the hyaluronidase. In an embodiment, the disclosed formulation permits for faster delivery of the full volume from a HVAI than a comparable formulation that does not comprise the hyaluronidase which results in less pain and discomfort for the subject.

EXAMPLES

The following examples are included for illustrative purposes only and are not intended to limit the scope of the invention.

Example 1: Tolerability of Sacituzumab Govitecan Following Subcutaneous Administration with and without Recombinant Human Hyaluronidase PH20 (rHuPH20)

High volume auto-injectors (HVAIs) are in development for subcutaneous (SC) delivery of biotherapeutics. However, traditional volumetric limitations have kept the development of these devices to around 2.5 to 5 milliliters (mL). Recombinant human hyaluronidase PH20 (rHuPH20) has been shown to facilitate the SC delivery of large volumes (from 5-600 mL) in clinical applications and may facilitate the delivery of large volumes of biotherapeutics using an HVAI. Both pre-clinical and clinical testing of a prototype HVAI device has demonstrated its capacity to deliver a 10 mL volume of test solution in approximately a 15-45 second timeframe.

This study investigated the local tolerability of subcutaneous (SC) administration of an antibody drug conjugate (ADC) both with and without recombinant human hyaluronidase PH20 (rHuPH20). An HVAI was used to deliver the test solutions. The HVAI had an exposed needle length of 10 mm and was vertically inserted through the dermis. Minipigs were used in this study due to the similarity of the SC skin architecture to humans. Each animal received two 10 mL SC injections into the lower abdominal region using the prototype HVAI. The first injection contained the ADC alone followed by the second injection on the contralateral side of the animal which contained the ADC+rHuPH20 at 2000 U/mL.

The duration of each injection was measured and recorded. Additional endpoints included measurement of post-injection back-leakage, local injection site measurements (bleb area and volume), qualitative scoring assessment of the local tissue for erythema, swelling size and induration, and standard imaging to quantitate post-injection changes of the skin. Qualitative assessments were taken at approximately one, two- and three-days post-injection. After the final imaging timepoint the animal was humanely euthanized and full skin thickness punch biopsies were collected of the injection sites.

Subcutaneous administration of large volumes of antibodies has been shown to be feasible when the antibody solution is co-formulated with recombinant human hyaluronidase PH20 (rHuPH20). rHuPH20 has been shown to facilitate SC administration of fluids and drugs by transiently and locally depolymerizing hyaluronan (HA) in the extracellular matrix (ECM) thereby reducing tissue backpressure in the SC space permitting rapid, large volume administration of fluid. Using this technology, subcutaneous administration of large volumes of antibody has become possible and is replacing intravenous administration as a treatment paradigm. Currently there are numerous approved antibody therapies that utilize rHuPH20 to enable subcutaneous administration including Herceptin® SC, Darzalex® SC, Phesgo™ and Hyqvia®.

A novel class of antibody-based therapeutics has been developed and recently approved by the FDA for the management or treatment of cancer. These therapeutics combine monoclonal antibodies specific to surface antigens present on particular tumor cells with highly potent anti-cancer agents linked via a chemical linker to form an antibody drug conjugate (ADC). Because these novel therapeutics are now being considered for SC administration it was important to assess their local tolerability using an appropriate animal model. Non-clinical local tolerance testing is intended to support human exposure to a compound at contact sites of the body and should reflect the proposed clinical administration. The swine model was chosen for this assessment due to the high similarity of the skin and subcutaneous space between humans and swine. Previous studies using a minipig model have demonstrated the translatability of the model for use in pre-clinical (Kang et al., 2013) and auto-injector studies.

This study utilized the FDA-approved drug Sacituzumab govitecan (Trodelvy®) as a representative ADC. This antibody was used in a prior study that demonstrated the local tolerability both alone and in combination with rHuPH20 after SC administration. However, this study was limited to a four-hour exposure and this follow-on study evaluated the local tolerability of larger dose volumes and longer exposure times.

In this study three animals were treated to assess the local tolerability of SC administration of either the antibody solution co-mixed with rHuPH20 or the antibody solution alone. Two SC injections were administered to the abdomen of each animal with one injection located on the lower left abdomen of the animal and the other injection located on the lower right of the abdomen of the animal. The injection volume was 10 mL. The test solution was delivered using a prototype high volume auto-injector (HVAI) that had been successfully used in previous preclinical and clinical studies to reproducibly deliver a 10 mL injection volume in an approximate 30 second timeframe.

After test solution administration, the injection site was monitored over a period of 72h with daily observations, photographing and qualitative assessments taken of the injection site. After the last timepoint, each animal was humanely euthanized and full thickness punch biopsies of each injection site were obtained post-mortem and preserved in 10% formalin for histological analyses using hematoxylin and eosin (H&E) staining.

Test Articles

Antibody Drug Conjugate (ADC)—Sacituzumab Govitecan (Trodelvy®)

Description: Clear colorless liquid

Lot number: S23C008A

Concentration: 10 mg/mL

Formulation: Reconstituted in 20 mL of 0.9% NaCl for Injection, USP

Storage Conditions: 2-8° C.

Handling Conditions: Standard laboratory precautions

Supplier: Pharmaceutical Buyers, Inc.

Recombinant Human Hyaluronidase (rHuPH20)

Description: Clear colorless liquid

Lot number: 1-FIN-3928

Concentration: 1,039,763 U/mL; 10 mg/mL

Formulation: 10 mM Histidine, 130 mM sodium chloride, pH 6.5

Storage Conditions: <70° C.

Handling Conditions: Standard laboratory precautions

Supplier: Halozyme, Inc.

0.9% Sodium Chloride

Description: Clear colorless liquid

Lot number: GX9803

Expiration date: 1 Jan. 2025

Storage Conditions: Room temperature

Handling Conditions: Standard laboratory precautions

Supplier: Hospira

Preparation of Test Solutions. The two test solutions administered in this study were Trodelvy alone and Trodelvy+rHuPH20. Three vials of Trodelvy were reconstituted according to manufacturer's instructions using 20.2 mL of 0.9% Sodium Chloride to the lyophilized product in each vial to produce 60.6 mL of Trodelvy that was used to prepare (3) syringes of Trodelvy and (3) syringes of Trodelvy+rHuPH20.

Preparation of Syringes Containing Trodelvy Alone

After reconstitution, three syringes were prepared that contained 10.1 mL each of Trodelvy. After filling each syringe, it was capped and stored at 2-8° C.

Preparation of Syringes Containing Trodelvy+rHuPH20

To prepare Trodelvy+rHuPH20, 0.062 mL of rHuPH20 was added to the remaining 30.3 mL of Trodelvy. This was used to fill three syringes with 10.1 mL each of Trodelvy+rHuPH20. After filling each syringe, it was capped and stored at 2-8° C.

Device Preparation

Assembly of all devices occurred in a sterile fill and finish hood under aseptic conditions. COC syringes were used to contain test solutions in the HVAI device. Springs used in this study had the same k spring constant as the devices used in a previous study using the HVAI (Studies 22148 and 23027). Prior to final assembly COC syringes were brought to room temperature for at least 30 minutes. The syringe cap was removed and replaced with a 25G×1-inch Becton Dickinson needle and loaded into a jig where the HVAI was assembled by Halozyme engineering staff. After final assembly of the HVAI a needle guard was placed over the needle to bring the exposed needle depth to 10 mm+1 mm. The length of each needle was recorded.

Animal Description

Species: Pig (Sus scrofa domestica)

Strain: Yucatan miniature

Sex: Female

Age: ~4-6 months

Body weight: ~18-22 kg

Quantity: 3

Source: Premier BioSource (Ramona, CA)

Husbandry: The animals were housed in steel pens with automatic water provided ad libitum. The animals were fed twice daily (AM and PM) but kept NPO after midnight on the day of the study to prevent anesthesia complications. The room environment was set to maintain a temperature of 19-23° C. and a relative humidity of 40-70%, with a 12-hour light/12-hour dark time cycle. The animals were acclimated to the vivarium for a minimum of 3 days prior to study start.

Test Materials

TABLE 1

Summary of test materials

| Test Material | Supplier | Catalog # |
|---|---|---|
| High Volume Auto-Injector (HVAI) | Halozyme | N/A |
| COC syringes | SCHOTT, Inc. | N/A |
| Sterile rubber plunger for COC syringes | SCHOTT, Inc. | N/A |
| Rubber plunger positioning platform | Halozyme | N/A |
| Syringe caps | Becton Dickinson | 305819 |
| 25G × 1 inch Precision Glide needle | Becton Dickinson | 305125 |
| Surgical Eye Spears | BVI Merocel ® | 400101 |
| Standard Digital Camera | Canon | S120 |
| Digital Caliper | Fisher | 06-664-16 |
| 12 mm biopsy punch | Accuderm | NC9253254 |
| 10% neutral buffered formalin | Fisher Scientific | 22-026-435 |

This study assessed the local tolerability of an approved antibody-drug conjugate Sacituzumab govitecan (Trodelvy®) with and without rHuPH20 over time after subcutaneous administration. In this study three animals were used. Each animal received a SC injection to their abdomen of Trodelvy alone followed by a SC injection of Trodelvy+rHuPH2 on the contralateral side of the abdomen. The dose volume was 10 mL and was delivered using a HVAI. The treatment groups are shown in Table 2.

TABLE 2

Description of treatment groups.

| Cohort [N/group] | Test Solution | Dose Volume (mL) | rHuPH20 (U/mL) | Evaluation Times (h/d) |
|---|---|---|---|---|
| 1 [3] | Sacituzumab govitecan (Trodelvy) | 10 | 0 | T0, 1 d, 2 d, 3 d |
| 2 [3] | Sacituzumab govitecan + rHuPH20 (Trodelvy + rHuPH20) | 10 | 2000 | T0, 1 d, 2 d, 3 d |

The duration of the injection was measured using a hand-held stopwatch (Fisher). Following administration any back-leakage was collected for a period of 30 seconds and weighed using an analytical balance with a sensitivity of 0.1 mg. Qualitative assessments and photographic images were taken immediately post-injection, and at intervals of 1 d, 2 d and 3 d. After the final imaging timepoint, each animal was humanely euthanized and punch biopsies (12 mm) of each injection site were obtained and fixed in 10% neutral buffered formalin for histological processing and subsequent pathological analyses.

Prior to the start of study, the animals were assessed for general health, and body weights collected. All anesthesia was administered and monitored. One day prior to the study, syringes were filled with appropriate test solutions and assembled into HVAIs then stored at 2-8° C. Devices were allowed to acclimate to room temperature for at least 30 minutes prior to use and used within 2 hours. After anesthetization the animal was placed in dorsal recumbence on a heated surgical table and was maintained under isoflurane gas for the entire duration of the procedure. Following anesthetization, the abdominal region was cleaned with Nolvasan followed by wiping the injection site with gauze containing 70% isopropanol and wiped dry with sterile gauze. Injection sites were located on the left and right abdominal regions, ~5 cm cranially from the inguinal fold towards the midline and ~3 cm towards the midline of the animal. Each of the injection sites were marked with a permanent marker and then photographed with the standard and 3D cameras prior to needle insertion. Once injections were completed, two additional devices were brought to room temperature for use with the next animal.

HVAI Needle Lengths

The needle length of each HVAI was measured prior to use and is shown in Table 3.

TABLE 3

Summary of needle lengths

| Animal ID# | Left Side | Needle Length (mm) | Right Side | Needle Length (mm) |
|---|---|---|---|---|
| 4493 | Trodelvy | 10.0 | Trodelvy + rHuPH20 | 10.0 |
| 4498 | Trodelvy + rHuPH20 | 10.0 | Trodelvy | 9.5 |
| 4593 | Trodelvy | 9.5 | Trodelvy + rHuPH20 | 10.0 |

The needle was inserted vertically into the marked injection site and the HVAI held in place by hand. Target needle insertion depth was ~10 mm. Injections were timed using a stopwatch. Upon completion of the injection the needle was removed and the HVAI device discarded. Test solution back-leakage was then absorbed to a tared eye-spear for 30 seconds on the injection site and the weight of the eye spear was measured using an analytical balance. The margins of the injection site bleb were marked with a permanent marker and measured for length, width, and height using a digital caliper and recorded then photographed with the standard and 3D cameras. Caliper measurements and photographs were taken immediately post-injection. Local injection sites were qualitatively assessed and graded daily for erythema severity, swelling size appearance, and firmness, using a scoring system described in Table 4 Table 5, and Table 6, respectively.

TABLE 4

Grading scale for erythema formation

| Scale | Description |
|---|---|
| 0 | No erythema |
| 1 | Very slight erythema (barely perceptible) |
| 2 | Well defined erythema |
| 3 | Moderate to severe erythema |
| 4 | Severe erythema (beet redness) to slight eschar formation |

TABLE 5

Grading scale for swelling formation

| Scale | Description |
|---|---|
| 0 | No swelling |
| 1 | Very slight swelling |
| 2 | Slight swelling |
| 3 | Moderate swelling |
| 4 | Severe swelling |

TABLE 6

Grading scale for swelling firmness (induration)

| Scale | Description |
|---|---|
| 0 | No perceptible difference in firmness after injection |
| 1 | Very slightly firm (barely perceptible) |
| 2 | Mildly firm |
| 3 | Moderately firm |
| 4 | Very firm |

Approximately, 24 hours post-dosing of the first injection, each animal was re-anesthetized, and injection sites assessed for erythema, induration and swelling, then photographed and returned to its cage. The scoring and evaluations continued daily up to approximately three days (72h).

Following the assessment after day three, the animal was humanely euthanized using an injectable euthanasia drug provided by the vivarium staff. Following euthanasia full thickness punch biopsies of the injection site were taken (12 mm) and placed in 10% formalin. After obtaining the punch biopsies the animal carcass was removed and disposed of as biohazardous waste. Sections were made from tissue samples and assessed for histopathology using hematoxylin and eosin staining methods. Analyses were performed on each injection site (2 biopsies) and one untreated site. Three tissue depths were examined from each tissue section following level sectioning technique, representing the beginning, middle and end of each section.

Assessment of Injection Time. The duration of the injection was measured using a digital stopwatch with resolution of 0.1 seconds.

Assessment of Local Swelling Volume and Area Using Caliper Measurement and 3D Imaging. Volume and area of post-injection swelling were measured using both caliper measurement and 3D camera image analysis. For caliper measurements a digital caliper was utilized to measure length, width and height of the bleb that formed post-injection. The length and width are defined as the edge to edge measurements of the bleb (i.e., diameter) along their longest axes. These values were manually recorded, and the volume determined using the formula for half of an ellipsoid $Vol=(2/3)*\pi*A*B*C$ where A=Length/2, B=Width/2 and C=Height.

3D imaging was applied as a longitudinal methodology to measure post-injection swelling. By obtaining high definition pre- and post-injection 3D images the distances between two registered surfaces can be determined. The camera captures images using a factory calibrated bifocal imaging system to measure distance between surfaces. Surface registration was performed using a multipoint method that utilized common landmarks between the pre-injection image and the post-injection image. Using the proprietary software, the volume, area and height of the post-injection swelling was calculated for each injection (Canfield Biosciences, Inc.).

Caliper measurement and 3D imaging measurement yield different values for volume, area, and bleb height. The differences are a result of the difference in the bleb size measurement. The 3D measurement calculates bleb height based on the top of the bleb to the original skin position, while the bleb height from caliper measurements measure from the top of the bleb to the height at the edge of the bleb. Due to skin curvature, this may yield an overall increase in bleb height for the caliper measurements compared to the 3D measurements, resulting in greater bleb volume and height. However, the measurements are consistent with each other and therefore differ only due to the methodology.

Statistical comparisons for Trodelvy and Trodelvy+rHuPH20 were performed using an unpaired parametric t-test (Prism v10.1.1, GraphPad Software, Inc., San Diego, California). All hypotheses' tests were performed at a 5% significance level, thus considered significant if $p<0.05$.

Pre- and Post-Injection Quantitative Measurements

Quantitative measurements were taken immediately post-injection (T0) and daily afterwards up to ~72 hours.

Duration of Injection

The duration of each injection was measured using a hand-held stopwatch with a precision of 0.1 seconds. The duration of the injections for each test solution is shown in Table 7 and individual animal data shown in FIG. 1.

TABLE 7

| Measurement of injection time | | |
|---|---|---|
| Test Solution | Injection Time (sec) | % Decrease |
| Trodelvy | 22.9 ± 0.6 | — |
| Trodelvy + rHuPH20 | 20.6 ± 2.1 | −10% |

Assessment of Post-Injection Back-Leakage. The back-leakage was collected using a pre-weighed eye spear for 30 seconds post-injection. The eye spear was then re-weighed, and the weight of the back-leakage recorded. The amount of back-leakage for each test solution is shown in Table 8 and individual animal data shown in FIG. 2.

TABLE 8

| Measurement of back-leakage | | |
|---|---|---|
| Test Solution | Back-Leakage (mg ± SEM) | % Decrease |
| Trodelvy | 37.0 ± 32.0 | — |
| Trodelvy + rHuPH20 | 0.9 ± 1.0 | −98% |

Figure 3:
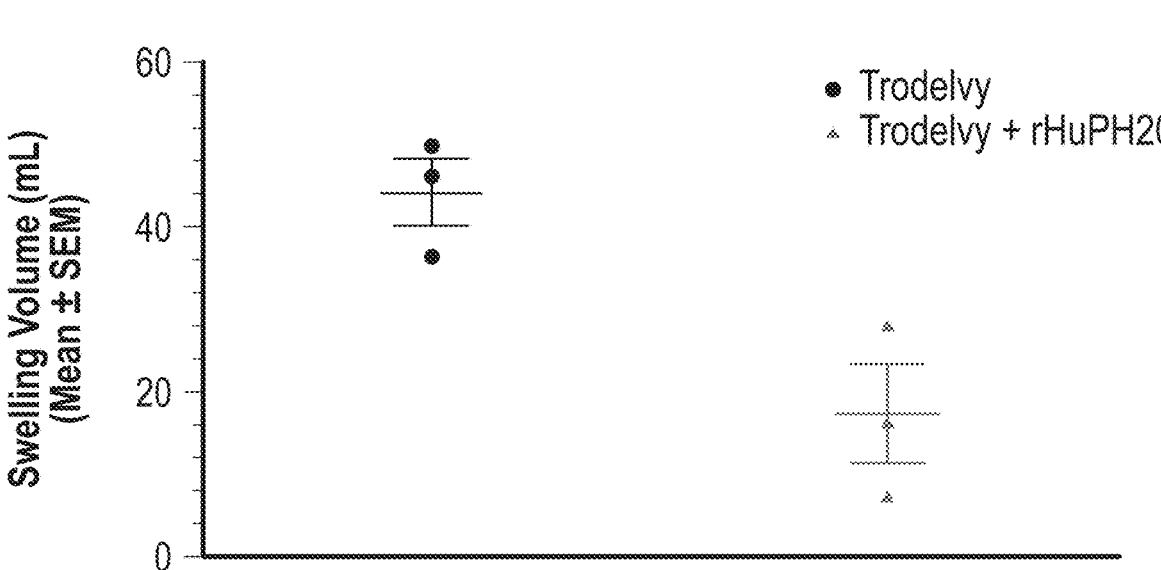
FIG. 3 is a chart of individual swelling volumes (mL) after SC Injection of Trodelvy and Trodelvy+rHuPH20–caliper measurement.
Figure 4:
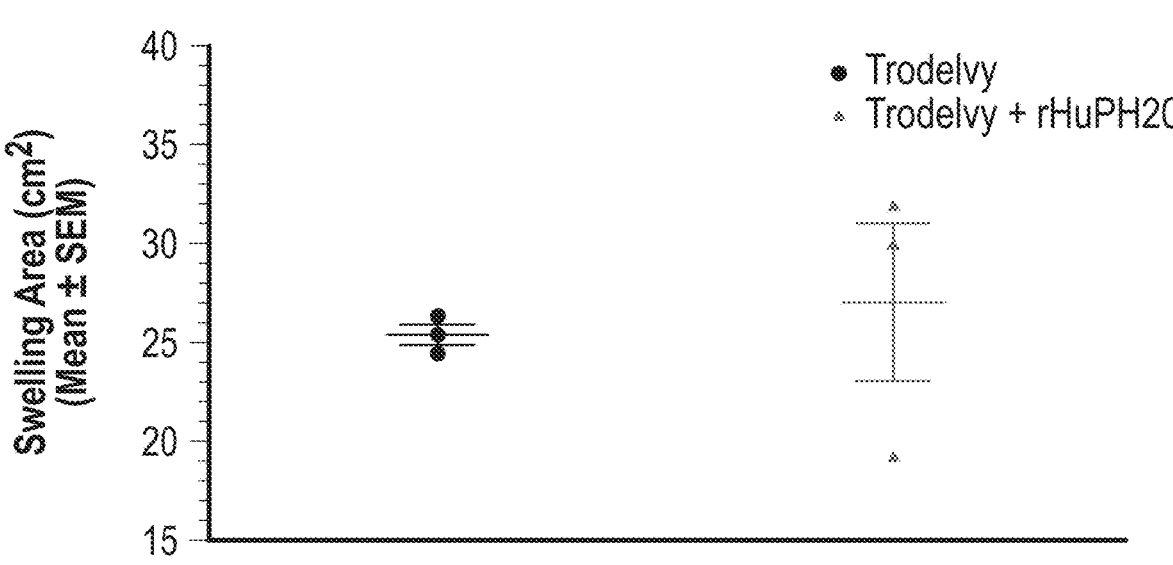
FIG. 4 is a chart of individual swelling area (cm) after SC injection of Trodelvy and Trodelvy+rHuPH20–caliper measurement.
Figure 5:
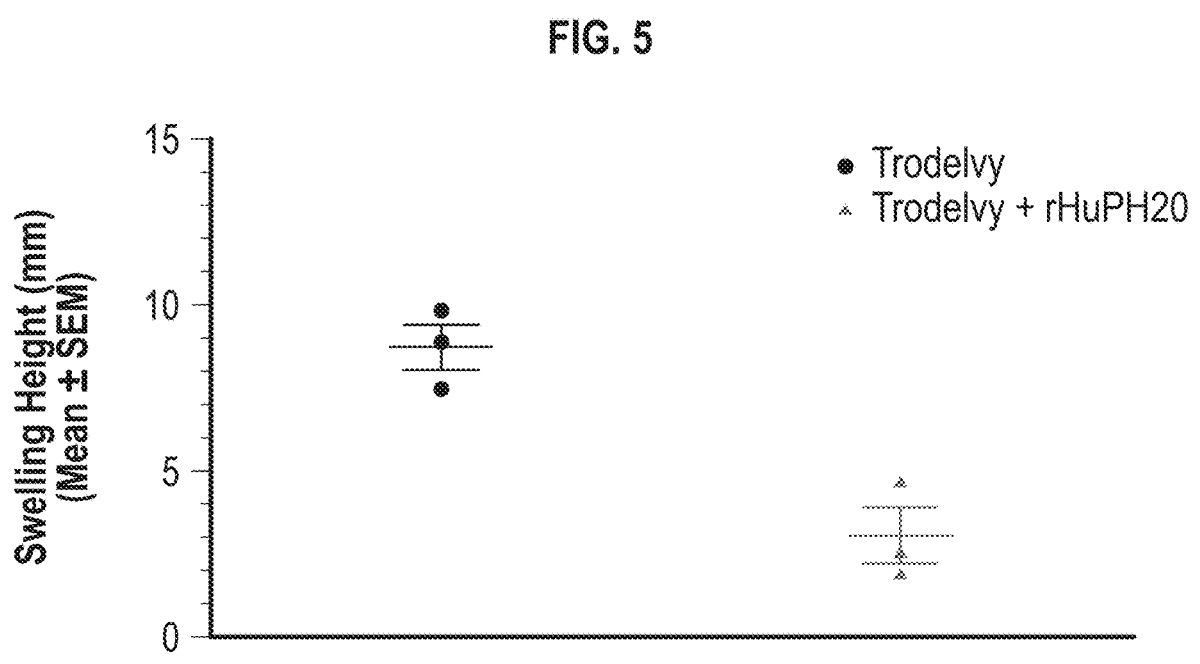

Assessment of Post-Injection Bleb Volume, Area and Height (Caliper Measurements). The local injection site swelling (bleb) was marked and measured using a digital caliper. Bleb volume dispersion area and swelling height of each bleb are summarized in Table 9. Mean and individual post-injection bleb volume, area and height values are shown in FIG. 3, FIG. 4, and FIG. 5.

TABLE 9

| | | Post-Injection Bleb Volume, Area and Height - Caliper Measurements (Mean ± SEM) | | |
|---|---|---|---|---|
| | | | Mean ± SEM | |
| Cohort # | Test Solution | Volume | Area | Height |
| 1 | Trodelvy | 44.3 ± 4.0 | 25.4 ± 0.5 | 8.7 ± 0.7 |
| 2 | Trodelvy + rHuPH20 | 17.3 ± 6.0 | 27.0 ± 3.9 | 3.1 ± 0.8 |
| | % Decrease + rHuPH20 | −61% | +6% | −64% |

Assessment of Post-Injection Bleb Shape, Volume, Area and Height (3D Imaging). Pre- and post-injection photographs were taken using a 3D imaging system (Canfield Scientific). This technology permits point-to-point alignment of these two images through multipoint surface registration. The distance between any two points is then represented using a colorimetric surface contour map. Regions where there is no difference between the two images are displayed in gray. Where the post-injection image is higher than the pre-injection image, the region is displayed in shades of blue. Where the post-injection image is lower than the pre-injection image the distance is displayed in shades of orange. The color intensity is proportional to the amount of distance measured between images with darker blue color indicating greater distance from the pre-injection image. Out of range measurements (distances greater than 6 mm) are depicted in white. Bleb measurements of volume and height include regions out of range.

Figure 6A:
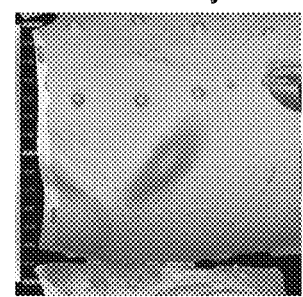
FIGS. 6A and 6B are composite 3D images of the minipigs by treatment.
Figure 6A:
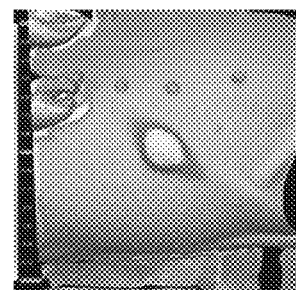
Figure 6A:
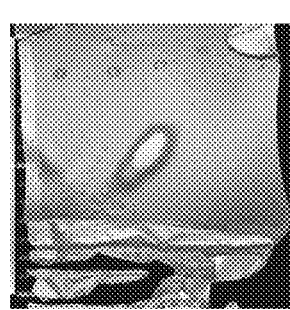
Figure 6B:
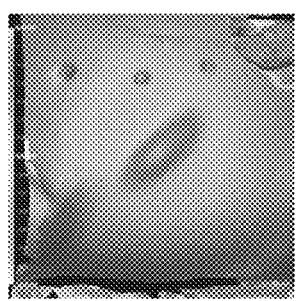
Figure 6B:
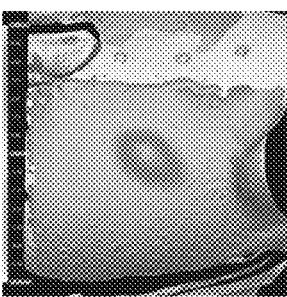

Each animal had a pre-injection 3D image taken of the injection site followed by a second image taken immediately post-injection and these images were mapped to each other using multipoint registration. These registered pre-/post-injection images were then used to calculate the bleb volume, height, circumference, length, and width for each bleb using proprietary software (Vectra H1 software; Canfield Sciences). Colorimetric surface contour maps of each post-injection bleb for Trodelvy and Trodelvy+rHuPH20 are shown in FIGS. 6A and 6B, respectively.

Figures 7, 8:
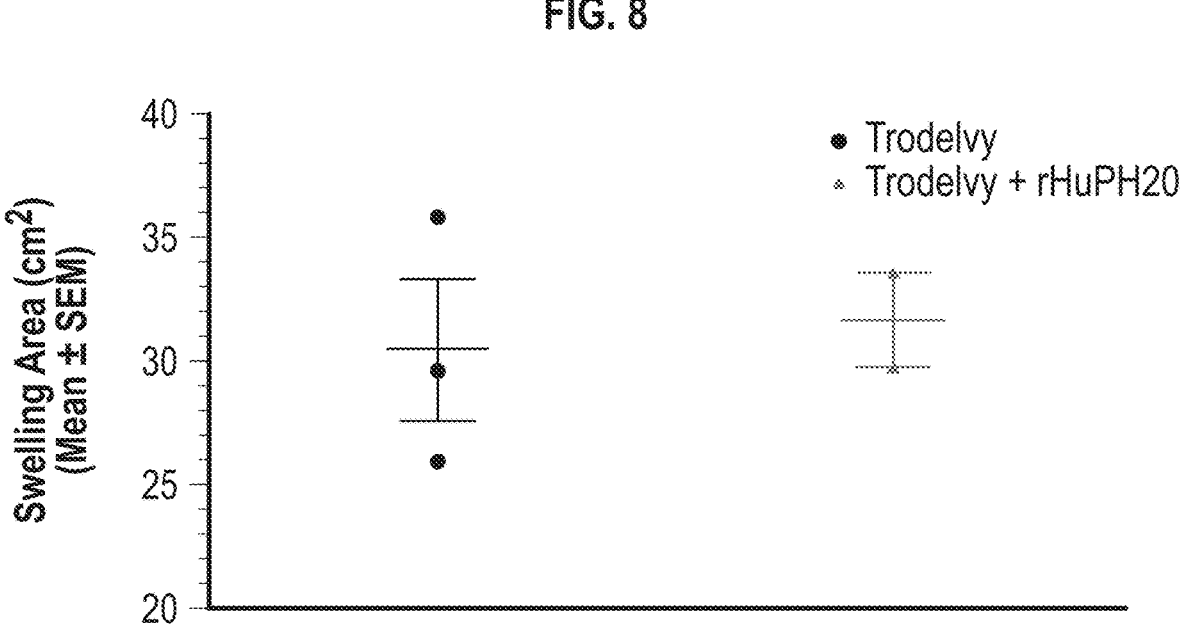
FIG. 7 is a chart of individual bleb volume (mL) after SC injection of Trodelvy and Trodelvy+rHuPH20–3D imaging.
FIG. 8 is a chart of individual bleb area (cm2) after SC injection of Trodelvy and Trodelvy+rHuPH20–3D imaging.
Figure 9:
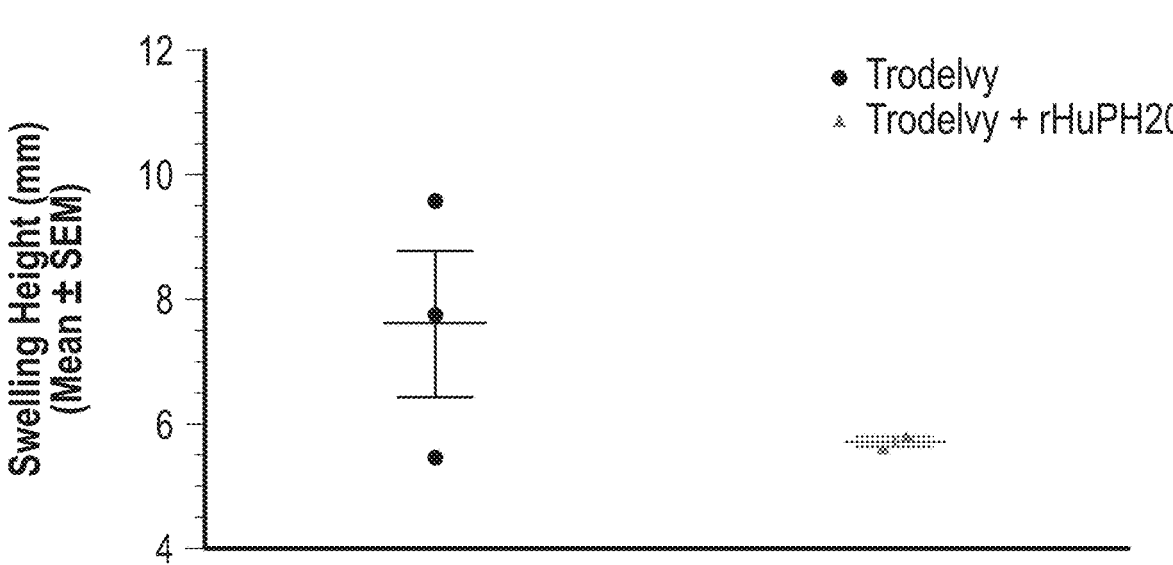
FIG. 9 is a chart of individual bleb height (mm) after SC injection of Trodelvy and Trodelvy+rHuPH20–3D imaging.

Post-injection bleb volume, area, and height for Trodelvy and Trodelvy+rHuPH20 calculated from the 3D images are summarized in Table 10. Individual post-injection bleb volume, area, and height are shown graphically in FIG. 7, FIG. 8, and FIG. 9. Because the pre-injection photo for AID #4493R was not able to be processed by the Vectra 3D software, the values for the Trodelvy+rHuPH20 are shown as the mean of the two measured values.

TABLE 10

| | | Swelling volume after injection of Ig-120 and Ig-120 + rHuPH20 over time using caliper measurement (Mean ± SEM) | |
|---|---|---|---|
| | | Mean ± SEM | |
| Test Solution | Volume (mL) | Area (cm$^2$) | Height (mm) |
| Trodelvy | 8.1 ± 0.7 | 30.5 ± 2.9 | 7.6 ± 1.2 |
| Trodelvy + rHuPH20[a] | 7.2 ± 0.5 | 31.7 ± 1.9 | 5.7 ± 0.1 |
| % Decrease + rHuPH20 | −11% | +4% | −25% |

[a]N = 2

Qualitative Assessment of Local Injection Sites

Qualitative assessments were taken immediately post-injection (T0) and daily thereafter. No erythema, swelling or induration was detected on D1, D2 or D3 post-injection.

Post-Injection Erythema

No erythema was observed for either test solution following injection at any timepoint.

Post-Injection Swelling Size

Figure 10:
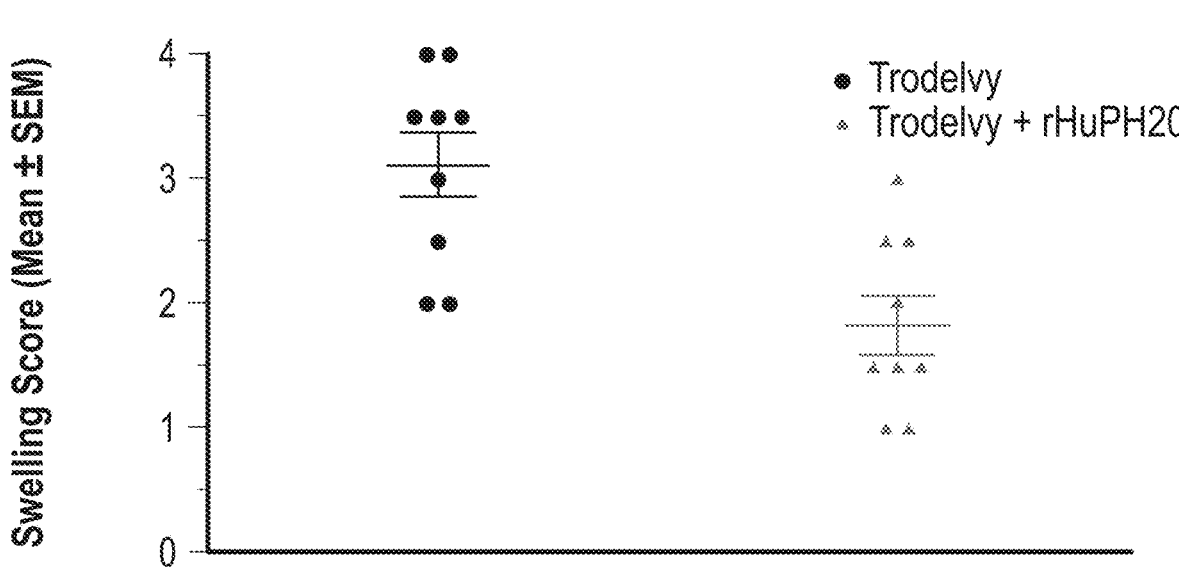
FIG. 10 is a chart of the qualitative assessment of post-injection swelling size.
Figures 12A, 12B:
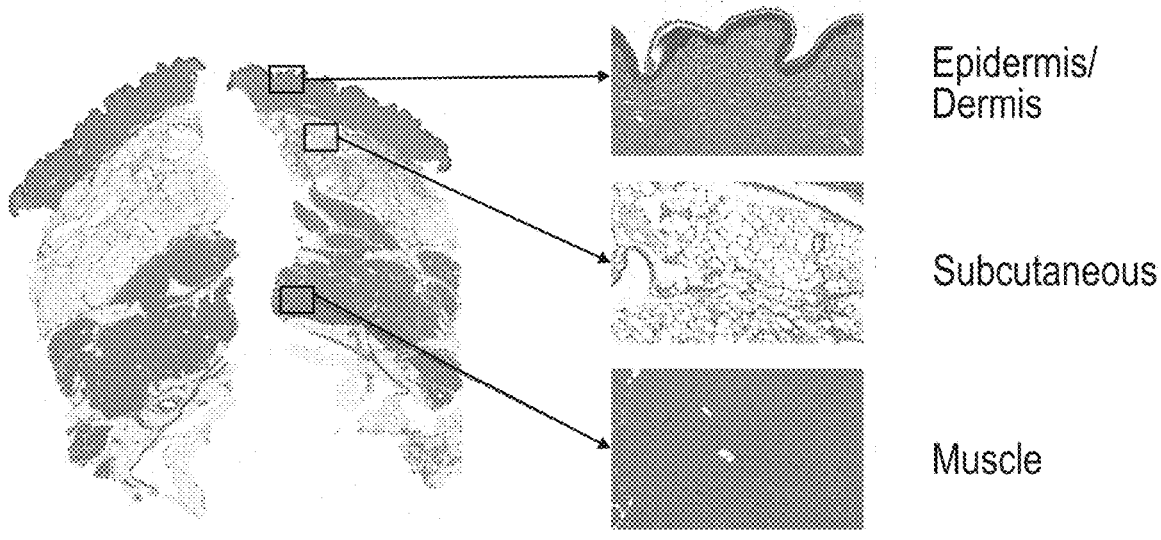
FIGS. 12A-12I are images of the histological staining of the minipigs taken from injection sites and naïve skin.
Figure 12C:
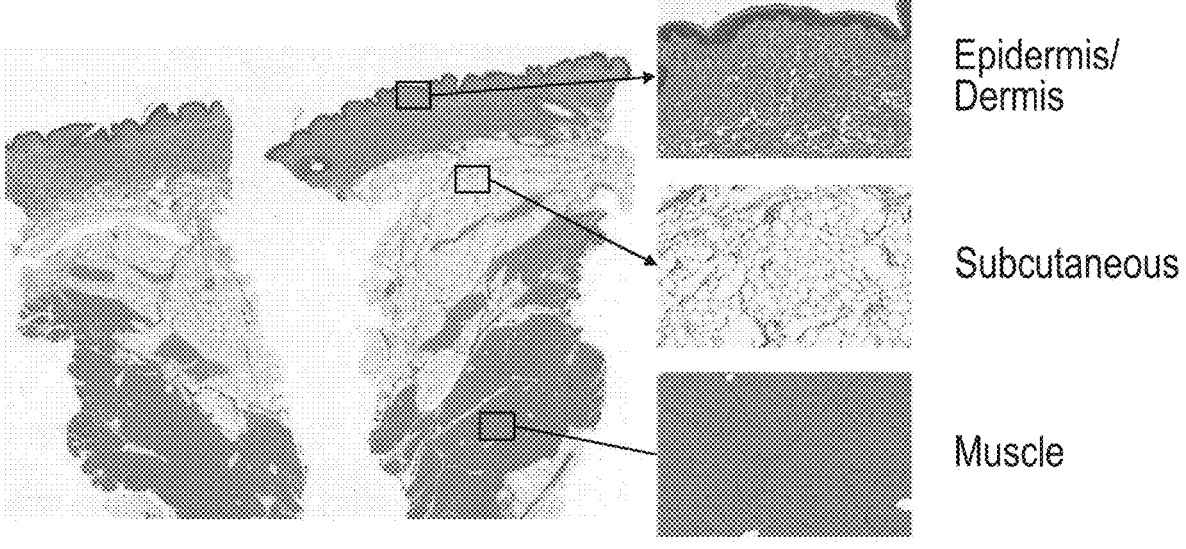
Figure 12D:
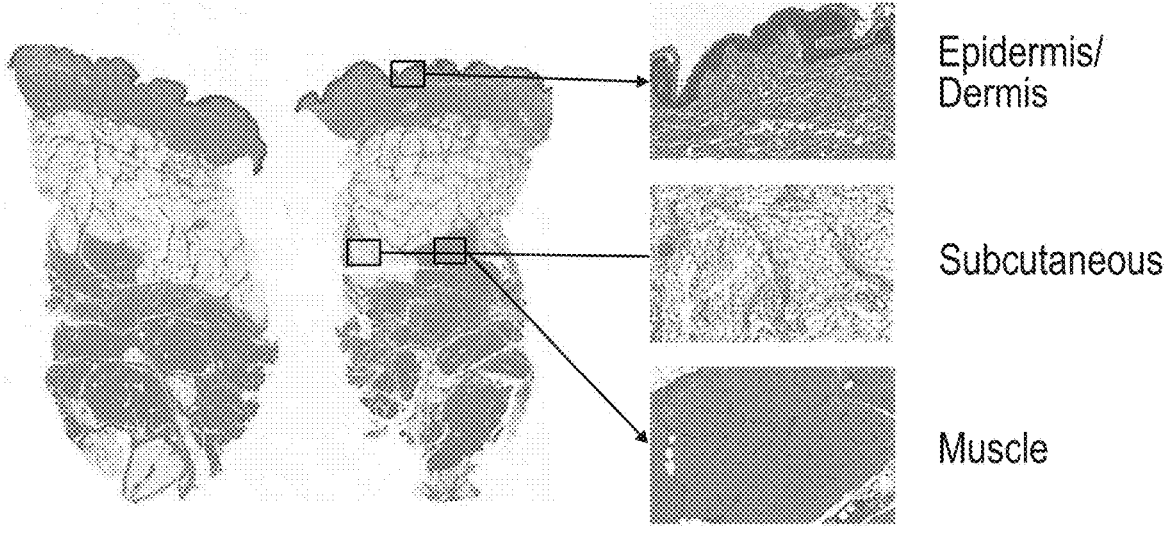
Figure 12E:
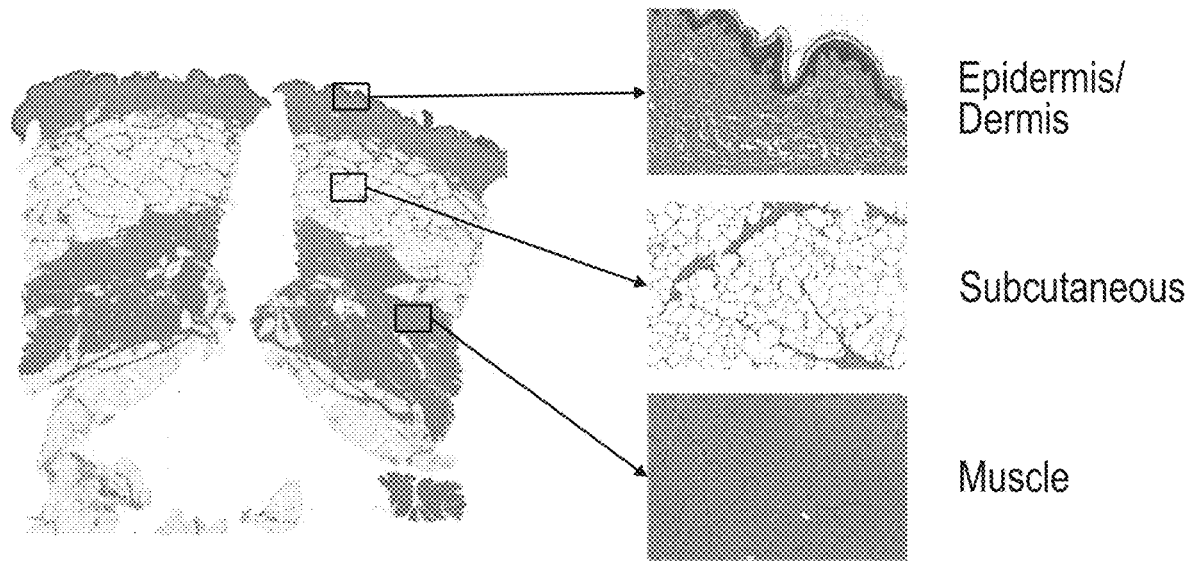
Figure 12F:
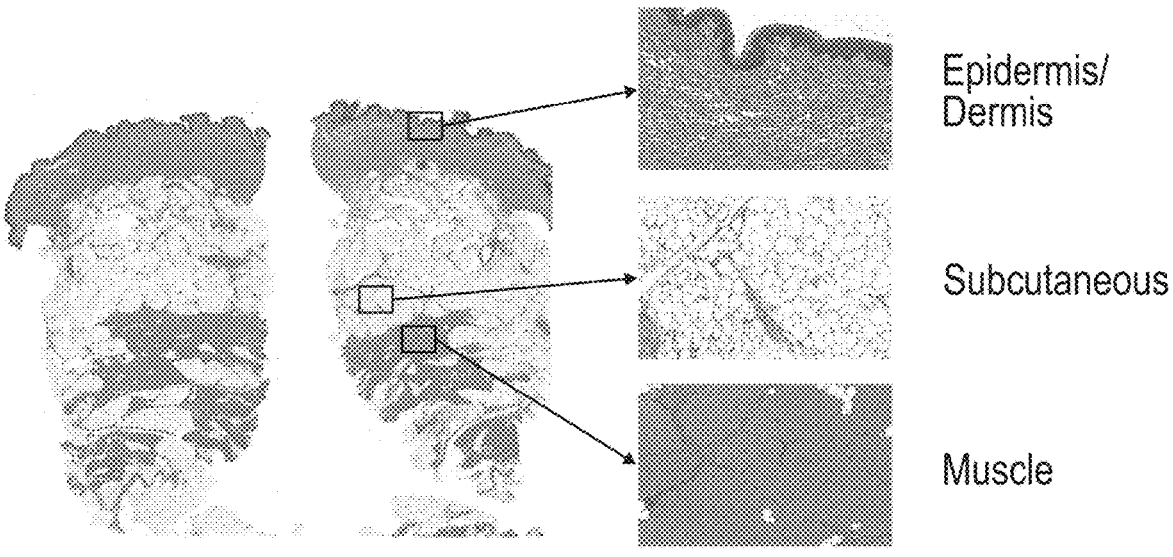
Figure 12G:
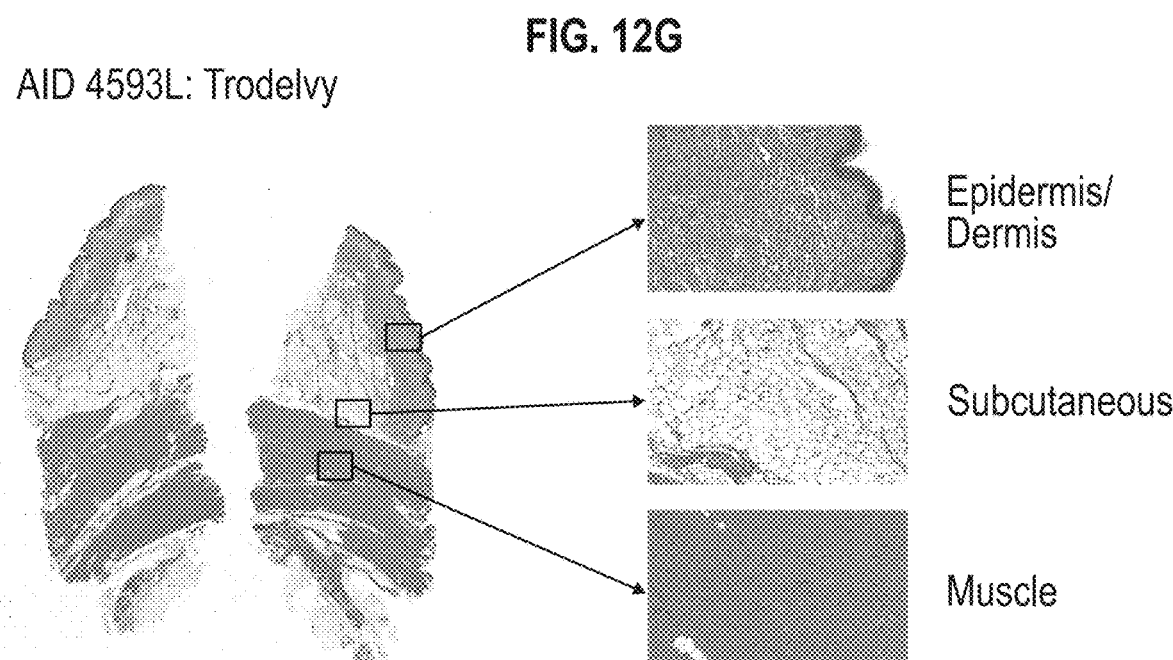
Figure 12H:
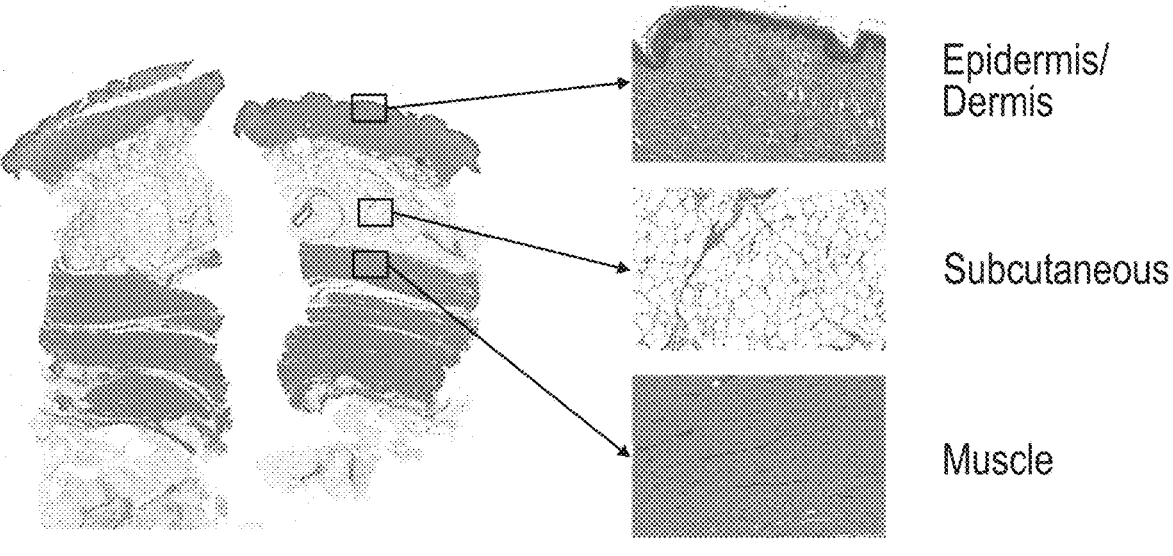
Figure 12I:
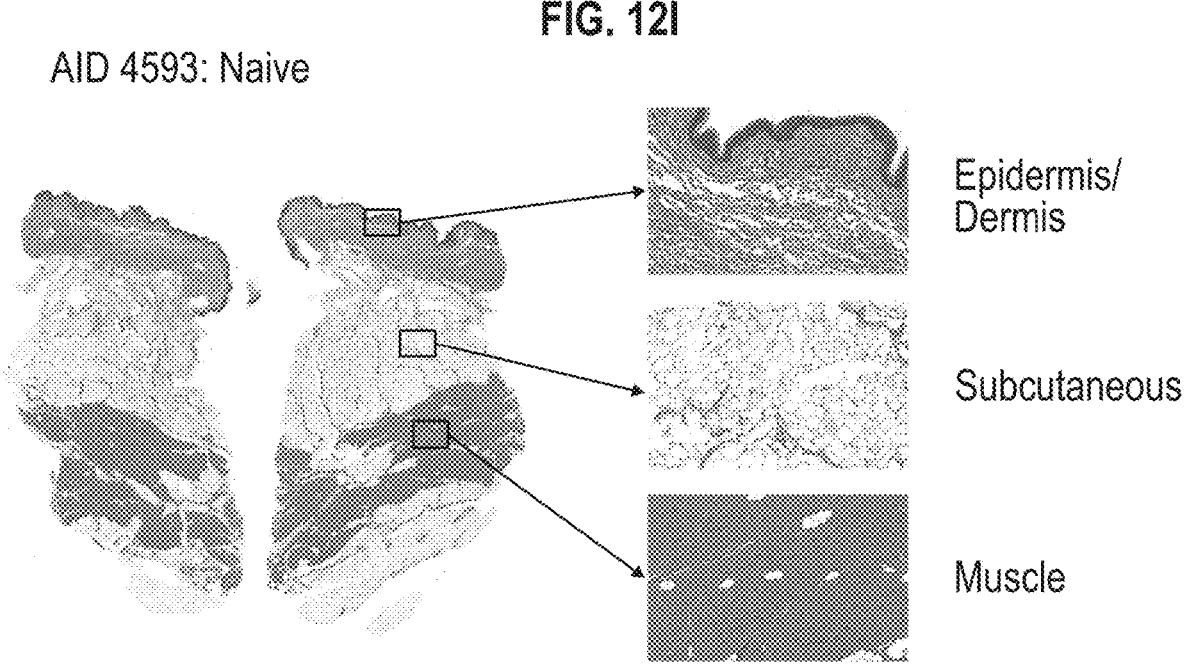

Post-injection swelling size ranged from slight (2) to severe (4) for Trodelvy alone and from very slight (1) to moderate (3) for injections of Trodelvy+rHuPH20. Scoring by three evaluators for swelling size (Mean±SEM) are summarized in Table 11 and shown in FIG. 10. No swelling was detected at the 24, 48 or 72 hour timepoints.

TABLE 11

| Swelling Scored Post-Injection for Trodelvy and Trodelvy + rHuPH20 (Mean ± SEM) | | |
| --- | --- | --- |
| Test Solution | Swelling Score (Mean ± SEM) | % Decrease |
| Trodelvy | 3.1 ± 0.3 | — |
| Trodelvy + rHuPH20 | 1.8 ± 0.2 | −42% |

Post-Injection Firmness (Induration)

Figure 11:
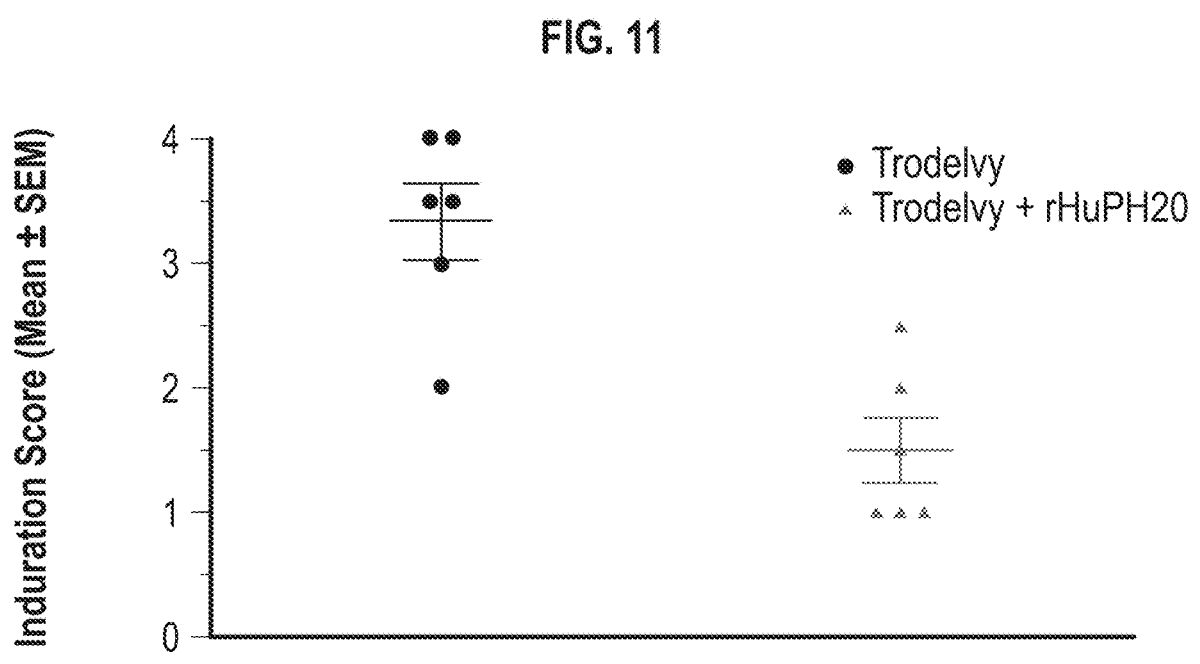

The hardness (induration) of the post-injection blebs for Trodelvy alone were found to be significantly firmer than the blebs that resulted from injection of Trodelvy+rHuPH20 (p.3.5). No induration was detected at the 24, 48 or 72 hour timepoints. Only two evaluators were available to score for induration and the values (Mean±SEM) are summarized in Table 12 and individual values are shown in FIG. 11. No induration was detected at the 24, 48 or 72 hour timepoints.

TABLE 12

| Induration Scores Post-Injection for Trodelvy and Trodelvy + rHuPH20 (Mean ± SEM) | | |
| --- | --- | --- |
| Test Solution | Induration Score (Mean ± SEM) | % Decrease |
| Trodelvy | 3.3 ± 0.3 | — |
| Trodelvy + rHuPH20 | 1.5 ± 0.3 | −55% |

Histological Analysis of Post-Injection Tissue Samples

After fixation the samples were processed and embedded into paraffin to make formalin fixed paraffin embedded (FFPE) tissues sections Each tissue section was evaluated at three different tissue depths (1-2-3; low-medium-high). In addition to tissue samples from the injection site, a sample was taken from naïve untreated tissue for comparison. A summary of the histological findings is shown in Table 13.

TABLE 13

| Summary of histological findings | | | | |
| --- | --- | --- | --- | --- |
| Sample ID | Level | Necrosis | Cell Infil-trates | Other/Comments |
| 4493L | 1 | 0 | 0 | 0 |
| Trodelvy | 2 | 0 | 0 | 0 |
| | 3 | 0 | 0 | 0 |
| 4493 | 1 | 0 | 0 | 0 |
| Naïve | 2 | 0 | 0 | 0 |
| | 3 | 0 | 0 | 0 |
| 4493R | 1 | 0 | 0 | 0 |
| Trodelvy + | 2 | 0 | 0 | 0 |
| rHuPH20 | 3 | 0 | 0 | 0 |
| 4498R | 1 | 0 | 2 focal SC | Multiple foci in SC; mild focal epithelial keratosis |
| Trodelvy | 2 | 0 | 2 focal SC | Multiple foci in SC; mild focal epithelial keratosis |
| | 3 | 0 | 2 focal SC | Multiple foci in SC; mild focal epithelial keratosis |
| 4498 | 1 | 0 | 0 | 0 |
| Naïve | 2 | 0 | 0 | 0 |
| | 3 | 0 | 0 | 0 |
| 4498L | 1 | 0 | 0 | 0 |
| Trodelvy + | 2 | 0 | 0 | 0 |
| rHuPH20 | 3 | 0 | 0 | 0 |
| 4593L | 1 | 0 | 0 | 0 |
| Trodelvy | 2 | 0 | 0 | 0 |
| | 3 | 0 | 0 | 0 |
| 4593 | 1 | 0 | 0 | 0 |
| Naïve | 2 | 0 | 0 | 0 |
| | 3 | 0 | 0 | 0 |

TABLE 13-continued

| Summary of histological findings | | | | |
| --- | --- | --- | --- | --- |
| Sample ID | Level | Necrosis | Cell Infil-trates | Other/Comments |
| 4583R | 1 | 0 | 0 | 0 |
| Trodelvy + | 2 | 0 | 0 | 0 |
| rHuPH20 | 3 | 0 | 0 | 0 |

Notably no findings occurred with the injections of Trodelvy+rHuPH20 whereas ⅓ of the injections of Trodelvy alone showed mild focal epithelial keratosis in all levels of the tissue sample. In addition, there were 2 focal instances of [immune] cell infiltrates in the SC space. Histological images of tissue sections stained with hematoxylin and eosin (H&E) together with magnified images of the dermis, subcutaneous and muscle tissues (5×) of biopsies taken from the Trodelvy±rHuPH20 injection sites and naïve skin are shown in FIGS. 12A-12I.

The addition of rHuPH20 to the 10 mL dose of Trodelvy was well tolerated when delivered subcutaneously. In addition to the tolerability this study showed:

HVAI devices with Trodelvy+rHuPH20 had a reduced mean time of delivery (−10%) compared to injection times for Trodelvy alone.

Back-leakage was extremely low and showed significantly less variability for HVAI injections with Trodelvy+rHuPH20, whereas injections of Trodelvy alone had substantial and highly variable amounts of back-leakage.

Post-injection bleb volume and height using caliper measurements were found to be significantly less for injections of Trodelvy+rHuPH20 compared to Trodelvy alone.

Post-injection bleb height showed significantly less variability between injection sites that contained rHuPH20 compared to those without.

Qualitative scoring of post-injection swelling size using a 5-point modified Draize scale showed that Trodelvy+rHuPH20 blebs were −42% compared to the size of blebs of Trodelvy alone. Qualitative scoring of post-injection induration showed that the Trodelvy+rHuPH20 blebs were consistently softer (−55%) than the blebs that were assessed after injection of Trodelvy alone.

Histopathological analysis showed that one of the injection sites with Trodelvy alone resulted in subcutaneous injection site findings that included mild focal keratosis and immune cell infiltrates which may be indicative of a wound response to an acute buildup of injection pressure in the extracellular matrix.

No signs of tissue necrosis were observed suggesting that the payload of the ADC was intact and dispersed from the injection site.

Example 2: Evaluation of Subcutaneous Administration of an Antibody Drug Conjugate (Trodelvy®) with and without Recombinant Human Hyaluronidase Ph20 (Rhuph20)

This study utilized all the same protocols and parameters as set forth in Example 1 unless disclosed otherwise. As in the previous Example, prior to study start, the enzyme activity of the test solution was measured using an in vitro activity assay (VV-QWUAL-006751 formerly TM010) to confirm the concentration of rHuPH20 in the co-mix drug solution.

Pre-study Enzymatic Activity Testing of rHuPH20 in Test Solutions. A sample of the ADC+rHuPH20 was tested for hyaluronidase activity and found to be acceptable for use. The pre-study enzyme activity is shown in Table 14.

TABLE 14

| Pre-study enzymatic activity testing of rHuPH20 in test solution. | |
| --- | --- |
| Test Solution | Pre-study Enzyme Activity (U/mL ± SD) |
| ADC + rHuPH20 | 2270 ± 19 |

Pre- and Post-Injection Quantitative Measurements

Quantitative measurements were taken immediately post-injection (T0) and daily afterwards up to ~72 hours.

Figure 13:
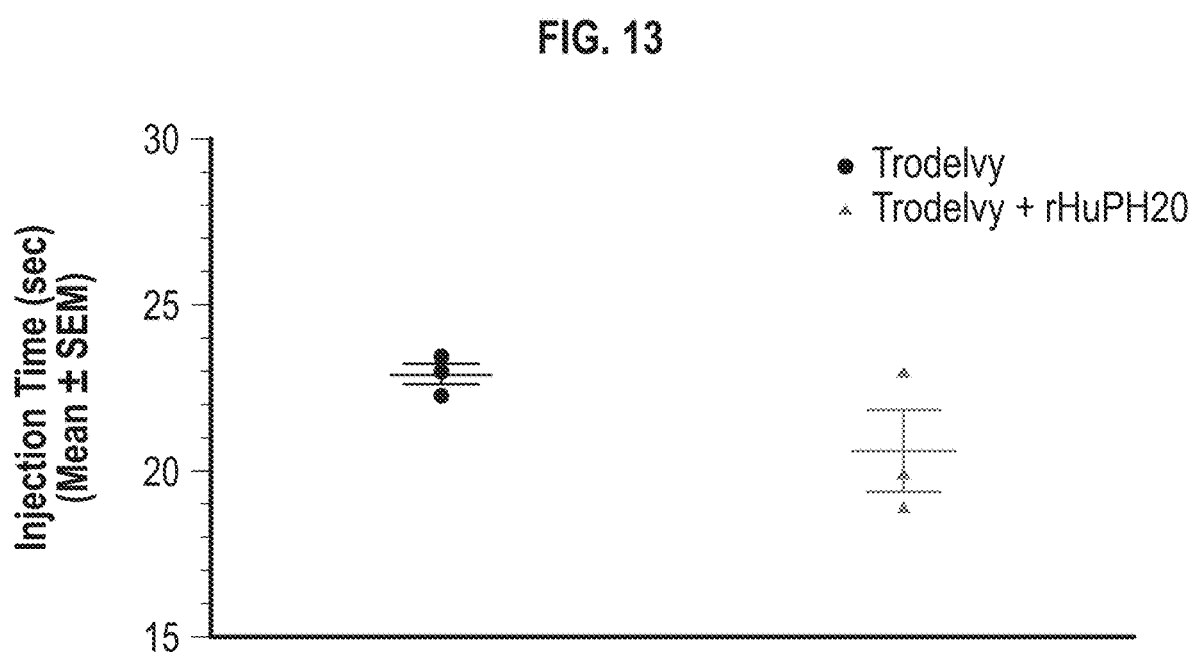

Duration of Injection. The duration of each injection was measured using a hand-held stopwatch with a precision of 0.1 seconds. The duration of the injections for each test solution is shown in Table 15 and individual animal data shown in FIG. 13.

TABLE 15

| Measurement of injection time | | |
| --- | --- | --- |
| Test Solution | Injection Time (sec) | % Decrease |
| ADC | 22.9 ± 0.6 | — |
| ADC + rHuPH20 | 20.6 ± 2.1 | −10% |

Figure 14:
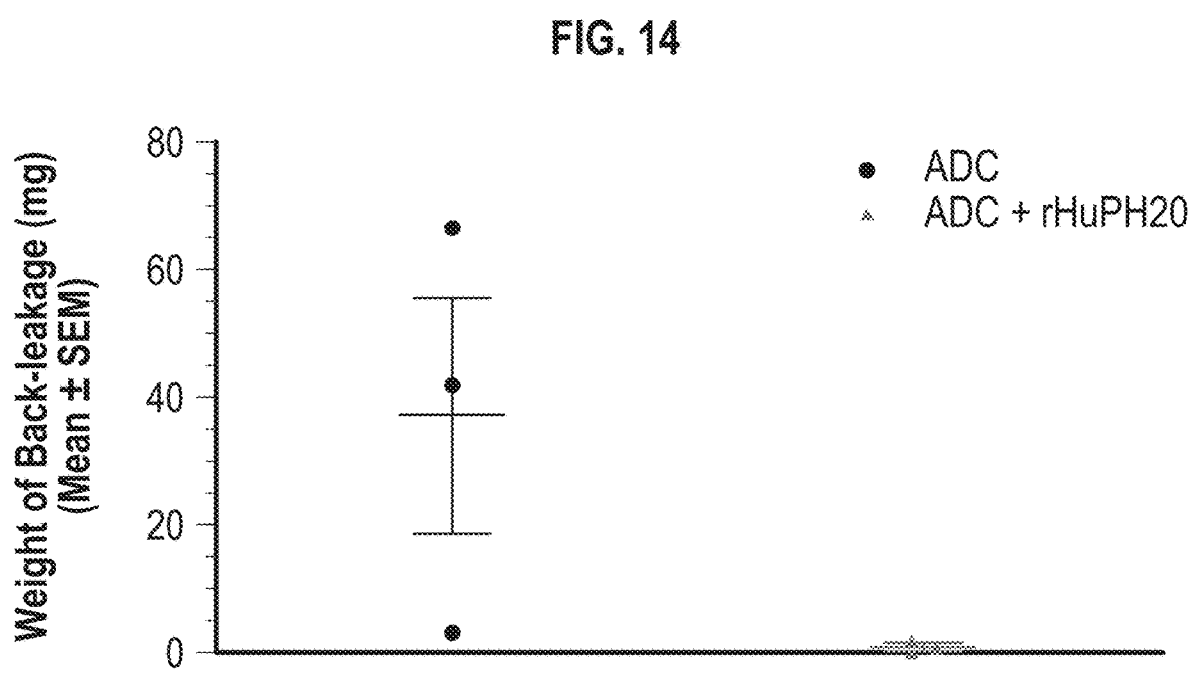

Assessment of Post-Injection Back-Leakage. The back-leakage was collected using a pre-weighed eye spear for 30 seconds post-injection. The eye spear was then re-weighed, and the weight of the back-leakage recorded. The amount of back-leakage for each test solution is shown in Table 16 and individual animal data shown in FIG. 14.

TABLE 16

| Measurement of back-leakage | | |
| --- | --- | --- |
| Test Solution | Back-Leakage (mg ± SEM) | % Decrease |
| ADC | 37.0 ± 32.0 | — |
| ADC + rHuPH20 | 0.9 ± 1.0 | −98% |

Figure 15A:
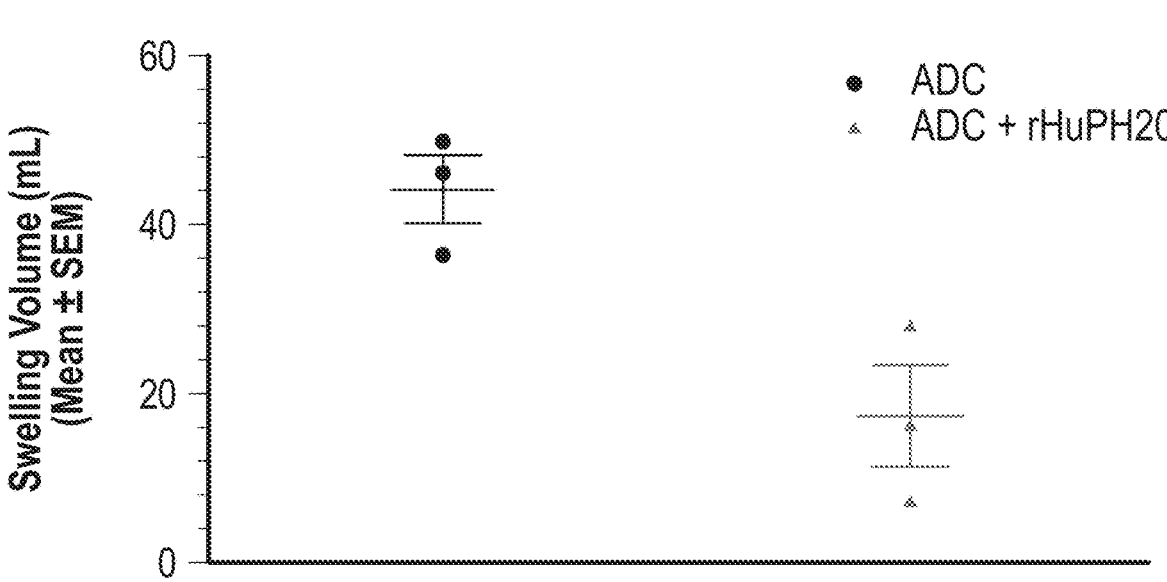
Figure 15B:
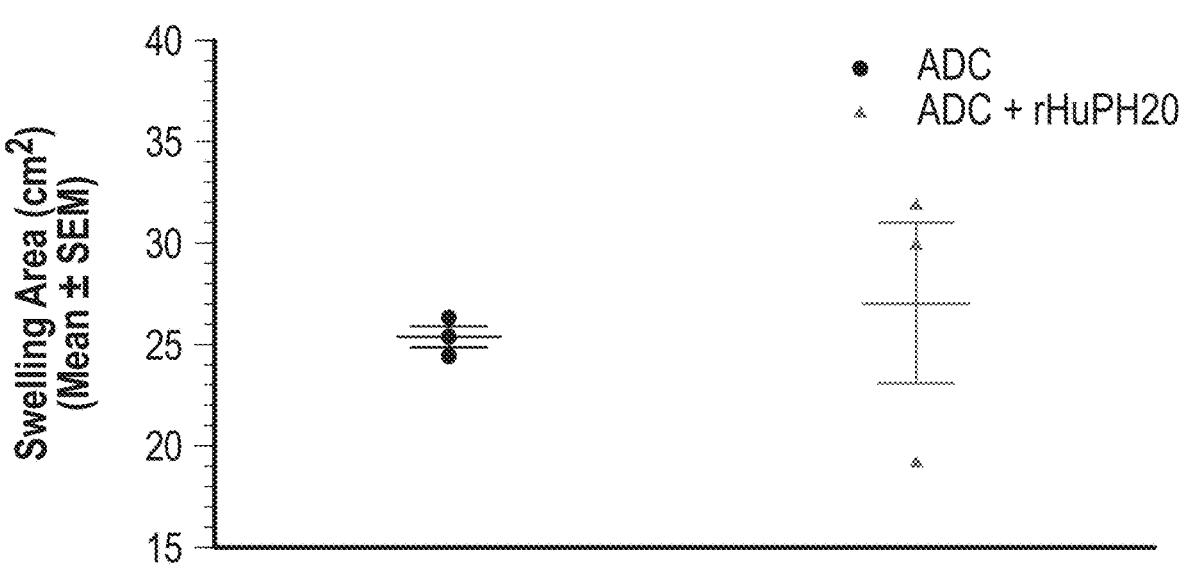
Figure 15C:
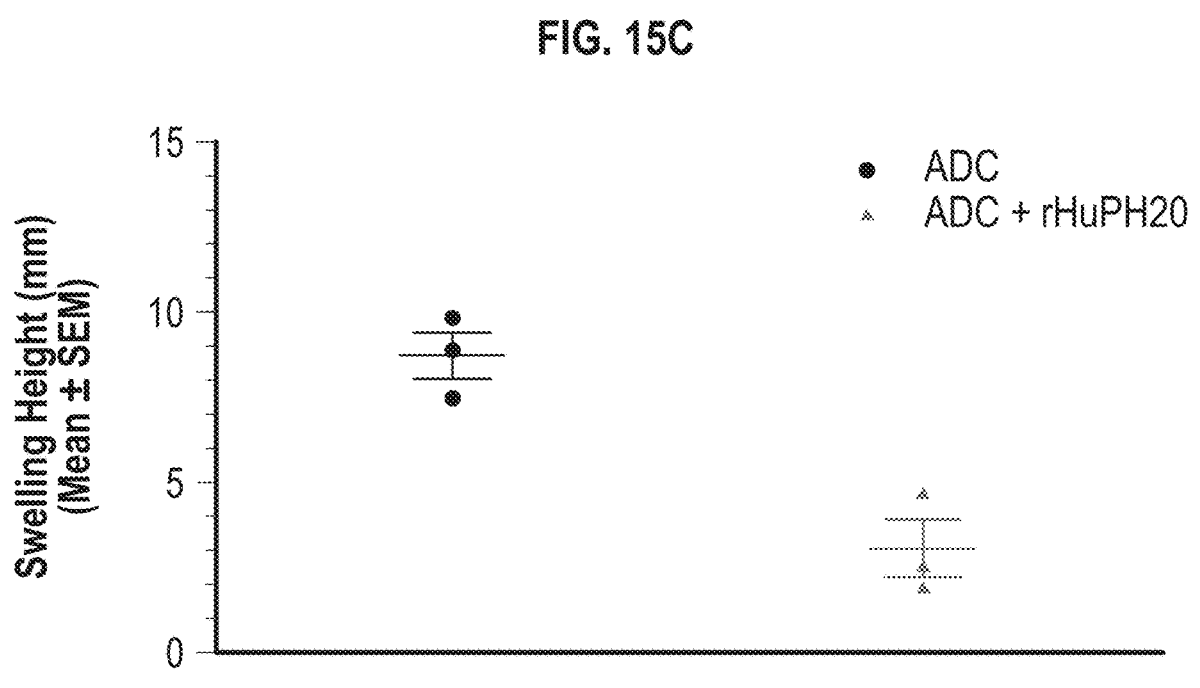

Assessment of Post-Injection Bleb Volume, Area and Height (Caliper Measurements). The local injection site swelling (bleb) was marked and measured using a digital caliper. Bleb volume dispersion area and swelling height of each bleb was determined as described in Section Section 6.2 and are summarized in Table 17. Mean and individual post-injection bleb volume, area and height values are shown in FIG. 15A, FIG. 15B, and FIG. 15C, respectively.

TABLE 17

| Post-injection bleb volume, area, and height - caliper measurements (mean ± SEM) | | | | |
| --- | --- | --- | --- | --- |
| | | | Mean ± SEM | |
| Cohort # | Test Solution | Volume | Area | Height |
| 1 | ADC | 44.3 ± 4.0 | 25.4 ± 0.5 | 8.7 ± 0.7 |
| 2 | ADC + rHuPH20 | 17.3 ± 6.0 | 27.0 ± 3.9 | 3.1 ± 0.8 |
| | % Increase/Decrease | −61% | +6% | −64% |

Figure 16:
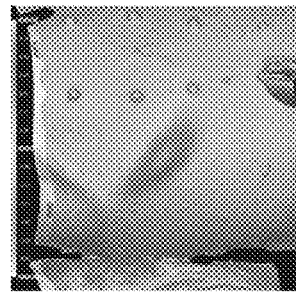
FIG. 16 shows a composite of 3D images of injection sites by treatment and AID #.
Figure 16:
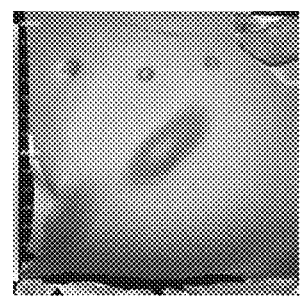
Figure 16:
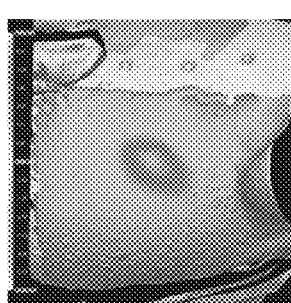

Each animal had a pre-injection 3D image taken of the injection site followed by a second image taken immediately post-injection and these images were mapped to each other using multipoint registration. These registered pre-/post-injection images were then used to calculate the bleb volume, height, circumference, length, and width for each bleb using proprietary software (Vectra H1 software; Canfield Sciences). Colorimetric surface contour maps of each post-injection bleb for ADC and ADC+rHuPH20 are shown in FIG. 16.

Figure 17A:
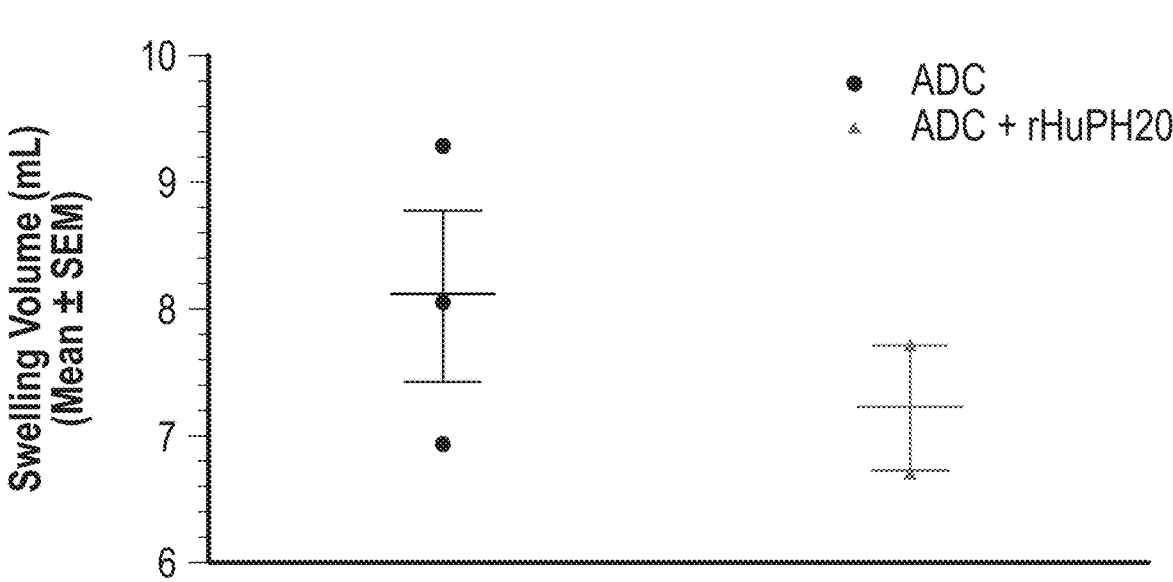
Figure 17B:
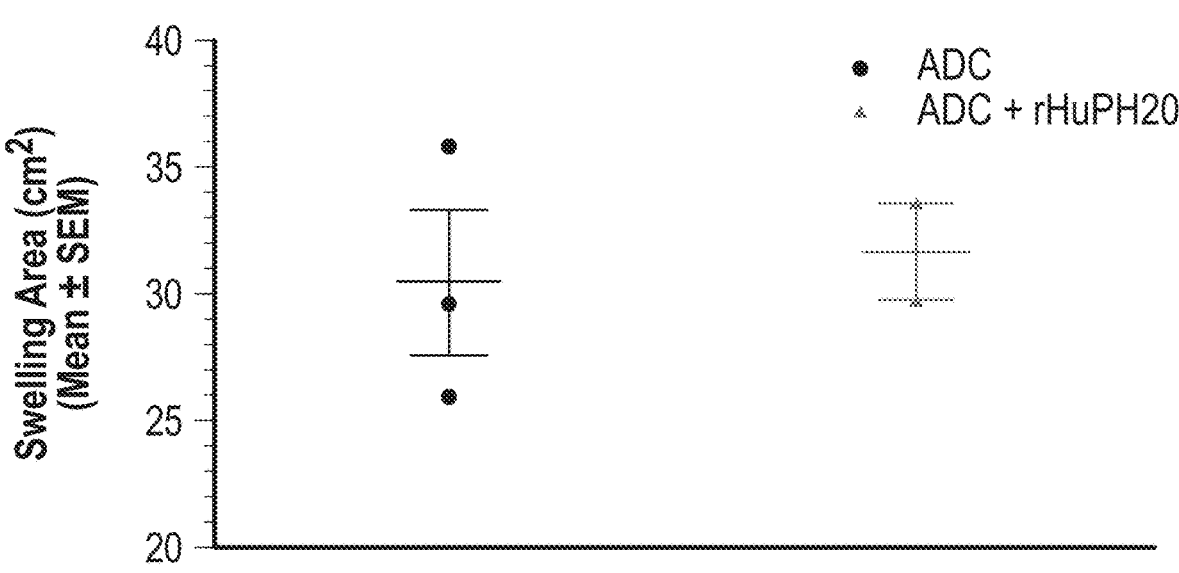
Figure 17C:
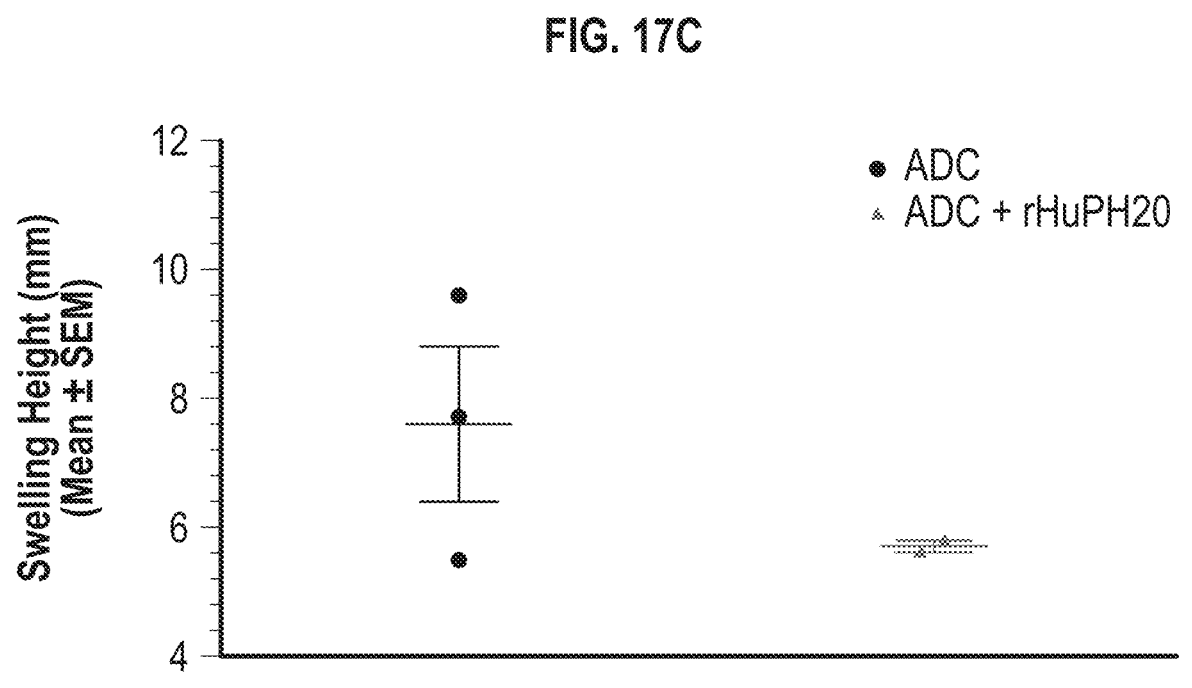

Post-injection bleb volume, area, and height for ADC and ADC+rHuPH20 calculated from the 3D images are summarized in Table 18. Individual post-injection bleb volume and height are shown graphically in FIG. 17A, FIG. 17B, and FIG. 17C. Because the pre-injection photo for AID #4493R was not able to be processed by the Vectra 3D software, the values for the ADC+rHuPH20 are shown as the mean of the two measured values.

TABLE 18

| Bleb volume, area and height after injection of ADC and ADC + rHuPH20 assessed using 3D imaging (mean ± SEM) | | | |
| --- | --- | --- | --- |
| | | Mean ± SEM | |
| Test Solution | Volume (mL) | Area (cm$^2$) | Height (mm) |
| ADC | 8.1 ± 0.7 | 30.5 ± 2.9 | 7.6 ± 1.2 |
| ADC + rHuPH20[a] | 7.2 ± 0.5 | 31.7 ± 1.9 | 5.7 ± 0.1 |
| % Increase/Decrease | −11% | +4% | −25% |

[a] n = 2

Qualitative assessments were taken immediately post-injection (T0) and daily thereafter. No erythema, swelling or induration was detected on D1, D2 or D3 post-injection (data not shown).

Post-Injection Erythema. No erythema was observed for either test solution following injection at any timepoint (data not shown).

Post-Injection Swelling Size. Post-injection swelling size ranged from slight (2) to severe (4) for ADC alone and from very slight (1) to moderate (3) for injections of ADC+rHuPH20.

Figure 18:
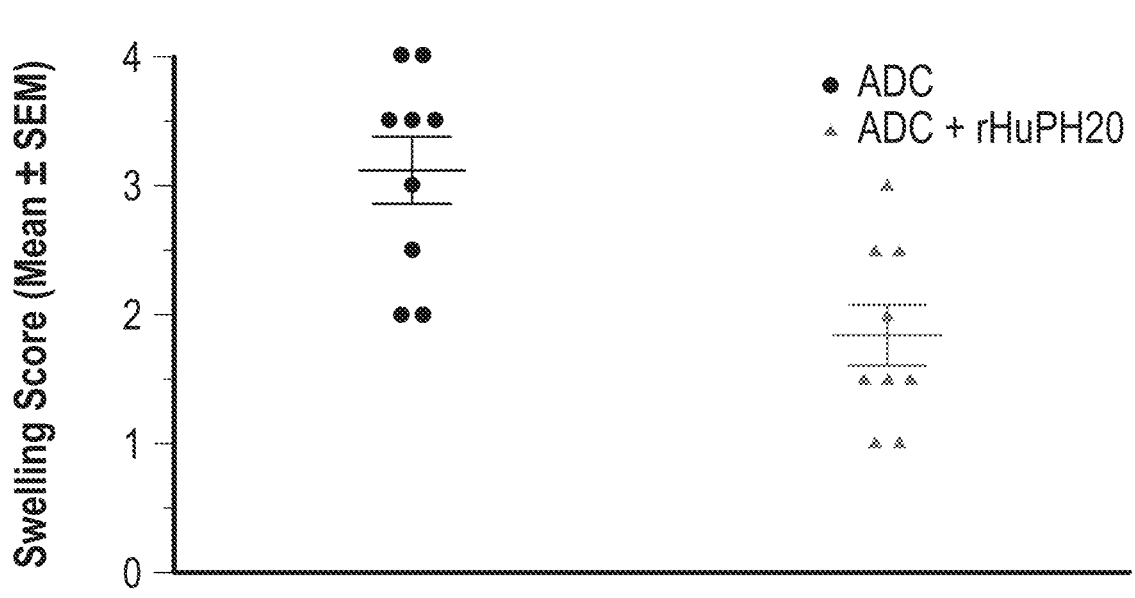
FIG. 18 is a chart of a qualitative assessment of post-injection swelling size measured by swelling score.

Scoring by three evaluators for swelling size (Mean±SEM) are summarized in Table 19 and shown in FIG. 18. No swelling was detected at the 24 h, 48h or 72h timepoints (data not shown).

TABLE 19

| Swelling scored post-injection for ADC and ADC + rHuPH20 (mean ± SEM) | | |
| --- | --- | --- |
| Test Solution | Swelling Score (Mean ± SEM) | % Decrease |
| ADC | 3.1 ± 0.3 | — |
| ADC + rHuPH20 | 1.8 ± 0.2 | −42% |

Figure 19:
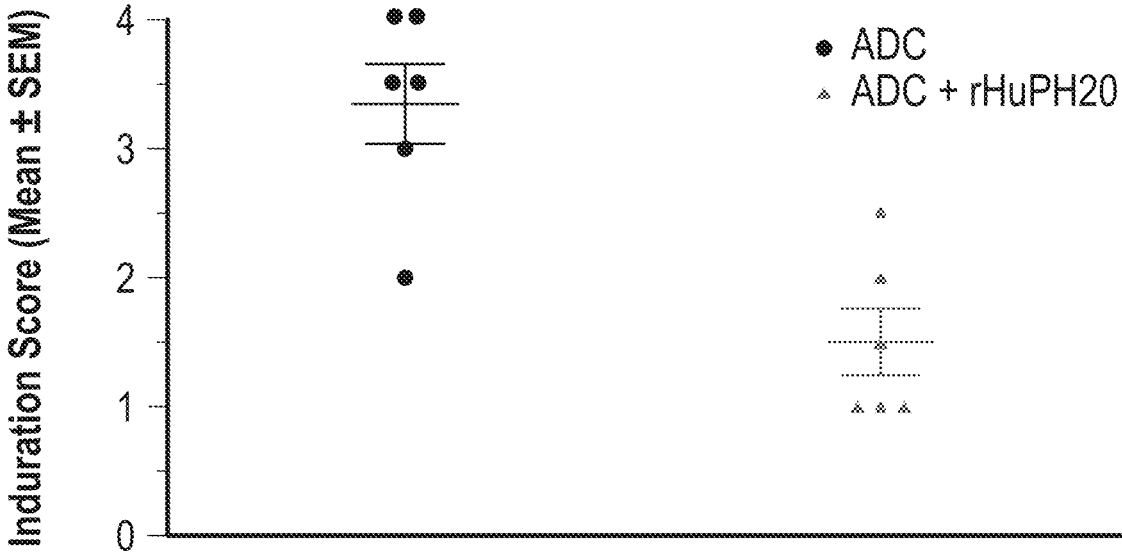
FIG. 19 is a chart showing qualitative assessment of post-injection induration (firmness) measured by induration score.
Figure 20A:
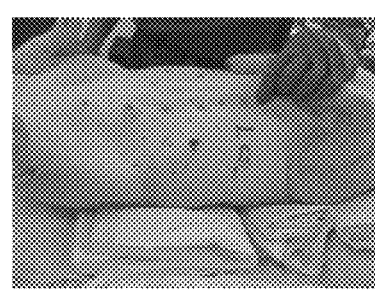
FIGS. 20A-20F show injection sites post-injection for different treatments and AID #.
Figure 20A:
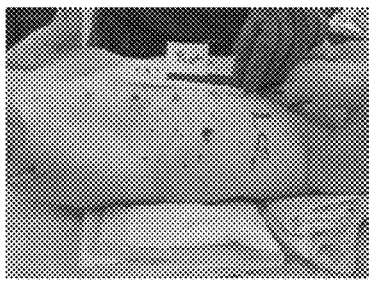
Figure 20A:
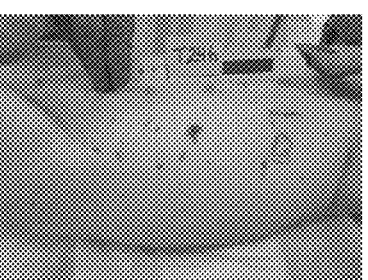
Figure 20A:
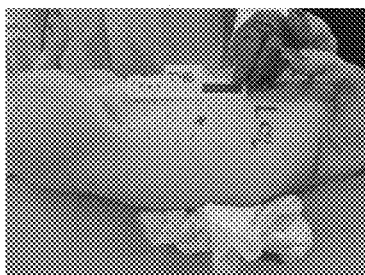
Figure 20A:
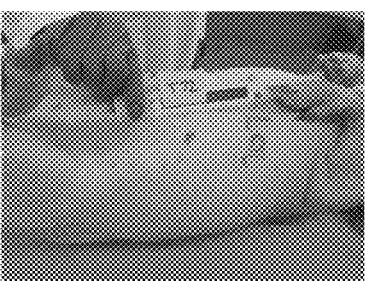
Figure 20B:
Figure 20B:
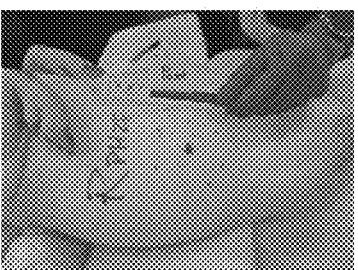
Figure 20B:
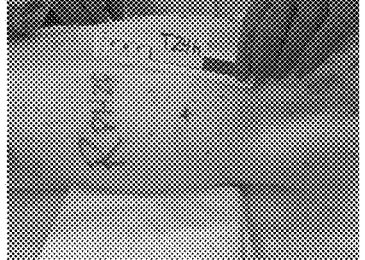
Figure 20B:
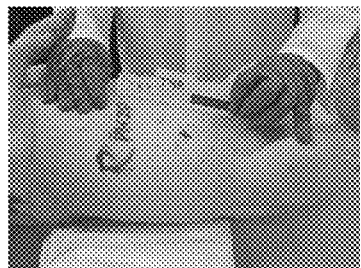
Figure 20B:
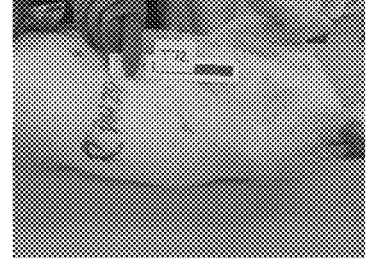
Figure 20C:
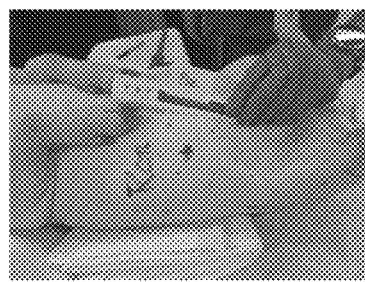
Figure 20C:
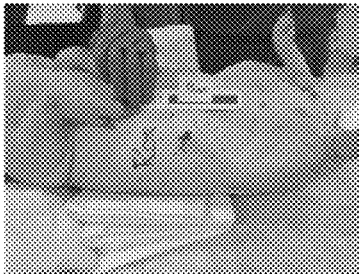
Figure 20C:
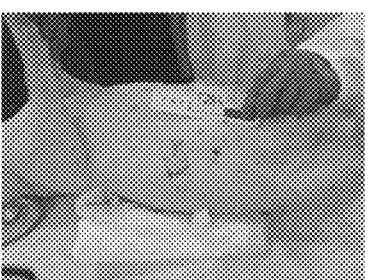
Figure 20C:
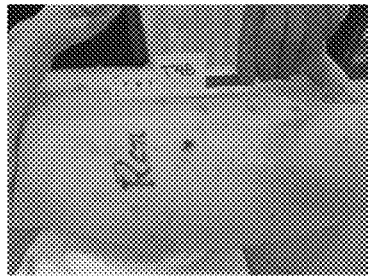
Figure 20C:
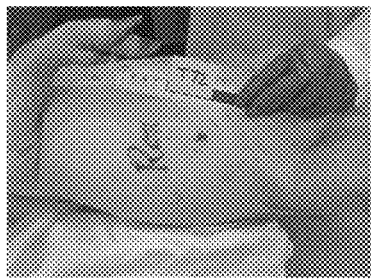
Figure 20D:
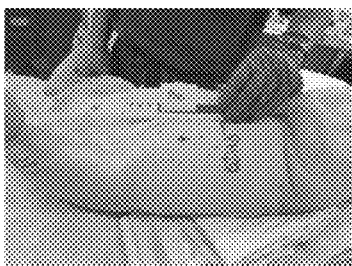
Figure 20D:
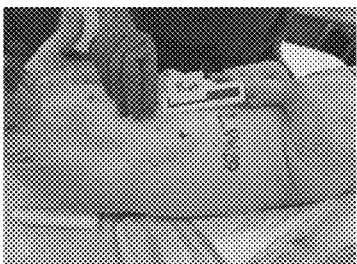
Figure 20D:
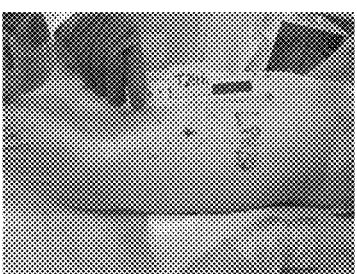
Figure 20D:
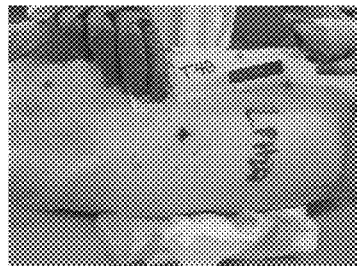
Figure 20D:
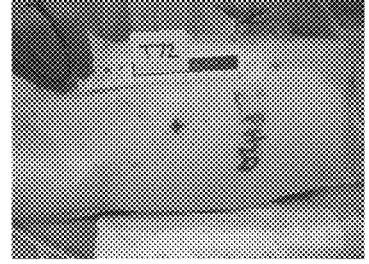
Figure 20E:
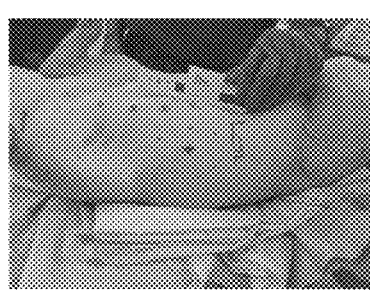
Figure 20E:
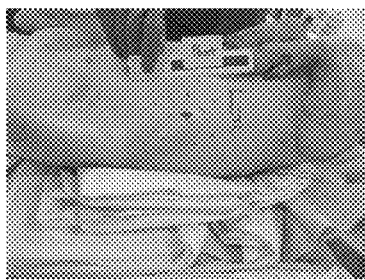
Figure 20E:
Figure 20E:
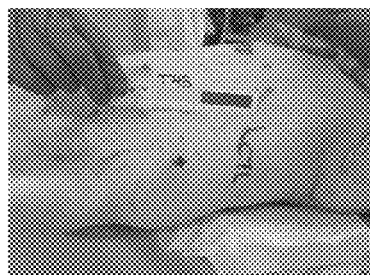
Figure 20E:
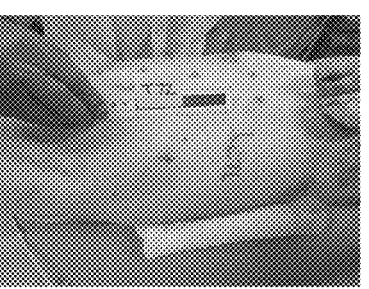
Figure 20F:
Figure 20F:
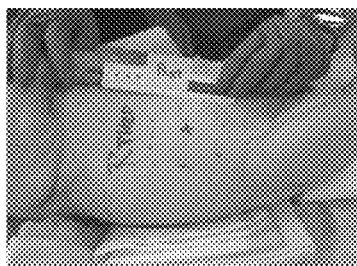
Figure 20F:
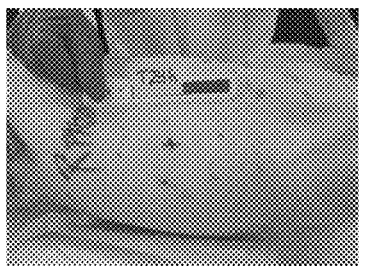
Figure 20F:
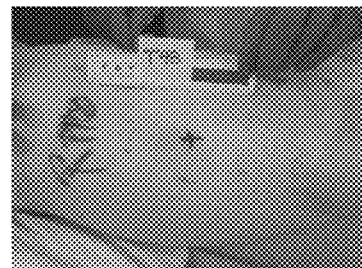
Figure 20F:
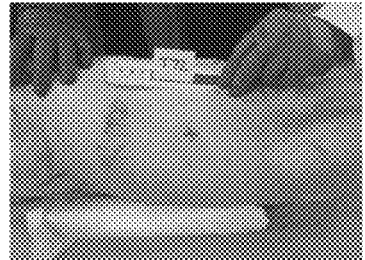
Figures 21A, 21B:
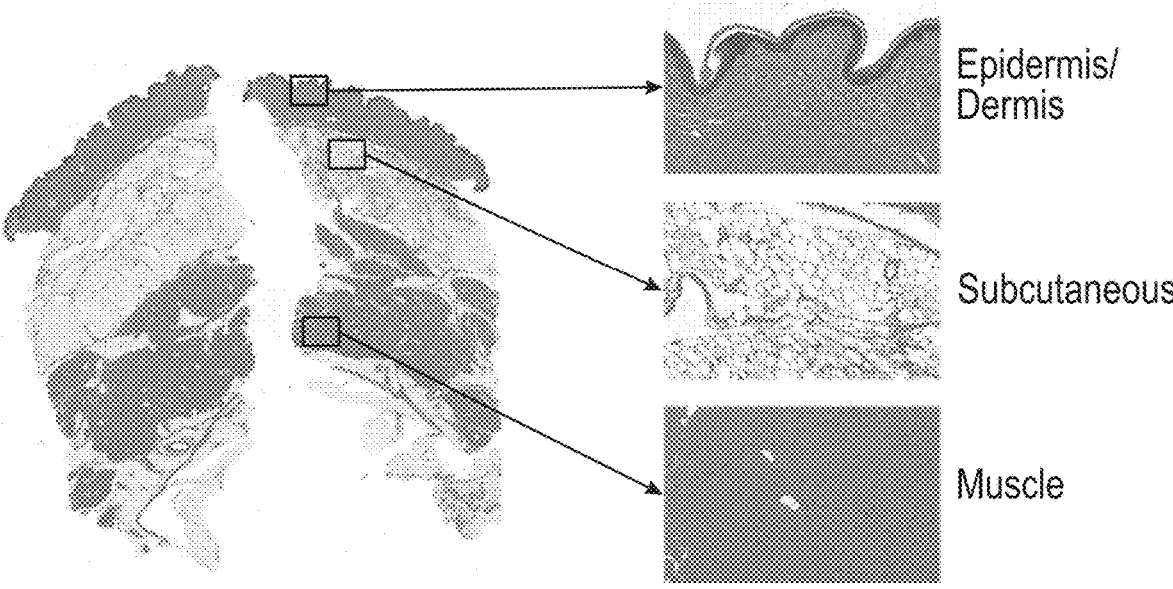
FIGS. 21A-21I show histological staining of tissues taken from injection sites post-injection for different treatments and AID #.
Figure 21C:
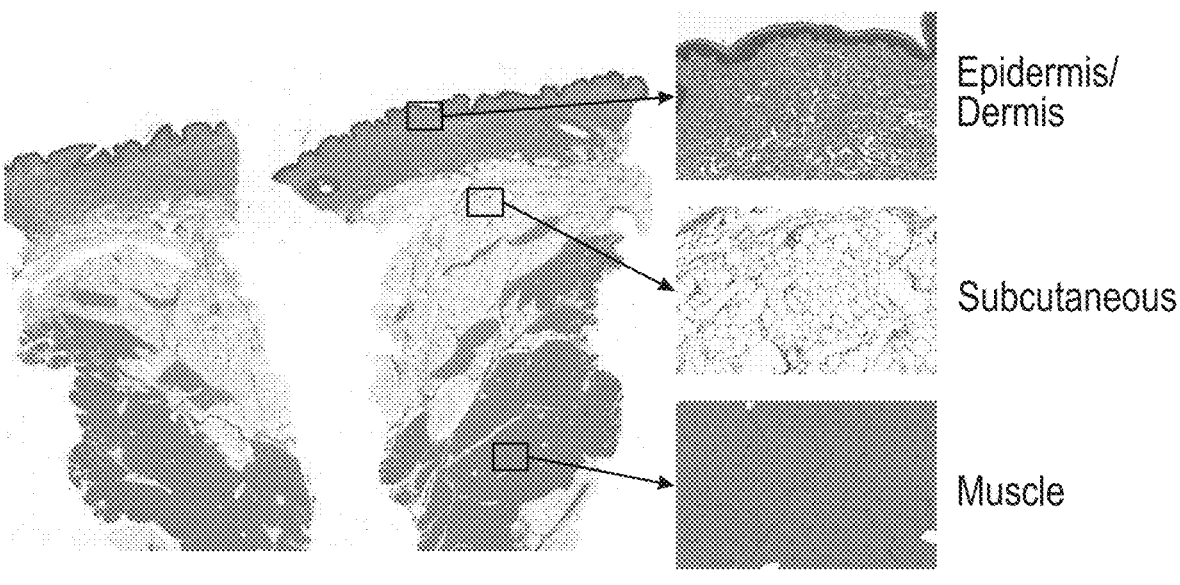
Figure 21D:
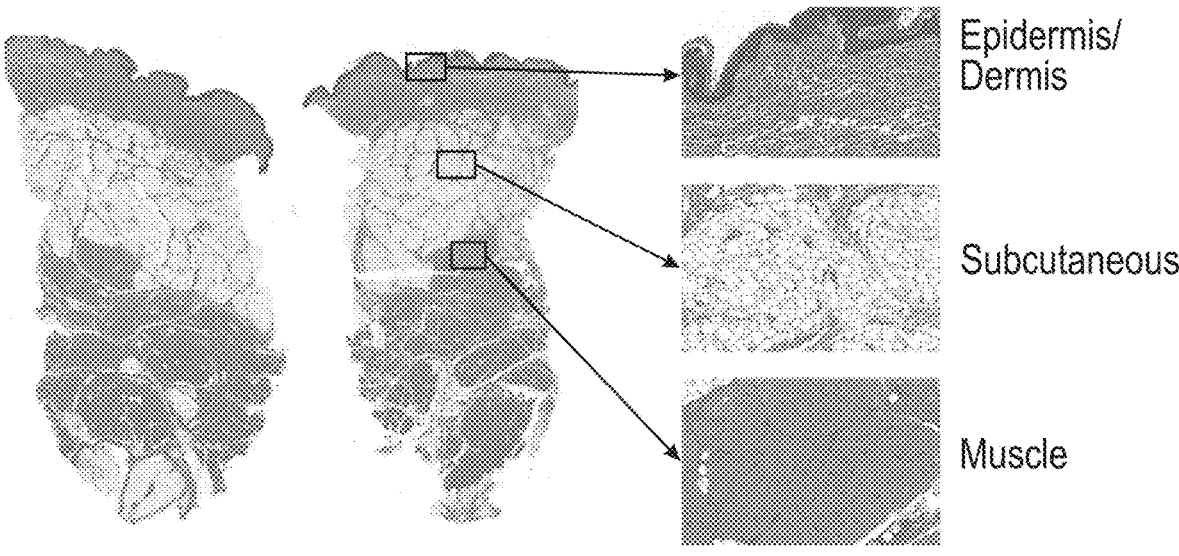
Figure 21E:
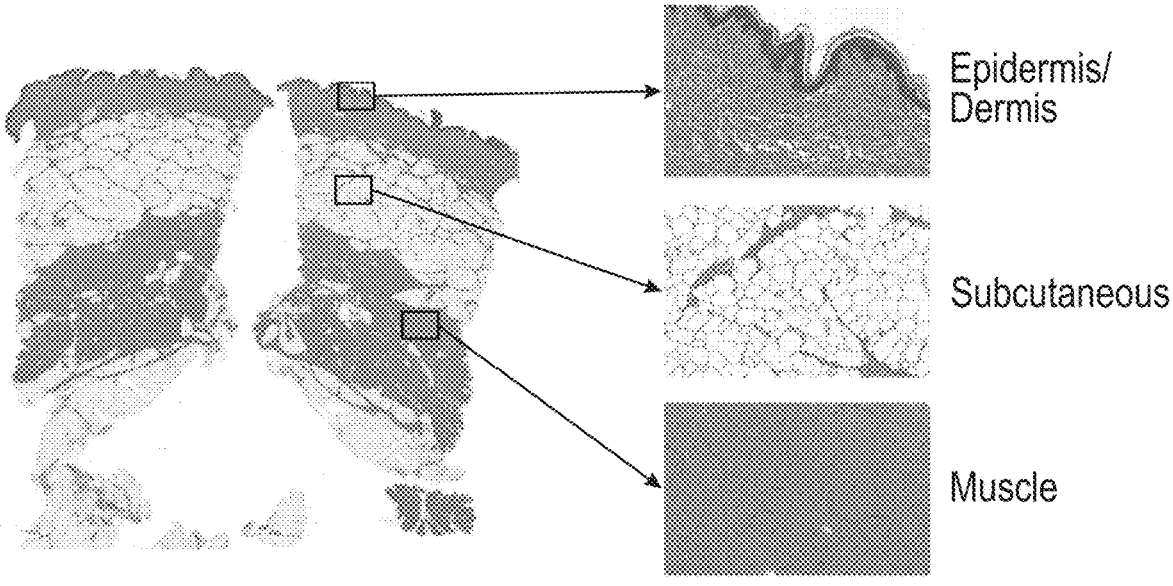
Figure 21F:
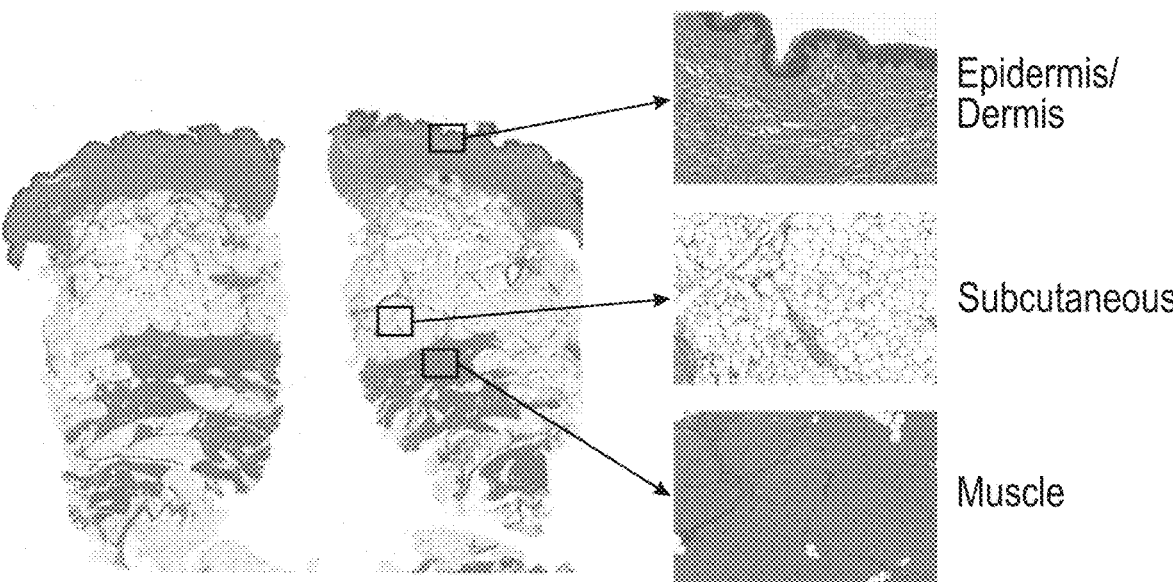
Figure 21G:
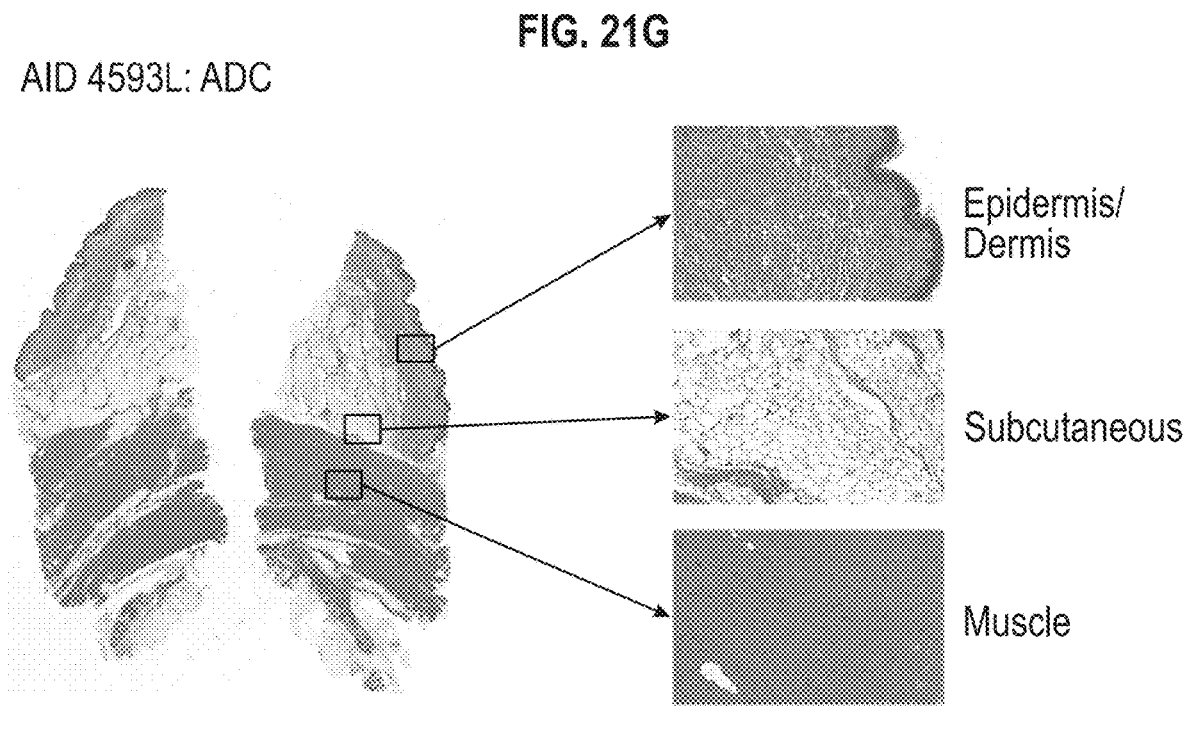
Figure 21H:
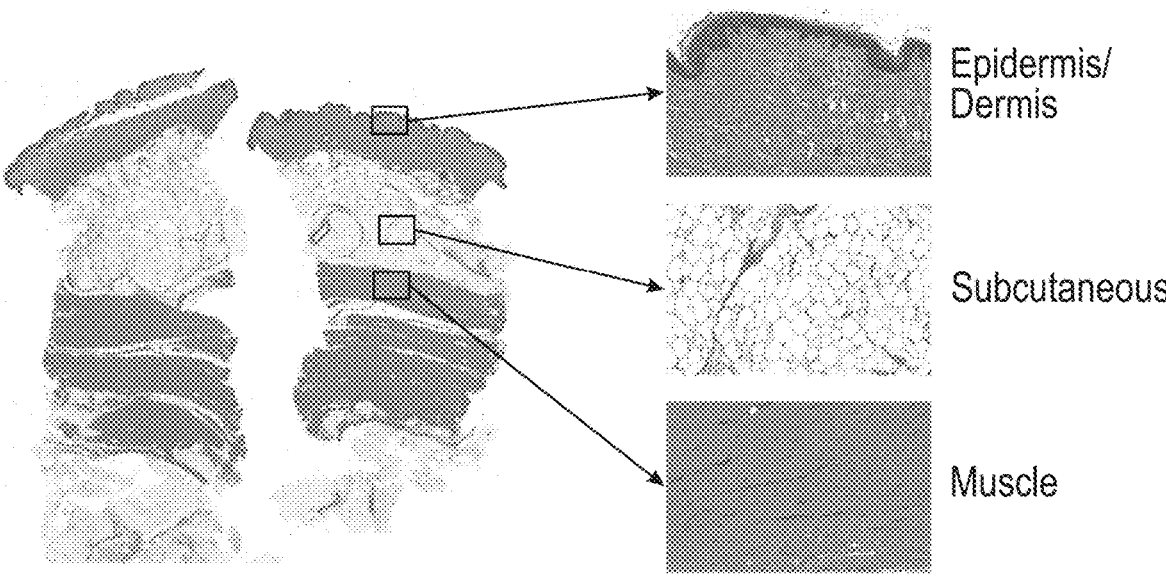
Figure 21I:
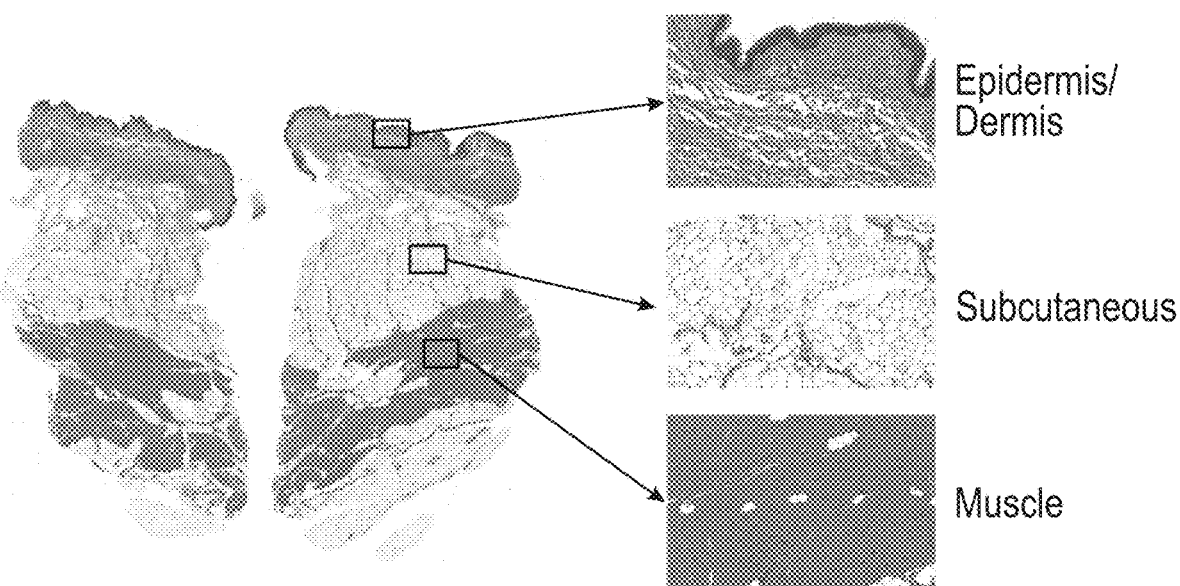

Post-Injection Firmness (Induration). The hardness (induration) of the post-injection blebs for ADC alone were found to be significantly firmer than the blebs that resulted from injection of ADC+rHuPH20 (p<0.05). No induration was detected at the 24 h, 48h or 72h timepoints (data not shown). Only two evaluators were available to score for induration and the values (Mean±SEM) are summarized in Table 20 and individual values are shown in FIG. 19. No induration was detected at the 24 h, 48h or 72h timepoints (data not shown).

TABLE 20

| Induration scores post-injection for ADC and ADC + rHuPH20 (mean ± SEM). | | |
|---|---|---|
| Test Solution | Induration Score (Mean ± SEM) | % Decrease |
| ADC | 3.3 ± 0.3 | — |
| ADC + rHuPH20 | 1.5 ± 0.3 | −55% |

The injection sites were photographed before and imme-diately post-injection and then at daily intervals up to 72 hours post-injection. Photographic images are shown in FIGS. 20A-20F. Histological Analysis of Post-Injection Tis-sue Samples. After fixation the samples were processed and embedded into paraffin to make formalin fixed paraffin embedded (FFPE) tissues sections Each tissue section was evaluated at three different tissue depths (1-2-3; low-me-dium-high). In addition to tissue samples from the injection site, a sample was taken from naïve untreated tissue for comparison. A summary of the histological findings is shown in Table 21.

TABLE 21

| Summary of Histological Findings | | | | |
|---|---|---|---|---|
| Sample ID | Level | Necrosis | Cell Infiltrates | Other/Comments |
| 4493L | 1 | 0 | 0 | 0 |
| ADC | 2 | 0 | 0 | 0 |
| | 3 | 0 | 0 | 0 |
| 4493 | 1 | 0 | 0 | 0 |
| Naïve | 2 | 0 | 0 | 0 |
| | 3 | 0 | 0 | 0 |
| 4493R | 1 | 0 | 0 | 0 |
| ADC + | 2 | 0 | 0 | 0 |
| rHuPH20 | 3 | 0 | 0 | 0 |
| 4498R | 1 | 0 | 2 focal SC | Multiple foci in SC; mildfocal epithelial keratosis |
| ADC | | | | |
| | 2 | 0 | 2 focal SC | Multiple foci in SC; mildfocal epithelial keratosis |
| | 3 | 0 | 2 focal SC | Multiple foci in SC; mildfocal epithelial keratosis |
| 4498 | 1 | 0 | 0 | 0 |
| Naïve | 2 | 0 | 0 | 0 |
| | 3 | 0 | 0 | 0 |
| 4498L | 1 | 0 | 0 | 0 |
| ADC + | 2 | 0 | 0 | 0 |
| rHuPH20 | 3 | 0 | 0 | 0 |
| 4593L | 1 | 0 | 0 | 0 |
| ADC | 2 | 0 | 0 | 0 |
| | 3 | 0 | 0 | 0 |
| 4593 | 1 | 0 | 0 | 0 |
| Naïve | 2 | 0 | 0 | 0 |
| | 3 | 0 | 0 | 0 |
| 4583R | 1 | 0 | 0 | 0 |
| ADC + | 2 | 0 | 0 | 0 |
| rHuPH20 | 3 | 0 | 0 | 0 |

Notably no findings occurred with the injections of ADC+ rHuPH20 whereas ⅓ of the injections of ADC alone showed mild focal epithelial keratosis in all levels of the tissue sample. In addition, there were 2 focal instances of [im-mune] cell infiltrates in the SC space. Histological images of tissue sections stained with hematoxylin and eosin (H&E) together with magnified images of the dermis, subcutaneous and muscle tissues (5×) of biopsies taken from the ADC±rHuPH20 injection sites and naïve skin are shown in FIG. 21A-21I.

The addition of rHuPH20 to the 10 mL dose of ADC was well tolerated when delivered subcutaneously. In addition to the tolerability this study showed:

HVAI devices with ADC+rHuPH20 had a reduced mean time of delivery (−10%) compared to injection times for ADC alone.

Back-leakage was extremely low and showed signifi-cantly less variability for HVAI injections with ADC+ rHuPH20, whereas injections of ADC alone had sub-stantial and highly variable amounts of back-leakage.

Post-injection bleb volume and height using caliper mea-surements were found to be significantly less for injec-tions of ADC+rHuPH20 compared to ADC alone.

Post-injection bleb height showed significantly less vari-ability between injection sites that contained rHuPH20 compared to those without.

Qualitative scoring of post-injection swelling size using a 5-point modified Draize scale showed that ADC+rH-uPH20 blebs were −42% compared to the size of blebs of ADC alone.

Qualitative scoring of post-injection induration showed that the ADC+rHuPH20 blebs were consistently softer (−55%) than the blebs that were assessed after injection of ADC alone.

Histological analysis showed that one of the injection sites with ADC alone resulted in histopathological findings that included mild focal keratosis and immune cell infiltrates in the subcutaneous space which may be indicative of a wound response to an acute buildup of injection pressure in the extracellular matrix.

No signs of tissue necrosis were observed suggesting that the payload of the ADC was intact and dispersed from the injection site.

Example 3: Evaluation of Subcutaneous Administration of an Antibody Drug Conjugate (Trodelvy®) with and without Recombinant Human Hyaluronidase PH20 (RhuPH20)

The objective of this study was to determine the local injection site tolerability following a subcutaneous admin-istration of an antibody drug conjugate (ADC). The ADC was administered either alone or co-mixed with recombinant human hyaluronidase PH20 (rHuPH20). For this study the ADC Sacituzumab govitecan was chosen as a representative test solution. This study utilized all the same protocols and parameters as set forth in Example 1 unless disclosed otherwise.

In this initial study one animal was used to assess the local tolerability of subcutaneous administration of the ADC delivered either alone or co-mixed with rHuPH20. For comparison, the animal also received SC administration of the antibody solution alone. Eight SC injections were administered on the abdomen of the animal; four injections were the ADC solution alone and four injections were the ADC co-mixed with rHuPH20. Each injection was one mL and was delivered using a pre-filled 3-cc syringe using a 26G×⅝-inch needle. Injection times were staggered in order to result in various exposure times to the test solutions and resulted in exposures of 0.5, 1, 2 and 4 hours. After the last timepoint, the animal was humanely euthanized. Following euthanasia, punch biopsies of each injection site were obtained and preserved in 10% formalin for histological analyses. Formalin-fixed paraffin sections (FFPE) were pre-pared of each tissue sample and used to prepare slides that were examined for any morphological changes that occurred as a result of the exposure to ADC alone or ADC+rHuPH20 co-mix.

Formulation

Prior to study start, the enzyme activity of the test solution was measured using an in vitro activity assay (VV-QWUAL-006751 formerly TM010) to confirm the concentration of rHuPH20 in the co-mix drug solution.

Pre-study Enzymatic Activity Testing of rHuPH20 in Test Solutions. A sample of the ADC+rHuPH20 was tested for hyaluronidase activity and the enzyme activity is shown in Table 22.

TABLE 22

| Pre-study enzymatic activity testing of rHuPH20 in test solution. | |
| --- | --- |
| Test Solution | Pre-study Enzyme Activity (U/mL ± SD) |
| ADC + rHuPH20 | 2237 ± 42 |

This exploratory study assessed the local tolerability of an approved antibody-drug conjugate (Sacituzumab govitecan) with and without rHuPH20. In this initial study one animal was treated and received four 1-mL injections of the ADC alone and four 1-mL injections of the co-mix of ADC+rHuPH20. Injection times were staggered in order to result in various exposure times to the test solution and resulted in exposures of approximately 0.5, 1, 2 and 4 hours. The ADC was co-mixed with rHuPH20 so that the final concentration was approximately 2000 U/mL (Table 23).

TABLE 23

| | | Description of Treatments. | | | |
| --- | --- | --- | --- | --- | --- |
| Cohort | Test Solution | Dose Volume (mL) | # of Injections | [rHuPH20] (U/mL) | Exposure Time (h) |
| 1 | ADC | 1.0 | 4 | 0 | 0.5, 1, 2, 4 |
| 2 | ADC + rHuPH20 | 1.0 | 4 | 2000 | 0.5, 1, 2, 4 |

At each timepoint two injections were given to the animal: one of the ADC solution alone and one of the ADC solution co-mixed with rHuPH20 on the diagonal contralateral side of the animal.

Each injection was one mL and was delivered using a pre-filled 1-cc syringe. After the last timepoint, the animal was humanely euthanized. After euthanasia, punch biopsies of each injection site were obtained and preserved in 10% formalin for histological analyses.

Figure 22:
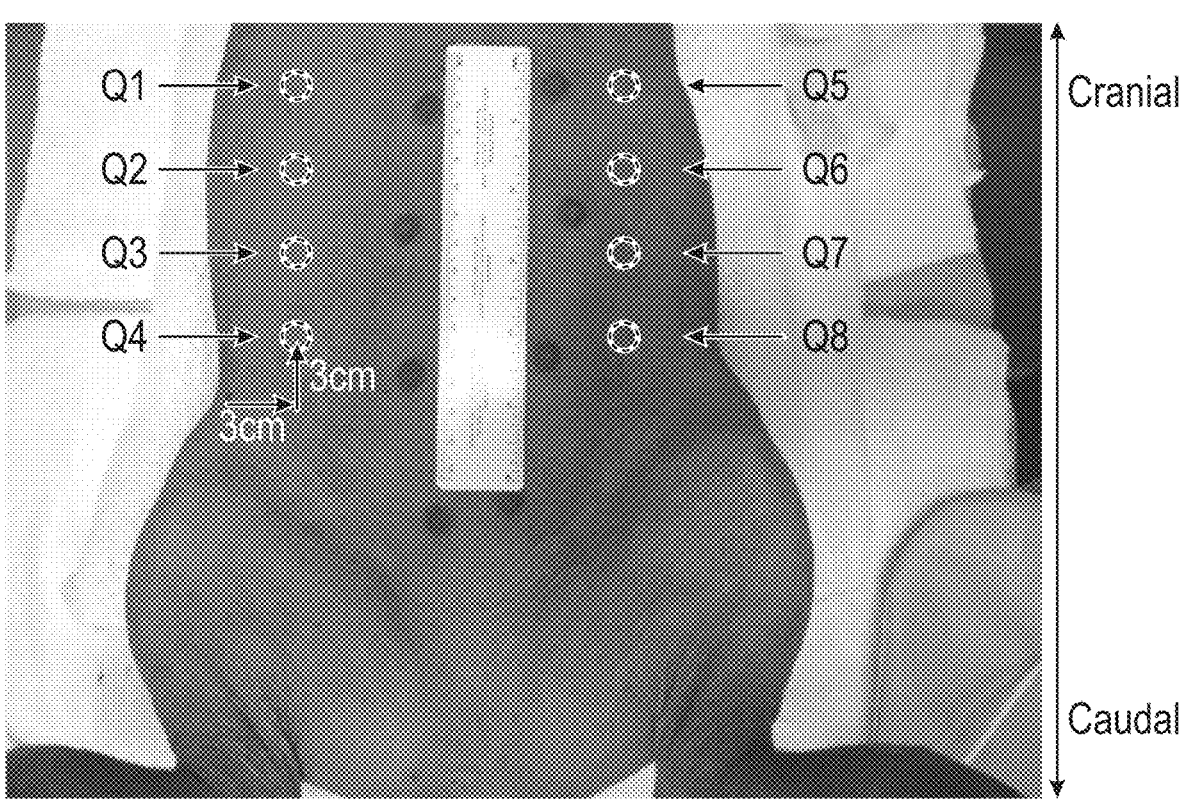
FIG. 22 shows injection sites Q1-Q8 before injection.

Following anesthetization, the abdominal region was cleaned with Nolvasan followed by wiping the injection site with gauze containing 70% isopropanol and wiped dry with sterile gauze. After drying the eight injection sites were marked (Q1-Q8) and are shown in FIG. 22.

The SC injections were administered on the abdomen of the animal. At each timepoint two injections were given to the animal—one injection of Sacituzumab govitecan alone followed by one injection on the diagonal contralateral side of the animal of Sacituzumab govitecan+rHuPH20.

Four injection sites were located on each side of the animal (Q1-Q4: right abdomen; Q5-Q8: left abdomen) with the lowest sites located 3 cm toward the midline of the animal from the midpoint of the inguinal fold and approximately 3 cm cranially (see below; sites Q7 & Q8). Injection sites (Q1-Q4 & Q5-Q8) were spaced approximately 4 cm apart. The test article and injection time associated for each of the injection sites are described in Table 24.

TABLE 24

| | | Summary of Injection Sites. | |
| --- | --- | --- | --- |
| Cohort | Test Solution | Injection Site | Total Exposure Time |
| 1 | ADC | Q1 | 4 h |
| | | Q5 | 2 h |
| | | Q3 | 1 h |
| | | Q7 | 0.5 h |
| 2 | ADC + rHuPH20 | Q8 | 4 h |
| | | Q4 | 2 h |
| | | Q6 | 1 h |
| | | Q2 | 0.5 h |

Each of the injection sites were marked with a permanent marker and then photographed prior to needle insertion. The procedure began with the injection at Injection Site Q1 with the injection of 1 mL SC injection of ADC followed by an injection on the diagonal contralateral side (Q8) which received a 1 mL SC injection of ADC+rHuPH20. Additional injections followed at sites Q5-Q4, Q3-Q7 and Q7-Q2 for exposure times of 2, 1 and 0.5 hours, respectively. Injection sites were photographed at each timepoint. At the end of study, the animal was humanely euthanized. After euthanasia 12 mm punch biopsies were obtained from each injection site and preserved in 10% formalin for tissue processing, paraffin embedding and eventual histological analyses by a licensed pathologist. After obtaining the punch biopsies the animal carcass was removed and disposed.

Figure 23:
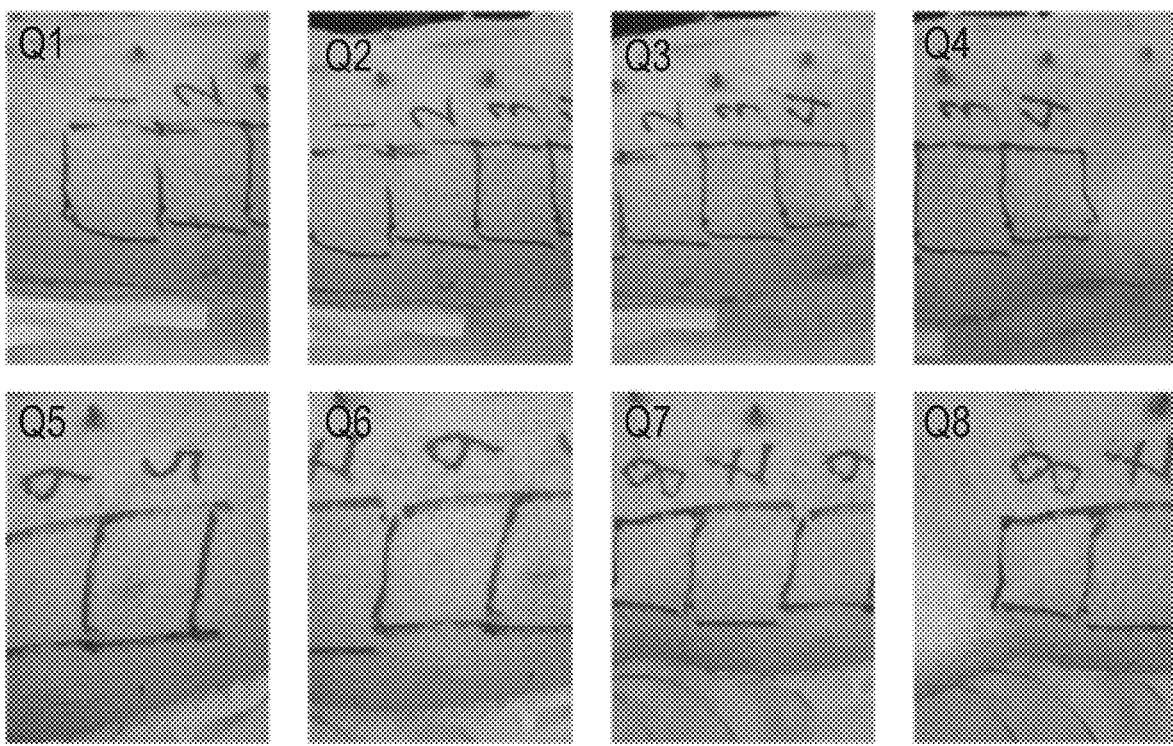
FIG. 23 shows close-up views of injection sites Q1-Q8 before injection.
Figure 24:
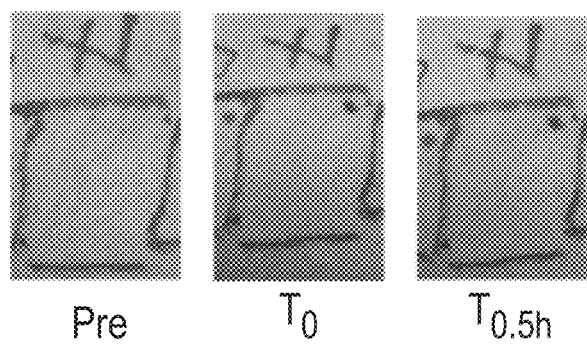
FIG. 24 shows injection site Q7 (ADC) and Q2 (ADC+rHuPH20): 0-0.5 h.
Figure 24:
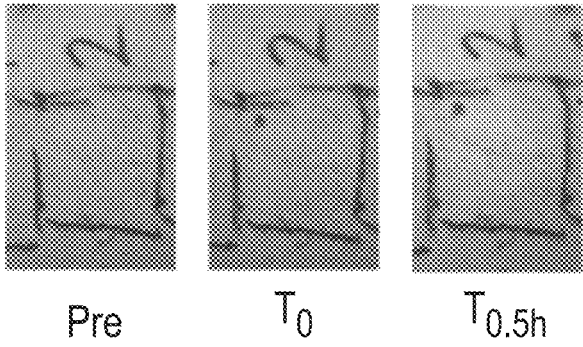
Figure 25:
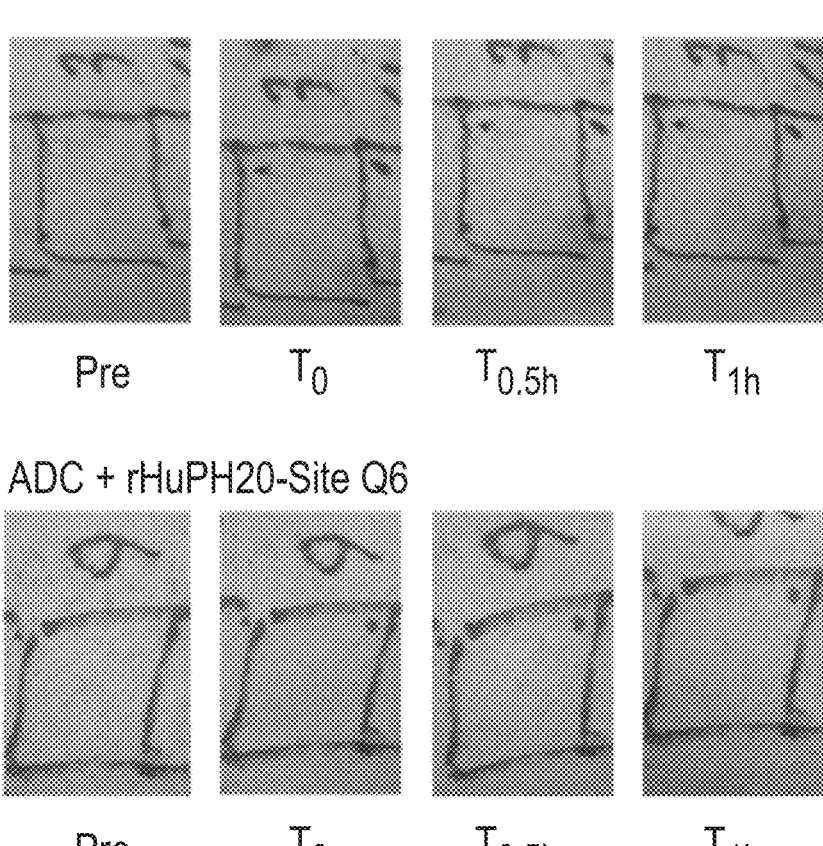
FIG. 25 shows injection site Q3 (ADC) and Q6 (ADC+rHuPH20): 0-1 h.
Figure 26:
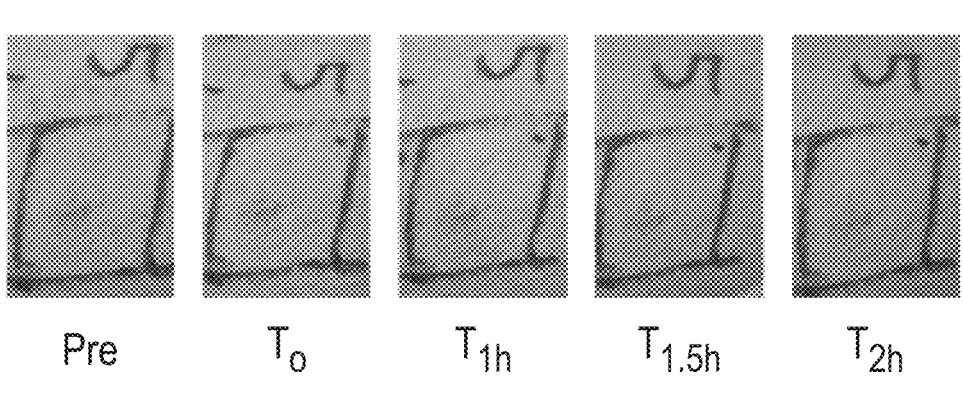
FIG. 26 shows injection site Q5 (ADC) and Q4 (ADC+rHuPH20): 0-2 h.
Figure 26:
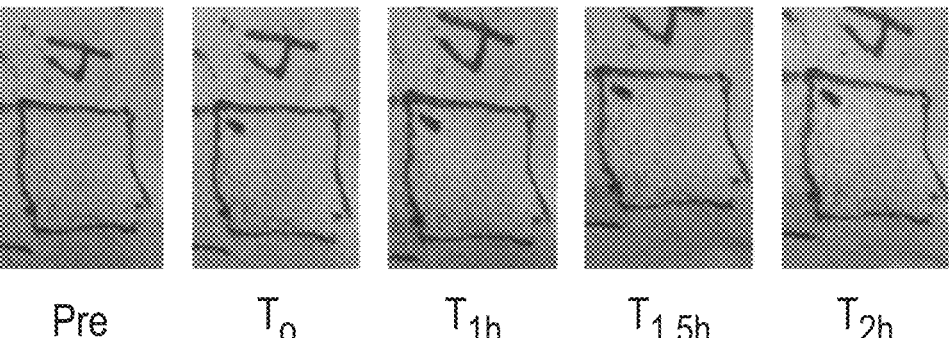
Figure 27:
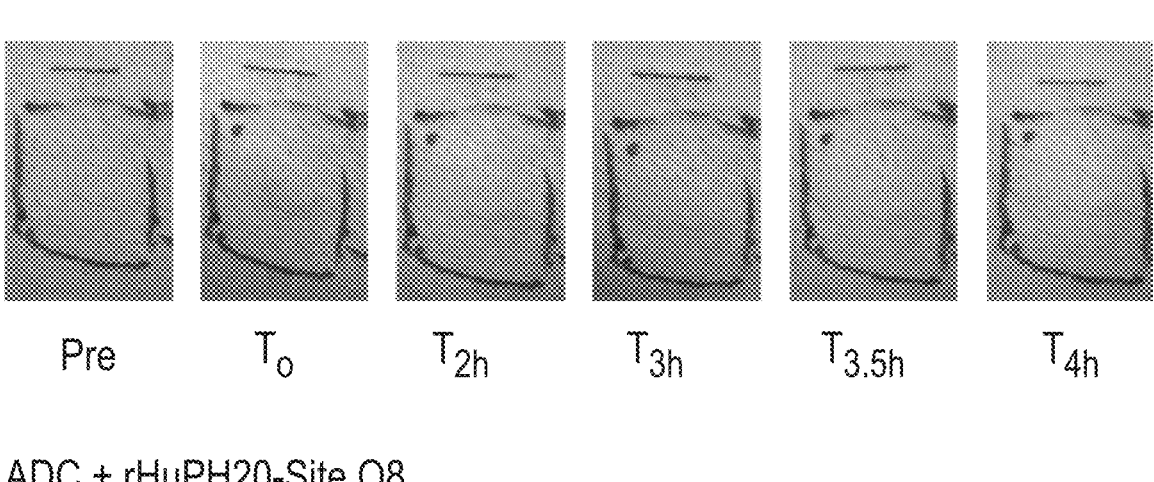
FIG. 27 shows injection site Q1 (ADC) and Q8 (ADC+rHuPH20): 0-4 h.
Figure 27:
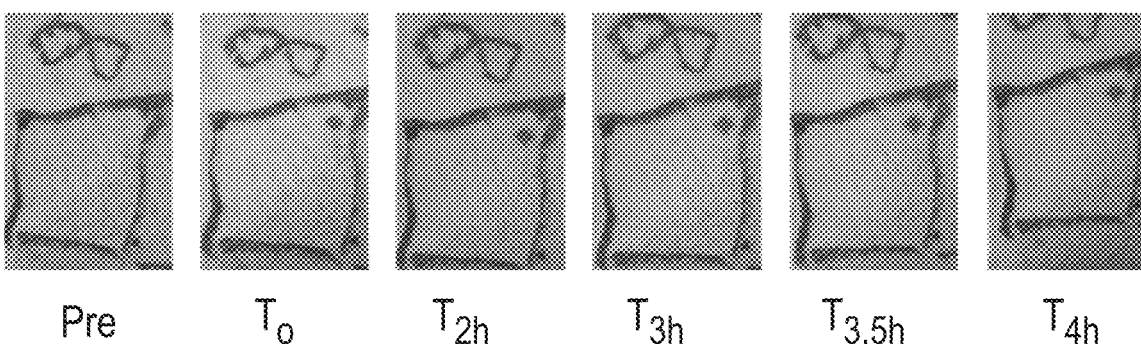
Figure 28A:
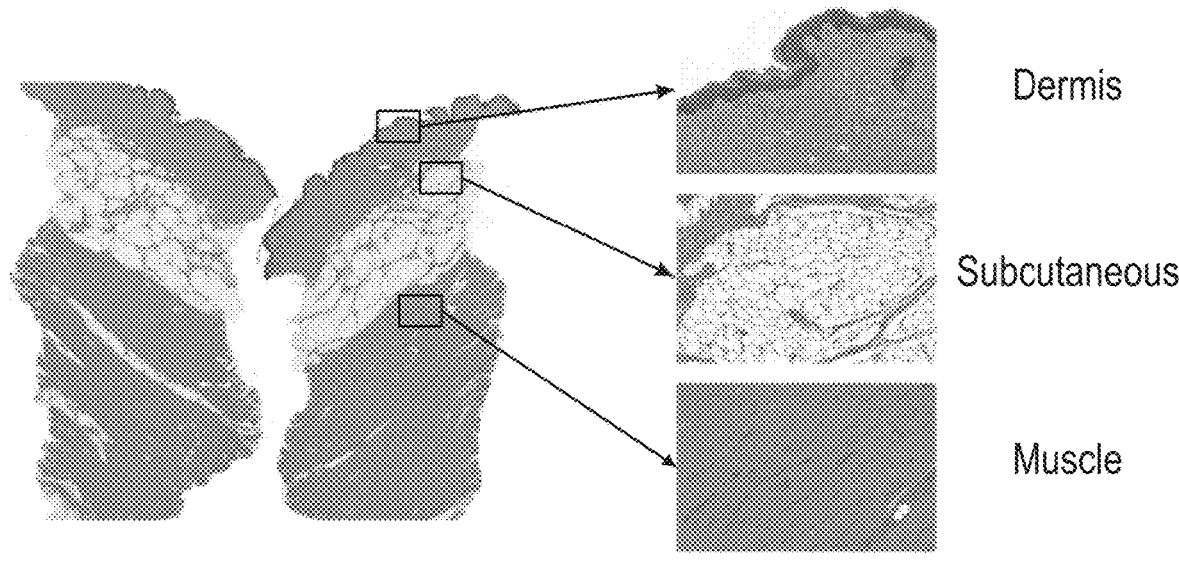
FIGS. 28A-28J show histological staining of tissue samples taken from injection sites.
Figure 28B:
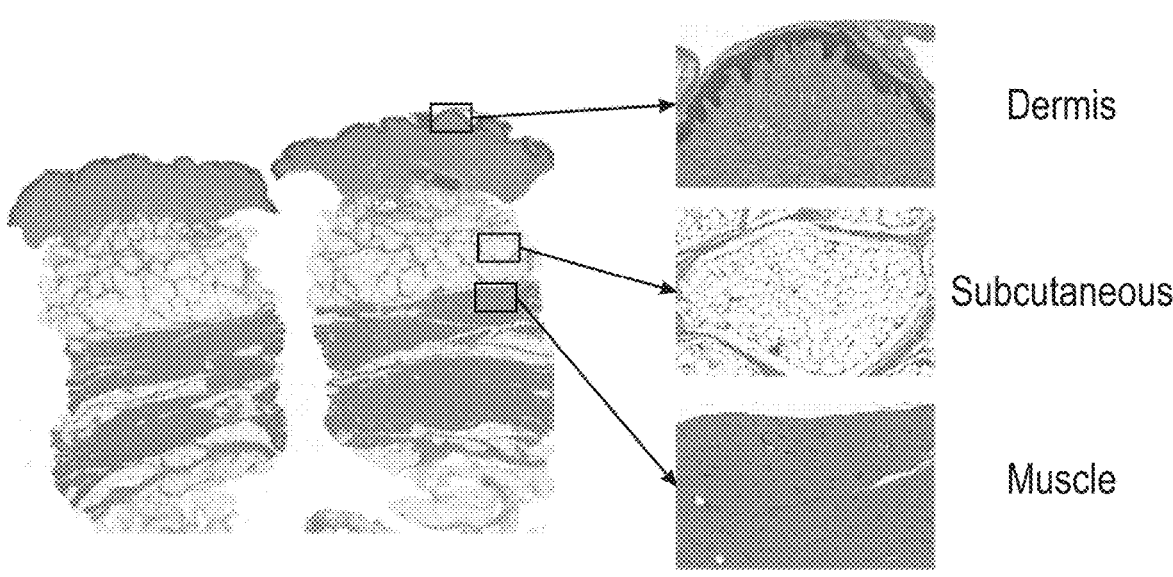
Figure 28C:
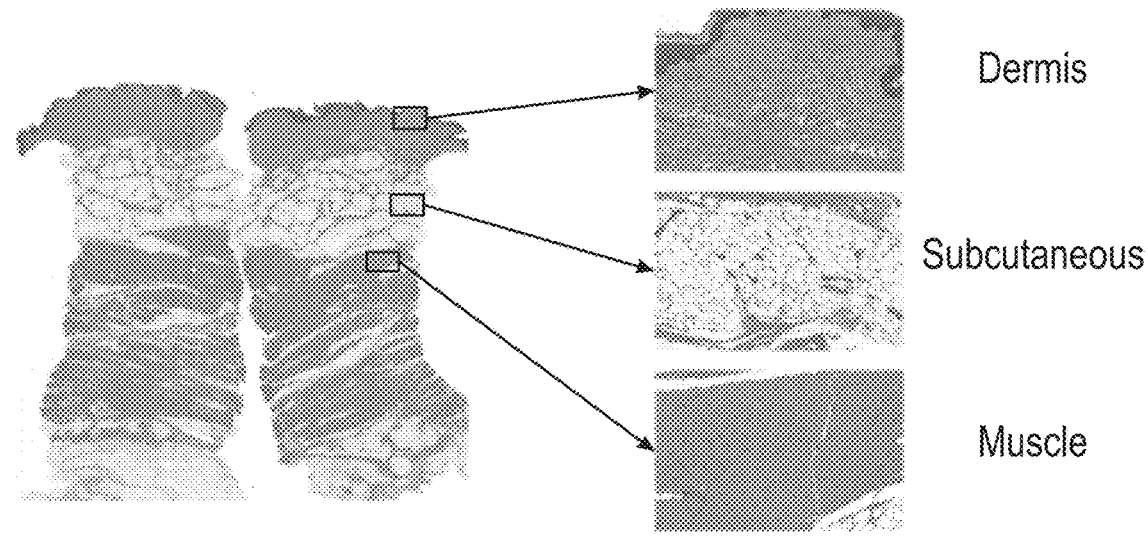
Figure 28D:
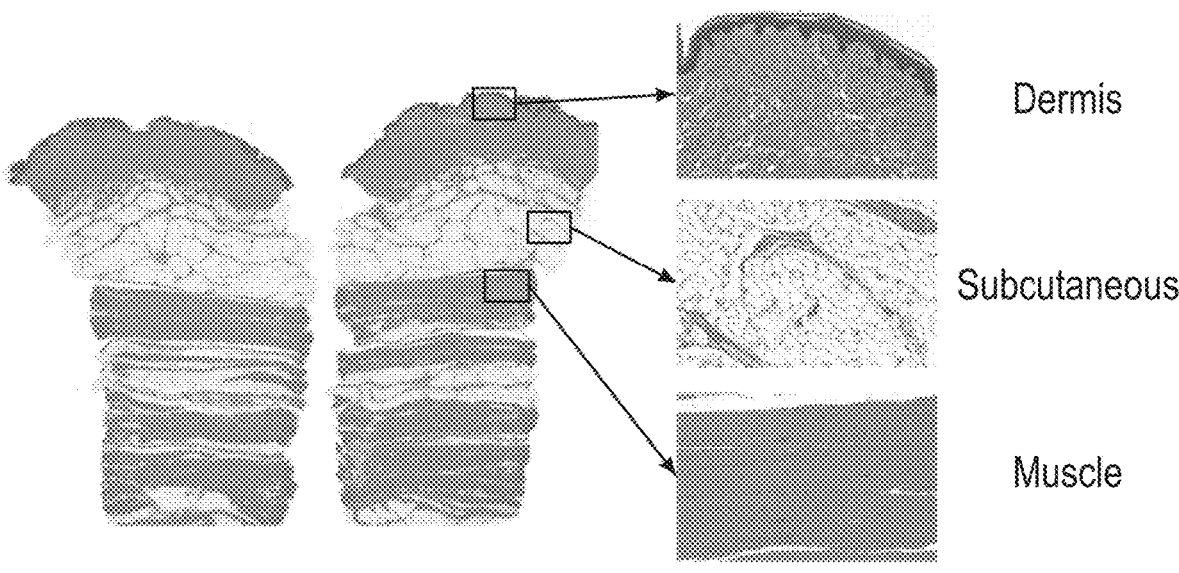
Figure 28E:
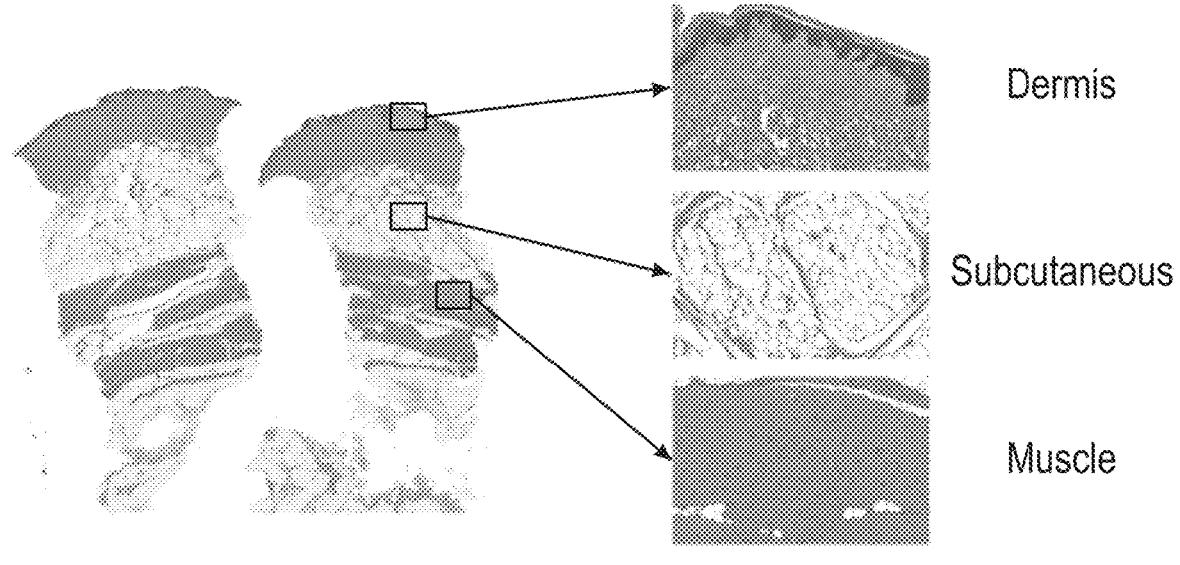
Figure 28F:
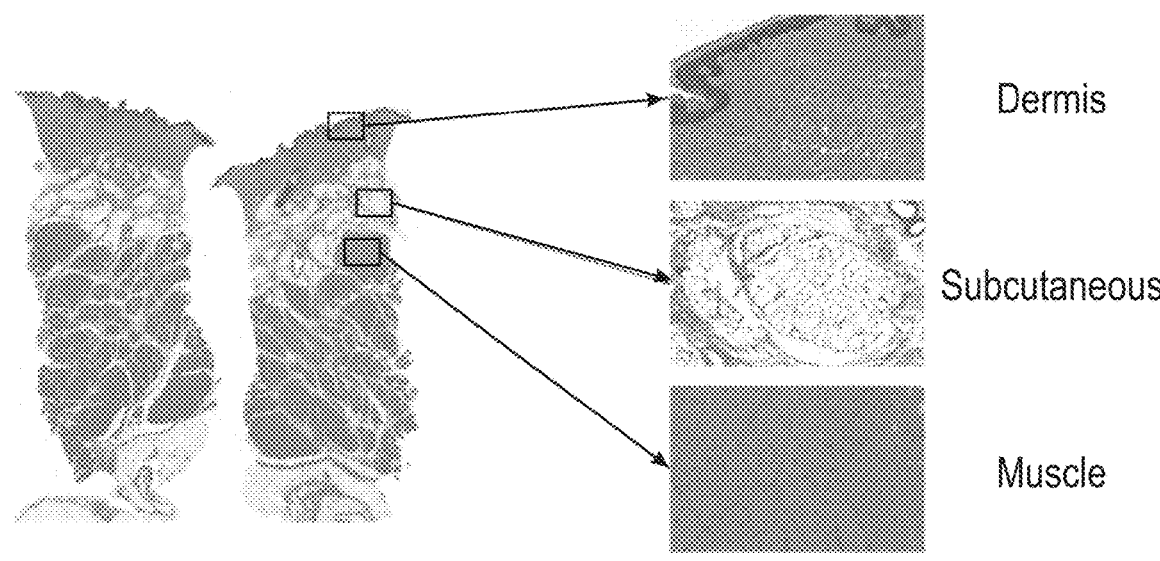
Figure 28G:
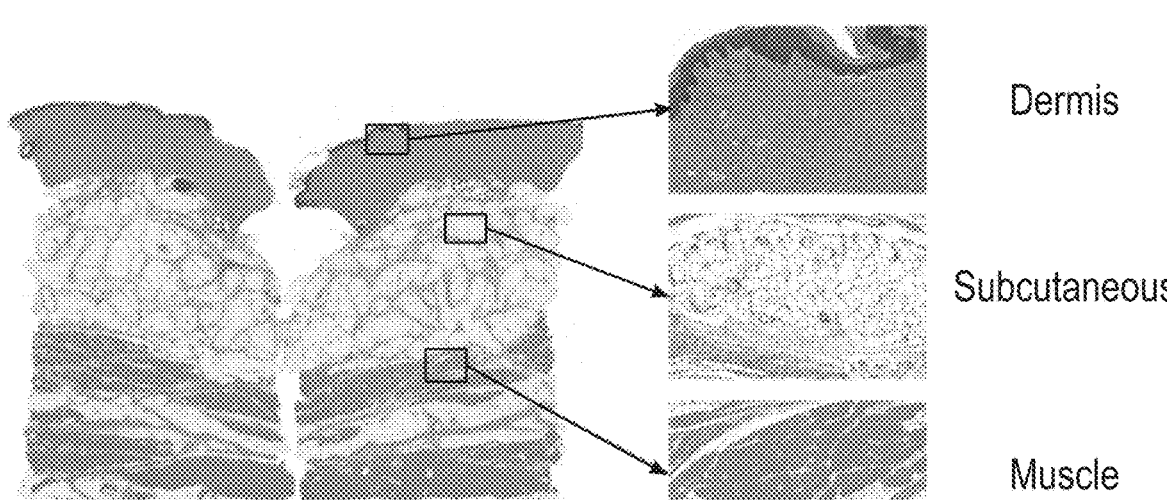
Figure 28H:
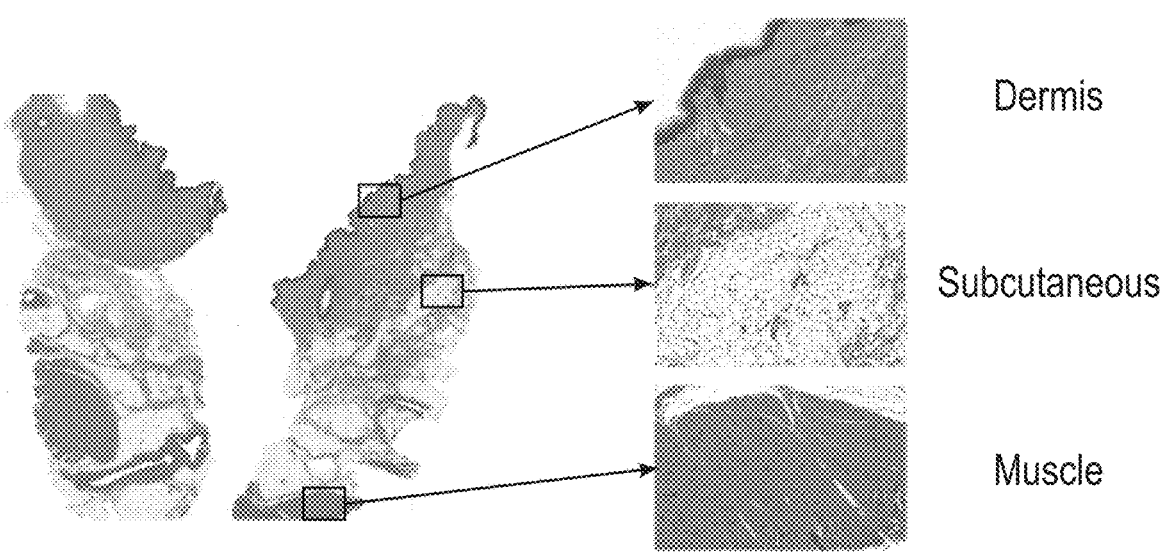
Figure 28I:
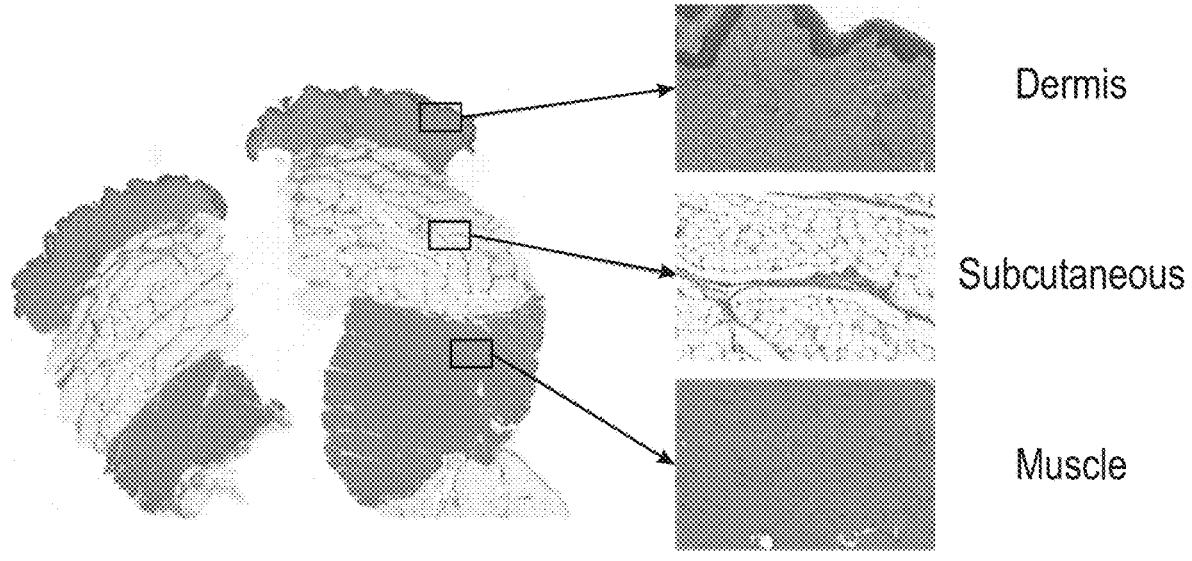
Figure 28J:
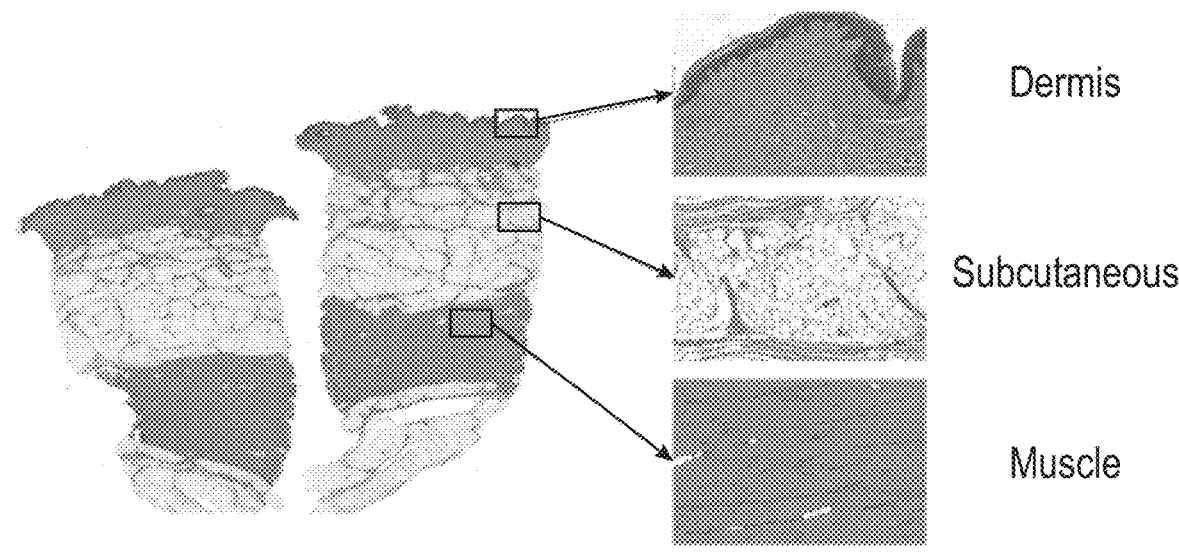

The injection sites were photographed at each timepoint. The pre-injection photos are shown in FIG. 23. The shortest exposure was 0.5 hours and images of the injection site at $T_0$ and $T_{0.5}$ h are shown in FIG. 24. Images of injection site Q3 (ADC) and Q6 (ADC+rHuPH20) taken at $T_0$ and T1h are shown in FIG. 25. Images of injection site Q5 (ADC) and Q4 (ADC+rHuPH20) taken at $T_0$, T1h and T2h are shown in FIGS. 26 and images of injection site Q1 (ADC) and Q8 (ADC+rHuPH20 taken at $T_0$, T1h, T2h and T4h are shown in FIG. 27.

After fixation, the samples were processed and embedded into paraffin to make formalin fixed paraffin embedded (FFPE) tissues sections Each tissue section was evaluated at three different tissue depths (1-2-3; low-medium-high). In addition to tissue samples from the injection site, a sample was taken from two naïve untreated tissue sites for comparison. Tissue sections were prepared and stained with hematoxylin and eosin for pathohistological evaluation. Notably no findings occurred with the injections of either Sacituzumab govitecan or Sacituzumab govitecan+rHuPH20. Histological images of tissue sections stained with hematoxylin and eosin (H&E) together with magnified images of the dermis, subcutaneous and muscle tissue (5×) of biopsies taken from the Trodelvy±rHuPH20 injection sites and naïve skin are shown in FIGS. 28A-28J.

Both injections of the ADC alone and the ADC co-mixed with rHuPH20 demonstrated local skin tolerability when exposure times were 4 hours or less. In addition to this tolerability, this study showed No pathophysiological findings in any skin component (epidermis-dermis, subcutaneous space or muscle layer).

Histological comparison of skin sections from both the ADC and the ADC+rHuPH20 appear comparable.

Longer exposures may be required to demonstrate if differences can be detected between treatment groups.

Example 4: Summary of Large Volume ADC Studies

This study utilized all the same protocols and parameters as set forth in Example 1 unless disclosed otherwise.

Study #1

Objectives

Assess local tolerability of high dose ADC vs. ADC+ rHuPH20

20 mL injection volume; 7.5 mm injection depth; 23G B-D needle

Delivery: 10 mg/mL; 5 mL/min (~10 mg/kg)

Endpoints

Back-Leakage measured post-injection (30 sec)

Bleb Size (Volume, Area, Height) measured at T0, T15, T30

Qualitative assessment of Erythema, Swelling and Induration overtime (T0, T15, T30, T2h and T24h); Daily observations through 72 h Test Articles: ADC (10 mg/mL)±rHuPH20 (2000 U/mL)

Figure 29:
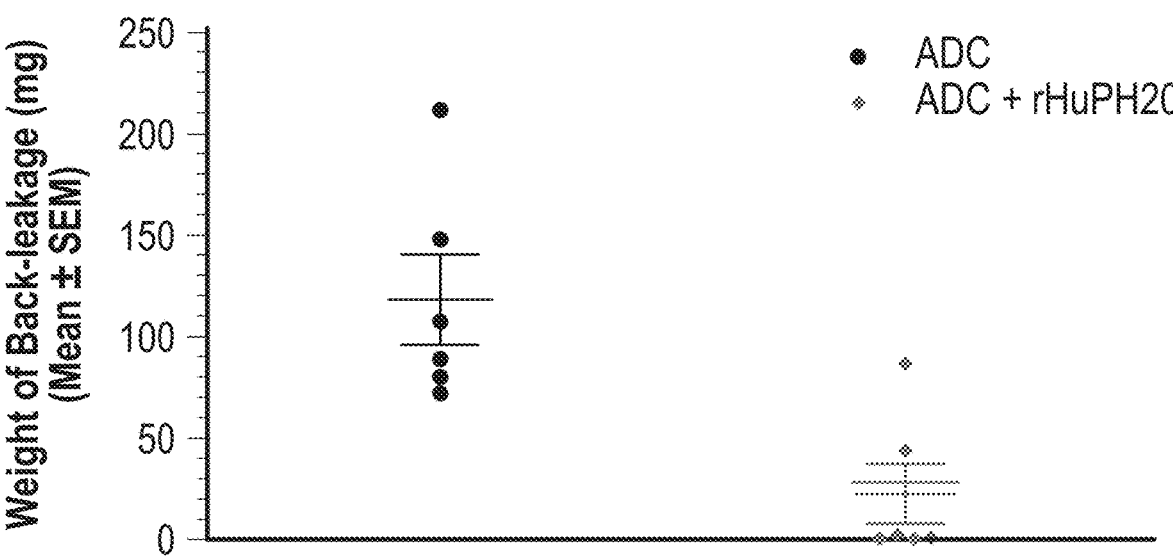
FIG. 29 is a chart of post-injection back-leakage of ADC and ADC+rHuPH20.

Results: Post-injection Back-leakage is significantly reduced with rHuPH20 (Table 25, FIG. 29).

TABLE 25

| Test Solution | Back-leakage (mg ± SEM) | % Decrease |
|---|---|---|
| ADC | 118.4 ± 21.8 | ~81%* |
| ADC + rHuPH20 | 22.5 ± 14.7 | |

Figure 30A:
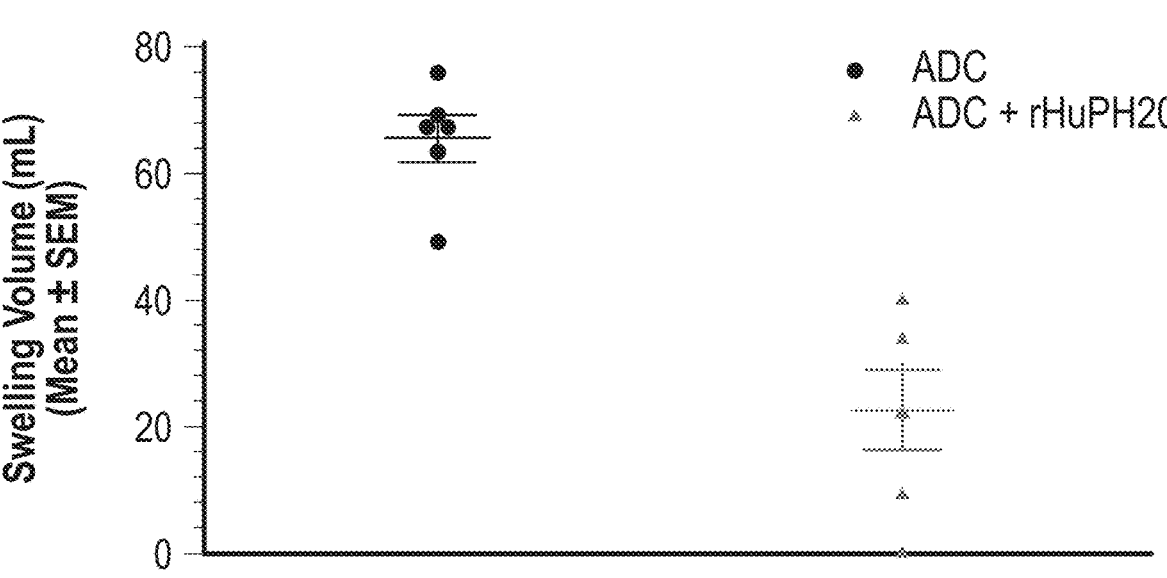
FIG. 30A is a chart of bleb volume of ADC and ADC+rHuPH20.
Figure 30B:
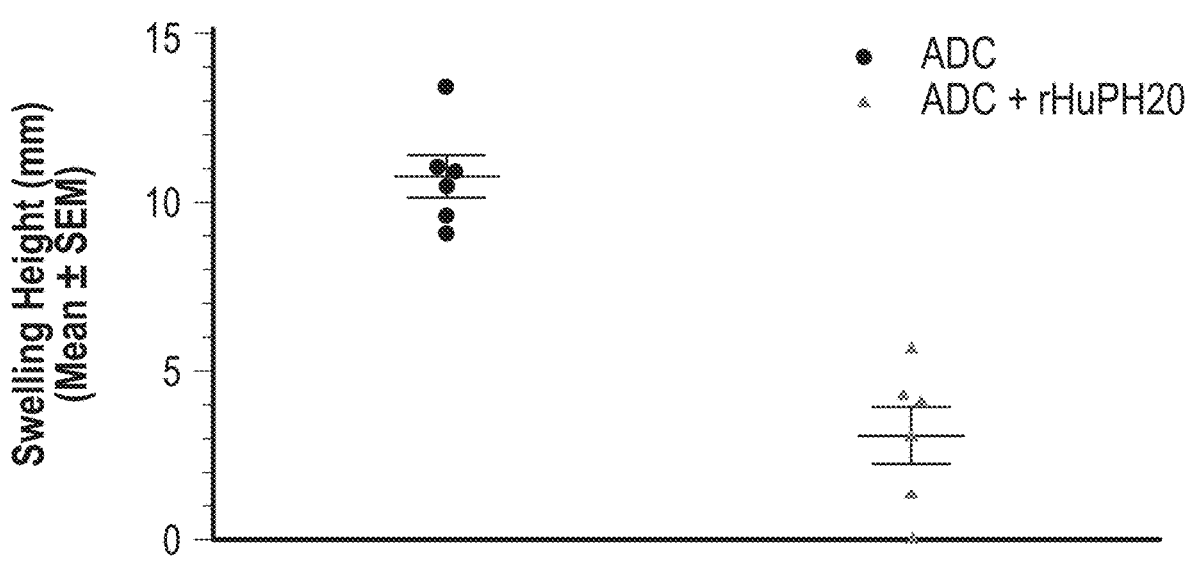

Bleb volume (FIG. 30A) and height (FIG. 30B) are significantly reduced with rHuPH20 (Table 26). Reduced bleb height largest contributing factor to reduced bleb volume.

TABLE 26

| Test Solution | Volume (cc) (Mean ± SEM) | % Decrease Bleb Volume | Height (mm) (Mean ± SEM) | % Decrease Bleb Height |
|---|---|---|---|---|
| ADC | 65.5 ± 3.6 | ~66% | 10.8 ± 0.6 | ~70% |
| ADC + rHuPH20 | 22.5 ± 6.2 | | 3.1 ± 0.8 | |

Figure 31:
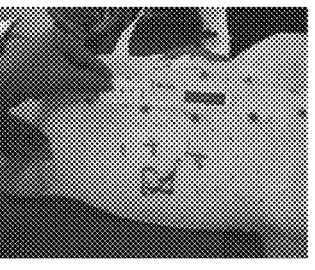
FIG. 31 shows a comparison of injection site of ADC and ADC+rHuPH20 from 0-2h.
Figure 31:
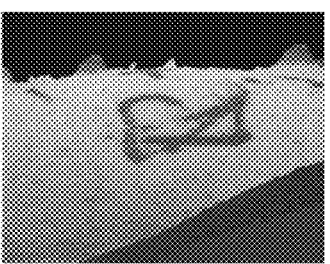
Figure 31:
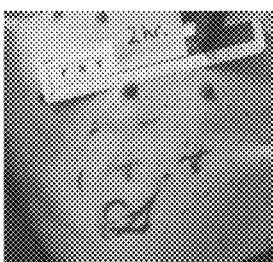
Figure 32A:
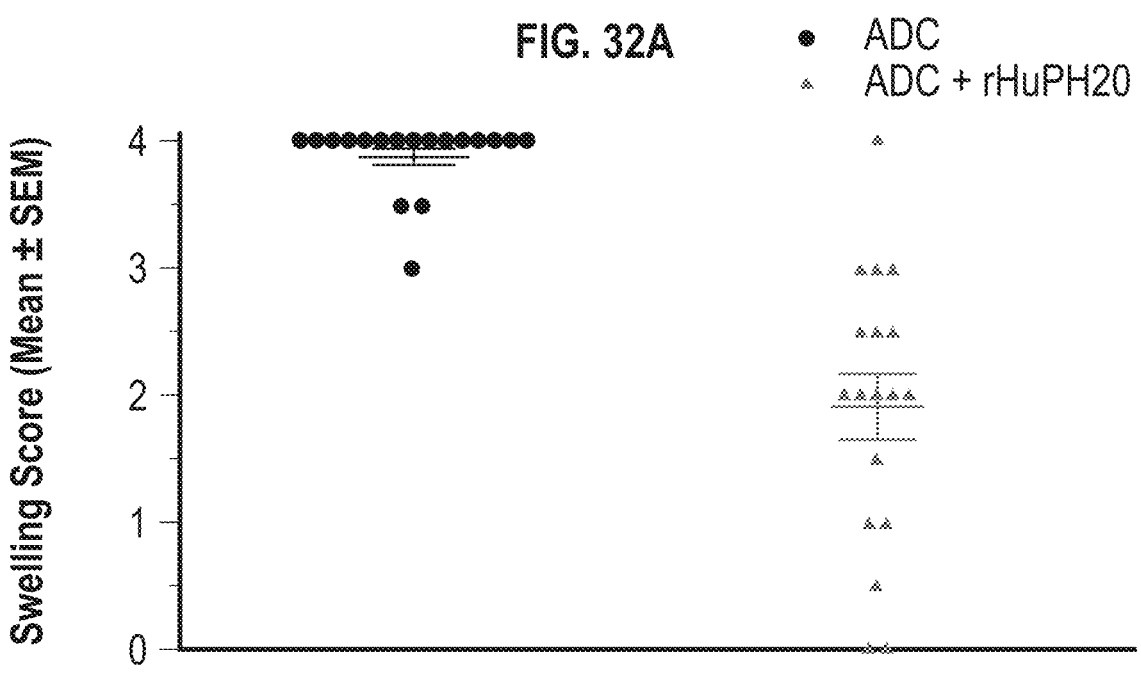
FIGS. 32A-32D compare swelling and induration post-injection with ADC and ADC+rHuPH20.
Figure 32B:
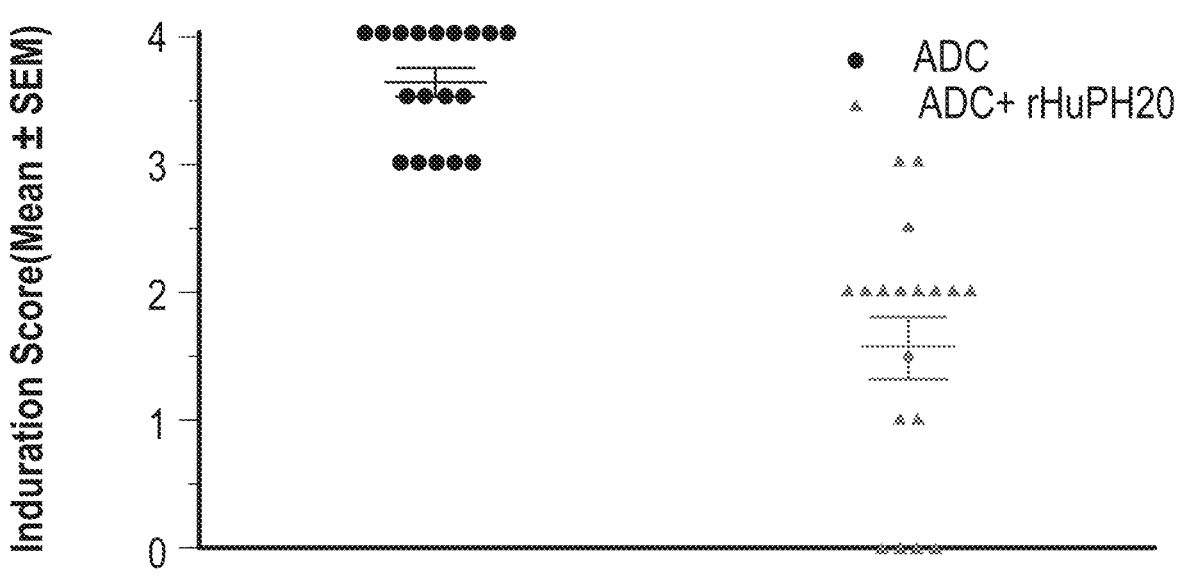
Figure 32C:
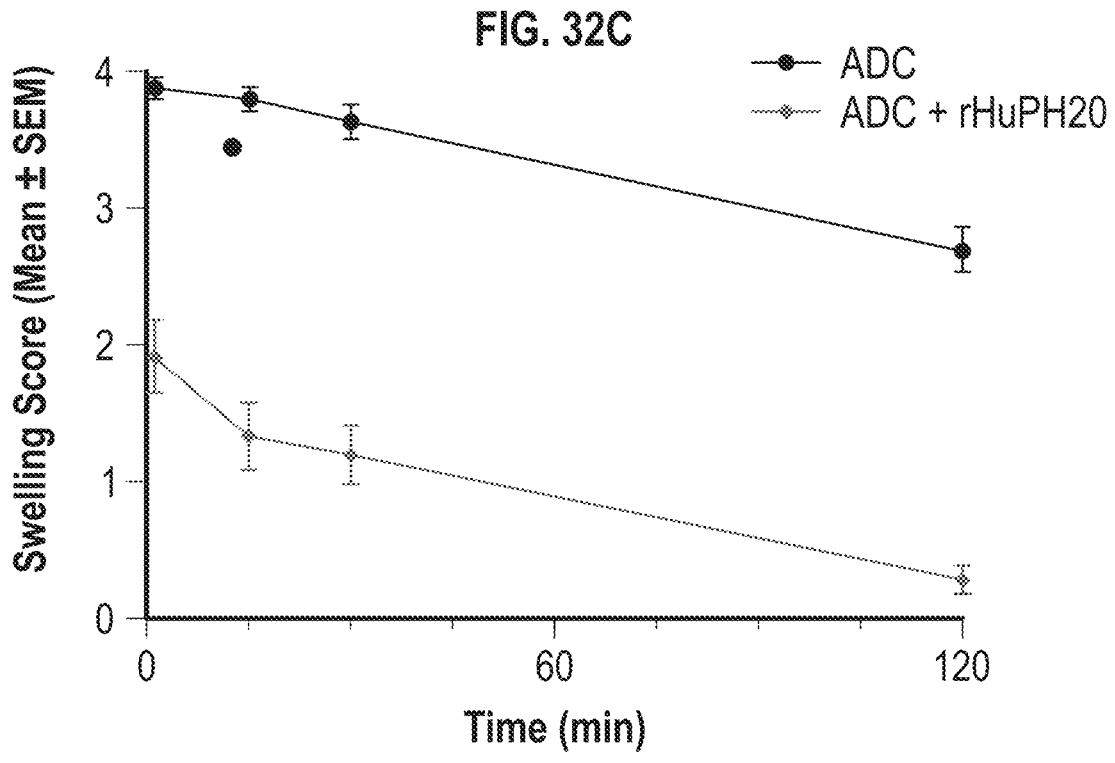
Figure 32D:
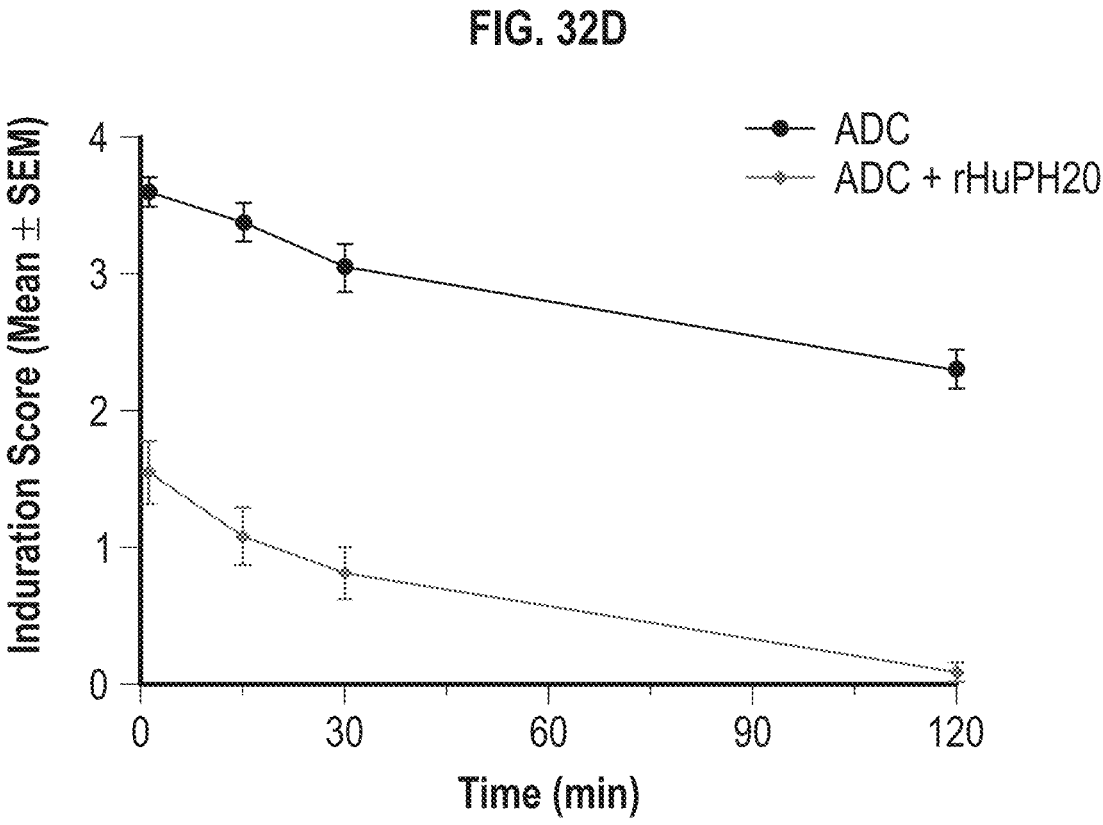

Large volume SC delivery of ADC+rHuPH20 shows minimal post-injection swelling in photographs in FIG. 31. Post-injection site swelling and induration are rapidly reduced with rHuPH20. For injections of ADC+rHuPH20, swelling (FIG. 32A) and induration (FIG. 32B) were lower than for control injections at T0, swelling was <1 for injections containing rHuPH20 by 2h (FIG. 32C), and induration was significantly reduced by 30 min and <1 by 2h (FIG. 32D). Score scales for swelling and induration are in Table 27 and 28, respectively.

TABLE 27

| Swelling Score Scale | |
|---|---|
| Scale | Description |
| 0 | No swelling |
| 1 | Very slight swelling |
| 2 | Slight swelling |
| 3 | Moderate swelling |
| 4 | Severe swelling |

TABLE 28

| Induration Score Scale | |
|---|---|
| Scale | Description |
| 0 | No perceptible difference in firmness |
| 1 | Very slightly firm (barely perceptible) |

TABLE 28-continued

| Induration Score Scale | |
|---|---|
| Scale | Description |
| 2 | Mildly firm |
| 3 | Moderately firm |
| 4 | Very firm |

SUMMARY

Back-leakage was significantly reduced for all ADC+ rHuPH20 injections

Bleb volume and height were reduced for rHuPH20-mediated injections

Qualitative assessment of post-injection swelling and induration demonstrated improvements for injections containing rHuPH20

Initial bleb size was smaller for rHuPH20-mediated injections with reduced firmness rHuPH20 increased the rate of bleb resolution over time Study #2

Objective

Assess local tolerability of high dose ADC vs. ADC+ rHuPH20

20 mL injection volume 10 mg/mL; 5 mL/min (~10 mg/kg)

Endpoints

Back-Leakage measured post-injection (30 sec)

Bleb Size (Volume, Area, Height) measured at T0, T15, T30

Qualitative assessment of Erythema, Swelling and Induration overtime (T0, T15, T30, T2h and T24h)

Test Articles: ADC (50 mg/mL)±rHuPH20 (2000 U/mL)

Figure 33:
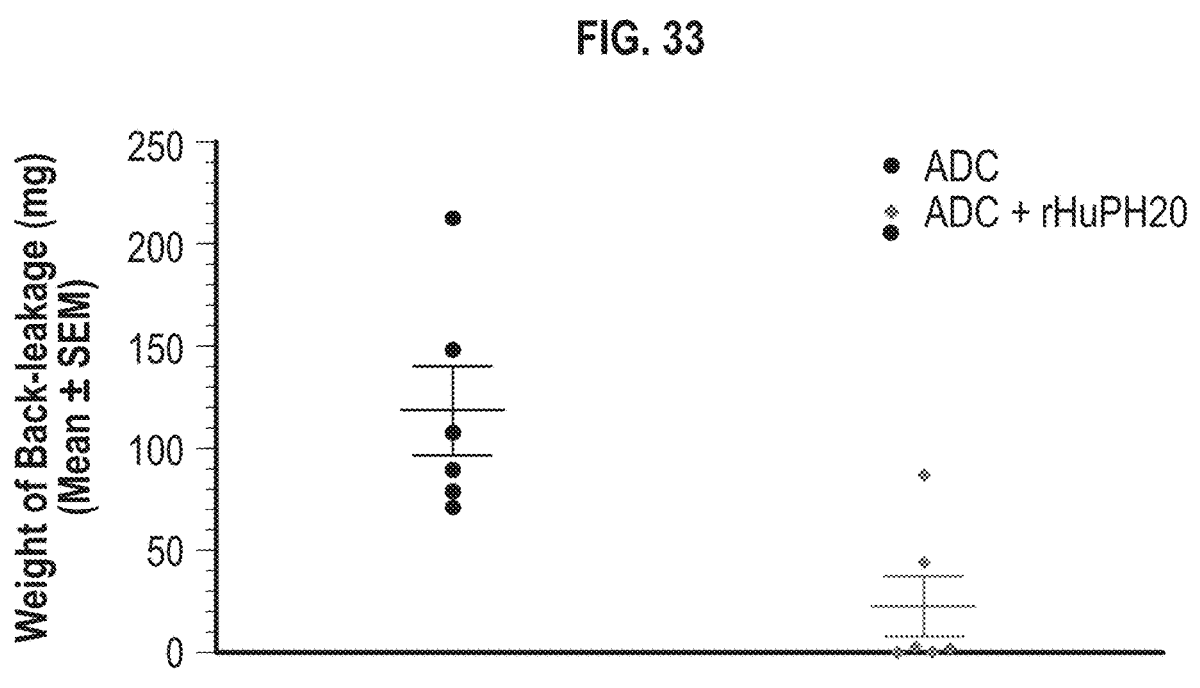

Results: Post-injection Back-leakage is significantly reduced with rHuPH20 (FIG. 33, Table 29).

TABLE 29

| Post-injection back-leakage | | |
|---|---|---|
| Test Solution | Back-leakage (mg ± SEM) | % Decrease |
| ADC | 118.4 ± 21.8 | ~81%* |
| ADC + rHuPH20 | 22.5 ± 14.7 | |

*p < 0.01

Figure 34A:
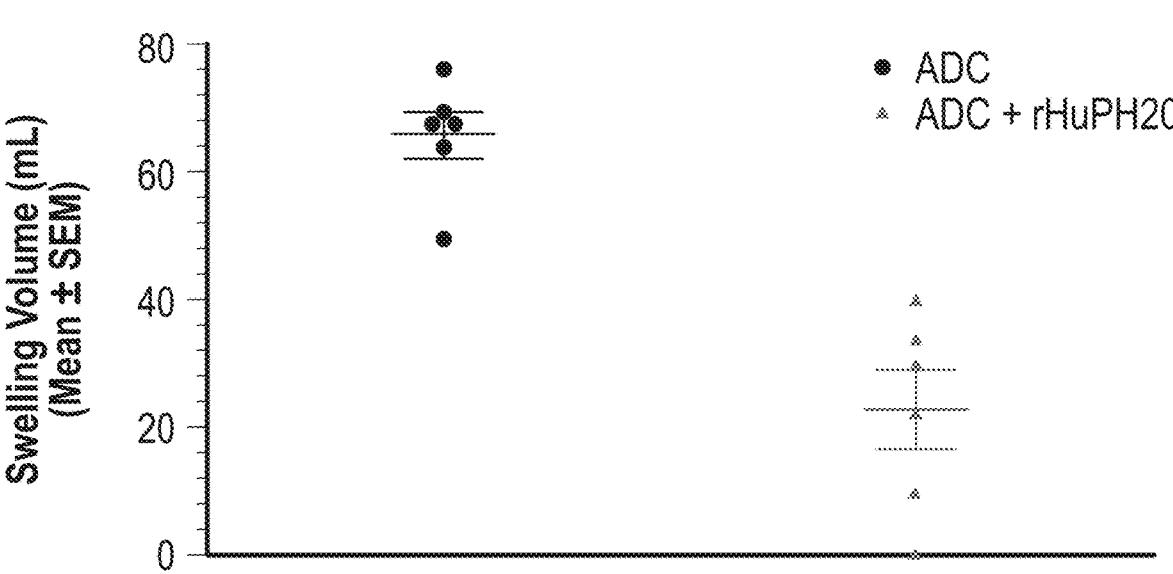
FIGS. 34A and 34B show comparisons of bleb size post-injection with ADC and ADC+rHuPH20.
Figure 34B:
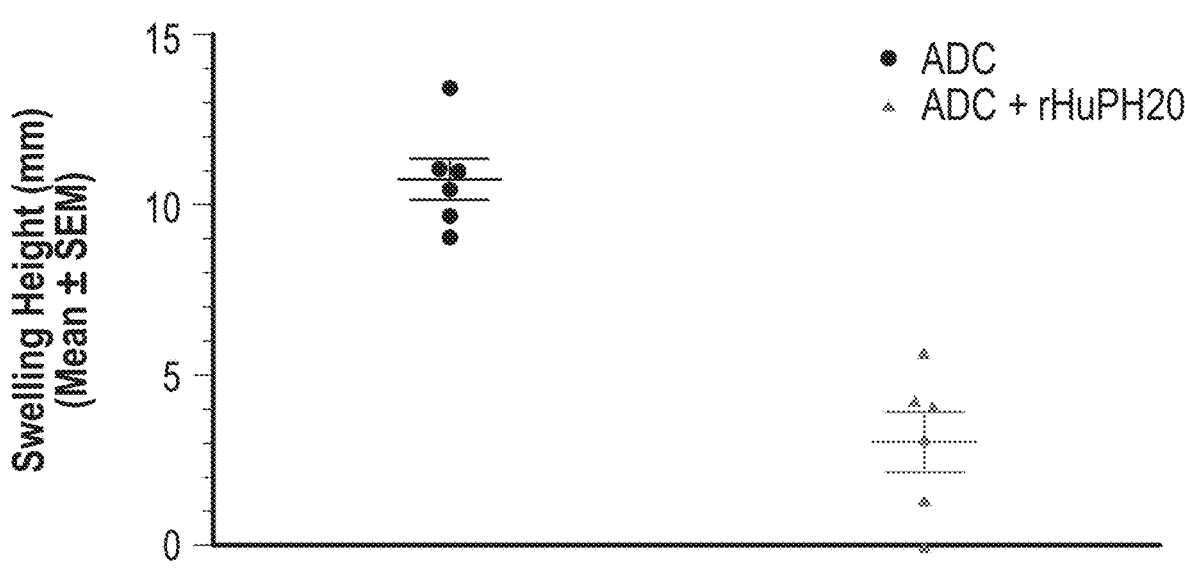

Bleb volume and height are significantly reduced with rHuPH20 (FIG. 34A, Table 30). Reduced bleb height largest contributing factor to reduced bleb volume (FIG. 34B, Table 30).

TABLE 30

| Bleb volume and height | | | | |
|---|---|---|---|---|
| Test Solution | Volume (cc) (Mean ± SEM) | % Decrease | Height (mm) (Mean ± SEM) | % Decrease |
| ADC | 65.5 ± 3.6 | ~66% | 10.8 ± 0.6 | ~70% |
| ADC + rHuPH20 | 22.5 ± 6.2 | | 3.1 ± 0.8 | |

Figure 35A:
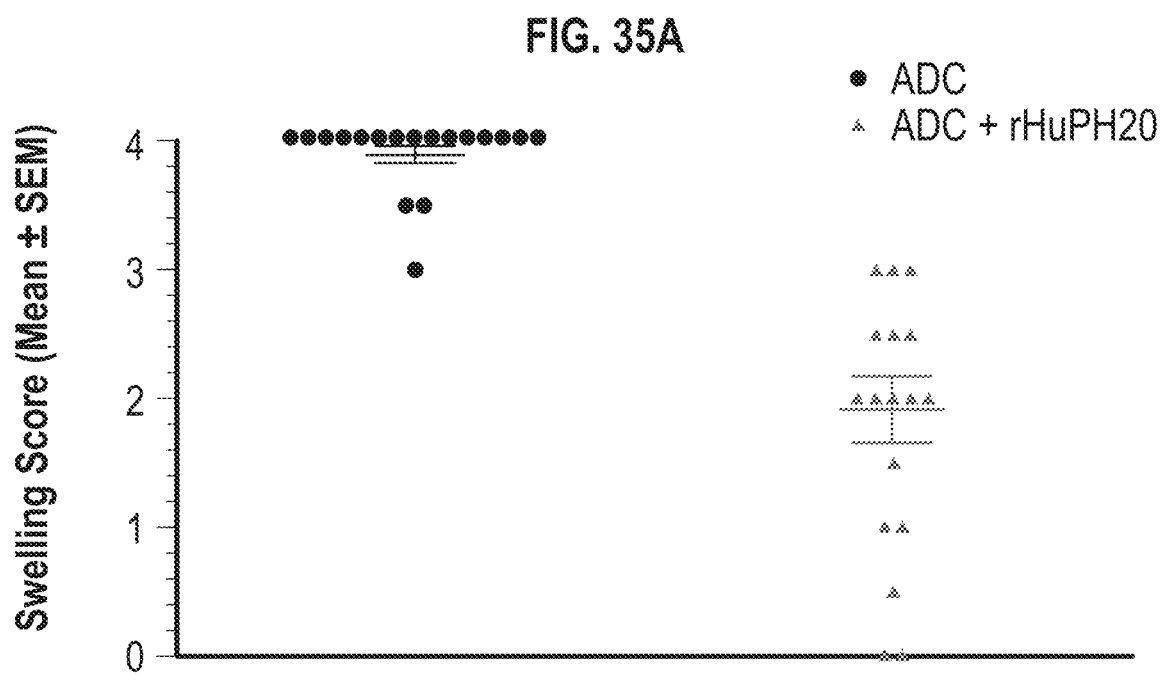
FIGS. 35A-35D compare swelling and induration post-injection post-injection with ADC and ADC+rHuPH20.
Figure 35B:
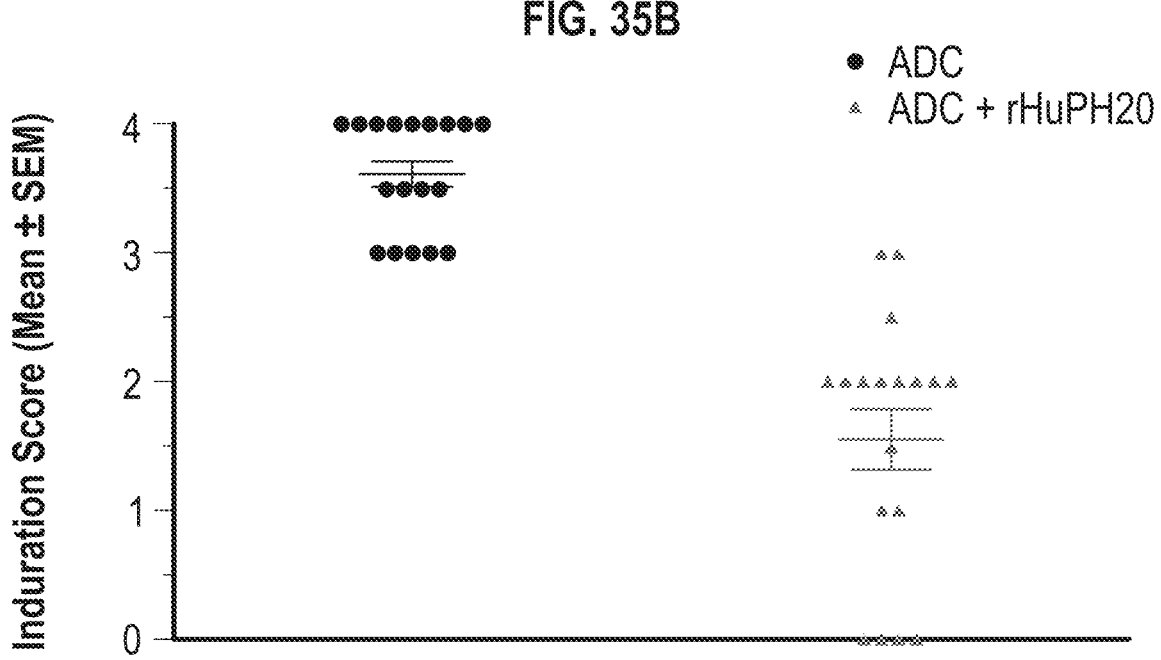
Figure 35C:
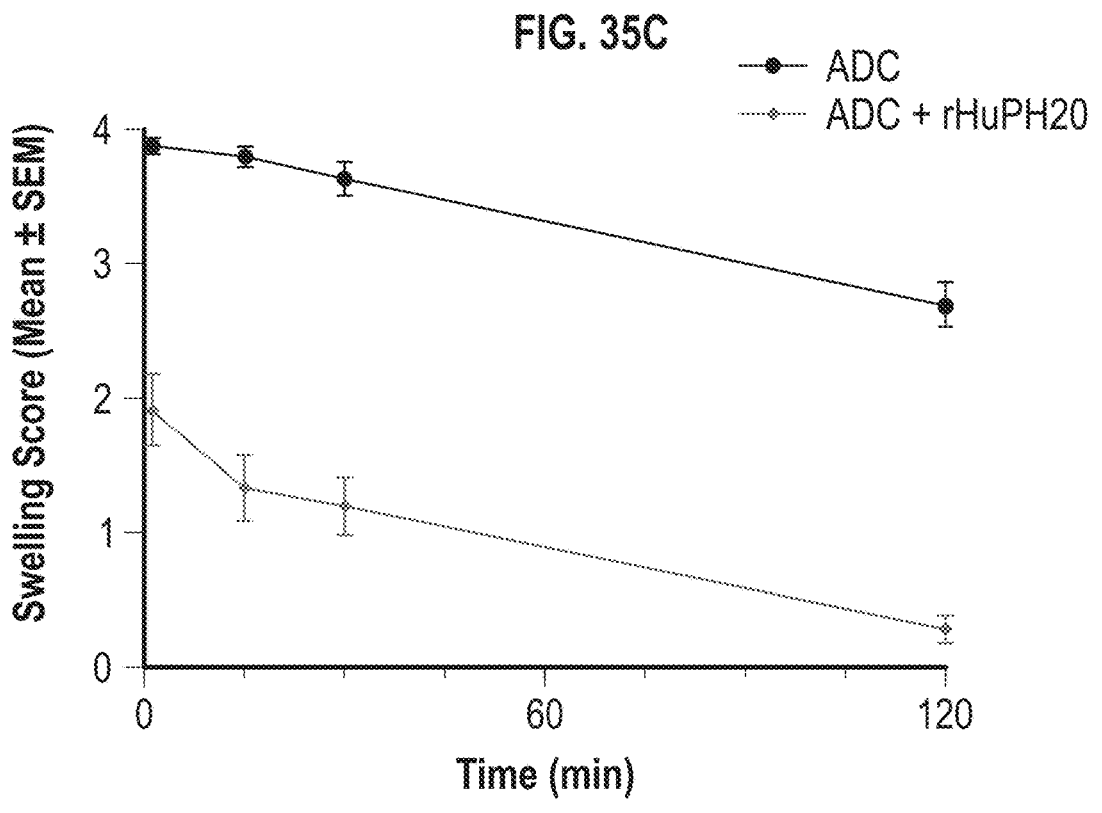
Figure 35D:
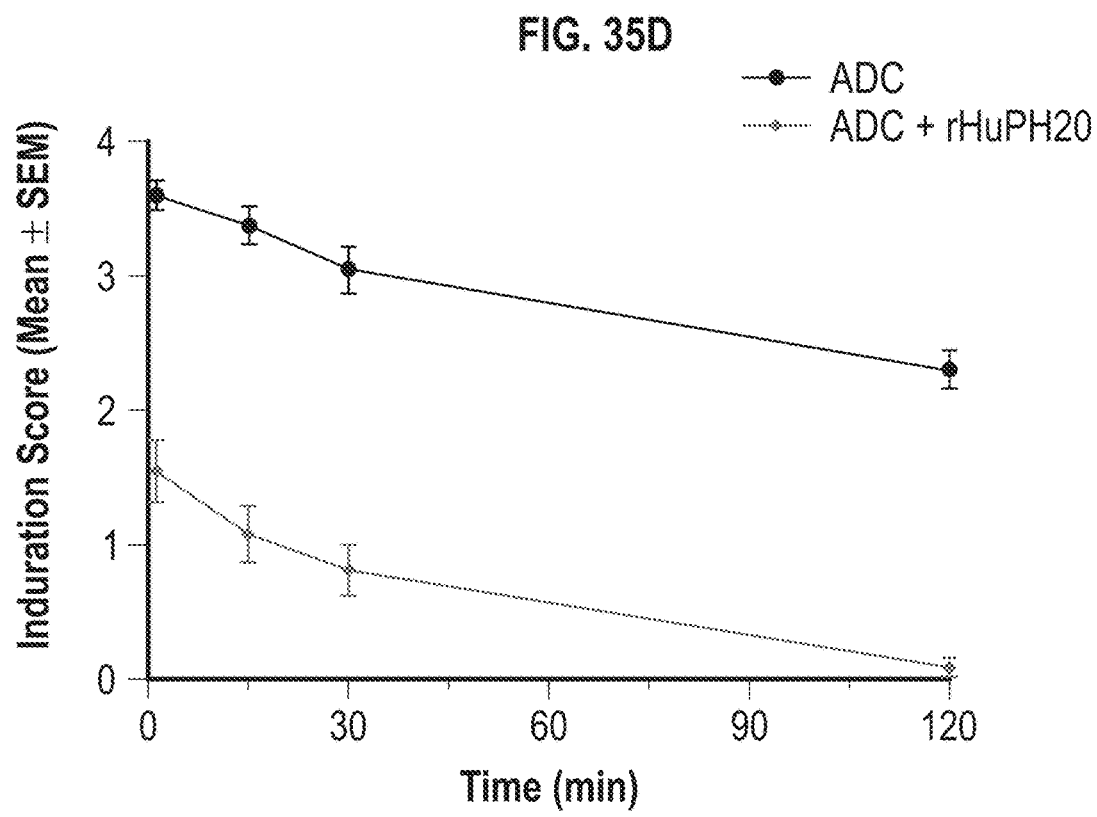

Post-injection site swelling and induration are rapidly reduced with rHuPH20. For injections of ADC+rHuPH20, swelling (FIG. 35A) and induration (FIG. 35B) were lower than for control injections at T0, swelling was <1 for injections containing rHuPH20 by 2h (FIG. 35C), and induration was significantly reduced by 30 min and <1 by 2h (FIG. 35D). Summary Back-leakage was significantly reduced for all ADC+rHuPH20 injections Bleb volume and height were reduced for rHuPH20-mediated injections Qualitative assessment of post-injection swelling and induration demonstrated improvements for injections containing rHuPH20

Initial bleb size was smaller for rHuPH20-mediated injections with reduced firmness rHuPH20 increased the rate of bleb resolution over time

Example 5: Tolerability of an ADC+rHuPH20 Over Time Following SC Administration This study utilized all the same protocols and parameters as set forth in Example 1 unless disclosed otherwise.

Objective

Assess local injection site tolerability following SC administration of an ADC±rHuPH20 over 72h 10 mL injection volume; 2000 U/mL rHuPH20

HVAI used for injections

Endpoints

Time to deliver measured for each injection

Back-Leakage measured immediately post-injection

Bleb Size (Volume, Area, Height) measured at T0

Qualitative assessment of Erythema, Swelling and Induration (T0, T24h, T48h, T72h)

Test Solutions: Sacituzumab govitecan (Trodelvy®)±rHuPH20 @2000 U/mL

Figure 36A:
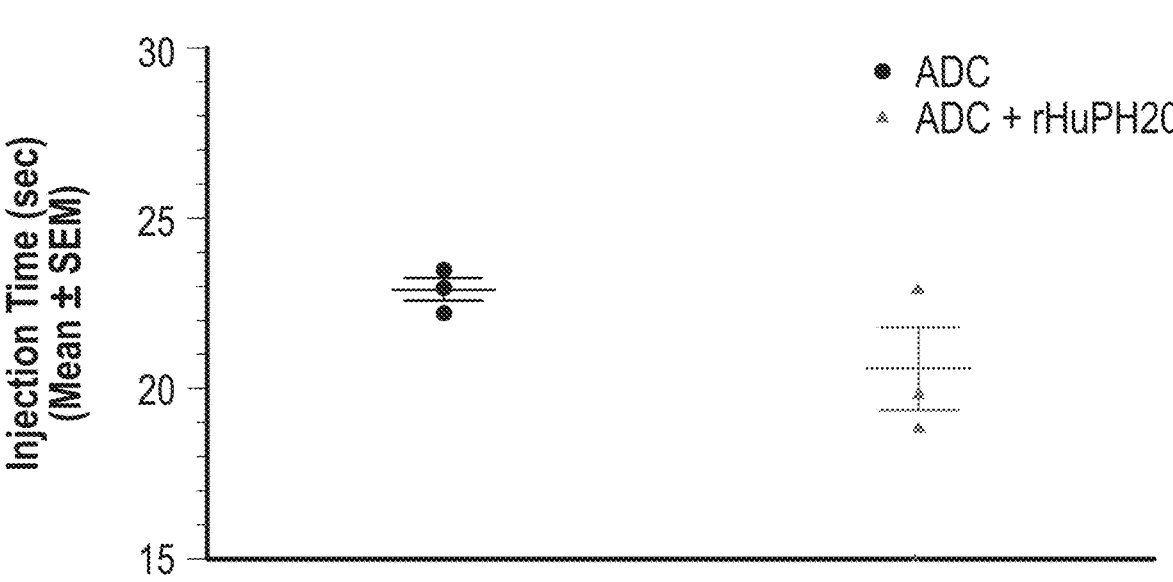
FIGS. 36A-36A show a comparison of delivery time and back leakage of injection with ADC and ADC+rHuPH20.
Figure 36B:
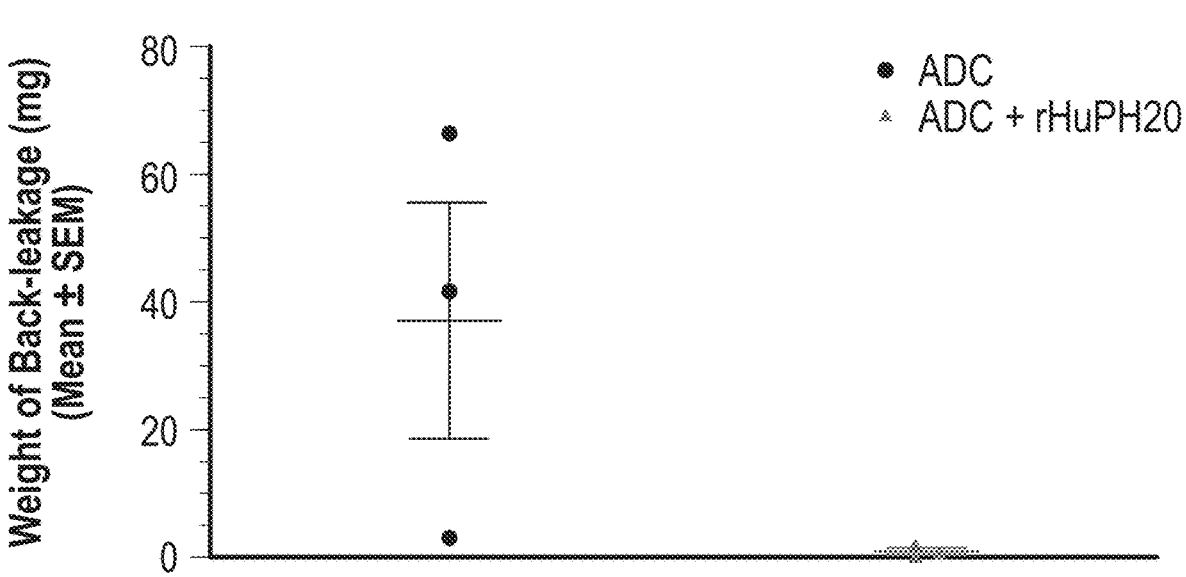
FIG. 36B is a chart comparing back leakage of ADC v. ADC+rHuPH20.

Results: rHuPH20 reduced delivery time and back-leakage (FIGS. 36A and 36B, Table 31).

TABLE 31

| | Delivery time and back-leakage. | | | |
|---|---|---|---|---|
| Test Solution | Delivery Time (sec) | % Decrease | Back-leakage (mg) | % Decrease |
| ADC* | 22.9 ± 0.6 | −10% | 37.0 ± 32.0 | −98% |
| ADC + rHuPH20 | 20.6 ± 2.1 | | 0.9 ± 1.0 | |

Figure 37A:
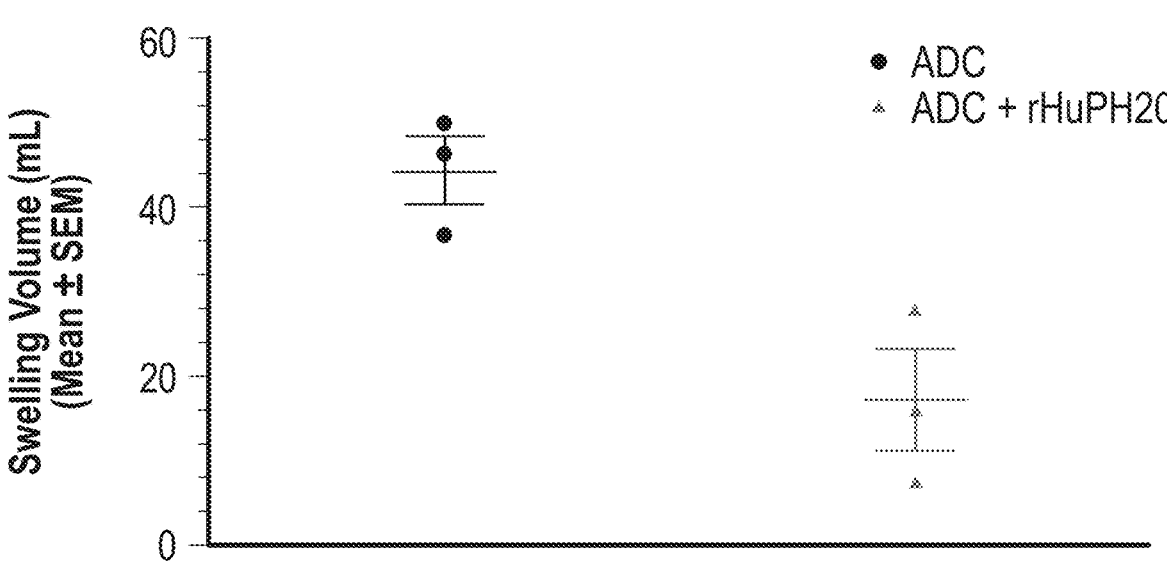
FIGS. 37A-37C show a comparison of bleb size post-injection with ADC and ADC+rHuPH20.
Figure 37B:
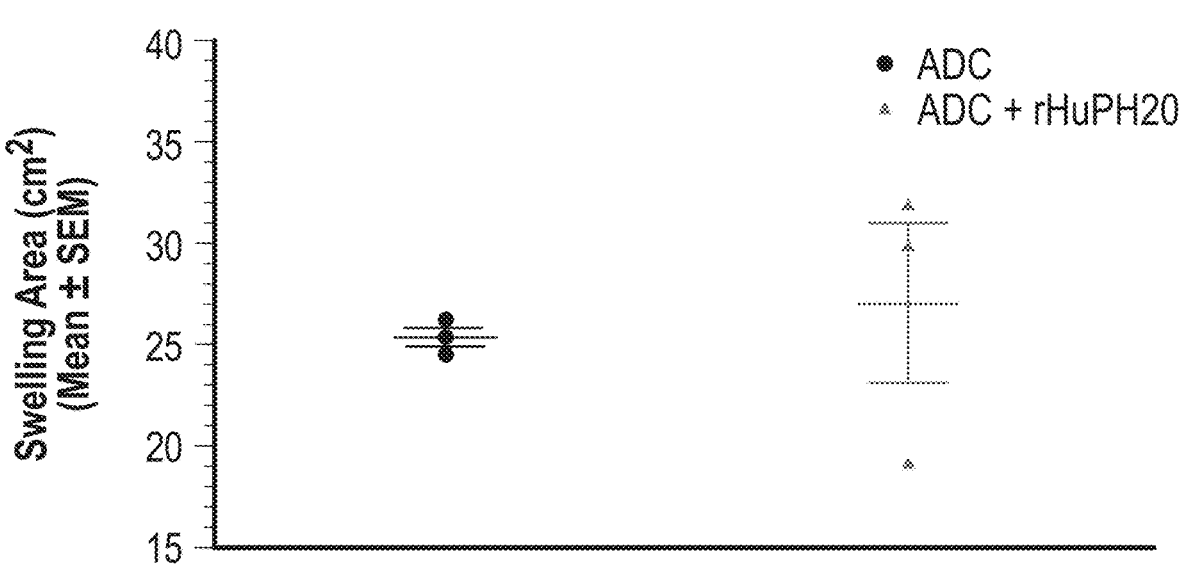
Figure 37C:
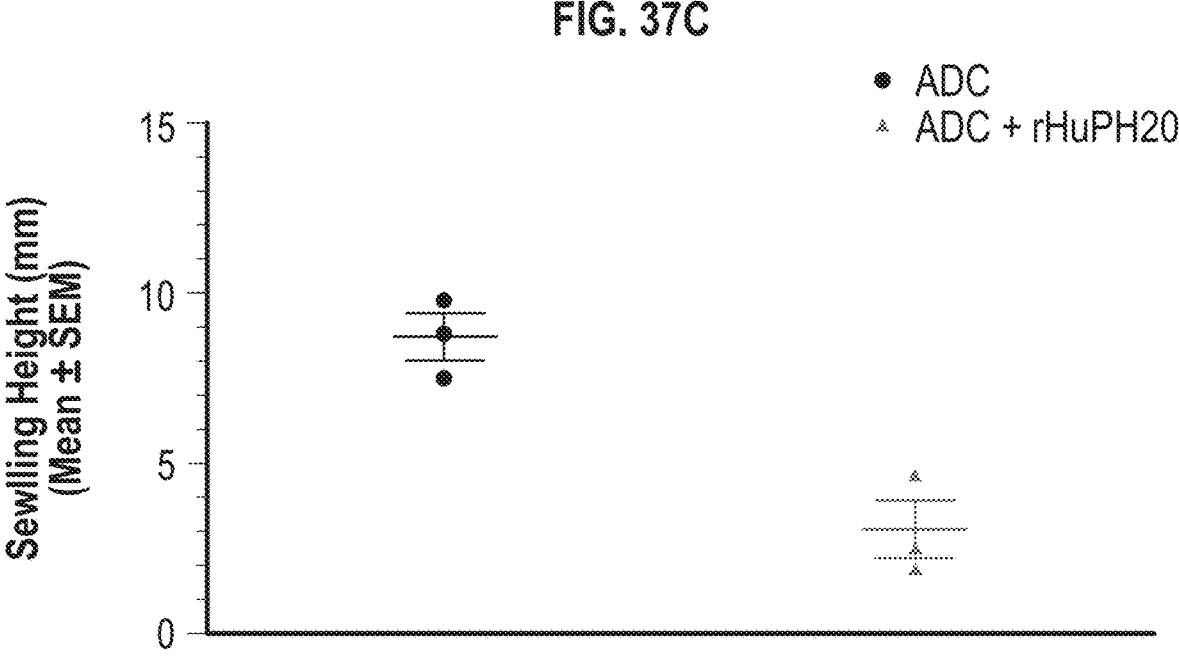

Bleb volume (FIG. 37A), area (FIG. 37B), and height (FIG. 37C) are reduced with rHuPH20 (Table 32). Reduced bleb height largest contributing factor to reduced bleb volume.

TABLE 32

| | Bleb size | | |
|---|---|---|---|
| Test Solution | Volume | Area | Height |
| ADC | 44.3 ± 4.0 | 25.4 ± 0.5 | 8.7 ± 0.7 |
| ADC + rHuPH20 | 17.3 ± 6.0 | 27.0 ± 3.9 | 3.1 ± 0.8 |
| % Increase/Decrease | −61% | +6% | −64% |

Figure 38A:
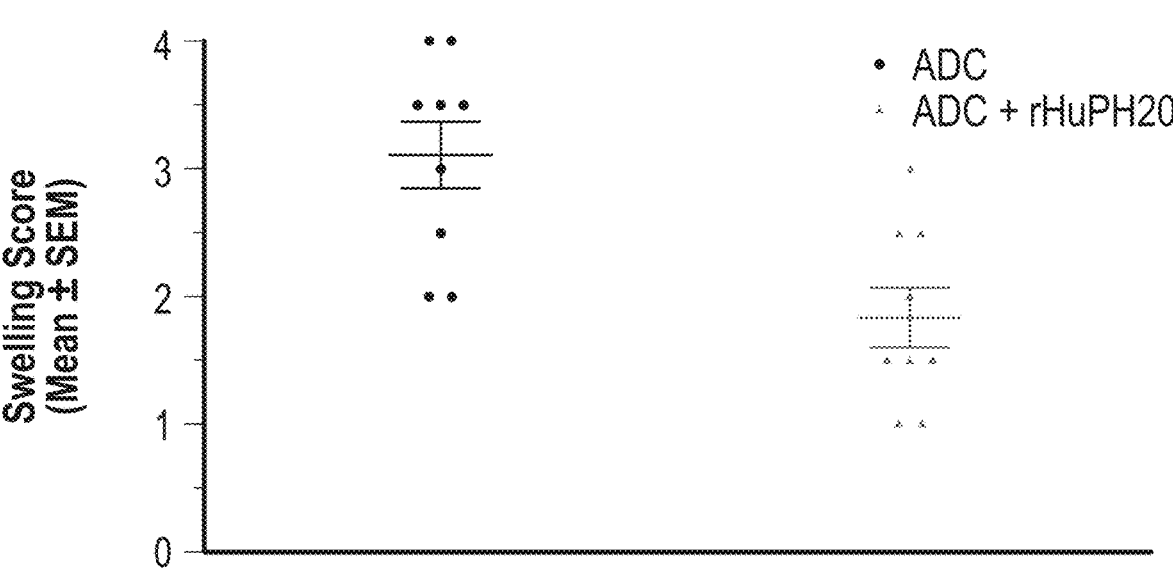
FIGS. 38A-38B compare swelling and induration post-injection with ADC and ADC+rHuPH20.
Figure 38B:
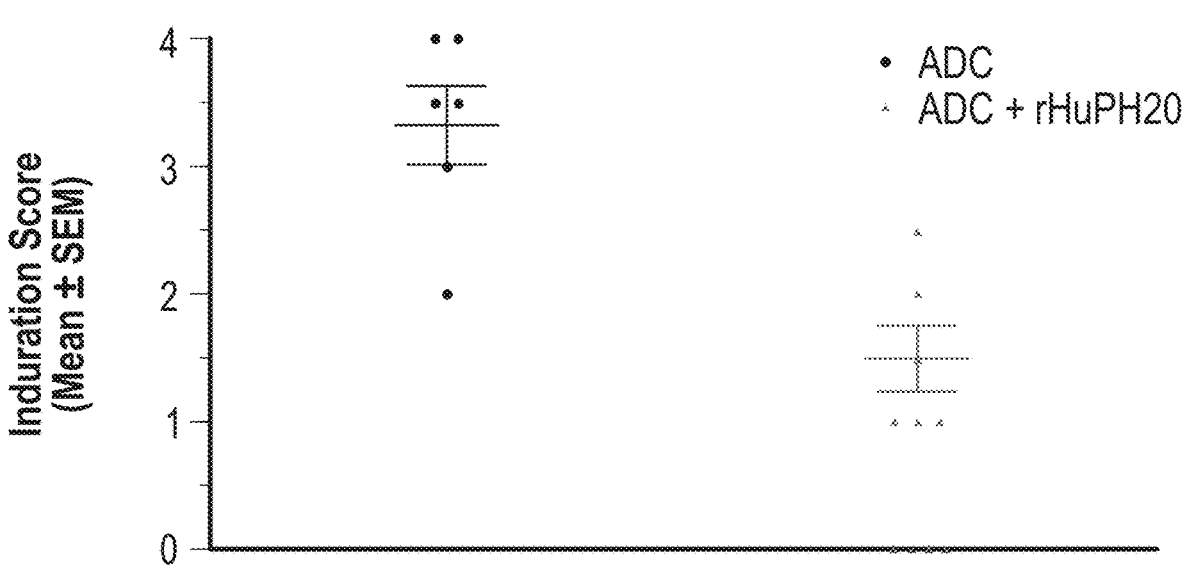

Post-injection site swelling and induration are reduced with rHuPH20. Swelling (FIG. 38A) and induration (FIG. 38B) were lower for ADC+rHuPH20 injections compared to ADC alone injections (Table 33). Score scales for swelling and induration are in Table 43 and 44, respectively.

TABLE 33

| | Swelling and induration post-injection | |
|---|---|---|
| Test Solution | Swelling Size | Induration |
| ADC | 3.1 ± 0.3 | 3.3 ± 0.3 |
| ADC + rHuPH20 | 1.8 ± 0.2 | 1.5 ± 0.3 |
| Induration Score | −42% | −55% |

Figure 39:
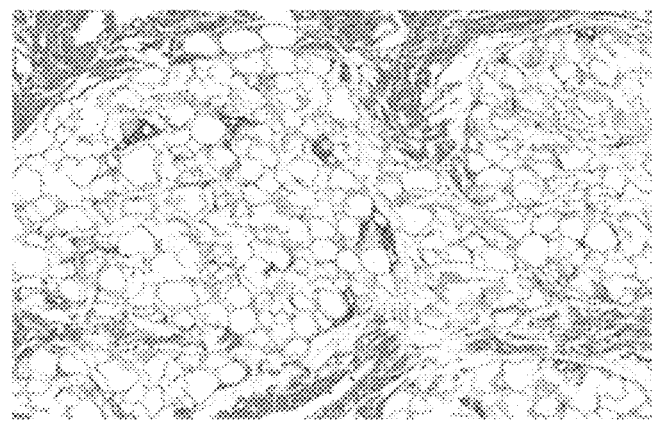
FIG. 39 shows a histological evaluation of skin after SC administration of ADC and ADC+rHuPH20.
Figure 39:
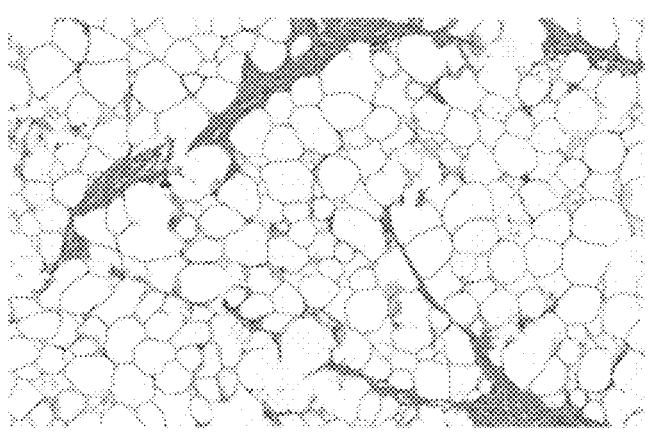
Figure 39:
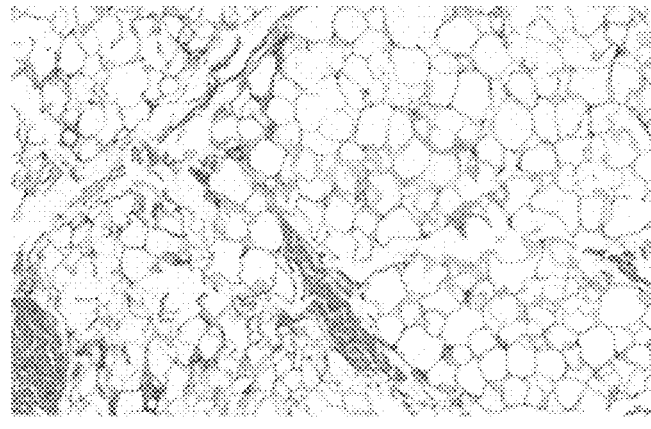

Histological Evaluation of Skin After SC Administration of ADC±rHuPH20. Method: After 72h, animals were euthanized and full-thickness punch biopsies taken (12 mm). FFPE sections were prepared from each injection site. Samples were evaluated at three different tissue depths. A sample of naïve skin was also included for comparison. Results: ⅓ tissue samples from ADC alone had multiple focal infiltrates in SC (all levels). 3/3 tissue samples from ADC+rHuPH2s were normal (no findings) (FIG. 39).

SUMMARY

Injection time for ADC was reduced ~10% with addition of rHuPH20. Back-leakage was significantly reduced for all ADC+rHuPH20 injections (~98%) with less variability. Bleb volume and height were reduced for rHuPH2-facilitate injections. Qualitative assessment of post-injection swelling and induration demonstrated improvements for injections with rHuPH2. Bleb sizes were smaller for rHuPH20-facilitated injections with reduced firmness. No erythema was observed for any injection. Histology demonstrated no findings for ADC+rHuPH2 injections whereas ⅓ injections of ADC alone had SC immune cell infiltrates.

Example 6: Toxicopathology Data of Porcine Skin Samples

This study utilized all the same protocols and parameters as set forth in Example 1 unless disclosed otherwise. A routine toxicopathology review was performed with emphasis on tissue integrity. Results of the review are in Table 34.

TABLE 34

| | Toxicopathology review | |
|---|---|---|
| Sample ID | Level | Microscopic Findings |
| 4081 | L Control | focal epithelial hyperplasia/hyperkeratosis minimal dermis, leukocyte infiltrates, focal, minimal subcutis, leukocytes, focal, minimal |
| | N Naïve | focal epithelial hyperplasia/hyperkeratosis minimal dermis, leukocyte infiltrates, focal, minimal subcutis, leukocytes, focal, minimal |
| | R PH20 | focal epithelial hyperplasia/hyperkeratosis minimal dermis, leukocyte infiltrates, focal, minimal subcutis, leukocytes, focal, minimal |
| 5055 | L PH20 | focal epithelial hyperplasia/hyperkeratosis minimal dermis, leukocyte infiltrates, focal, minimal subcutis, leukocytes, focal, minimal |
| | N Naïve | focal epithelial hyperplasia/hyperkeratosis minimal dermis, leukocyte infiltrates, focal, minimal subcutis, leukocytes, focal, minimal |
| | R Control | focal epithelial hyperplasia/hyperkeratosis minimal dermis, leukocyte infiltrates, focal, minimal subcutis, leukocytes, focal, minimal |
| 5061 | L Control | focal epithelial hyperplasia/hyperkeratosis minimal dermis, leukocyte infiltrates, focal, minimal subcutis, leukocytes, focal, minimal |
| | N Naïve | focal epithelial hyperplasia/hyperkeratosis minimal dermis, leukocyte infiltrates, focal, minimal subcutis, leukocytes, focal, minimal |

TABLE 34-continued

| | | Toxicopathology review |
| --- | --- | --- |
| Sample ID | Level | Microscopic Findings |
| | R PH20 | focal epithelial hyperplasia/hyperkeratosis minimal dermis, leukocyte infiltrates, focal, minimal subcutis, leukocytes, focal, minimal |
| 5069 | L PH20 | focal epithelial hyperplasia/hyperkeratosis minimal dermis, leukocyte infiltrates, focal, minimal subcutis, leukocytes, focal, minimal |
| | n Naïve | focal epithelial hyperplasia/hyperkeratosis minimal dermis, leukocyte infiltrates, focal, minimal subcutis, leukocytes, focal, minimal |
| | R Control | focal epithelial hyperplasia/hyperkeratosis minimal dermis, leukocyte infiltrates, focal, minimal subcutis, leukocytes, focal, minimal |
| 5083 | L Control | focal epithelial hyperplasia/hyperkeratosis minimal dermis, leukocyte infiltrates, focal, minimal subcutis, leukocytes, focal, minimal |
| | N Naïve | focal epithelial hyperplasia/hyperkeratosis minimal dermis, leukocyte infiltrates, focal, minimal subcutis, leukocytes, focal, minimal |
| | R PH20 | focal epithelial hyperplasia/hyperkeratosis minimal dermis, leukocyte infiltrates, focal, minimal subcutis, leukocytes, focal, minimal |
| 5085 | L PH20 | focal epithelial hyperplasia/hyperkeratosis minimal dermis, leukocyte infiltrates, focal, minimal subcutis, leukocytes, focal, minimal |
| | N Naïve | focal epithelial hyperplasia/hyperkeratosis minimal dermis, leukocyte infiltrates, focal, minimal subcutis, leukocytes, focal, minimal |
| | R Control | focal epithelial hyperplasia/hyperkeratosis minimal dermis, leukocyte infiltrates, focal, minimal subcutis, leukocytes, focal, minimal |

Example 7: Tolerability of Full Dose Sacituzumab Govitecan Following Subcutaneous Administration with and without Recombinant Human Hyaluronidase Ph20 (Rhuph20)

This study utilized all the same protocols and parameters as set forth in Example 1 unless disclosed otherwise. The objective of this study is to investigate the local tolerability of subcutaneous (SC) administration of an antibody drug conjugate (ADC) both with and without recombinant human hyaluronidase PH20 (rHuPH20). Minipigs are used in this study due to the similarity of the SC skin architecture to humans. Each animal receives two 20 mL SC injections into the lower abdominal region using a high-speed syringe pump. The needle is inserted vertically into the SC space using a custom 3D printed adapter to maintain the needle at a target needle depth of 7.5 mm.

The first injection is the ADC alone on the lower abdominal region of the animal. Following the injection of the ADC on one side of the animal, the animal receives a second SC injection of ADC+rHuPH20 on the contralateral side of the abdomen. Endpoints include measurement of applied force during the injection, as well as measurement of post-injection back-leakage, local injection site measurements (bleb area and volume), qualitative scoring assessment of the local tissue for erythema, swelling size and induration, and 3D imaging to quantitate post-injection changes of the skin. Qualitative assessments are taken at approximately one, two and three days post-injection. After the final timepoint the animals are humanely euthanized and full skin thickness punch biopsies are taken of the injection site for subsequent histopathological analyses.

This study utilizes an FDA approved antibody drug conjugate as a representative ADC. This antibody was used in prior studies that demonstrated the local tolerability both when administered in combination with rHuPH20 after SC administration. The objective of this follow-on study is to evaluate the local tolerability of full dose volumes.

Each animal receives two subcutaneous injections—one of the ADC alone and one of the ADC co-mixed with rHuPH20. The ADC alone injection precedes the ADC+rHuPH20 injection. A summary of the Description of Treatments for each cohort is shown in Table 35.

TABLE 35

| | | Description of Treatments | | | |
| --- | --- | --- | --- | --- | --- |
| Cohort # | Test Solution | N/group | Dose Volume (mL) | rHuPH20 (U/mL) | Evaluation Times (h/d) |
| 1 | ADC | 6 | 20 | 0 | 2 h, 1 d, 2 d, 3 d |
| 2 | ADC + rHuPH20 | 6 | 20 | 2000 | 2 h, 1 d, 2 d, 3 d |

Each injection is administered using a syringe pump at a flow rate of 5 mL/min. The applied force is measured during the injection via a load cell attached to the end of the syringe barrel. Following administration any back-leakage is collected for a period of 30 seconds and weighed using an analytical balance with a sensitivity of 0.1 mg. The animal is monitored & photographed at approximately 2h post dose, and 1 d, 2 d and 3 d. After the final timepoint, the animals are humanely euthanized and punch biopsies (12 mm) of each injection site are obtained and preserved in 10% formalin for future histological analyses. For comparison, a full thickness punch biopsy is taken from a non-treated portion of the abdomen after the animal is euthanized.

One day prior to the study, syringes are filled with ~22 mL of the appropriate test solutions, capped, and stored at 2-8° C. Syringes are allowed to acclimate to room temperature for at least 30 minutes prior to use and used within 2 hours. Once the animal has received the two injections, two additional syringes are brought to room temperature as described above for use with the next animal.

After anesthetization the animal is placed in dorsal recumbence on a heated surgical table and is maintained under isoflurane gas for the entire duration of the procedure. Following anesthetization the abdominal region is cleaned with Nolvasan followed by wiping the injection site with gauze containing 70% isopropanol and wiped dry with sterile gauze. Injection sites are located on the left and right abdominal regions, ~5 cm cranially from the inguinal fold and ~3 cm towards the midline of the animal. Each of the injection sites are marked with a permanent marker and then photographed with the standard and 3D cameras prior to needle insertion.

Immediately prior to use the syringe containing the test solution is mounted to a load cell in an adapter and then placed on the end of the syringe barrel. The syringe cap is then removed and replaced with a 23G×12-inch BD Vacutainer Blood Collection Set. The infusion set is primed to the needle tip. The syringe is then loaded into a high-pressure syringe pump. The load cell is then zeroed and the pump block then pushed to abut the end of the syringe barrel and locked in place. Load cell measurements are taken at a sampling rate of 2 Hz.

A custom 3D printed adapter is used to hold the needle at a precise depth of 7.5 mm. Approximate needle depths are recorded. The skin at the injection site is then pinched and the needle inserted vertically into the SC space and the skin is then allowed to relax into normal position. The 3D printed adapter is held in place during the injection flush against the skin but without exerting excessive downward pressure.

Upon completion of the injection the needle is removed from the skin and the syringe with infusion set discarded. Test solution samples from at least 3 out of 6 ADC+ rHuPH20 syringes will be retained for post-study enzymatic testing. Test solution back-leakage is then absorbed to a tared eye-spear for 30 seconds on the injection site. The weight of the eye spear is then recorded using an analytical balance. The margins of the injection site bleb are marked with a permanent marker and measured for length, width, and height using a digital calliper and recorded then photographed with the standard and 3D cameras. The margins of the injection site blebs are also measured using a digital calliper at T15 and T30 timepoints. Local injection sites are then qualitatively assessed and graded for erythema severity, swelling size appearance, and firmness, using a scoring system described in Example 1.

Approximately 24 hours post-dosing of the first injection, injection sites for each animal are inspected, photographed, and assessed for erythema, induration, and swelling. The scoring and evaluation continue daily for up to approximately three days (72h). Following the assessment after day three, the animal is humanely euthanized using an injectable euthanasia drug provided by the vivarium staff Following euthanasia punch biopsies of the injection site are taken (12 mm). For comparison, a punch biopsy from an untreated area of the abdomen is obtained for each animal. After obtaining the punch biopsies the animal carcass is removed and disposed of as biohazardous waste.

Example 7: Pharmacokinetics of Dupilumab Administration Following Subcutaneous Administration with and without Recombinant Human Hyaluronidase PH20 (rHuPH20)

The objective of this study was to investigate the pharmacokinetics (PK) of a monoclonal antibody dupilumab (Dupixent®) following subcutaneous (SC) administration alone or co-administered with recombinant human hyaluronidase PH20 (rHuPH20; 5000 U/mL). This study compared the PK of a standard clinical dose of 2 mL of dupilumab alone versus the PK of a 5 mL bolus of dupilumab co-mixed with rHuPH20. The 2 mL doses were administered using a pre-filled syringe (PFS) while the larger dose volume was administered using a prototype HVAI with a 5 mL fill. Blood was collected prior to the start of the study (pre-dose), and at 6 hours (h), 1 day(d), 2d, 3d, 4d, 5d and 7d post-injection. Blood was collected via jugular vein stick into serum separation tubes (SSTs) and allowed to remain at room temperature for thirty minutes whereupon they were then placed on ice until processed for serum collection. Samples were divided into duplicates and stored at −80° C. until used for bioanalysis. The concentration of functional Dupixent® of individual serum sample was quantitatively detected using Dupilumab ELISA kit, abx395100, Abbexa LLC.

Ten animals were administered a single injection of either dupilumab alone (5 animals) or with dupilumab+rHuPH20 (5 animals). Prior to injection pre-treatment blood samples were obtained from each animal. After test solution injection blood samples were obtained at 6h, 1 d, 2d, 3d, 4d, 5d and 7d post-injection. Blood was collected into serum separator tubes, centrifuged, and stored at −80° C. for bioanalytical analysis.

The concentration of functional Dupixent® in serum sample was quantitatively detected using a competitive Dupilumab ELISA kit (abx395100, Abbexa LLC). Briefly, Dupixent® in serum sample was bound to its antigen immobilized on 96-well plate, which competes the binding of detection reagent, biotin labeled Dupilumab. After incubation and washing to remove unbound Dupilumab from 96-well plate, the bound biotin labeled Dupilumab was visualized by horseradish peroxidase substate and Dupilumab concentration was calculated from a 4PL fitted standard curve.

The two test solutions administered in this study were dupilumab alone and dupilumab co-mixed with rHuPH20. Dupilumab alone was administered as commercially packaged in a 2 mL PFS. To prepare the co-mix, the antibody solution was pooled from dupilumab syringes (28 mL). To the pooled dupilumab, 0.157 mL of rHuPH20 (10 mg/mL) was added to yield 28.157 mL of test solution. A sample of the co-mix was used for enzymatic activity testing.

All device syringes were filled in a sterile fill and finish hood under aseptic conditions. Cyclic olefin copolymer (COC) syringes were filled with 5.1 mL of the co-mix of dupilumab+rHuPH20. To fill the syringes a sterile rubber plunger was initially inserted into the sterile syringe barrel and pushed to a preset depth for filling, The co-mix of dupilumab+rHuPH20 was then pumped into the syringe at a flow rate of 2 mL/min. After adding the test solution to the syringe, the rubber plunger was brought to the final loading position (to remove residual air in the syringe). Syringes were then capped and stored at 2-8° C. until removed and brought to room temperature prior to use in device assembly.

Assembly of all devices occurred in a sterile fill and finish hood under aseptic conditions. The syringe cap was removed and replaced using a 25G×1-inch Becton Dickinson (BD) needle. The needle remained capped until immediately prior to use. The needle and syringe were placed in a proprietary assembly jig with the HVAI for final assembly, which included the placement of a needle guard that brought the exposed needle depth to 10 mm. The length of each needle in the completed device was measured prior to use and all were found to be 10.0 mm. Devices were discarded after use.

This study measured the pharmacokinetics of dupilumab alone or dupilumab co-mixed with rHuPH20 following subcutaneous administration. The dose volume for dupilumab alone was 2 mL (300 mg) while the dose volume for dupilumab+rHuPH20 was 5 mL (750 mg). Five animals were injected with dupilumab alone and five animals were injected with dupilumab+rHuPH20. The treatment groups are shown in Table 36.

TABLE 36

| | Description of Treatments | | | | |
|---|---|---|---|---|---|
| Cohort | Test Solution | N | Dose Volume (mL) | rHuPH20 (U/mL) | Blood Sampling Times (h/d) |
| 1 | dupilumab alone | 5 | 2 | 0 | 6 h, 1 d, 2 d, 3 d, 4 d, 5 d, 7 d |
| 2 | dupilumab + rHuPH20 | 5 | 5 | 5000 | 6 h, 1 d, 2 d, 3 d, 4 d, 5 d, 7 d |

Each animal received a single SC injection to their left lower abdominal region. For Cohort #1, injections were administered using the manufacturer's pre-filled syringe (2 mL). For Cohort #2, injections of dupilumab+rHuPH20 were delivered using an HVAI device (5 mL). The duration of all injections was timed using a hand-held stopwatch. Following administration any back-leakage was collected for a period of 30 seconds and weighed using an analytical balance. Approximately 3 mL of blood was collected from each animal at intervals of 6 h, 1 d, 2 d, 3 d, 4 d, 5 d, and 7 d via jugular venipuncture. After the final blood collection timepoint, the animal was humanely euthanized.

Prior to the start of study, animals were assessed for general health, body weight recorded, and a pre-treatment baseline blood sample obtained and collected into serum separating tubes (SSTs). Blood samples were processed according to manufacturer's instructions (centrifugation for 10 min @1250 rcf,) and serum removed and stored at –80° C. until used for bioanalysis. Additionally, blood collections were obtained from each animal at 6h post injection, and on day 1, 2, 3, 4, 5 and 7.

One day prior to the study, syringes were filled with appropriate test solutions and assembled into HVAIs then stored at 2-8° C. Devices were allowed to acclimate to room temperature for at least 30 minutes prior to use and used within 2 hours.

On the day of the procedure, animals were anesthetized and placed in dorsal recumbence on a heated surgical table and maintained under isoflurane gas for the entire duration of the procedure. Following anesthetization, the abdominal region was cleaned with Nolvasan followed by wiping the injection site with gauze containing 70% isopropanol and wiped dry with sterile gauze. Injection sites were located on the lower left abdominal regions, –5 cm cranially from the inguinal fold towards the midline and ~3 cm towards the midline of the animal. Each injection site was marked with a permanent marker and then photographed prior to needle insertion and immediately post-injection.

Animals in Cohort #1 received a single SC injection of dupilumab alone administered via a PFS using a standard skin pinch method. Animals in Cohort #2 received a single SC injection of dupilumab+rHuPH20 administered via an HVAI. For HVAI injections, the skin was briefly tented for vertical needle insertion and allowed to relax while holding the device in place against the skin prior to activating device.

Injections were timed using a stopwatch. Upon completion of the injection, the needle and HVAI were removed and discarded. Test solution back-leakage was then absorbed to a tared eye-spear for 30 seconds on the injection site and the weight of the eye spear was measured using an analytical balance. The margins of the injection site bleb were marked with a permanent marker and measured for length, width, and height using a digital caliper and recorded then photographed with the standard camera. Caliper measurements and photographs were taken only immediately post-injection. Local injection sites were qualitatively assessed and graded immediately post-injection (T0) for erythema severity, swelling size appearance, and firmness, using a scoring system described in Example 1. Following the blood sampling obtained on d7, the animal was humanely euthanized using an injectable euthanasia drug provided by the vivarium staff.

Figure 40A:
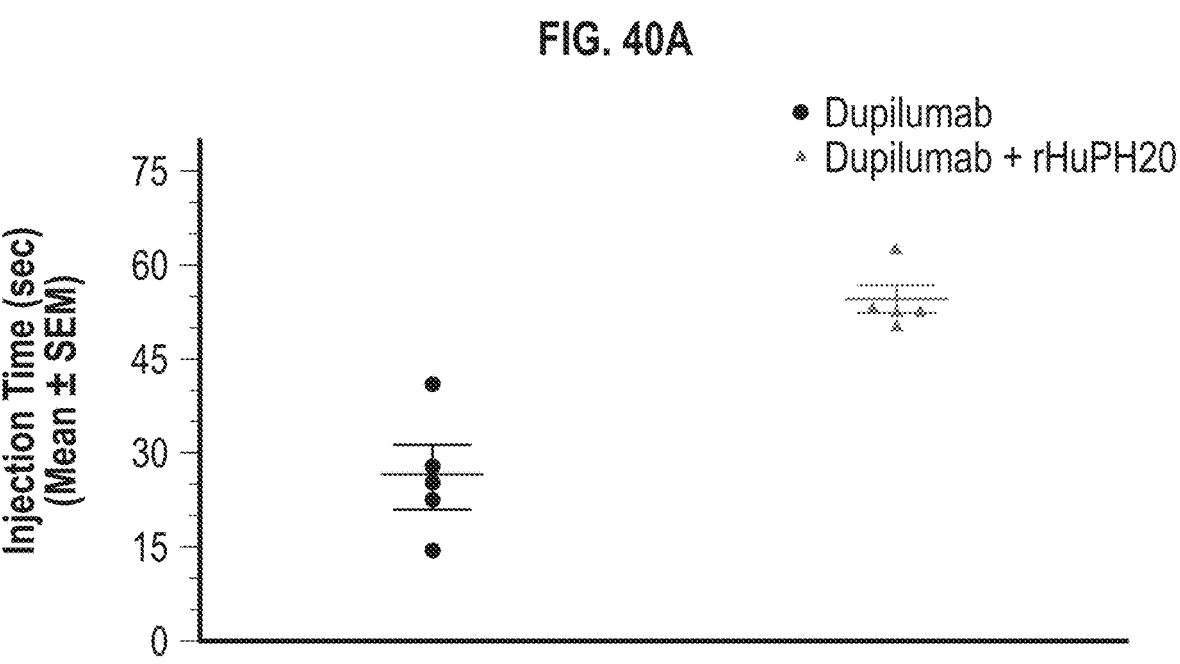
FIGS. 40A-40B show the individual animal data for the enzymatic activity of the co-mix of dupilumab+rHuPh20.

Pre-study hyaluronidase activity testing of dupilumab+rHuPH20 Co-mix. The enzymatic activity of the co-mix of dupilumab+rHuPH20 was tested using VV-QWUAL-006751 formerly TM010) The pre-study testing results are shown in Table 37 and individual animal data is shown in FIG. 40A.

TABLE 37

| Summary of Pre-study Enzymatic Activity Testing | |
| --- | --- |
| Test Solution | Pre-study Concentration (U/mL ± SD) |
| Dupilumab + rHuPH20 | 5637 ± 22 |

Figure 40B:
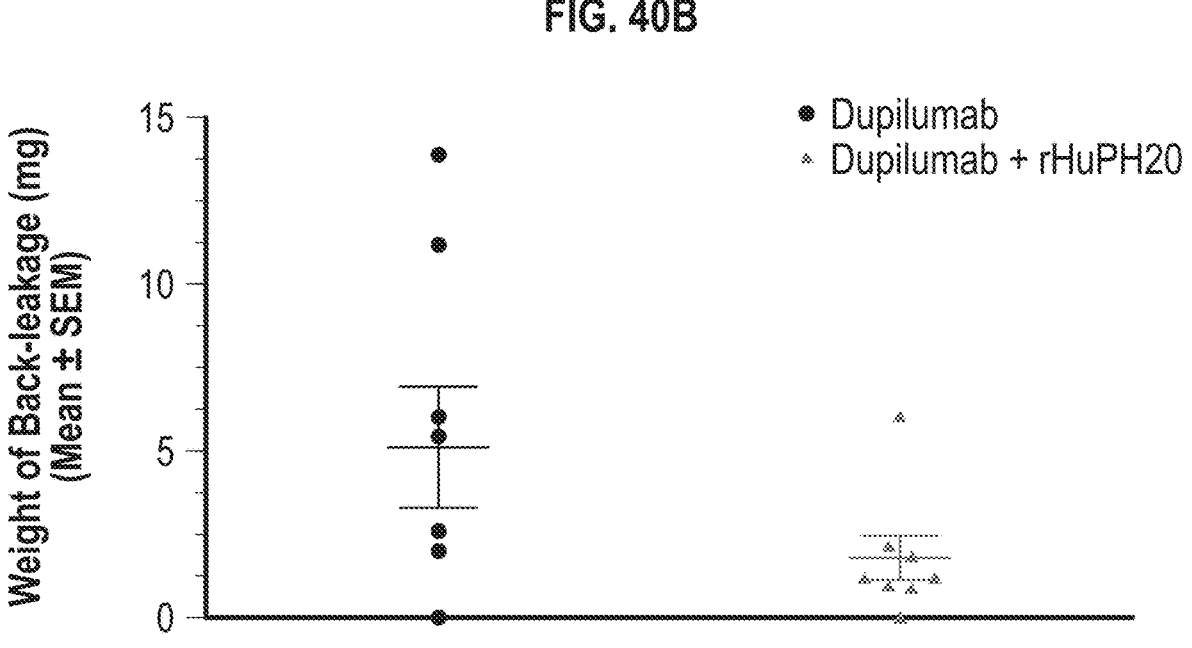

The duration of each injection was measured using a hand-held stopwatch with a precision of 0.1 seconds. The pre-study testing results are shown in Table 38 and individual animal data is shown in FIG. 40B.

TABLE 38

| Measurement of Injection Time | |
| --- | --- |
| Test Solution | Injection Time (sec ± SEM) |
| Dupilumab | 27.3 ± 4.3 |
| Dupilumab + rHuPH20 | 54.5 ± 2.1 |

The back-leakage was collected using a pre-weighed eye spear for 30 seconds post-injection. The eye spear was then re-weighed, and the weight of the back-leakage recorded. The amount of back-leakage for each test solution is shown in Table 39.

TABLE 39

| Measurement of Back-Leakage | |
| --- | --- |
| Test Solution | Back-Leakage (mg ± SEM) |
| Dupilumab | 1.9 ± 1.0 |
| Dupilumab + rHuPH20 | 5.4 ± 2.6 |

Figure 41A:
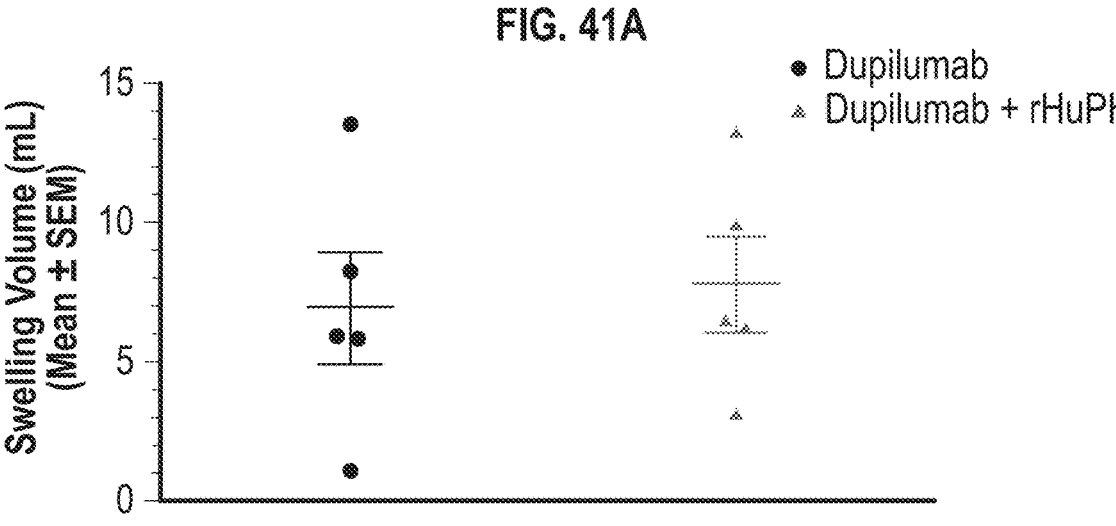
FIGS. 41A-41C show the mean and individual post-injection bleb volume, area and height values of the co-mix of dupilumab+rHuPh20, respectively.
Figure 41B:
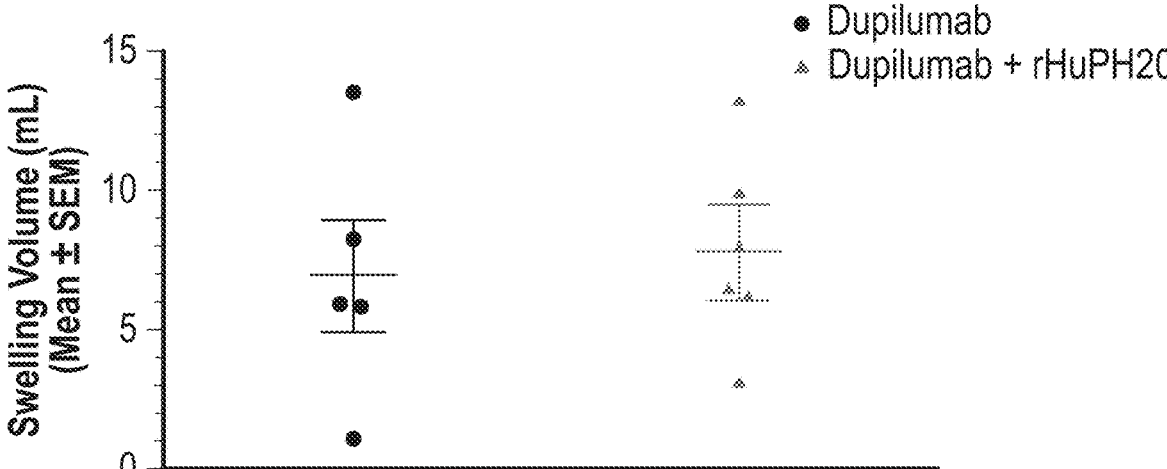
Figure 41C:
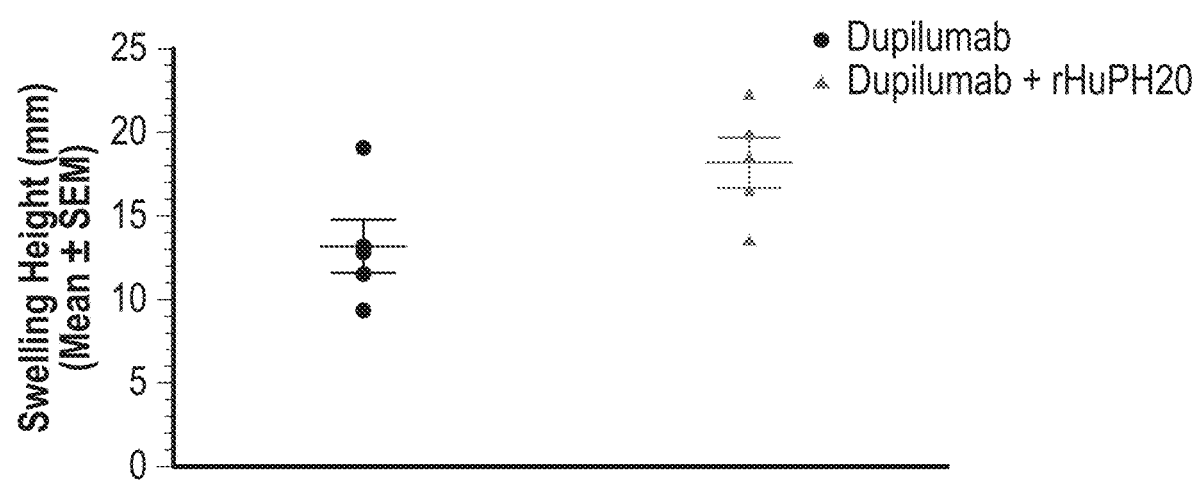

The local injection site swelling (bleb) was marked and measured using a digital caliper. Bleb volume dispersion area and swelling height of each bleb was determined as described above. Mean and individual post-injection bleb volume, area and height values are shown in FIG. 41A-C, respectively.

TABLE 40

| Post-Injection Bleb Volume, Area, Height - Caliper Measurements | | | | |
| --- | --- | --- | --- | --- |
| | | Mean ± SEM | | |
| Cohort # | Test Solution | Volume | Area | Height |
| 1 | Dupilumab | 7.0 ± 1.8 | 13.1 ± 1.4 | 2.5 ± 0.5 |
| 2 | Dupilumab + rHuPH20 | 7.8 ± 1.6 | 18.2 ± 1.3 | 2.3 ± 0.6 |

Qualitative assessments were taken immediately post-injection (T0) and daily thereafter. No erythema, swelling or induration was detected on D1, D2 or D3 post-injection (data not shown). No post-injection erythema was observed for any injection.

Figure 42:
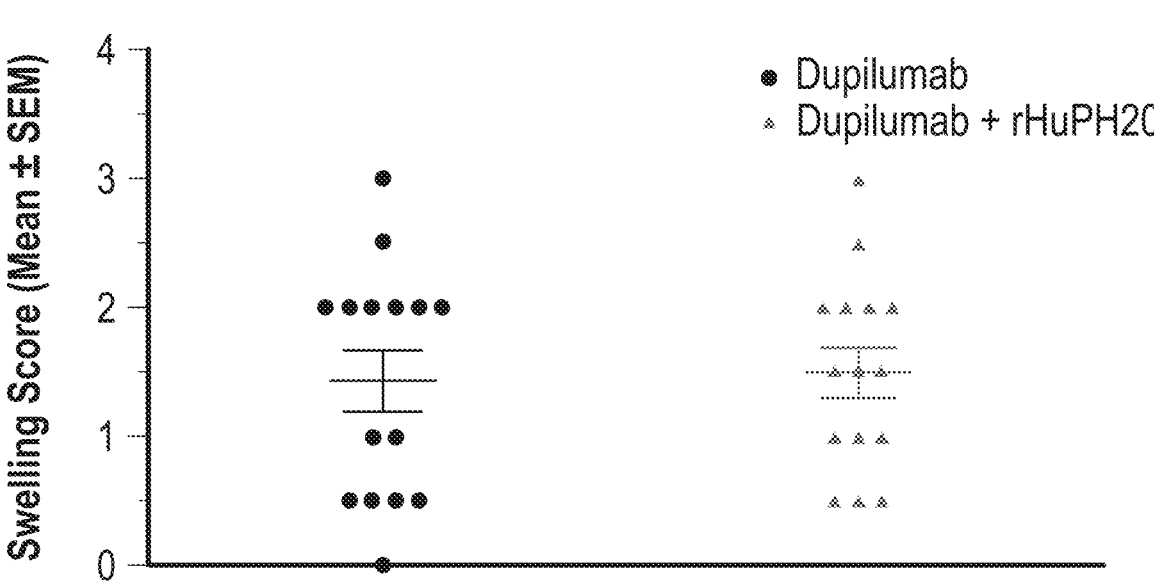
FIG. 42 shows individual animal data for scoring by three evaluators for swelling size using the modified Draize scoring system as summarized in Table 60.

Scoring by three evaluators for swelling size using the modified Draize scoring system are summarized in Table 41 and individual animal data shown in FIG. 42. No swelling was detected at the 24 h, 48h or 72h timepoints (data not shown).

TABLE 41

| Post-Injection Swelling of Dupilumab and Dupilumab + rHuPH20 | |
| --- | --- |
| Test Solution | Swelling Score (Mean ± SEM) |
| Dupilumab | 1.4 ± 0.2 |
| Dupilumab + rHuPH20 | 1.5 ± 0.2 |

Figure 43:
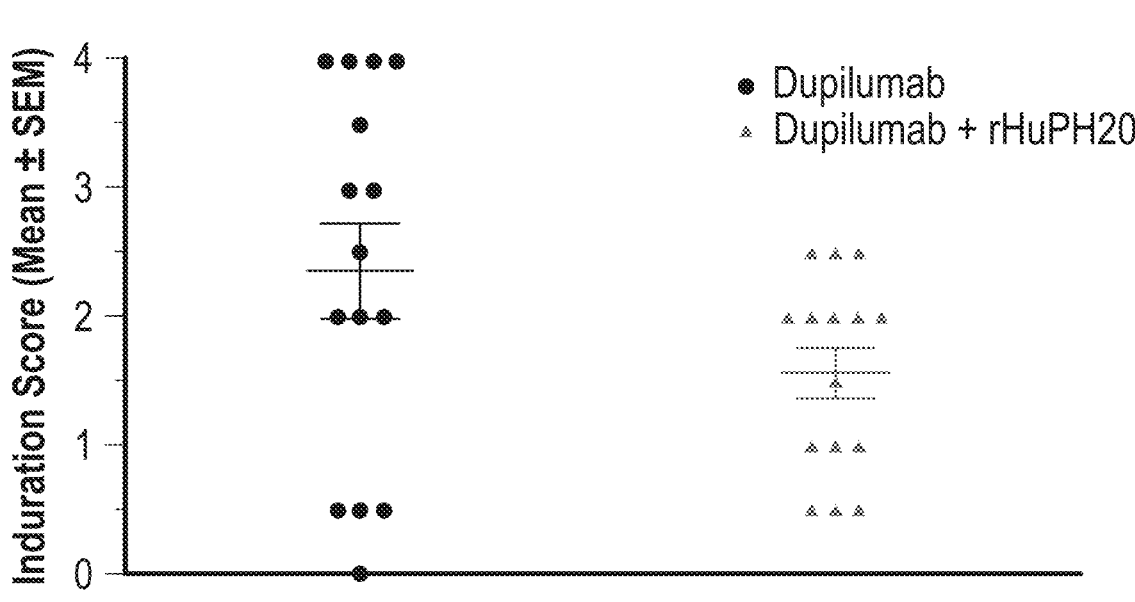
FIG. 43 shows individual animal data for scoring by three evaluators for bleb induration as summarized in Table 61.

Post-Injection Induration. Scoring by three evaluators for bleb induration was performed and is summarized in Table 42 and shown in FIG. 43.

TABLE 42

| Post-Injection Induration After SC Administration of Dupilumab and Dupilumab + rHuPH20 | |
| --- | --- |
| Test Solution | Induration Score (Mean ± SEM) |
| Dupilumab | 2.4 ± 0.4 |
| Dupilumab + rHuPH20 | 1.6 ± 0.2 |

Notably, despite dupilumab+rHuPH20 having injection volumes 2.5× that of the dupilumab alone, the induration of the larger volume appeared to be markedly reduced. Five animals received a 2 mL dose of dupilumab (Cohort 1) and five animals received a 5 mL dose of dupilumab+rHuPH20 (Cohort 2). The serum concentrations of dupilumab were measured using Dupilumab ELISA, Abx395100, Lot E2402922A, Exp. September 2024. The Concentration was calculated using a 4-PL model, SoftMax Pro, Molecule Device.

Figure 45:
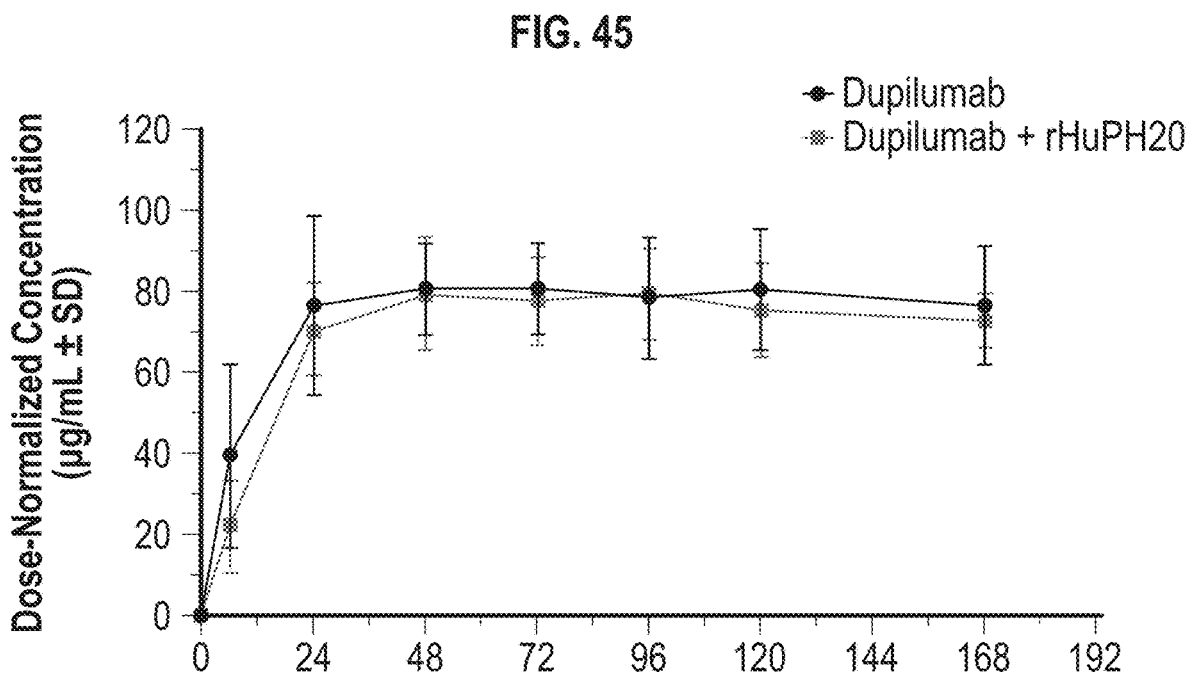
FIG. 45 shows the dose-normalized concentration versus time profiles for the two treatment groups.

Cohort #2). A similar calculation was performed for standard deviation values. The dose-normalized concentration versus time profiles for the two treatment groups is shown in FIG. 45. Individual pharmacokinetic parameters were determined by non-compartmental analyses in Excel and are presented in Table 44.

TABLE 44

| | | | Dose Normalized | | Dose Normalized |
| --- | --- | --- | --- | --- | --- |
| Group | Animal ID | $AUC_{0-168}$ (µg*hr/mL) | $AUC_{0-168}$ (µg*hr/mL) | $C_{max}$ (µg/mL) | $C_{max}$ (µg/mL) |
| 1 | 4497 | 22473 | 11237 | 163 | 81 |
| 1 | 4499 | 32651 | 16325 | 211 | 105 |
| 1 | 4500 | 22164 | 11082 | 173 | 86 |
| 1 | 4501 | 24181 | 12090 | 163 | 81 |
| 1 | 4590 | 24279 | 12140 | 179 | 89 |
| Group Mean | | 25150 | 12575 | 178 | 89 |
| Standard Deviation | | 4302 | 2151 | 20 | 10 |
| Coefficient of Variation % | | 17 | 17 | 11 | 11 |
| 2 | 4483 | 52071 | 10414 | 349 | 70 |
| 2 | 4485 | 59498 | 11900 | 407 | 81 |
| 2 | 4494 | 53126 | 10625 | 374 | 75 |
| 2 | 4495 | 73157 | 14631 | 492 | 98 |
| 2 | 4496 | 59626 | 11925 | 432 | 86 |
| Group Mean | | 59496 | 11899 | 411 | 82 |
| Standard Deviation | | 8402 | 1680 | 56 | 11 |
| Coefficient of Variation % | | 14 | 14 | 14 | 14 |

Pharmacokinetic Parameters for Individual Animals

TABLE 43

Concentrations of Dupixent in Individual Pig Serum

| Cohort | Time Points Post Injection (hr) | 4497 | 4499 | 4500 | 4501 | 4590 | Mean | SD | CV % |
| --- | --- | --- | --- | --- | --- | --- | --- | --- | --- |
| 1 | 0 | 0 | 0 | 0 | 0 | 0 | 0.0 | 0.0 | n/a |
| 1 | 6 | 84.7 | 130 | 10.9 | 62.8 | 105.6 | 78.8 | 45.4 | 57.6 |
| 1 | 24 | 162.9 | 203.2 | 88.1 | 129.3 | 178.9 | 152.5 | 44.9 | 29.4 |
| 1 | 48 | 154.7 | 198.9 | 138.5 | 156.3 | 158.2 | 161.3 | 22.4 | 13.9 |
| 1 | 72 | 141.7 | 192.9 | 172.9 | 159.1 | 142.2 | 161.8 | 21.7 | 13.4 |
| 1 | 96 | 134.6 | 208 | 150.2 | 152.9 | 138.4 | 156.8 | 29.6 | 18.9 |
| 1 | 120 | 133 | 210.9 | 152.3 | 162.6 | 147.4 | 161.2 | 29.7 | 18.4 |
| 1 | 168 | 121 | 201.5 | 150.9 | 150.8 | 142.4 | 153.3 | 29.6 | 19.3 |

Dupixent Concentrations (µg/mL) Animal ID — Dupixent Concentrations (µg/mL)

| | Post Injection (hr) | 4483 | 4485 | 4494 | 4495 | 4496 | Mean | SD | CV % |
| --- | --- | --- | --- | --- | --- | --- | --- | --- | --- |
| 2 | 0 | 0 | 0 | 0 | 0 | 0 | 0 | 0.0 | n/a |
| 2 | 6 | 113.7 | 118.9 | 77.5 | 195.5 | 43.9 | 109.9 | 56.6 | 51.5 |
| 2 | 24 | 332.3 | 366.8 | 301.5 | 448.7 | 316.3 | 353.12 | 58.7 | 16.6 |
| 2 | 48 | 318.7 | 403.2 | 345.7 | 492.4 | 431.8 | 398.36 | 69.1 | 17.3 |
| 2 | 72 | 332.7 | 363.1 | 373.6 | 474.5 | 403.2 | 389.42 | 53.8 | 13.8 |
| 2 | 96 | 348.7 | 406.5 | 353.1 | 486.4 | 386.8 | 396.3 | 55.8 | 14.1 |
| 2 | 120 | 320.8 | 355.6 | 341.4 | 466.7 | 404 | 377.7 | 58.4 | 15.5 |
| 2 | 168 | 340.7 | 392.5 | 326.5 | 404.5 | 357.9 | 364.42 | 33.3 | 9.1 |

Animal ID — Dupixent Concentrations (µg/mL)

Figure 44:
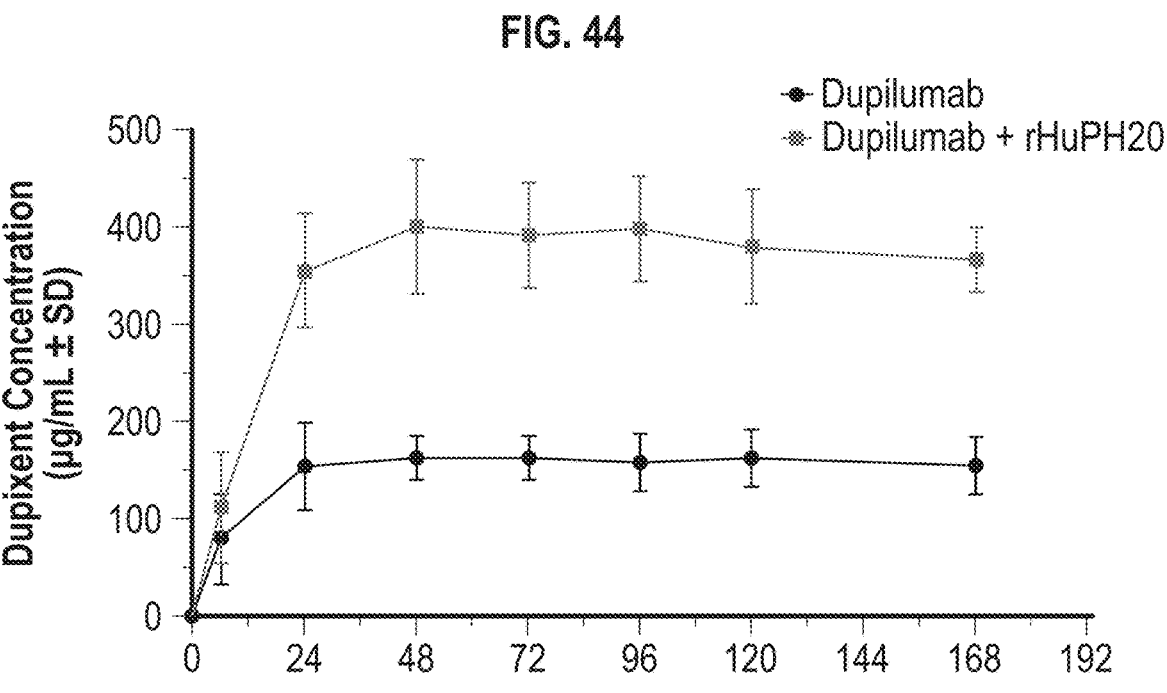
FIG. 44 shows the concentration—time profiles of dupilumab and dupilumab+rHuPH20.

The concentration—time profiles of dupilumab and dupilumab+rHuPH20 are shown in FIG. 44. The concentration of dupilumab at each timepoint was dose-normalized for both treatment groups. To obtain dose-normalized values, the serum values for dupilumab concentration were divided by 2 (dose volume for Cohort #1) or by 5 (dose volume for A prototype HVAI was able to successfully deliver 5 mL of dupilumab in approximately 55 seconds using rHuPH20. Despite having a dose volume 2.5× greater than that of dupilumab alone, dupilumab+rHuPH20 resulted in similar post-injection bleb size. Post-injection induration was reduced by the addition of rHuPH20 compared to dupilumab alone. Basic pharmacokinetic parameters derived from the two dose groups indicate similar dose-normalized PK profiles, with no significant differences in dose-normalized $AUC_{0-168}$ or $C_{max}$ observed.

Example 8: Pharmacokinetic Models

The following simulations were conducted for TRODELVY and eight examples (see Table below). Commercially-approved or clinically-evaluated IV dosing regimens were defined for each ADC, along with PK parameters (e.g. volume of distribution and clearance), based on publicly available information (e.g. from package inserts or peer-reviewed publications). Two-compartment PK models were constructed for each ADC based on this information. Simulations were then generated for each ADC to compare the PK profiles of the current IV regimen and SC regimen(s) when co-administered with rHuPH20. Doses of the ADC administered SC with rHuPH20 were chosen to match the AUC (the typical driver of efficacy) of the current IV regimen and simulations of ADCs SC with rHuPH20 were generated for the current schedule (Q3W), as well as less (e.g., Q4W) and more (e.g, Q2W) frequent schedules.

| Example # | Generic Name | Trade Name | FIGURE |
|---|---|---|---|
| i | patritumab deruxtecan | N/A | 47 |
| ii | datopotamab deruxtecan | N/A | 48 |
| iii | brentuximab vedotin | ADCETRIS | 49 |
| iv | trastuzumab emtansine | KADCYLA | 50 |
| v | trastuzumab deruxtecan | ENHERTU | 51 |
| vi | tisotumab vedotin | TIVDAK | 52 |
| vii | mirvetuximab soravtansine | ELAHERE | 53 |
| viii | loncastuximab tesirine | ZYNLONTA | 54 |

Figure 46:
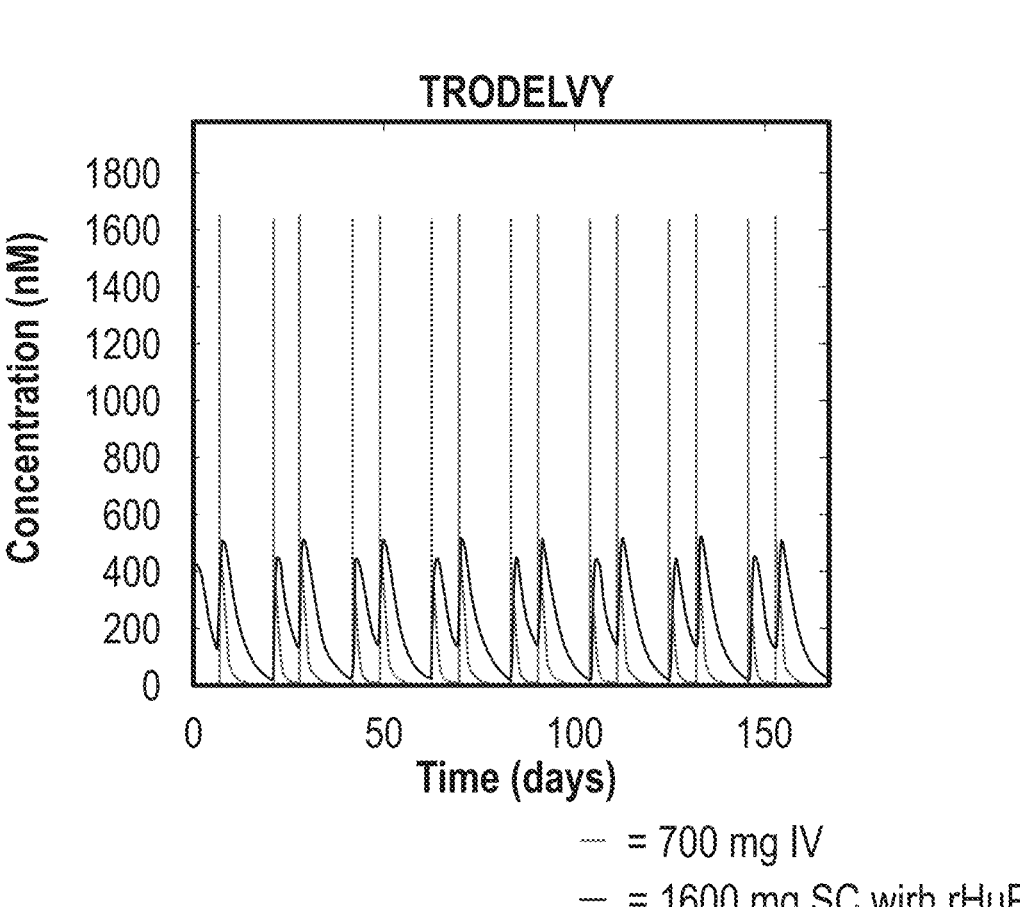
FIG. 46 shows a simulation for conversion of an IV dosing regimen of TRODELVY to a SC regimen with rHuPH20, with equivalent AUC and lower $C_{max}$.
Figure 47:
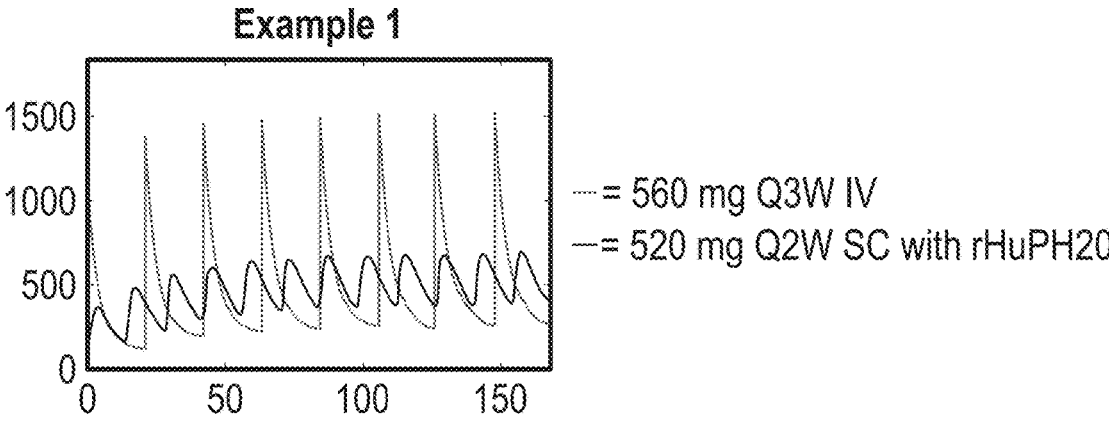
FIG. 47 shows a simulation for conversion of an IV dosing regimen of patritumab deruxtecan to a SC regimen with rHuPH20, with equivalent AUC and lower $C_{max}$.
Figure 47:
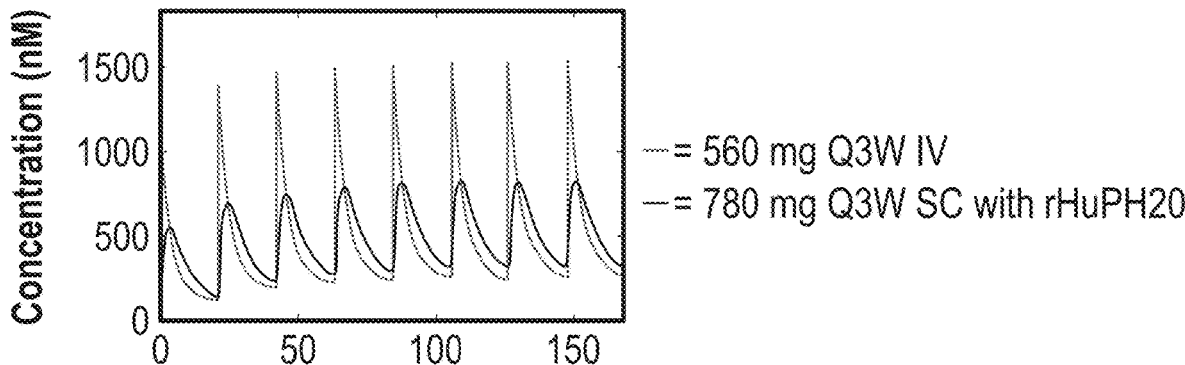
Figure 47:
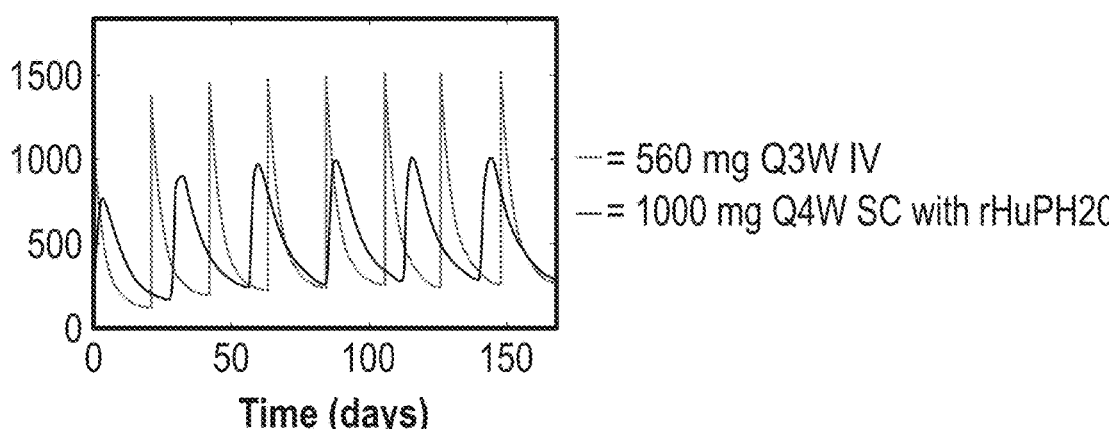
Figure 48:
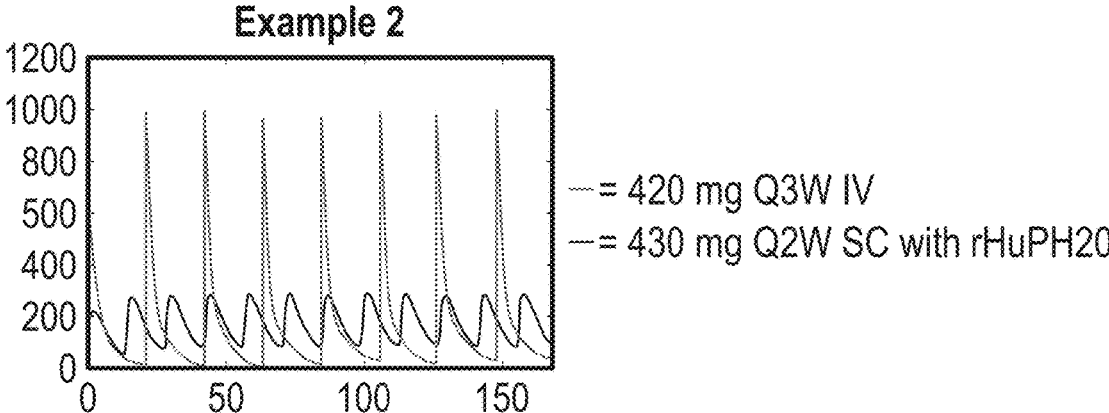
FIG. 48 shows a simulation for conversion of an IV dosing regimen of datopotamab deruxtecan to a SC regimen with rHuPH20, with equivalent AUC and lower $C_{max}$.
Figure 48:
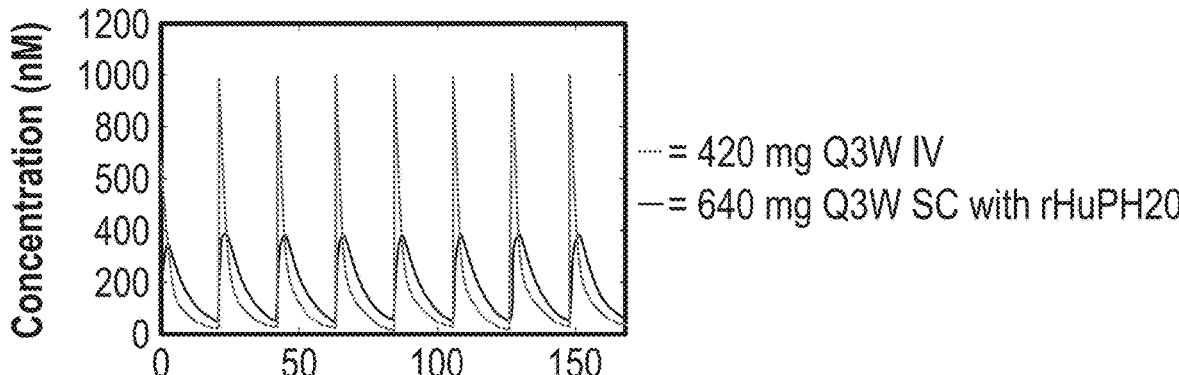
Figure 48:
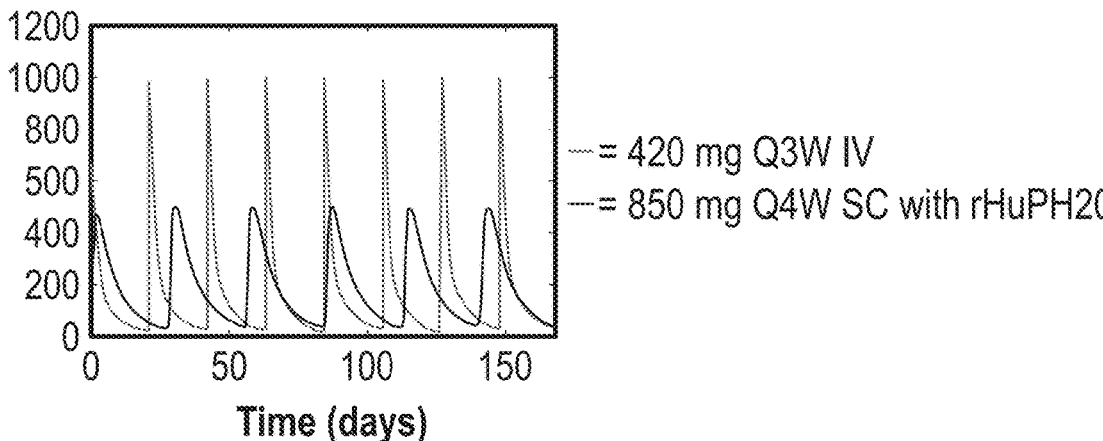
Figure 49:
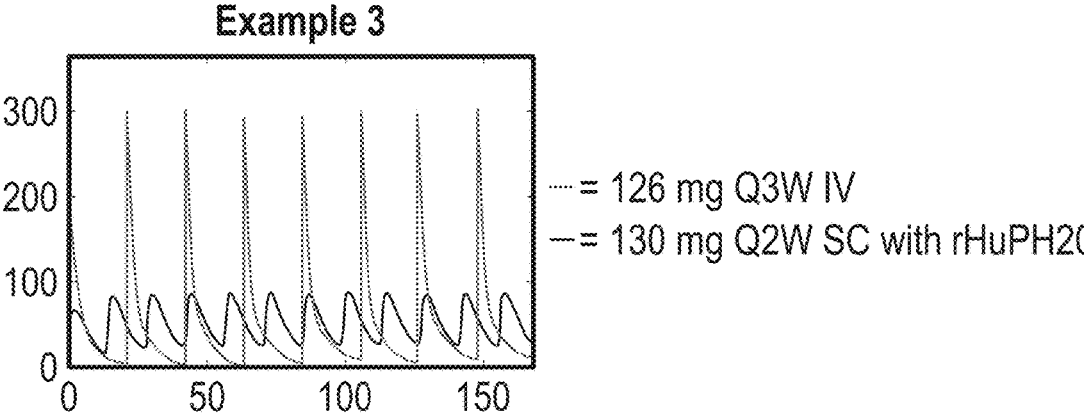
FIG. 49 shows a simulation for conversion of an IV dosing regimen of brentuximab vedotin to a SC regimen with rHuPH20, with equivalent AUC and lower $C_{max}$.
Figure 49:
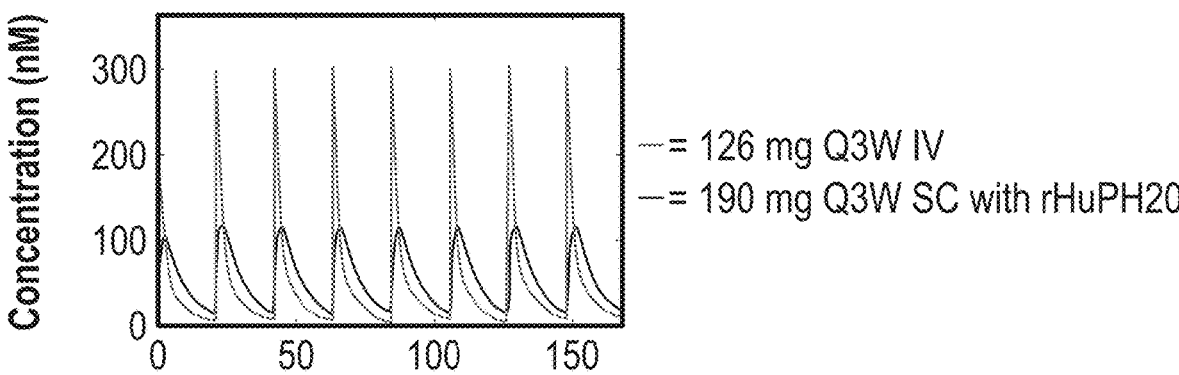
Figure 49:
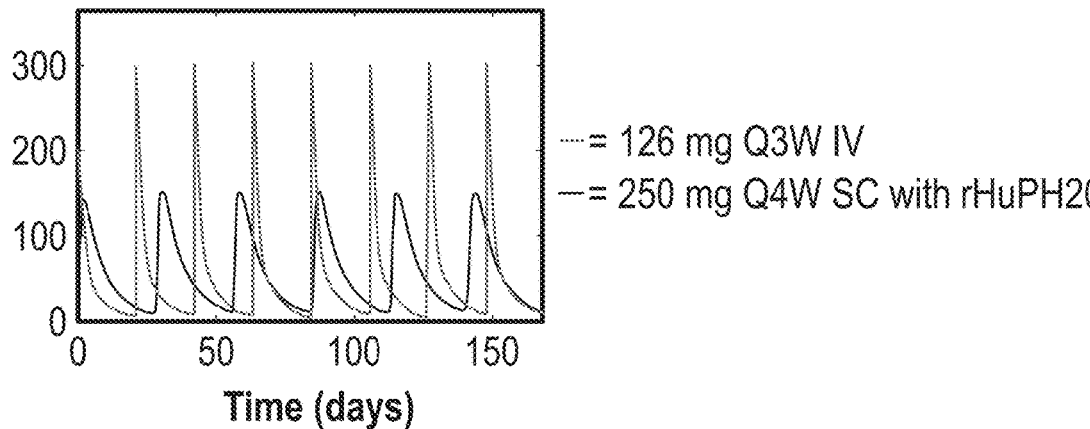
Figure 50:
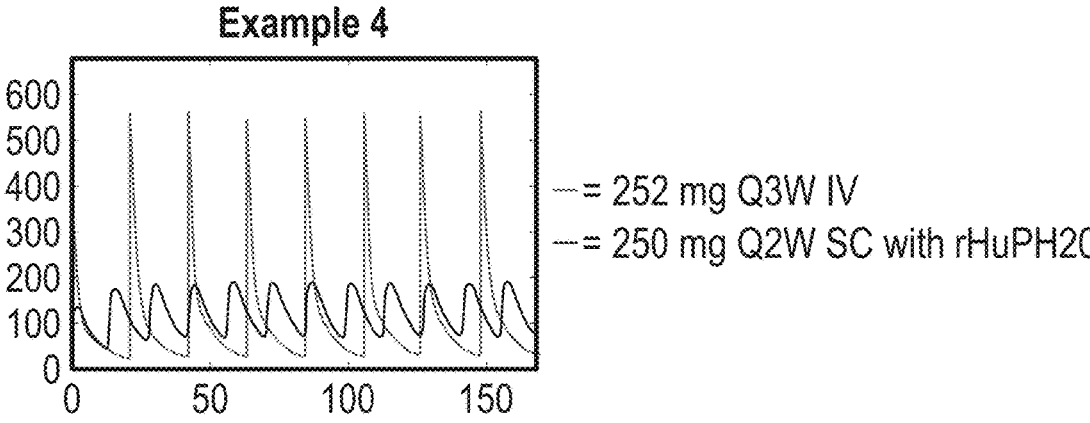
FIG. 50 shows a simulation for conversion of an IV dosing regimen of trastuzumab emtansine to a SC regimen with rHuPH20, with equivalent AUC and lower $C_{max}$.
Figure 50:
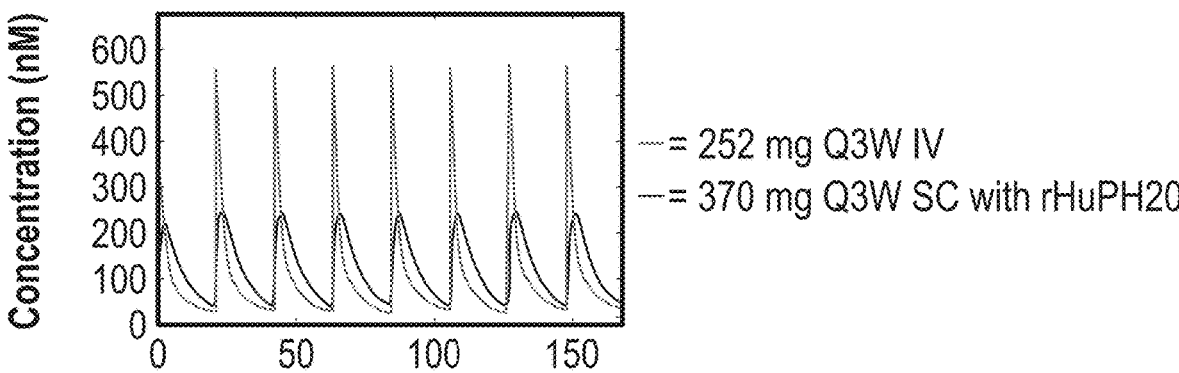
Figure 50:
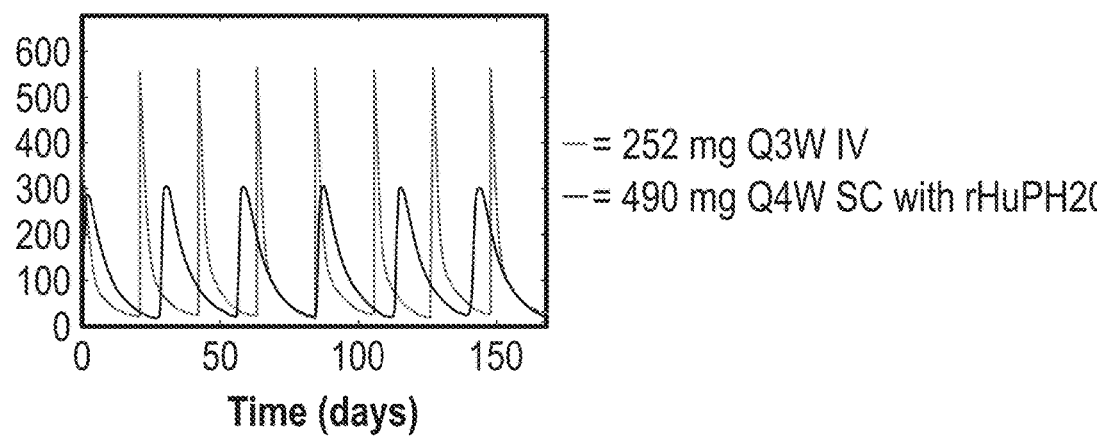
Figure 51:
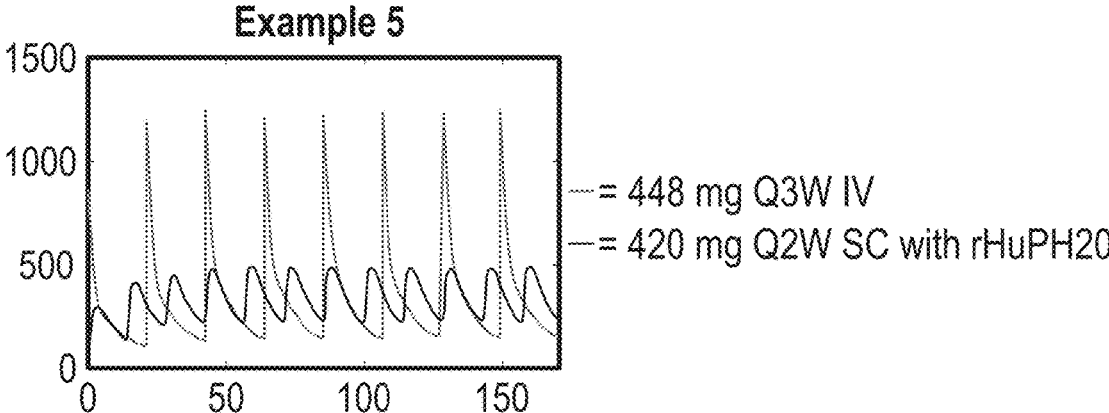
FIG. 51 shows a simulation for conversion of an IV dosing regimen of trastuzumab deruxtecan to a SC regimen with rHuPH20, with equivalent AUC and lower $C_{max}$.
Figure 51:
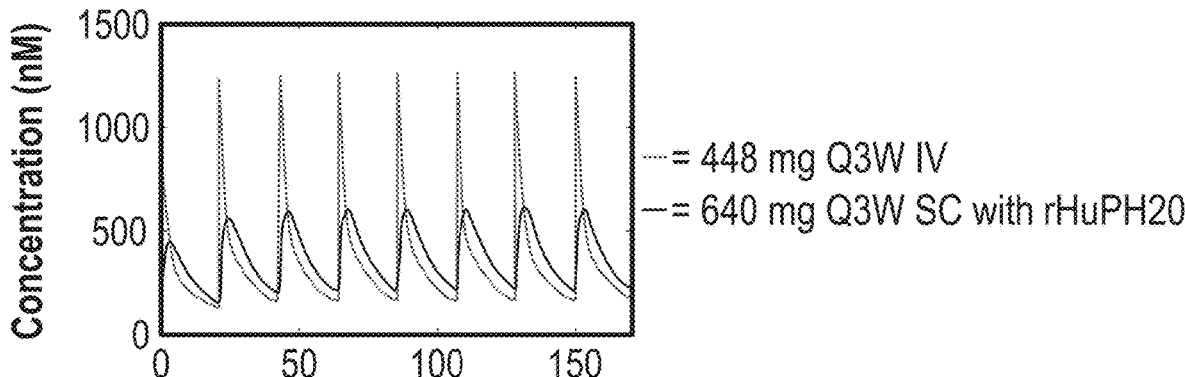
Figure 51:
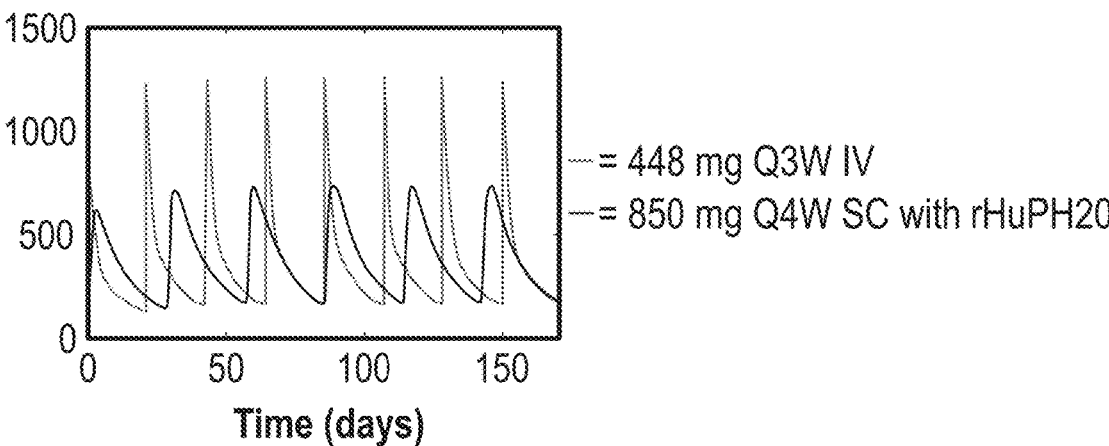
Figure 52:
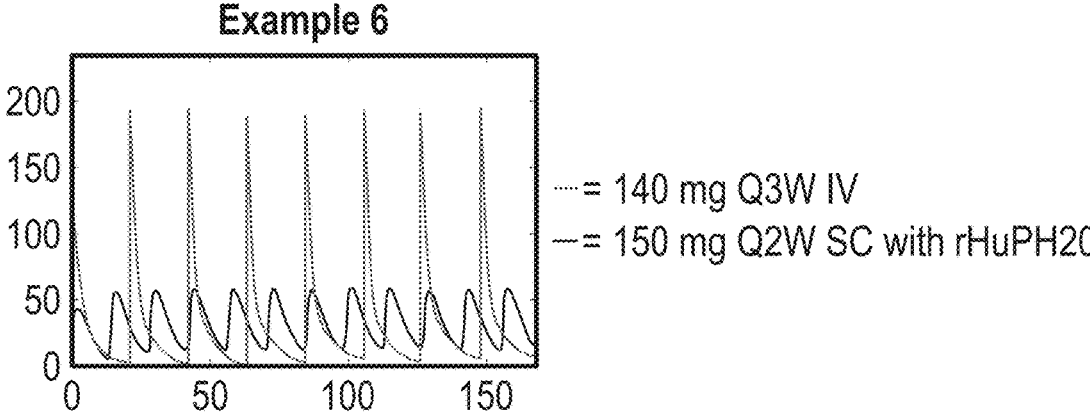
FIG. 52 shows a simulation for conversion of an IV dosing regimen of tisotumab vedotin to a SC regimen with rHuPH20, with equivalent AUC and lower $C_{max}$.
Figure 52:
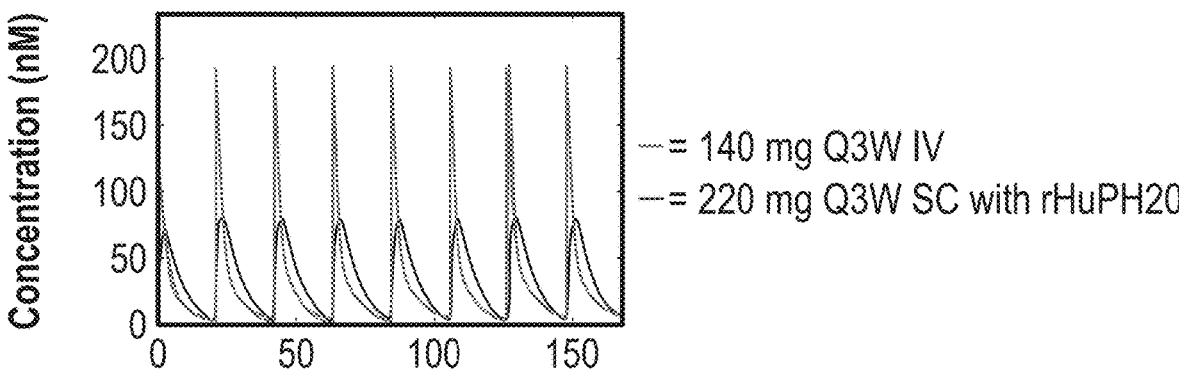
Figure 52:
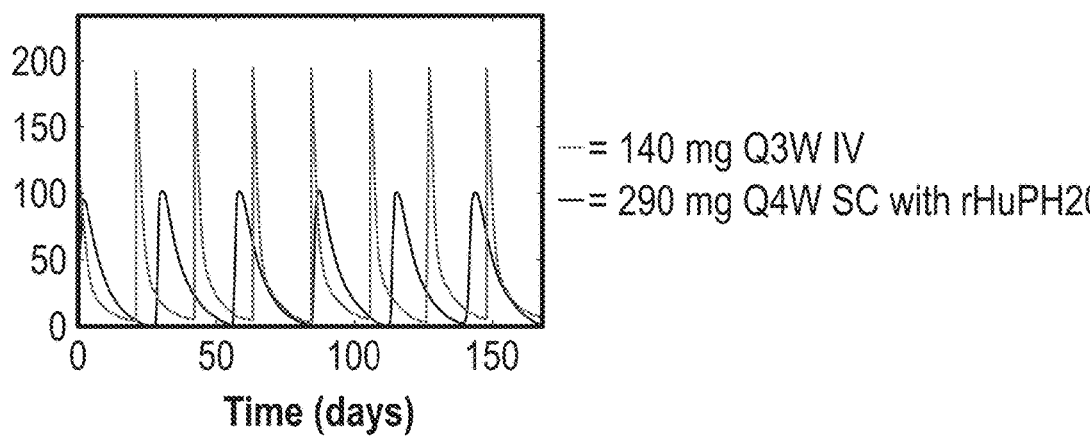
Figure 53:
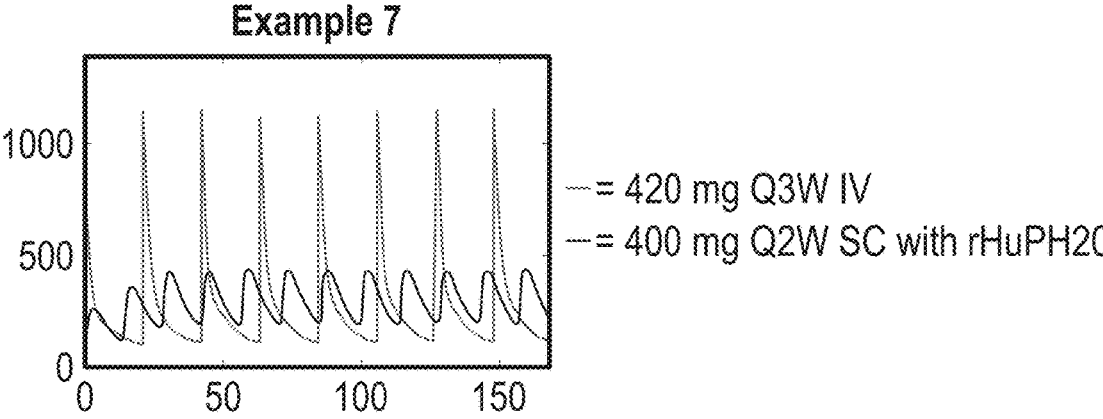
FIG. 53 shows a simulation for conversion of an IV dosing regimen of mirvetuximab soravtansine to a SC regimen with rHuPH20, with equivalent AUC and lower $C_{max}$.
Figure 53:
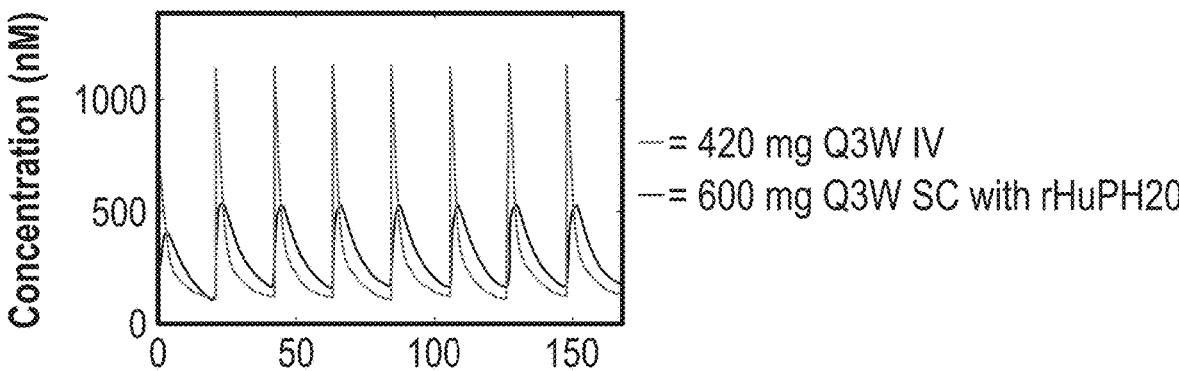
Figure 53:
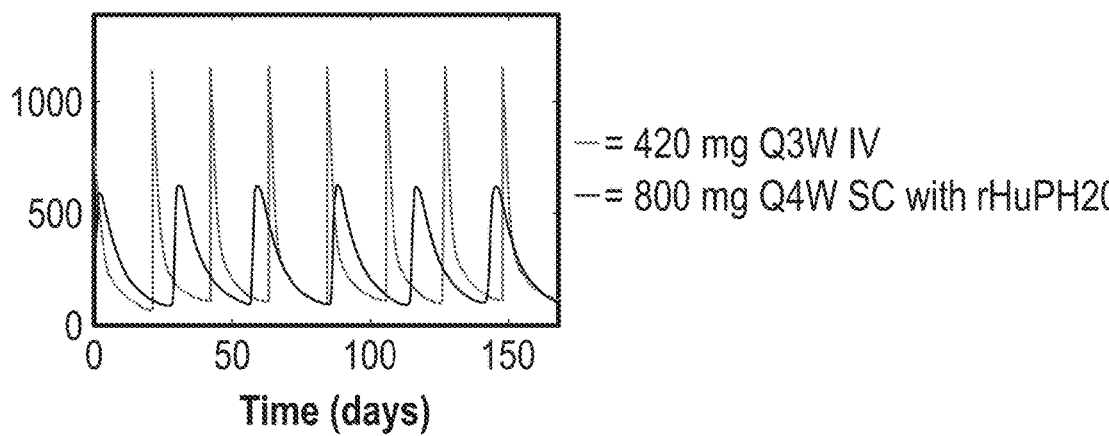
Figure 54:
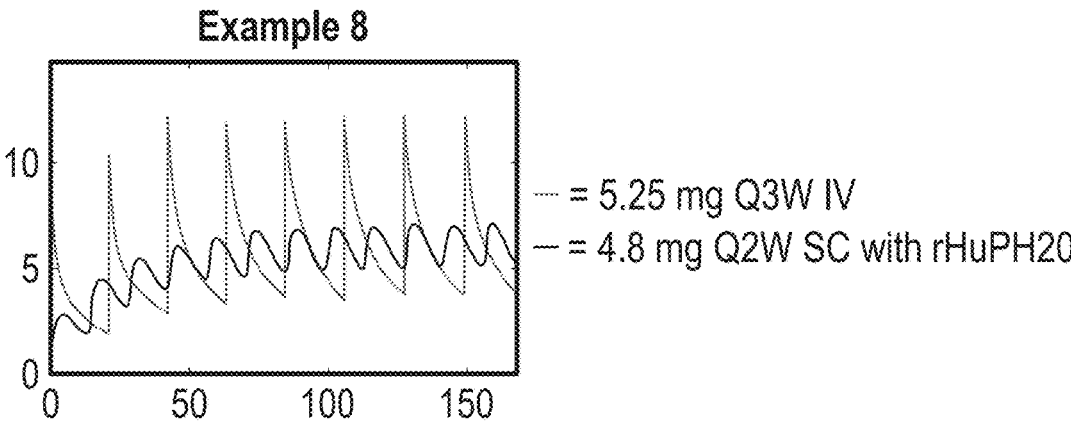
FIG. 54 shows a simulation for conversion of an IV dosing regimen of loncastuximab tesirine to a SC regimen with rHuPH20, with equivalent AUC and lower $C_{max}$.
Figure 54:
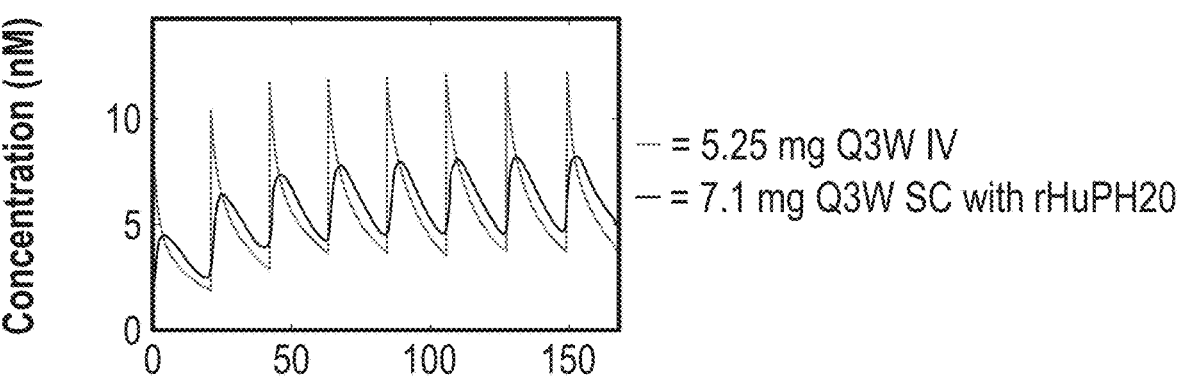
Figure 54:
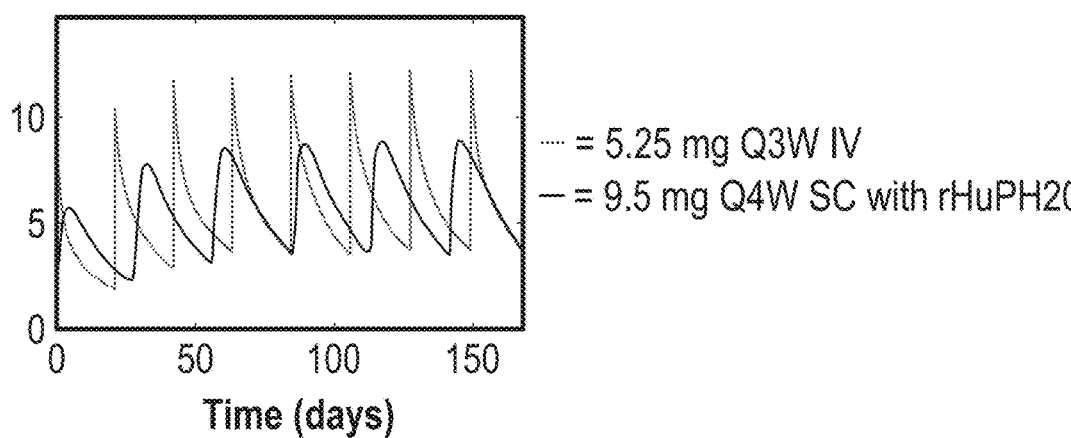

All simulations, for TRODELVY (FIG. 46) and eight others (FIG. 47-54), demonstrated the ability to convert the current IV dosing regimen to a SC regimen with rHuPH20, with equivalent AUC and lower $C_{max}$. Since $C_{max}$ is typically a driver of systemic toxicities for ADCs, this suggests the regimen of SC with rHuPH20 could provide an improved safety profile. Additionally, all eight simulated examples demonstrated the ability of a SC regimen with rHuPH20 to maintain this equivalent AUC and lower $C_{max}$ compared to IV, at at less and more frequent dosing schedules, enabling more options for optimizing the safety and/or efficacy profile of the ADC.

The invention claimed is:

1. A combination dosing regimen, comprising:

(i) subcutaneously administering to a patient in need thereof a composition comprising (a) a soluble hyaluronidase comprising a sequence of amino acids that has at least 85% sequence identity to a sequence of amino acids that contains at least amino acids 36-464 of SEQ ID NO: 1 and retains hyaluronidase activity, and (b) an effective dose of an antibody-drug conjugate (ADC); or (ii) (a) subcutaneously administering to a patient in need thereof a first composition comprising a soluble hyaluronidase comprising a sequence of amino acids that has at least 85% sequence identity to a sequence of amino acids that contains at least amino acids 36-464 of SEQ ID NO: 1 and retains hyaluronidase activity, and (b) subcutaneously administering to the patient in need thereof a second composition comprising the effective dose of the ADC, wherein:

the subcutaneous administration of the combination dosing regimen is administered in an amount that yields an area under the curve (AUC) of the ADC that is equal or greater than an AUC of an intravenous administration of a dosing regimen comprising the effective dose of the ADC without the soluble hyaluronidase, and the subcutaneous administration of the combination dosing regimen yields a maximum concentration ($C_{max}$) of the ADC that is lower than the $C_{max}$ of the ADC obtained from the intravenous administration of the dosing regimen without the soluble hyaluronidase.

2. The combination dosing regimen of claim 1, wherein the ADC comprises an antibody and a payload conjugated to the antibody via a cleavable linker, wherein free antibody and free payload are released upon cleavage of the cleavable linker, and wherein the subcutaneous administration of the combination dosing regimen yields an AUC of the free payload in blood that is about 50% to about 90% of an AUC of an intravenous administration of a dosing regimen comprising an equivalent dose of the ADC without the soluble hyaluronidase.

3. The combination dosing regimen of claim 1, wherein the ADC comprises an antibody and a payload conjugated to the antibody via a cleavable linker, wherein free antibody and free payload are released upon cleavage of the cleavable linker, and wherein the subcutaneous administration of the combination dosing regimen yields a $C_{max}$ of the free payload in blood that is about 30% to about 80% of a $C_{max}$ of an intravenous administration of a dosing regimen comprising an equivalent dose of the ADC without the soluble hyaluronidase.

4. The combination dosing regimen of claim 1, wherein the subcutaneous administration of the combination dosing regimen yields a $C_{max}$ of the ADC that is about 20% to about 55% of the $C_{max}$ of the ADC obtained from an intravenous administration of an equivalent dose of the dosing regimen without the soluble hyaluronidase.

5. The combination dosing regimen of claim 1, wherein:

(a) the soluble hyaluronidase has an amino acid sequence selected from amino acids 36-465 of SEQ ID NO: 1, 36-466 of SEQ ID NO: 1, 36-467 of SEQ ID NO: 1, 36-468 of SEQ ID NO: 1, 36-469 of SEQ ID NO: 1, 35-470 of SEQ ID NO: 1, 36-471 of SEQ ID NO: 1, 36-472 of SEQ ID NO: 1, 36-474 of SEQ ID NO: 1, 36-475 of SEQ ID NO: 1, 36-476 of SEQ ID NO: 1, 35-477 of SEQ ID NO: 1, 36-478 of SEQ ID NO: 1 (i.e., SEQ ID NO: 8), 36-479 of SEQ ID NO: 1 (i.e., SEQ ID NO: 7), 36-480 of SEQ ID NO: 1 (i.e., SEQ ID NO: 6), 36-481 of SEQ ID NO: 1 (i.e., SEQ ID NO: 5), 36-482 of SEQ ID NO: 1 (i.e., SEQ ID NO: 4), 36-483 of SEQ ID NO: 1 (i.e., SEQ ID NO: 46), 35-484 of SEQ ID NO: 1, 36-485 of SEQ ID NO: 1, 36-486 of SEQ ID NO: 1, 36-487 of SEQ ID NO: 1, 36-488 of SEQ ID NO: 1, 36-489 of SEQ ID NO: 1, 36-490 of SEQ ID NO: 1, 35-491 of SEQ ID NO: 1, 36-492 of SEQ ID NO: 1, 36-493 of SEQ ID NO: 1, 36-494 of SEQ ID NO: 1, 36-495 of SEQ ID NO: 1, 36-496 of SEQ ID NO: 1, 36-497 of SEQ ID NO: 1, 35-498 of SEQ ID NO: 1, 36-499 of SEQ ID NO: 1, and 36-500 of SEQ ID NO: 1; or (b) the soluble hyaluronidase is a variant soluble hyaluronidase that has at least 91% sequence identity to a reference soluble hyaluronidase having the amino acid sequence of (a).

6. The combination dosing regimen of claim 5, wherein the soluble hyaluronidase comprises a modified PH20 hyaluronidase with amino acid substitution F204P, and has increased stability relative to an unmodified PH20 hyaluronidase that does not comprise F204P; and wherein the modified PH20 hyaluronidase comprises one or more further replacements selected from:

(a) T341S, L342W, S343E, I344N, M345T, S347T, M348K, K349E, L352Q, L353A, L354I, D355K, N356E, E359D and I361T;

(b) L342W, S343E, I344N, M345T, S347T, M348K, K349E, L352Q, L353A, L354I, D355K, N356E, E359D and I361T;

(c) M345T, S347T, M348K, K349E, L352Q, L353A, L354I, D355K, N356E, E359D, I361T and N363G;

(d) T341G, L342W, S343E, I344N, M345T, S347T, M348K, K349E, L352Q, L353A, L354I, D355K, N356E, E359D and I361T;

(e) T341A, L342W, S343E, I344N, M345T, S347T, M348K, K349E, L352Q, L353A, L354I, D355K, N356E, E359D and I361T;

(f) T341C, L342W, S343E, I344N, M345T, S347T, M348K, K349E, L352Q, L353A, L354I, D355K, N356E, E359D and I361T;

(g) T341D, L342W, S343E, I344N, M345T, S347T, M348K, K349E, L352Q, L353A, L354I, D355K, N356E, E359D and I361T;

(h) I344N, M345T, S347T, M348K, K349E, L352Q, L353A, L354I, D355K, N356E, E359D and I361T; and (i) S343E, I344N, M345T, S347T, M348K, K349E, L352Q, L353A, L354I, D355K, N356E, E359D and I361T, and wherein increased stability is measured as increased stability in a denaturing condition or at elevated temperatures.

7. The combination dosing regimen of claim 5, wherein:

the soluble hyaluronidase is a variant modified polypeptide or catalytically active portion thereof that comprises one or more amino acid substitutions selected from among T341A, T341C, T341D, T341G, T341S, L342W, S343E, I344N, M348K, and N363G, wherein amino acid numbering is with reference to SEQ ID NO:1; and the variant modified polypeptide has an N-terminus at amino acid 36, 37, 38, 39, or 40 and a C-terminus at an amino acid corresponding to amino acids 465 to 500 with reference to SEQ ID NO: 1, optionally wherein the C-terminus of the variant modified polypeptide is at an amino acid corresponding to amino acid 467, 468, 469, 470, or 471 with reference to SEQ ID NO:1.

8. The combination dosing regimen of claim 1, wherein:

the soluble hyaluronidase is administered at a dose of 2,000 to 96,000 U; and the ADC is administered at a dose of at least or at 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 30 mg/kg, 40 mg/kg, 50 mg/kg, 60 mg/kg, 70 mg/kg, 80 mg/kg, 90 mg/kg, or 100 mg/kg; optionally at a dose of 10 mg/kg.

9. The combination dosing regimen of claim 1, wherein the soluble hyaluronidase and the ADC are administered once per day on at least two days in a treatment cycle.

10. The combination dosing regimen of claim 1, wherein the soluble hyaluronidase and the ADC are administered once a day (Q1).

11. The combination dosing regimen of claim 1, wherein the ADC is selected from sacituzumab govitecan, patritumab deruxtecan, datopotamab deruxtecan, brentuximab vedotin, trastuzumab emtansine, trastuzumab deruxtecan, tisotumab vedotin, mirvetuximab soravtansine, and loncastuximab tesirine.

12. The combination dosing regimen of claim 1, wherein the AUC is a weekly average AUC.

13. The combination dosing regimen of claim 1, wherein the AUC is measured over a time interval selected from a group consisting of twenty-four (24) hours, forty-eight (48) hours, seventy-two (72) hours, ninety-six (96) hours, one-hundred-and-twenty (120) hours, one-hundred-and-forty-four (144) hours, and one-hundred-and-sixty-eight (168) hours.

14. The combination dosing regimen of claim 1, wherein the AUC is measured over a time interval selected from a group consisting of seven (7) days, fourteen (14) days, twenty-one (21) days, twenty-eight (28) days, eighty-four (84) days, and one-hundred-and-sixty-eight (168) days.

15. The combination dosing regimen of claim 1, wherein the sequence of amino acids of the soluble hyaluronidase has at least 86% sequence identity to the sequence of amino acids that contains at least amino acids 36-464 of SEQ ID NO:1.

16. The combination dosing regimen of claim 15, wherein the sequence of amino acids of the soluble hyaluronidase has at least 87% sequence identity to the sequence of amino acids that contains at least amino acids 36-464 of SEQ ID NO:1.

17. The combination dosing regimen of claim 16, wherein the sequence of amino acids of the soluble hyaluronidase has at least 88% sequence identity to the sequence of amino acids that contains at least amino acids 36-464 of SEQ ID NO:1.

18. The combination dosing regimen of claim 17, wherein the sequence of amino acids of the soluble hyaluronidase has at least 89% sequence identity to the sequence of amino acids that contains at least amino acids 36-464 of SEQ ID NO:1.

19. The combination dosing regimen of claim 18, wherein the sequence of amino acids of the soluble hyaluronidase has at least 90% sequence identity to the sequence of amino acids that contains at least amino acids 36-464 of SEQ ID NO:1.

20. The combination dosing regimen of claim 19, wherein the sequence of amino acids of the soluble hyaluronidase has at least 91% sequence identity to the sequence of amino acids that contains at least amino acids 36-464 of SEQ ID NO:1.

21. The combination dosing regimen of claim 20, wherein the sequence of amino acids of the soluble hyaluronidase has at least 92% sequence identity to the sequence of amino acids that contains at least amino acids 36-464 of SEQ ID NO:1.

22. The combination dosing regimen of claim 21, wherein the sequence of amino acids of the soluble hyaluronidase has at least 93% sequence identity to the sequence of amino acids that contains at least amino acids 36-464 of SEQ ID NO:1.

23. The combination dosing regimen of claim 22, wherein the sequence of amino acids of the soluble hyaluronidase has at least 94% sequence identity to the sequence of amino acids that contains at least amino acids 36-464 of SEQ ID NO:1.

24. The combination dosing regimen of claim 23, wherein the sequence of amino acids of the soluble hyaluronidase has at least 95% sequence identity to the sequence of amino acids that contains at least amino acids 36-464 of SEQ ID NO:1.

25. The combination dosing regimen of claim 24, wherein the sequence of amino acids of the soluble hyaluronidase has at least 96% sequence identity to the sequence of amino acids that contains at least amino acids 36-464 of SEQ ID NO:1.

26. The combination dosing regimen of claim 25, wherein the sequence of amino acids of the soluble hyaluronidase has at least 97% sequence identity to the sequence of amino acids that contains at least amino acids 36-464 of SEQ ID NO:1.

27. The combination dosing regimen of claim 26, wherein the sequence of amino acids of the soluble hyaluronidase has at least 98% sequence identity to the sequence of amino acids that contains at least amino acids 36-464 of SEQ ID NO:1.

28. The combination dosing regimen of claim 27, wherein the sequence of amino acids of the soluble hyaluronidase has at least 99% sequence identity to the sequence of amino acids that contains at least amino acids 36-464 of SEQ ID NO:1.

29. The combination dosing regimen of claim 9, wherein the soluble hyaluronidase and the ADC are administered on day one (1) and day eight (8) of a twenty-one (21) day treatment cycle for three (3) cycles.

30. The combination dosing regimen of claim 9, wherein the soluble hyaluronidase and the ADC are administered on day one (1) and day fifteen (15) of a twenty-one (21) day treatment cycle.

31. The combination dosing regimen of claim 9, wherein the soluble hyaluronidase and the ADC are administered on day one (1), day fifteen (15), and day twenty-nine (29) of a forty-two (42) day treatment cycle.

32. The combination dosing regimen of claim 9, wherein the soluble hyaluronidase and the ADC are administered on day one (1), day eight (8), and day fifteen (15) of a twenty-eight (28) day treatment cycle.

33. The combination dosing regimen of claim 9, wherein the soluble hyaluronidase and the ADC are administered on day one (1), day four (4), and day seven (7) of an induction cycle.

34. The combination dosing regimen of claim 1, wherein the soluble hyaluronidase and the ADC are administered twice a day (Q2).

35. The combination dosing regimen of claim 1, wherein the soluble hyaluronidase and the ADC are administered three times a day (Q3).

36. The combination dosing regimen of claim 1, wherein the soluble hyaluronidase and the ADC are administered four times a day (Q4).

37. The combination dosing regimen of claim 1, wherein the subcutaneous administration of the combination dosing regimen yields an AUC of the ADC in blood that is about 50% to about 90% of an AUC of an intravenous administration of a dosing regimen comprising an equivalent dose of the ADC without the soluble hyaluronidase.

* * * * *